(12) United States Patent
Babb et al.

(10) Patent No.: US 11,142,578 B2
(45) Date of Patent: Oct. 12, 2021

(54) ANTI-MET ANTIBODIES, BISPECIFIC ANTIGEN BINDING MOLECULES THAT BIND MET, AND METHODS OF USE THEREOF

(71) Applicant: Regeneron Pharmaceuticals, Inc., Tarrytown, NY (US)

(72) Inventors: Robert Babb, River Edge, NJ (US); Gang Chen, Yorktown Heights, NY (US); Christopher Daly, New York, NY (US); John DaSilva, Somers, NY (US); Douglas MacDonald, New York, NY (US); Thomas Nittoli, Pearl River, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 273 days.

(21) Appl. No.: 15/814,095

(22) Filed: Nov. 15, 2017

(65) Prior Publication Data

US 2018/0134794 A1     May 17, 2018

Related U.S. Application Data

(60) Provisional application No. 62/423,068, filed on Nov. 16, 2016, provisional application No. 62/479,516, filed on Mar. 31, 2017.

(51) Int. Cl.

| | |
|---|---|
| *C07K 16/28* | (2006.01) |
| *A61K 47/68* | (2017.01) |
| *A61P 35/00* | (2006.01) |
| *A61K 31/537* | (2006.01) |
| *C07K 16/30* | (2006.01) |

(52) U.S. Cl.
CPC ........ *C07K 16/2863* (2013.01); *A61K 31/537* (2013.01); *A61K 47/6803* (2017.08); *A61K 47/6849* (2017.08); *A61K 47/6857* (2017.08); *A61K 47/6863* (2017.08); *A61K 47/6879* (2017.08); *A61K 47/6889* (2017.08); *A61P 35/00* (2018.01); *C07K 16/3023* (2013.01); *C07K 16/3046* (2013.01); *C07K 2317/31* (2013.01); *C07K 2317/34* (2013.01); *C07K 2317/35* (2013.01); *C07K 2317/565* (2013.01); *C07K 2317/73* (2013.01); *C07K 2317/76* (2013.01); *C07K 2317/92* (2013.01)

(58) Field of Classification Search
CPC ............ A61K 47/6889; A61K 47/6803; A61K 47/6879; A61K 47/6849; A61K 31/537; A61K 39/395; A61K 39/3955; A61K 39/39558; C07K 2317/31; C07K 16/2863

See application file for complete search history.

(56) References Cited

U.S. PATENT DOCUMENTS

| | | | |
|---|---|---|---|
| 5,208,020 | A | 5/1993 | Chari et al. |
| 5,639,879 | A | 6/1997 | Mease et al. |
| 5,646,036 | A | 7/1997 | Schwall et al. |
| 5,686,292 | A | 11/1997 | Schwall et al. |
| 5,707,624 | A | 1/1998 | Nickoloff et al. |
| 5,714,586 | A | 2/1998 | Kunstmann et al. |
| 6,099,841 | A | 8/2000 | Hillan et al. |
| 6,207,152 | B1 | 3/2001 | Schwall et al. |
| 6,214,344 | B1 | 4/2001 | Schwall et al. |
| 6,468,529 | B1 | 10/2002 | Schwall et al. |
| 7,087,411 | B2 | 8/2006 | Daly et al. |
| 7,476,724 | B2 | 1/2009 | Dennis et al. |
| 7,498,420 | B2 | 3/2009 | Michaud et al. |
| 7,556,804 | B2 | 7/2009 | Prat |

(Continued)

FOREIGN PATENT DOCUMENTS

| | | |
|---|---|---|
| EP | 1636593 B9 | 12/2009 |
| EP | 2127683 | 12/2009 |

(Continued)

OTHER PUBLICATIONS

Ferrucci et al (Clinical Cancer Research, 2014, vol. 20, pp. 5796-5807) (Year: 2014).*

(Continued)

*Primary Examiner* — Karen A. Canella
(74) *Attorney, Agent, or Firm* — FisherBroyles, LLP; Cara L. Crowley-Weber; Robert Chang

(57) ABSTRACT

Provided herein are antibodies and bispecific antigen-binding molecules that bind MET and methods of use thereof. The bispecific antigen-binding molecules comprise a first and a second antigen-binding domain, wherein the first and second antigen-binding domains bind to two different (preferably non-overlapping) epitopes of the extracellular domain of human MET. The bispecific antigen-binding molecules are capable of blocking the interaction between human MET and its ligand HGF. The bispecific antigen-binding molecules can exhibit minimal or no MET agonist activity, e.g., as compared to monovalent antigen-binding molecules that comprise only one of the antigen-binding domains of the bispecific molecule, which tend to exert unwanted MET agonist activity. Also included are antibody-drug conjugates (ADCs) comprising the antibodies or bispecific antigen-binding molecules provided herein linked to a cytotoxic agent, radionuclide, or other moiety, as well as methods of treating cancer in a subject by administering to the subject a bispecific antigen-binding molecule or an ADC thereof.

26 Claims, 20 Drawing Sheets

Specification includes a Sequence Listing.

(56) References Cited

U.S. PATENT DOCUMENTS

| | | |
|---|---|---|
| 7,615,529 B2 | 11/2009 | Kong-Beltran et al. |
| 7,714,016 B2 | 5/2010 | Gangwar et al. |
| 7,718,174 B2 | 5/2010 | Chung et al. |
| 7,750,116 B1 | 6/2010 | Doronina et al. |
| 7,754,681 B2 | 7/2010 | Feng |
| 7,892,550 B2 | 2/2011 | Dennis et al. |
| 7,892,770 B2 | 2/2011 | Cao et al. |
| 8,039,598 B2 | 10/2011 | Cao |
| 8,101,727 B2 | 1/2012 | Stover et al. |
| 8,133,867 B2 | 3/2012 | Otsuka et al. |
| 8,163,280 B2 | 4/2012 | Michaud et al. |
| 8,217,148 B2 | 7/2012 | Davies et al. |
| 8,309,315 B2 | 11/2012 | Cao et al. |
| 8,329,173 B2 | 12/2012 | Goetsch |
| 8,388,958 B2 | 3/2013 | Comoglio et al. |
| 8,398,974 B2 | 3/2013 | Davies et al. |
| 8,455,623 B2 | 6/2013 | Van Der Horst et al. |
| 8,501,917 B2 | 8/2013 | Kim et al. |
| 8,536,118 B2 | 9/2013 | Kong-Beltran et al. |
| 8,545,839 B2 | 10/2013 | Goetsch et al. |
| 8,546,544 B2 | 10/2013 | Cheong et al. |
| 8,562,985 B2 | 10/2013 | Michaud et al. |
| 8,563,696 B2 | 10/2013 | Cheong et al. |
| 8,623,359 B2 | 1/2014 | Goetsch |
| 8,637,027 B2 | 1/2014 | Hultberg et al. |
| 8,673,302 B2 | 3/2014 | Goetsch et al. |
| 8,741,290 B2 | 6/2014 | Goetsch et al. |
| 8,747,850 B2 | 6/2014 | Goetsch et al. |
| 8,765,128 B2 | 7/2014 | Goetsch et al. |
| 8,821,869 B2 | 9/2014 | Michaud et al. |
| 8,871,909 B2 | 10/2014 | Goetsch |
| 8,871,910 B2 | 10/2014 | Goetsch |
| 8,889,832 B2 | 11/2014 | Goetsch |
| 8,900,582 B2 | 12/2014 | Cheong et al. |
| 9,011,865 B2 | 4/2015 | Goetsch |
| 9,062,104 B2 | 6/2015 | Garcia-Martinez et al. |
| 9,068,011 B2 | 6/2015 | Neijssen et al. |
| 9,101,610 B2 | 8/2015 | Cheong et al. |
| 9,107,907 B2 | 8/2015 | Goetsch |
| 9,120,852 B2 | 9/2015 | Jouhanneaud |
| 9,150,655 B2 | 10/2015 | Wu et al. |
| 9,169,329 B2 | 10/2015 | Johns et al. |
| 9,192,666 B2 | 11/2015 | Kim et al. |
| 9,201,074 B2 | 12/2015 | Davies et al. |
| 9,213,031 B2 | 12/2015 | Lee et al. |
| 9,233,155 B2 | 1/2016 | Kim et al. |
| 9,249,221 B2 | 2/2016 | Lee et al. |
| 9,260,531 B2 | 2/2016 | Beuerlein et al. |
| 9,296,817 B2 | 3/2016 | Kim et al. |
| 9,328,173 B2 | 5/2016 | Aldaz et al. |
| 9,359,437 B2 | 6/2016 | Davis et al. |
| 9,364,556 B2 | 6/2016 | Park et al. |
| 9,375,425 B2 | 6/2016 | Goetsch |
| 9,394,367 B2 | 7/2016 | Cheong et al. |
| 9,458,245 B2 | 10/2016 | Harms et al. |
| 9,469,691 B2 | 10/2016 | Cheong et al. |
| 9,481,725 B2 | 11/2016 | Dutzar et al. |
| 9,487,589 B2 | 11/2016 | Demeule et al. |
| 9,505,843 B2 | 11/2016 | Kim et al. |
| 9,535,055 B2 | 1/2017 | Kim et al. |
| 9,556,275 B2 | 1/2017 | Jeong et al. |
| 9,567,641 B2 | 2/2017 | Kim et al. |
| 9,572,878 B2 | 2/2017 | Lee et al. |
| 9,580,508 B2 | 2/2017 | Chiu et al. |
| 9,593,164 B2 | 3/2017 | Chiu et al. |
| 9,631,020 B2 | 4/2017 | Park et al. |
| 9,631,027 B2 | 4/2017 | Hultberg et al. |
| 9,637,541 B2 | 5/2017 | Kim et al. |
| 9,650,443 B2 | 5/2017 | Song et al. |
| 9,657,104 B2 | 5/2017 | Cho et al. |
| 9,657,107 B2 | 5/2017 | Neijssen et al. |
| 9,688,773 B2 | 6/2017 | Hultberg et al. |
| 9,695,228 B2 | 7/2017 | Mark et al. |
| 9,717,715 B2 | 8/2017 | Lee et al. |
| 9,725,497 B2 | 8/2017 | Anderson et al. |
| 9,730,926 B2 | 8/2017 | Lin et al. |
| 9,732,150 B2 | 8/2017 | Garcia-Martinez et al. |
| 9,783,603 B2 | 10/2017 | Garcia-Martinez et al. |
| 9,808,507 B2 | 11/2017 | Oh et al. |
| 9,884,917 B2 | 2/2018 | Hultberg et al. |
| 9,902,776 B2 | 2/2018 | Cho et al. |
| 9,931,400 B2 | 4/2018 | Jeong et al. |
| 9,950,076 B2 | 4/2018 | Nittoli et al. |
| 9,975,960 B2 | 5/2018 | Cho et al. |
| 9,994,644 B2 | 6/2018 | Wong et al. |
| 10,000,569 B2 | 6/2018 | Cheong et al. |
| 10,100,108 B2 | 10/2018 | Dutzar et al. |
| 10,106,622 B2 | 10/2018 | Yoo et al. |
| 10,143,749 B2 | 12/2018 | Cho et al. |
| 10,214,593 B2 | 2/2019 | Jung et al. |
| 10,246,507 B2 | 4/2019 | Lee et al. |
| 10,570,151 B2 | 2/2020 | Nittoli et al. |
| 2004/0166544 A1 | 8/2004 | Morton et al. |
| 2005/0233960 A1 | 10/2005 | Kong-Beltran et al. |
| 2007/0258987 A1 | 11/2007 | Francisco et al. |
| 2007/0280945 A1 | 12/2007 | Stevens et al. |
| 2008/0305497 A1 | 12/2008 | Kosmeder et al. |
| 2009/0068179 A1 | 3/2009 | Nayeri et al. |
| 2009/0142354 A1 | 6/2009 | Papadopoulos et al. |
| 2009/0226443 A1 | 9/2009 | Filvaroff et al. |
| 2009/0226455 A1 | 9/2009 | Filvaroff |
| 2009/0297439 A1 | 12/2009 | Comoglio et al. |
| 2010/0016241 A1 | 1/2010 | Kong-Beltran et al. |
| 2010/0129314 A1 | 5/2010 | Singh et al. |
| 2010/0254988 A1 | 10/2010 | Bossenmaier et al. |
| 2010/0256339 A1 | 10/2010 | Bossenmaier et al. |
| 2011/0027286 A1 | 2/2011 | Thurston et al. |
| 2011/0104161 A1 | 5/2011 | Burgess et al. |
| 2011/0104166 A1 | 5/2011 | Stankovic et al. |
| 2011/0229469 A1 | 9/2011 | Johns |
| 2011/0239316 A1 | 9/2011 | Goetsch et al. |
| 2011/0287003 A1 | 11/2011 | Patel et al. |
| 2012/0134996 A1 | 5/2012 | Comoglio et al. |
| 2012/0171210 A1 | 7/2012 | Kong-Beltran et al. |
| 2012/0237524 A1 | 9/2012 | Boccaccio et al. |
| 2013/0089542 A1 | 4/2013 | Lee et al. |
| 2013/0101546 A1 | 4/2013 | Yurkovetskiy et al. |
| 2013/0102494 A1 | 4/2013 | Jouhanneaud |
| 2013/0109840 A1 | 5/2013 | Goetsch et al. |
| 2013/0129718 A1 | 5/2013 | Wong et al. |
| 2013/0143813 A1 | 6/2013 | Kirchhofer et al. |
| 2013/0156772 A1 | 6/2013 | Bossenmaier et al. |
| 2013/0164281 A1 | 6/2013 | Cheong et al. |
| 2013/0171063 A1 | 7/2013 | Johns et al. |
| 2013/0209365 A1 | 8/2013 | Wu et al. |
| 2013/0216548 A1 | 8/2013 | Neijssen et al. |
| 2013/0315895 A1 | 11/2013 | Farrell et al. |
| 2013/0316450 A1 | 11/2013 | Van Der Horst et al. |
| 2014/0349310 A1 | 11/2014 | Davies et al. |
| 2015/0017170 A1 | 1/2015 | Oh et al. |
| 2015/0050275 A1 | 2/2015 | Wong et al. |
| 2015/0182622 A1 | 7/2015 | Lashkari |
| 2015/0197542 A1 | 7/2015 | Kim et al. |
| 2015/0284808 A1 | 10/2015 | Chung et al. |
| 2015/0299326 A1 | 10/2015 | Wu et al. |
| 2016/0222115 A1 | 8/2016 | Huang et al. |
| 2016/0354482 A1 | 12/2016 | Nittoli |
| 2016/0375147 A1 | 12/2016 | Nittoli |
| 2017/0137539 A1 | 5/2017 | Fu et al. |
| 2017/0209591 A1 | 7/2017 | Nittoli et al. |
| 2017/0233489 A1 | 8/2017 | Shim et al. |
| 2017/0281796 A1* | 10/2017 | Zhu .................. C07K 16/2863 |
| 2017/0283501 A1 | 10/2017 | Swanson et al. |
| 2017/0348429 A1 | 12/2017 | Reilly et al. |
| 2018/0110875 A1 | 4/2018 | Liu et al. |
| 2018/0134794 A1 | 5/2018 | Babb et al. |
| 2018/0250418 A1 | 9/2018 | Afar et al. |
| 2018/0280531 A1 | 10/2018 | Zhu et al. |
| 2018/0326085 A1 | 11/2018 | Doerner et al. |

(56) References Cited

U.S. PATENT DOCUMENTS

| | | |
|---|---|---|
| 2018/0327500 A1 | 11/2018 | Bouquin et al. |
| 2021/0077638 A1 | 3/2021 | Kelly et al. |

FOREIGN PATENT DOCUMENTS

| | | |
|---|---|---|
| EP | 0922102 B1 | 4/2010 |
| EP | 1641828 B1 | 4/2010 |
| EP | 1773885 B1 | 4/2010 |
| EP | 2188312 | 5/2010 |
| EP | 2316484 | 5/2011 |
| EP | 1981981 B1 | 6/2011 |
| EP | 2336178 A1 | 6/2011 |
| EP | 2575879 B1 | 6/2011 |
| EP | 1997511 B1 | 7/2011 |
| EP | 2367008 A2 | 9/2011 |
| EP | 1957102 B1 | 1/2012 |
| EP | 2195345 B1 | 5/2012 |
| EP | 2004693 B1 | 6/2012 |
| EP | 2500036 A1 | 9/2012 |
| EP | 2535356 | 12/2012 |
| EP | 2708556 A1 | 3/2014 |
| EP | 2787008 A1 | 10/2014 |
| EP | 1868648 B1 | 4/2015 |
| EP | 2358755 | 9/2015 |
| EP | 2963058 | 1/2016 |
| EP | 2635603 B1 | 3/2016 |
| EP | 2611928 B1 | 4/2016 |
| EP | 2635602 B1 | 9/2016 |
| EP | 2370468 B1 | 4/2017 |
| EP | 2824113 A1 | 5/2017 |
| EP | 2588497 | 6/2017 |
| EP | 2870178 | 7/2017 |
| EP | 3196211 A1 | 7/2017 |
| EP | 2786764 B1 | 8/2017 |
| EP | 2832748 A1 | 9/2017 |
| EP | 2784091 B1 | 11/2017 |
| EP | 2784092 B1 | 12/2017 |
| EP | 2467402 B1 | 1/2018 |
| EP | 2963058 | 2/2018 |
| EP | 3284751 A1 | 2/2018 |
| EP | 2786765 B1 | 3/2018 |
| EP | 2415785 | 4/2018 |
| EP | 2535357 | 8/2018 |
| EP | 2764026 A1 | 8/2018 |
| EP | 3135691 B1 | 8/2018 |
| EP | 2545077 B1 | 10/2018 |
| EP | 2922566 A1 | 10/2018 |
| EP | 2922872 B1 | 10/2018 |
| EP | 2937421 B1 | 10/2018 |
| EP | 2708556 B1 | 11/2018 |
| EP | 2992019 B1 | 3/2019 |
| EP | 2764024 A1 | 8/2019 |
| EP | 3544634 B1 | 4/2021 |
| WO | WO 2005/016382 A1 | 2/2005 |
| WO | 2005/058965 | 6/2005 |
| WO | 2005/089808 | 9/2005 |
| WO | 2006/015371 | 2/2006 |
| WO | 2008/122039 | 10/2008 |
| WO | WO 2009/111691 A2 | 9/2009 |
| WO | WO 2009/140549 A1 | 11/2009 |
| WO | 2010/010324 | 1/2010 |
| WO | WO 2010/045344 | 4/2010 |
| WO | WO 2010/045345 | 4/2010 |
| WO | 2010/115553 | 10/2010 |
| WO | WO 2010/115551 | 10/2010 |
| WO | WO 2010/115552 | 10/2010 |
| WO | WO 2010/115553 A1 | 10/2010 |
| WO | 2011/018611 | 2/2011 |
| WO | 2011/056983 | 5/2011 |
| WO | 2011/110642 | 9/2011 |
| WO | 2011/130598 | 10/2011 |
| WO | WO 2011/143665 | 11/2011 |
| WO | 2011/150454 | 12/2011 |
| WO | 2012/005982 | 1/2012 |
| WO | WO 2012/003338 | 1/2012 |
| WO | WO 2012/136685 | 10/2012 |
| WO | WO 2012/161372 | 11/2012 |
| WO | 2012/166559 | 12/2012 |
| WO | WO 2012/165925 | 12/2012 |
| WO | WO 2013/003680 A1 | 1/2013 |
| WO | WO 2013/043452 | 3/2013 |
| WO | WO 2013/043715 | 3/2013 |
| WO | 2013/053872 | 4/2013 |
| WO | 2013/053873 | 4/2013 |
| WO | 2013/055990 | 4/2013 |
| WO | 2013/055993 | 4/2013 |
| WO | WO 2013/051891 | 4/2013 |
| WO | WO-2013045707 A2 * | 4/2013 |
| WO | 2013/064701 | 5/2013 |
| WO | 2013/068874 | 5/2013 |
| WO | 2013/085925 | 6/2013 |
| WO | WO 2013/081379 | 6/2013 |
| WO | WO 2013/152252 A1 | 10/2013 |
| WO | WO 2013/169532 A1 | 11/2013 |
| WO | WO 2013/188752 | 12/2013 |
| WO | WO 2013/192594 | 12/2013 |
| WO | 2014/065661 | 5/2014 |
| WO | 2014/145090 | 9/2014 |
| WO | 2015/031396 | 3/2015 |
| WO | WO-2015031396 A1 * | 3/2015 |
| WO | WO 2015/081857 A1 | 6/2015 |
| WO | 2015/140212 | 9/2015 |
| WO | WO 2016/042412 A1 | 3/2016 |
| WO | WO 2016/060297 | 4/2016 |
| WO | 2016/094455 | 6/2016 |
| WO | WO 2016/094455 A1 | 6/2016 |
| WO | WO 2017/076492 A1 | 5/2017 |
| WO | WO 2017/087603 A1 | 5/2017 |
| WO | WO 2017/135791 A1 | 8/2017 |
| WO | WO 2017/201204 A1 | 11/2017 |
| WO | WO 2018/050733 A1 | 3/2018 |
| WO | WO 2018/068758 | 4/2018 |
| WO | WO 2018/069851 | 4/2018 |
| WO | 2018/093866 | 5/2018 |
| WO | WO 2018/098035 A1 | 5/2018 |
| WO | WO 2018/221969 A1 | 12/2018 |
| WO | WO 2018/223958 A1 | 12/2018 |
| WO | WO 2019/031965 A1 | 2/2019 |
| WO | WO 2019/066617 | 4/2019 |
| WO | WO 2019/066620 | 4/2019 |

OTHER PUBLICATIONS

Tsao et al (Human Pathology, 2001, vol. 32, pp. 57-65) (Year: 2001).*
Rock et al (Drug Metabolism and Disposition, 2015, vol. 43, pp. 1341-1344) (Year: 2015).*
Casi et al (Journal of Controlled Release, 2012, vol. 161, pp. 422-428) (Year: 2012).*
Kawakami et al (Cancers, 2014, vol. 6, pp. 1540-1552) (Year: 2014).*
Smith (1979) "In Vitro Properties of Epithelial Cell Lines Established from Human Carcinomas and Nonmalignant Tissue", J. Nat'l. Cancer Inst. 62(2): 225-230.
Nair et al., (1994) "Induction of squamous differentiation by interferon beta in a human non-small-cell lung cancer cell line", J. Nat'l. Cancer Inst. 86(5): 378-383.
International Search Report and Written Opinion, received for PCT/US2017/061757 dated Apr. 4, 2018, 22 pages.
Agarwal et al., (2013) "A Pictet-Spengler Ligation for Protein Chemical Modification", Proc. Natl. Acad. Sci., USA, 110:46-51.
Al-Lazikaniet al., (1997) "Standard Conformations for the Canonical Structures of Immunoglobulins", J. Mol. Biol. 273:927-948.
Altschul et al., (1990) "Basic Local Alignment Search Tool", J. Mol. Biol. 215:403-410.
Altschul et al., (1997) "Grapped Blast and PSI-Blast: a new generation of protein database search programs", Nucleic Acids Res. 25:3389-402.
Bean et al., (2007) "MET amplification occurs with or without T790M mutations in EGFR mutant lung tumors with acquired resistance to gefitinib or erlotinib," Proc. Natl. Acad. Sci., 104(52): 20932-20937.

(56) References Cited

OTHER PUBLICATIONS

Carrico et al., (2007) "Introducing genetically encoded aldehydes into proteins", Nat. Chem. Biol., 3:321-322.
Collins (2007) "Image J for microscopy", BioTechniques 43: S25-S30.
Dinter et al., (2015) "Inverse Agonistic Action of 3-Iodothyronamine at the Human Trace Amine-Associated Receptor 5", PLoS ONE 10(2): e0117774.
Ducry (2010) "Antibody—Drug Conjugates: Linking Cytotoxic Payloads to Monoclonal Antibodies", Bioconjugate Chem., 21:5-13.
Ehring (1999) "Hydrogen Exchange/Electrospray Ionization Mass Spectrometry Studies of Structural Features of Proteins and Protein/Protein Interactions", Analytical Biochemistry 267(2):252-259.
Engen and Smith (2001) "The Basics of Ion Chromatography", Anal. Chem. 73:256A-265A.
Gonnet et al., (1992) "Exhaustive Matching of the Entire Protein Sequence Database", Science 256: 1443-1445.
Greenall, et al. (2012) "Non-agonistic bivalent antibodies that promote c-MET degradation and inhibit tumor growth and others specific for tumor related c-MET", PLOS One, Public Library of Science, US, 7(4):E34658.1-E34658.10.
Hamblett et al., (2004) "Effects of drug loading on the antitumor activity of a monoclonal antibody drug conjugate", American Association for Cancer Research, 10(20):7063-7070.
Hochleitner et al., (2000) "Characterization of a discontinuous epitope of the human immunodeficiency virus (HIV) core protein p24 by epitope excision and differential chemical modification followed by mass spectrometric peptide mapping analysis", Protein Science 9:487-496.
Hofer et al., (2008) "An engineered selenocysteine defines a unique class of antibody derivatives", Proc. Natl. Acad. Sci., USA, 105:12451-12456.
Hollander et al., (2008) "Selection of Reaction Additives Used in the Preparation of Monomeric Antibody-Calicheamicin Conjugates", Bioconjugate Chem., 19:358-361.
Kazane et al., (2012) "Self-Assembled Antibody Multimers through Peptide Nucleic Acid Conjugation," J. Am. Chem. Soc. [Epub: Dec. 4, 2012].
Klein et al., (2012) Progress in overcoming the chain association issue in bispecific heterodimeric IgG antibodies, mAbs 4:6, 1-11.
Ku and Park (2005) "Biology of SNU cell lines", Cancer Res. Treat. 37(1): 1-19.
Kubo et al., (2009) "MET gene amplification or EGFR mutation activate MET in lung cancers untreated with EGFR tyrosine kinase inhibitors", Int. J. Cancer, 124(8): 1778-1784.
Liu, et al. (2014) "LY2875358, a Neutralizing and Internalizing Anti-MET Bivalent Antibody, Inhibits HGF-Dependent and HGF-Independent MET Activation and Tumor Growth", Clinical Cancer Research 20(23):6059-6070.
Lutterbach et al., (2007) "Lung cancer cell lines harboring MET gene amplification are dependent on Met for growth and survival", Cancer Res. 67(5):2081-2088.
Martin et al., (1989) "Modeling antibody hypervariable loops: A combined algorithm", Proc. Natl. Acad. Sci. USA 86:9268-9272.
Olopade et al., (1992) "Molecular Analysis of Deletions of the Short Arm of Chromosome 9 in Human Gliomas", Cancer Research 52: 2523-2529.
Pearson (1994) "Using the FASTA Program to Search Protein and DNA Sequence Database", Methods Mol. Biol. 24: 307-331.
Rabuka et al., (2012) "Site-specific chemical protein conjugation using genetically encoded aldehyde tags", Nat. Protocols, 10:1052-1067.
Reineke, (2004) "Antibody Epitope Mapping Using Arrays of Synthetic Peptides", Methods Mol Biol 248:443-463.
Rosen et al., (2017) "A First-in-Human Phase I Study of a Bivalent MET Antibody, Emibetuzumab (LY2875358), as Monotherapy and in Combination with Erlotinib in Advanced Cancer", Clin. Cancer Res., 23(8):1910-1919.
Ryan et al., (2001) "Polyclonal Antibody Production Against Chito-Oligosaccharides", Food & Agriculture Immunol., 13:127-130.
Sapra et al., (2013) "Monoclonal antibody-based therapies in cancer: Advances and challenges", Pharmacol. & Therapeutics, 138:452-469.
Schumacher et al. (2016) "Current Status: Site-Specific Antibody Drug Conjugates", J. Clin. Immunol. 36(Suppl 1):100-107.
Shaunak et al., (2006) "Site-specific PEGylation of native disulfide bonds in therapeutic proteins," Nat. Chem. Biol., 2:312-313.
Shields et al., (2002) "Lack of Fucose on Human IgG1 N-Linked Oligosaccharide Improves Bidning to Human FcγRIII and Antibody-dependent Cellular Toxicity," JBC 277:26733.
Sierra and Tsao (2011) "c-MET as a potential therapeutic target and biomarker in cancer", Ther. Adv. Med. Oncol., 3(1 Suppl): S21-S35.
Taylor et al. (1992) "A Transgenic mouse that expresss a diversity of human sequence heavy and light chain Immunoglobulins", Nucl. Acids Res. 20:6287-6295.
Vordermark and Brown (2003) "Evaluation of hypoxia-inducible factor-1α (HIF-1α) as an intrinsic marker of tumor hypoxia in U87 MG human glioblastoma: In vitro and xenograft studies", Int. J. Radiation Biol. 56(4): 1184-1193.
Xiang et al., (2013) "Onartuzumab (MetMAb): Using Nonclinical Pharmacokinetic and Concentration—Effect Data to Support Clinical Development", Clin. Cancer Res. 19(18): 5068-5078.
Junghans et al., (1990) "Anti-Tac-H, a Humanized Antibody to the Interleukin 2 Receptor with New Features for Immnotherapy in Malignant and Immune Disorders", Cancer Research 50:14951502.
Godar, et al. (2006) "Dual anti-idiotypic purification of a novel, native-format biparatopic anti-MET antibody with improved in vitro and in vivo efficacy", Scientific Reports, 6:31621; 1-12, DOI:10.1038/srep31621.
Andres et al. (2019) "Inhibition of the MET Kinase Activity and Cell Growth in METAddicted Cancer Cells by Bi-Paratopic Linking" Journal of Molecular Biology, 40 pages.
Bancroft et al., (1986) "Regulation of macrophage la expression in mice with severe combined immunodeficiency: induction of la expression by a T cell-independent mechanism", J. Immunol. 137(1): 4-9, 1986.
Boersma and Pluckhun (2011) "DARPins and other repeat protein scaffolds: advances in engineering and applications", Curr. Opin. Biotechnol. 22:849-857.
Camidge et al. (2018) "An Open-Label, Multicenter, Phase 1 Study of ABBV-399 (Telisotuzumab Vedotin, Teliso-V) as Monotherapy (T) and in Combination WithErlotinib (T+E) in Non-Small Cell Lung Cancer (NSCLC)" Presented at the European Society for Medical Oncology Annual Congress • Munich, Germany • Oct. 19-23, 2018.
Cheng et al. (2018) "Phase 2 Study of Tepotinib + Gefitinib in MET-Positive/Epidermal Growth Factor Receptor-Mutant NSCLC", Munich 2018 ESMO Congress, 15 pages.
Cho et al. (2018) "JNJ-61186372 (JNJ-372), an EGFR-cMET Bispecific Antibody, in Advanced Non-Small Cell Lung Cancer (NSCLC): An Update on Phase 1 Results" Presented at the 43rd Annual Congress of the European Society for Medical Oncology, Oct. 19-23, 2018, Munich, Germany.
Doronina et al., (2003) "Development of potent monoclonal antibody auristatin conjugates for cancer therapy", Nature Biotechnology, 21(7):778-784.
Godar, et al. (2016) "Dual anti-idiotypic purification of a novel, native-format biparatopic anti-MET antibody with improved in vitro and in vivo efficacy", Scientific Reports, 6:31621; 1-12, DOI:10.1038/srep31621.
Grandal et al. (2017) "Simultaneous Targeting of Two Distinct Epitopeson MET Effectively Inhibits MET-and HGF-Driven Tumor Growth by Multiple Mechanisms", Molecular Cancer Therapeutics, 16:2780-2791.
Jeger et al. (2010) "Site-Specific and Stoichiometric Modification of Antibodies by Bacterial Transglutaminase," Angew Chemie Inter Ed. 49:9995-9997.
Kabat (1991) "Sequences of Proteins of Immunological Interest," National Institutes of Health, Bethesda, Md.

(56) References Cited

OTHER PUBLICATIONS

Nakamura et al. (2010) "The discovery of Hepatocyte Growth Factor (HGF) and its significance for cell biology, life sciences and clinical medicine", Proc. Jpn. Acad., Ser. B 86:588.

Wang et al. (2016) "ABBV-399, a c-Met Antibody-Drug Conjugate that Targets Both MET-Amplified and c-Met-Overexpressing Tumors, Irrespective of MET Pathway Dependence", Clinical Cancer Research, 23(4):992-1000.

Wang et al. (2016) "Anti-c-Met monoclonal antibody ABT-700 breaks oncogene addiction in tumors with MET amplicfication", BMC Cancer, 16:105, pp. 1-14.

Widdison et al. (2006) "Semisynthetic maytansine analogues for the targeted treatment of cancer", J. Med. Chem., 49(14):4392-4408.

Wolf, et al. (2018) "Results of the Geometry Mono-1 Phase Ii Study For Evaluation Of The Met Inhibitor Capmatinib (INC280) In Patients With MetΔex14 Mutated Advanced Non-Small Cell Lung Cancer" Munich 2018 ESMO Congress, 19 pages.

Taylor et al. (2017) "AbbVie pairs up another ADC cancer drug with Bristol-Myers Squibb's Opdvio" FierceBiotech. https://www.fiercebiotech.com/biotech/abbvie-pairs-up-another-adc-cancer-drug-bms-opdivo.

Allen (1999) "The Art, Science and Technology of Pharmaceutical Compounding", Fifth Edition, American Pharmacists Association, Washington D.C.

Czyz (2018) "HGF/c-MET Signaling in Melanocytes and Melanoma", International Journal of Molecular Sciences, 19(12):3844-3856.

Ducry (2013) "Antibody-Drug Conjugates" Humana Press, Springer Protocols, 315 pages.

Han et al. (2017) "Analysis of Progress and Challenges for Various Patterns of c-MET-targeted Molecular Imaging: a Systematic Review", Ejnmmi Research, Biomed Central Ltd., 7(1):1-15.

Kazane et al. (2013) "Self-Assembled Antibody Multimers through Peptide Nucleic Acid Conjugation" J Am Chem Soc 135:340-346.

Martens et al. (2006) "A Novel One-Armed Anti-c-Met Antibody Inhibits Glioblastoma Growth In vivo", Clin Cancer Res,12(20): 6144-6152.

Padlan et al. (1995) "Identification of Specificity-Determining Residues in Antibodies", FASEB J. 9(1):133-139.

Pearson (2000) "Flexible Sequence Similarity Searching with the FASTA3 Program Package", Methods in Molecular Biology, 132:185-219.

Powell et al. (1998) "Compendium of excipients for parenteral formulations" PDA J Pharm Sci Technol 52:238-311.

Surriga, et al. (2013) "Crizotinib, a c-Met Inhibitor, Prevents Metastasis in a Metastatic Uveal Melanoma Model", Molecular Cancer Therapeutics, 12(12):2817-2826.

Tomer (2000) "Characterization of a Discontinuous Epitope of the Human Immunodeficiency Virus (HIV) Core Protein p24 by Eptiope Excision and Differential Chemical Modification Followed by Mass Spectrometric Peptide Mapping Analysis" Protein Science 9:487-496.

Vajdos et al. (2002) "Comprehensive Functional Maps of the Antigen-Binding Site of an Anti-ErbB2 Antibody Obtained with Shotgun Scanning Mutagenesis", J Mol Biol, 320:415-428.

International Search Report and Written Opinion for International Application No. PCT/US2020/050865 dated Dec. 1, 2020, 19 pages.

International Search Report and Written Opinion, for International Application No. PCT/US2020/019126 dated Jun. 18, 2020, 16 pages.

\* cited by examiner

FIG. 1

ANTI-MET ANTIBODIES, BISPECIFIC ANTIGEN BINDING MOLECULES THAT BIND MET, AND METHODS OF USE THEREOF

CROSS-REFERENCE TO RELATED APPLICATIONS

This application claims the benefit under 34 U.S.C § 119(e) of U.S. Provisional Application No. 62/423,068, filed Nov. 16, 2016, and U.S. Provisional Application No. 62/479,516, filed Mar. 31, 2017, both of which are herein specifically incorporated by reference in their entireties.

FIELD OF THE INVENTION

The present invention relates to antibodies, bispecific antibodies, and antigen-binding fragments thereof, as well as antibody-drug conjugates of such antibodies, which specifically bind the hepatocyte growth factor receptor (c-Met or MET) and modulate MET signal transduction, and methods of use thereof.

SEQUENCE LISTING

An official copy of the sequence listing is submitted concurrently with the specification electronically via EFS-Web as an ASCII formatted sequence listing with a file name of 10316US01_Sequence_Listing_ST25.TXT, a creation date of Nov. 15, 2017, and a size of about 136 kilobytes. The sequence listing contained in this ASCII formatted document is part of the specification and is herein incorporated by reference in its entirety.

BACKGROUND

Hepatocyte growth factor (HGF) (a.k.a. scatter factor [SF]) is a heterodimeric paracrine growth factor that exerts its activity by interacting with the HGF receptor (HGFR). HGFR is the product of the c-Met oncogene and is also known as MET. MET is a receptor tyrosine kinase consisting of a transmembrane beta chain linked via a disulfide bridge to an extracellular alpha chain. The binding of HGF to MET activates the kinase catalytic activity of MET resulting in the phosphorylation of Tyr 1234 and Tyr 1235 of the beta chain and subsequent activation of downstream signaling pathways.

MET and/or HGF overexpression, activation, or amplification has been shown to be involved in non-small cell lung carcinoma (NSCLC), gastric, ovarian, pancreatic, thyroid, breast, head and neck, colon and kidney carcinomas (Sierra and Tsao, Ther. Adv. Med. Oncol., 3(1 Suppl): S21-S35, 2011). MET amplification is thought to be a key driver of oncogenesis in NSCLCs and oesophagogastric malignancies. In addition, mutations resulting in exon 14 deletion of MET have been described as oncogenic drivers in a subset of NSCLC. Tumor cell lines having MET gene amplification are highly dependent on MET for growth and survival. Preclinical data implicate MET signaling in resistance to targeted therapies in multiple tumor types, such as NSCLC, colorectal cancer, and head and neck squamous-cell carcinoma (HNSCC).

Both preclinical and recent clinical results indicate that tumors harboring these genetic alterations respond to MET inhibitors, validating MET as a cancer driver. Various monovalent MET blocking antibodies are in clinical development for the treatment of various cancers (see U.S. Pat. Nos. 5,686,292; 5,646,036; 6,099,841; 7,476,724; 9,260,531; and 9,328,173; and U.S. Patent Application Publications No. 2014/0349310 and 2005/0233960). Those antibodies include onartuzumab (MetMab) and emibetuzumab, (Xiang et al., Clin. Cancer Res. 19(18): 5068-78, 2013, and Rosen et al., Clin. Cancer Res., Published Oct. 10, 2016, doi: 10.1158/1078-0432.CCR-16-1418). Some of these antibodies block ligand-dependent MET signaling, but are not as effective in blocking ligand-independent MET activation.

There remains a significant unmet medical need for improved anti-cancer drugs that potently block both ligand-dependent and ligand-independent MET signaling.

BRIEF SUMMARY

Provided herein are antibodies, antigen-binding fragments of antibodies, combinations of bivalent monospecific antibodies, and bispecific antibodies that bind human c-Met receptor protein (MET×MET). The antibodies are useful, inter alia, for targeting tumor cells that express MET. The anti-MET antibodies, and antigen-binding portions thereof, may be used alone in unmodified form, or may be included as part of an antibody-drug conjugate or a bispecific antibody.

Other embodiments will become apparent from a review of the ensuing detailed description.

BRIEF DESCRIPTION OF THE FIGURES

FIG. 1 is a matrix illustrating the components of 272 exemplary MET×MET bispecific antibodies disclosed herein. Each numbered cell of the matrix identifies a unique bispecific antibody comprising a "D1" antigen binding domain and a "D2" antigen binding domain, wherein the D1 antigen binding domain comprises the immunoglobulin variable domain (HCVR/LCVR amino acid sequence pair) or CDRs from the corresponding anti-MET antibody listed along the Y-axis, and wherein the D2 antigen binding domain comprises the immunoglobulin variable domain (HCVR/LCVR amino acid sequence pair) or CDRs from the corresponding anti-MET antibody listed along the X-axis.

FIGS. 3(A-B) are line graphs depicting relative luminosity units (RLU) representing SRE-luciferase expression as a function of antibody concentration in log moles per liter. Filled squares (■) represent parental bivalent monospecific antibody H4H13306P2, filled pyramids (▲) represent parental bivalent monospecific antibody H4H13312P2, filled circles (●) represent a monovalent antibody, filled diamonds (♦) represent isotype control, and filled inverted pyramids (▼) represent no ligand.

FIGS. 4(A-B) are a line graphs depicting relative luminosity units (RLU) representing SRE-luciferase expression as a function of antibody concentration in log moles per liter. Filled squares (■) represent an anti-MET monovalent antibody, filled circles (●) represent a MET×MET bispecific antibody, and filled diamonds (♦) represent parental antibody H4H13312P2.

FIGS. 6(A-B) contains bar charts depicting the relative cell growth of MET-amplified cells as a function of treatment with a MET×MET bispecific antibody, a control antibody and an anti-MET monovalent antibody.

FIGS. 13(A-B) contain bar charts depicting the relative cell growth of MET-amplified cells as a function of treatment with a MET×MET bispecific antibody, a control antibody and an anti-MET monovalent antibody.

DETAILED DESCRIPTION

Figure 2:
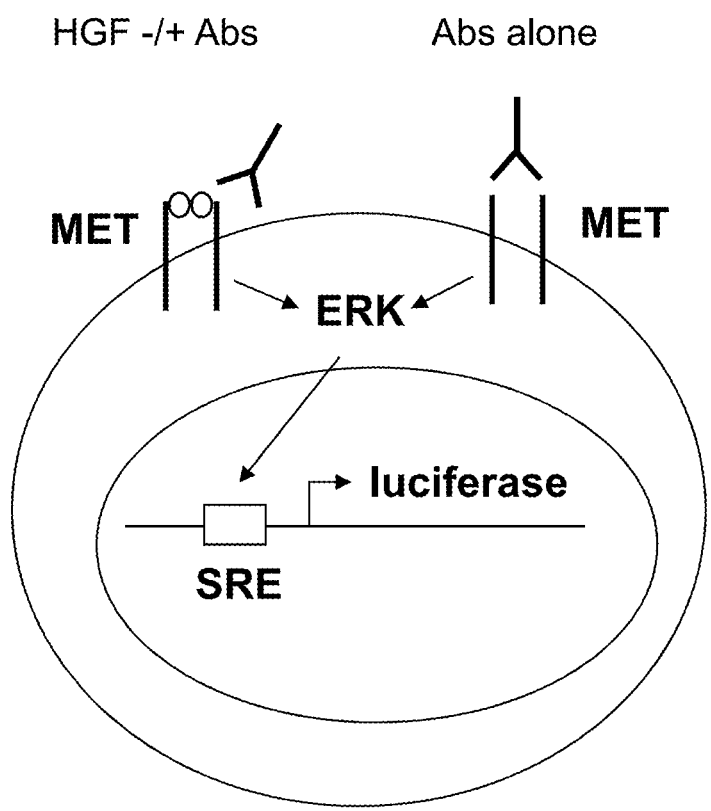
FIG. 2 is a schematic of a luciferase-based reporter assay used to assess antibody-induced MET pathway activation or antibody blockade of HGF-induced pathway activation in HEK293T cells containing an SRE-Luciferase reporter gene construct.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Met Protein

The expressions "MET," "c-Met," and the like, as used herein, refer to the human membrane spanning receptor tyrosine kinase comprising (1) the amino acid sequence as set forth in SEQ ID NO:145, and/or having the amino acid sequence as set forth in NCBI accession No. NM_001127500.2, representing the unprocessed prepropro- tein of isoform "a", (2) the amino acid sequence as set forth in SEQ ID NO:146, and/or having the amino acid sequence as set forth in NCBI accession No. NM_000236.2, repre- senting the unprocessed preproprotein of isoform "b", (3) the amino acid sequence as set forth in SEQ ID NO:147, and/or having the amino acid sequence as set forth in NCBI accession No. NM_001311330.1, representing the unpro- cessed preproprotein of isoform "c", and/or (3) the mature protein comprising the cytoplasmic alpha subunit (SEQ ID NO:148) shared by all three isoforms and the transmem- brane beta subunit (SEQ ID NO:149, 150, or 151 of isoform a, b and c, respectively). The expression "MET" includes both monomeric and multimeric MET molecules. As used herein, the expression "monomeric human MET" means a MET protein or portion thereof that does not contain or possess any multimerizing domains and that exists under normal conditions as a single MET molecule without a direct physical connection to another MET molecule. An exem- plary monomeric MET molecule is the molecule referred to herein as "hMET.mmh" comprising the amino acid sequence of SEQ ID NO:152 (see, e.g., Example 3, herein). As used herein, the expression "dimeric human MET" means a construct comprising two MET molecules con- nected to one another through a linker, covalent bond, non-covalent bond, or through a multimerizing domain such as an antibody Fc domain. An exemplary dimeric MET molecule is the molecule referred to herein as "hMET.mFc" comprising the amino acid sequence of SEQ ID NO:153 (see, e.g., Example 3, herein).

All references to proteins, polypeptides and protein frag- ments herein are intended to refer to the human version of the respective protein, polypeptide or protein fragment unless explicitly specified as being from a non-human species. Thus, the expression "MET" means human MET unless specified as being from a non-human species, e.g., "mouse MET," "monkey MET," etc.

As used herein, the expression "cell surface-expressed MET" means one or more MET protein(s), or the extracel- lular domain thereof, that is/are expressed on the surface of a cell in vitro or in vivo, such that at least a portion of a MET protein is exposed to the extracellular side of the cell membrane and is accessible to an antigen-binding portion of an antibody. A "cell surface-expressed MET" can comprise or consist of a MET protein expressed on the surface of a cell which normally expresses MET protein. Alternatively, "cell surface-expressed MET" can comprise or consist of MET protein expressed on the surface of a cell that normally does not express human MET on its surface but has been artifi- cially engineered to express MET on its surface.

Anti-Met Antibodies and Antigen-Binding Fragments Thereof

According to one aspect, anti-MET antibodies are pro- vided (e.g., monospecific anti-MET antibodies). Exemplary anti-MET antibodies according to this aspect are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-MET antibodies from which the bispecific antigen-binding molecules (used interchangeably herein with bispecific antigen-binding protein) disclosed herein may be derived. Table 2 sets forth the nucleic acid sequence identifiers of the HCVRs, LCVRs, HCDR1, HCDR2 HCDR3, LCDR1, LCDR2 and LCDR3 of the exemplary anti-MET antibodies.

Also provided herein are antibodies or antigen-binding fragments thereof that specifically bind MET and agonize (e.g., activate) the MET signaling pathway in cells, as well as the use of such antibodies in therapeutic settings where activation of MET signaling would be beneficial or thera- peutically useful. Non-limiting examples of such an agonist anti-MET antibodies include the antibody referred to herein as "H4H14636D," as well as antibodies and antigen-binding fragments thereof comprising the heavy and light chain CDRs (SEQ ID NOs: 28, 30, 32, 140, 142, 144) and/or heavy and light chain variable domains (SEQ ID NOs: 26/138) thereof.

Provided herein are antibodies or antigen-binding frag- ments thereof that specifically bind MET, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

Provided herein are antibodies or antigen-binding frag- ments thereof that specifically bind MET, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

Provided herein antibodies or antigen-binding fragments thereof that specifically bind MET, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, anti- bodies, or antigen-binding fragments thereof, comprise an HCVR/LCVR amino acid sequence pair contained within any of the exemplary anti-MET antibodies listed in Table 1. In certain embodiments, the HCVR/LCVR amino acid sequence pair is selected from the group consisting of: SEQ ID NO: 2/138, 10/138, 18/138, 26/138, 34/138, 42/138, 50/138, 58/138, 66/138, 74/138, 82/138, 90/138, 98/138, 106/138, 114/138, 122/138 and 130/138.

Also provided are antibodies or antigen-binding frag- ments thereof that specifically bind MET, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

Also provided are antibodies or antigen-binding frag- ments thereof that specifically bind MET, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

Also provided are antibodies or antigen-binding frag- ments thereof that specifically bind MET, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

Also provided are antibodies or antigen-binding fragments thereof that specifically bind MET, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

Also provided are antibodies or antigen-binding fragments thereof that specifically bind MET, comprising an HCDR1 and an LCDR1 amino acid sequence pair (HCDR1/LCDR1) comprising any of the HCDR1 amino acid sequences listed in Table 1 paired with any of the LCDR1 amino acid sequences listed in Table 1. According to certain embodiments, antibodies, or antigen-binding fragments thereof, comprise an HCDR3/LCDR3 amino acid sequence pair contained within any of the exemplary anti-MET antibodies listed in Table 1. In certain embodiments, the HCDR1/LCDR1 amino acid sequence pair is selected from the group consisting of: SEQ ID NO: 4/140, 12/140, 20/140, 28/140, 36/140, 44/140, 52/140, 60/140, 68/140, 76/140, 84/140, 92/140, 100/140, 108/140, 116/140, 124/140 and 132/140.

Also provided are antibodies or antigen-binding fragments thereof that specifically bind MET, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

Also provided are antibodies or antigen-binding fragments thereof that specifically bind MET, comprising an HCDR2 and an LCDR2 amino acid sequence pair (HCDR2/LCDR2) comprising any of the HCDR2 amino acid sequences listed in Table 1 paired with any of the LCDR2 amino acid sequences listed in Table 1. According to certain embodiments, antibodies, or antigen-binding fragments thereof, comprise an HCDR2/LCDR2 amino acid sequence pair contained within any of the exemplary anti-MET antibodies listed in Table 1. In certain embodiments, the HCDR2/LCDR2 amino acid sequence pair is selected from the group consisting of: SEQ ID NO: 6/142, 14/142, 22/142, 30/142, 38/142, 46/142, 54/142, 62/142, 70/142, 78/142, 86/142, 94/142, 102/142, 110/142, 118/142, 126/142, and 134/142.

Also provided are antibodies or antigen-binding fragments thereof that specifically bind MET, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

Also provided herein are antibodies or antigen-binding fragments thereof that specifically bind MET, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, antibodies, or antigen-binding fragments thereof, comprise an HCDR3/LCDR3 amino acid sequence pair contained within any of the exemplary anti-MET antibodies listed in Table 1. In certain embodiments, the HCDR3/LCDR3 amino acid sequence pair is selected from the group consisting of: SEQ ID NO: 8/144, 16/144, 24/144, 32/144, 40/144, 48/144, 56/144, 64/144, 72/144, 80/144, 88/144, 96/144, 104/144, 112/144, 120/144, 128/144 and 136/144.

Also provided herein are antibodies or antigen-binding fragments thereof that specifically bind MET, comprising a set of six CDRs (i.e., HCDR1-HCDR2-HCDR3-LCDR1-LCDR2-LCDR3) contained within any of the exemplary anti-MET antibodies listed in Table 1. In certain embodiments, the HCDR1-HCDR2-HCDR3-LCDR1-LCDR2-LCDR3 amino acid sequences set is selected from the group consisting of: SEQ ID NO: 4-6-8-140-142-144, 12-14-16-140-142-144, 20-22-24-140-142-144, 28-30-32-140-142-144, 36-38-40-140-142-144, 44-44-48-140-142-144, 52-54-56-140-142-144, 60-62-64-140-142-144, 68-70-72-140-142-144, 76-78-80-140-142-144, 84-86-88-140-142-144, 92-94-96-140-142-144, 100-102-104-140-142-144, 108-110-112-140-142-144, 116-118-120-140-142-144, 124-126-128-140-142-144 and 132-134-136-140-142-144.

In a related embodiment, antibodies, or antigen-binding fragments thereof that specifically bind MET, comprise a set of six CDRs (i.e., HCDR1-HCDR2-HCDR3-LCDR1-LCDR2-LCDR3) contained within an HCVR/LCVR amino acid sequence pair as defined by any of the exemplary anti-MET antibodies listed in Table 1. For example, antibodies or antigen-binding fragments thereof that specifically bind MET, comprise the HCDR1-HCDR2-HCDR3-LCDR1-LCDR2-LCDR3 amino acid sequences set contained within an HCVR/LCVR amino acid sequence pair selected from the group consisting of: SEQ ID NO: 4-6-8-140-142-144, 12-14-16-140-142-144, 20-22-24-140-142-144, 28-30-32-140-142-144, 36-38-40-140-142-144, 44-44-48-140-142-144, 52-54-56-140-142-144, 60-62-64-140-142-144, 68-70-72-140-142-144, 76-78-80-140-142-144, 84-86-88-140-142-144, 92-94-96-140-142-144, 100-102-104-140-142-144, 108-110-112-140-142-144, 116-118-120-140-142-144, 124-126-128-140-142-144 and 132-134-136-140-142-144.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Also provide herein are nucleic acid molecules encoding anti-MET antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

Also provided are nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

Also provided are nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

Also provided are nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

Also provided are nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

Also provided are nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

Also provided are nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

Also provided are nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

Also provided are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-MET antibodies listed in Table 1.

Also provided are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-MET antibodies listed in Table 1.

Also provided are nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect, the nucleic acid molecule encodes an HCVR and LCVR, wherein the HCVR and LCVR are both derived from the same anti-MET antibody listed in Table 1.

Also provided herein are recombinant expression vectors capable of expressing a polypeptide comprising a heavy or light chain variable region of an anti-MET antibody. For example, recombinant expression vectors comprise any of the nucleic acid molecules mentioned above, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

Provided herein are anti-MET antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Met×Met Bispecific Antigen-Binding Molecules

The present inventors have observed that certain monospecific anti-MET antigen binding molecules that block HGF binding to MET tend to potently activate MET signaling (an undesirable consequence for a therapeutic molecule). The present inventors have surprisingly discovered, however, that bispecific antigen-binding molecules that simultaneously bind to two separate epitopes on the MET protein extracellular domain are effective at blocking ligand binding to MET while causing little agonism of MET signaling.

Accordingly, provided herein are bispecific antigen binding molecules comprising a first antigen-binding domain (also referred to herein as "D1"), and a second antigen-binding domain (also referred to herein as "D2"). The simultaneous binding of the two separate MET epitopes by the bispecific antigen-binding molecule results in effective ligand blocking with minimal activation of MET signaling.

The bispecific antigen-binding molecules, which comprise a first antigen-binding domain (D1) which specifically binds a first epitope of human MET and a second antigen-binding domain (D2) which specifically binds a second epitope of human MET, may be referred to herein as "MET×MET bispecific antibodies," "MET×MET," or other related terminology. In some embodiments, the first epitope of human MET comprises amino acids 192-204 of SEQ ID NO:155. In some embodiments, the second epitope of human MET comprises amino acids 305-315 and 421-455 of SEQ ID NO:155. In some embodiments, the first epitope of human MET comprises amino acids 192-204 of SEQ ID NO:155; and the second epitope of human MET comprises amino acids 305-315 and 421-455 of SEQ ID NO:155.

In certain embodiments, D1 and D2 domains of a MET×MET bispecific antibody are non-competitive with one another. Non-competition between D1 and D2 for binding to MET means that, the respective monospecific antigen binding proteins from which D1 and D2 were derived do not compete with one another for binding to human MET. Exemplary antigen-binding protein competition assays are known in the art, non-limiting examples of which are described elsewhere herein.

In certain embodiments, D1 and D2 bind to different (e.g., non-overlapping, or partially overlapping) epitopes on MET, as described elsewhere herein.

MET×MET bispecific antigen-binding molecules may be constructed using the antigen-binding domains of two separate monospecific anti-MET antibodies. For example, a collection of monoclonal monospecific anti-MET antibodies may be produced using standard methods known in the art. The individual antibodies thus produced may be tested pairwise against one another for cross-competition to a MET protein. If two different anti-MET antibodies are able to bind to MET at the same time (i.e., do not compete with one another), then the antigen-binding domain from the first anti-MET antibody and the antigen-binding domain from the second, non-competitive anti-MET antibody can be engineered into a single MET×MET bispecific antibody in accordance with the present disclosure.

According to the present disclosure, a bispecific antigen-binding molecule can be a single multifunctional polypeptide, or it can be a multimeric complex of two or more polypeptides that are covalently or non-covalently associated with one another. As will be made evident by the present disclosure, any antigen binding construct which has the ability to simultaneously bind two separate, non-identical epitopes of the MET molecule is regarded as a bispecific antigen-binding molecule. Any of the bispecific antigen-binding molecules described herein, or variants thereof, may be constructed using standard molecular biological techniques (e.g., recombinant DNA and protein expression technology) as will be known to a person of ordinary skill in the art.

Antigen-Binding Domains

The bispecific antigen-binding molecules of the present disclosure comprise two separate antigen-binding domains (D1 and D2). As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., human MET). The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present disclosure include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. For example, an antigen-binding domain, as used in the context of the present disclosure, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

As indicated above, an "antigen-binding domain" (D1 and/or D2) may comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., human MET). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibodies provided herein (or antigen-binding portion thereof) may be identical to the human germline sequences, or may be naturally or artificially modified. An amino acid consensus sequence may be defined based on a side-by-side analysis of two or more CDRs.

The D1 and/or D2 components of the bispecific antigen-binding molecules provided herein may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The bispecific antigen-binding molecules provided herein may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The bispecific antigen-binding molecules of the present disclosure may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Methods for making bispecific antibodies are known in the art and may be used to construct bispecific antigen-binding molecules disclosed herein. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

Exemplary antigen-binding domains (D1 and D2) that can be included in the MET×MET bispecific antigen-binding molecules provided herein include antigen-binding domains derived from any of the anti-MET antibodies disclosed herein. For example, the present disclosure includes MET×MET bispecific antigen-binding molecules comprising a D1 or D2 antigen-binding domain comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

Also provided herein are MET×MET bispecific antigen-binding molecules comprising a D1 or D2 antigen-binding domain comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

Provided herein are MET×MET bispecific antigen-binding molecules comprising a D1 or D2 antigen-binding domain comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides MET× MET bispecific antigen-binding molecules comprising a D1 or D2 antigen-binding domain comprising an HCVR/LCVR amino acid sequence pair contained within any of the exemplary anti-MET antibodies listed in Table 1.

Also provided herein are MET×MET bispecific antigen-binding molecules comprising a D1 or D2 antigen-binding domain comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

Also provided are MET×MET bispecific antigen-binding molecules comprising a D1 or D2 antigen-binding domain comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

Also provided are MET×MET bispecific antigen-binding molecules comprising a D1 or D2 antigen-binding domain comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

Also provided are MET×MET bispecific antigen-binding molecules comprising a D1 or D2 antigen-binding domain comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

Also provided are MET×MET bispecific antigen-binding molecules comprising a D1 or D2 antigen-binding domain comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

Also provided are MET×MET bispecific antigen-binding molecules comprising a D1 or D2 antigen-binding domain comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

Also provided are MET×MET bispecific antigen-binding molecules comprising a D1 or D2 antigen-binding domain comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-MET antibodies listed in Table 1.

Also provided are MET×MET bispecific antigen-binding molecules comprising a D1 or D2 antigen-binding domain comprising a set of six CDRs (i.e., HCDR1-HCDR2-HCDR3-LCDR1-LCDR2-LCDR3) contained within any of the exemplary anti-MET antibodies listed in Table 1.

In a related embodiment, the present disclosure provides MET×MET bispecific antigen-binding molecules comprising a D1 or D2 antigen-binding domain comprising a set of six CDRs (i.e., HCDR1-HCDR2-HCDR3-LCDR1-LCDR2-LCDR3) contained within an HCVR/LCVR amino acid sequence pair as defined by any of the exemplary anti-MET antibodies listed in Table 1.

Figure 1:
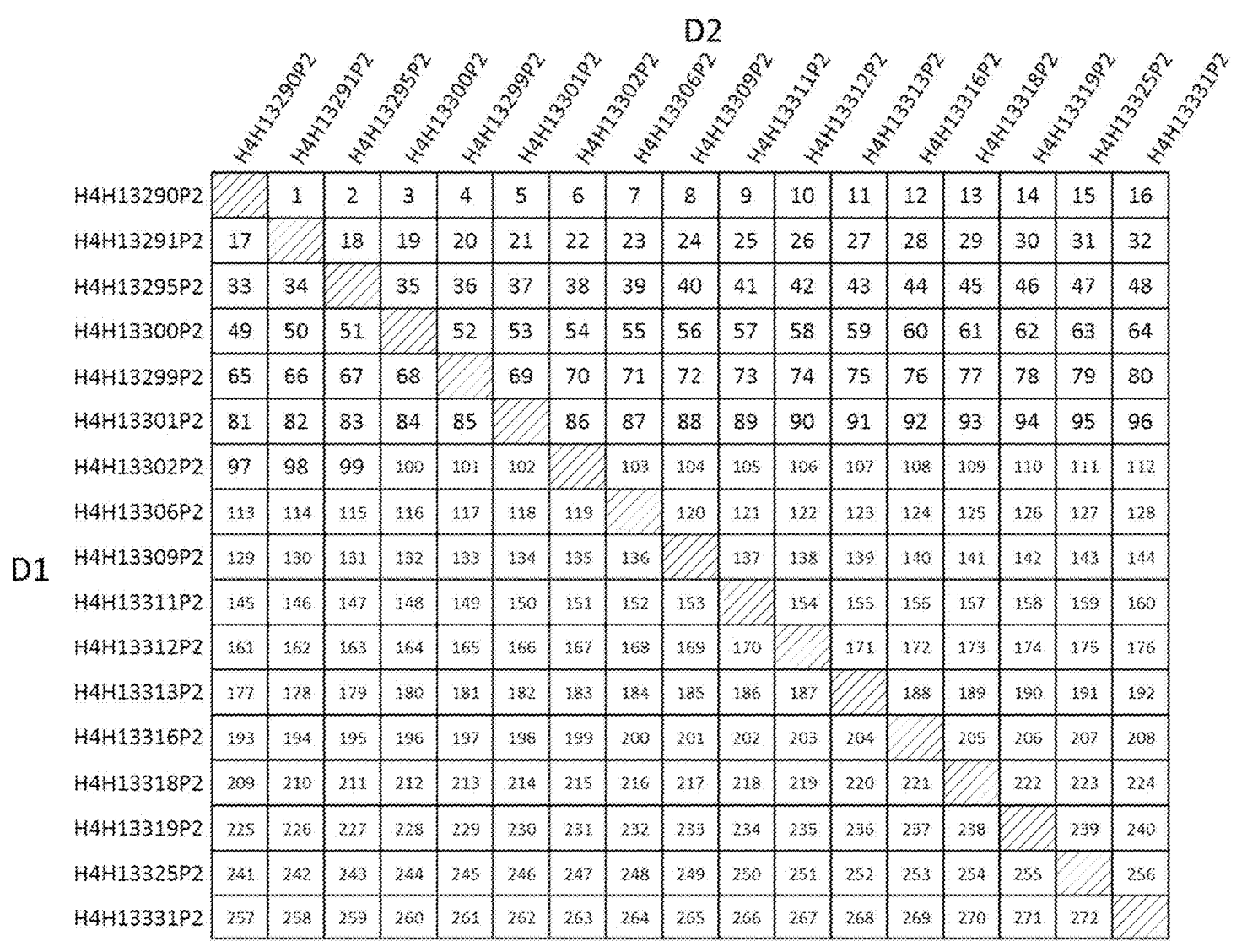

The MET×MET bispecific antigen-binding molecules provided herein may comprise a D1 antigen-binding domain derived from any of the anti-MET antibodies of Table 1, and a D2 antigen-binding domain derived from any other anti-MET antibody of Table 1. Non-limiting examples of MET× MET bispecific antibodies of the present disclosure are depicted in FIG. 1. FIG. 1 is a matrix illustrating the components of 272 exemplary MET×MET bispecific antibodies. Each numbered cell of the matrix (numbered 1 through 272) identifies a unique bispecific antibody comprising a "D1" antigen binding domain and a "D2" antigen binding domain, wherein the D1 antigen binding domain comprises the immunoglobulin variable domain (HCVR/LCVR amino acid sequence pair) or CDRs from the corresponding anti-MET antibody listed along the Y-axis, and wherein the D2 antigen binding domain comprises the immunoglobulin variable domain (HCVR/LCVR amino acid sequence pair) or CDRs from the corresponding anti-MET antibody listed along the X-axis. Thus, for example, the MET×MET bispecific antigen-binding molecule "number 10" shown in the matrix comprises a D1 antigen-binding domain comprising an HCVR/LCVR pair, or 6-CDR set, from the exemplary anti-MET antibody H4H13290P2, and a D2 antigen-binding domain comprising an HCVR/LCVR pair, or 6-CDR set, from the exemplary anti-MET antibody H4H13321P2. Additional examples of MET×MET bispecific antibodies provided herein are described in Example 4 herein.

As a non-limiting illustrative example, the present disclosure includes MET×MET bispecific antigen binding molecules comprising a D1 antigen-binding domain and a D2 antigen-binding domain, wherein the D1 antigen binding domain comprises an HCVR/LCVR amino acid sequence pair of SEQ ID NOs: 58/138, or a set of heavy and light chain CDRs (HCDR1-HCDR2-HCDR3-LCDR1-LCDR2-LCDR3) comprising SEQ ID NOs: 60-62-64-140-142-144, and wherein the D2 antigen-binding domain comprises an HCVR/LCVR amino acid sequence pair of SEQ ID NOs: 82/138, or a set of heavy and light chain CDRs (HCDR1-HCDR2-HCDR3-LCDR1-LCDR2-LCDR3) comprising SEQ ID NOs: 84-86-88-140-142-144. An exemplary MET× MET bispecific antibody having these sequence characteristics is the bispecific antibody designated H4H14639D, also referred to as bispecific antibody No. 122, which comprises a D1 derived from H4H13306P2 and a D2 derived from H4H13312P2 (see Example 4, Table 5 herein).

As a further non-limiting illustrative example, the present disclosure includes MET×MET bispecific antigen binding molecules comprising a D1 antigen-binding domain and a D2 antigen-binding domain, wherein the D1 antigen binding domain comprises an HCVR/LCVR amino acid sequence pair of SEQ ID NOs: 18/138, or a set of heavy and light chain CDRs (HCDR1-HCDR2-HCDR3-LCDR1-LCDR2-LCDR3) comprising SEQ ID NOs: 20-22-24-140-142-144, and wherein the D2 antigen-binding domain comprises an HCVR/LCVR amino acid sequence pair of SEQ ID NOs: 82/138, or a set of heavy and light chain CDRs (HCDR1-HCDR2-HCDR3-LCDR1-LCDR2-LCDR3) comprising SEQ ID NOs: 84-86-88-140-142-144. An exemplary MET× MET bispecific antibody having these sequence characteristics is the bispecific antibody designated H4H14635D, also referred to as bispecific antibody No. 42, which comprises a D1 derived from H4H13295P2 and a D2 derived from H4H13312P2 (see Example 4, Table 5 herein).

Multimerizing Components

The bispecific antigen-binding molecules provided herein, in certain embodiments, may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the bispecific antigen-binding molecules provided herein comprise two multimerizing domains, M1 and M2, wherein D1 is attached to M1 and D2 is attached to M2, and wherein the association of M1 with M2 facilitates the physical linkage of D1 and D2 to one another in a single bispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

The bispecific antigen-binding molecules of the disclosure may be "isolated." An "isolated bispecific antigen-binding molecule," as used herein, means a bispecific antigen-binding molecule that has been identified and separated and/or recovered from at least one component of its natural environment. For example, a bispecific antibody that has been separated or removed from at least one component of an organism, or from a tissue or cell in which the antibody is produced, is an "isolated bispecific antibody" for purposes of the present disclosure. An isolated bispecific antigen-binding molecule also includes molecules in situ within a recombinant cell. Isolated bispecific antigen-binding molecules are molecules that have been subjected to at least one purification or isolation step. According to certain embodiments, an isolated bispecific antigen-binding molecule may be substantially free of other cellular material and/or chemicals.

The bispecific antigen-binding molecules disclosed herein, or the antigen-binding domains thereof (D1 and/or D2) may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences disclosed herein to germline sequences available from, for example, public antibody sequence databases. The present disclosure includes bispecific antigen-binding molecules disclosed herein, or the antigen-binding domains thereof (D1 and/or D2), which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

A person of ordinary skill in the art, starting with the heavy and light chain variable region sequences disclosed herein, can easily produce numerous bispecific antigen-binding molecules, or antigen-binding domains thereof (D1 and/or D2), which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the bispecific antigen-binding molecules, or the antigen-binding domains thereof (D1 and/or D2), of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, bispecific antigen-binding molecules, or the antigen-binding domains thereof (D1 and/or D2), that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules, or the antigen-binding domains thereof (D1 and/or D2), obtained in this general manner are encompassed within the present disclosure.

Variants

The present disclosure also includes anti-MET antibodies and bispecific antigen-binding molecules comprising variants of any of the HCVR, LCVR, and/or CDR amino acid sequences disclosed herein. Exemplary variants included within this aspect include variants of any of the HCVR, LCVR, and/or CDR amino acid sequences disclosed herein having one or more conservative substitutions. For example, the present disclosure includes anti-MET antibodies and MET×MET bispecific antigen-binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

Exemplary variants included within this aspect of the disclosure also include variants having substantial sequence identity to any of the HCVR, LCVR, and/or CDR amino acid sequences disclosed herein. As used herein in the context of amino acid sequences, the term "substantial identity" or "substantially identical" means that two amino acid sequences, when optimally aligned, such as by the programs GAP or BESTFIT using default gap weights, share at least 95%, 98% or 99% sequence identity. In certain embodiments, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence identity between two different amino acid sequences is typically measured using sequence analysis software. Sequence analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence provided herein to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Anti-MET Antibodies and MET×MET Bispecific Antigen-Binding Molecules Comprising Fc Variants According to certain embodiments provided herein, anti-MET antibodies and MET×MET bispecific antigen binding proteins are provided comprising an Fc domain comprising one or more mutations which enhance or diminish antibody binding to the FcRn receptor, e.g., at acidic pH as compared to neutral pH. For example, the present disclosure includes anti-MET antibodies and MET×MET bispecific antigen binding proteins comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present disclosure includes anti-MET antibodies and MET×MET bispecific antigen binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Biological Characteristics of the Antigen-Binding Molecules Provided Herein

Provided herein are antibodies and antigen-binding fragments thereof that bind monomeric human MET with high affinity. For example, the present disclosure includes anti-MET antibodies that bind monomeric human MET (e.g., hMET.mmh) with a $K_D$ of less than about 230 nM as measured by surface plasmon resonance at 25° C. or 37° C., e.g., using an assay format as defined in Example 3 herein, or a substantially similar assay. According to certain embodiments, anti-MET antibodies are provided that bind monomeric human MET at 37° C. with a $K_D$ of less than about 230 nM, less than about 200 nM, less than about 150 nM, less than about 100 nM, less than about 50 nM, less than about 25 nM, less than about 20 nM, less than about 10 nM, Less than about 8 nM, less than about 6 nM, less than about 5 nM, less than about 4 nM, or less than about 3 nM, as measured by surface plasmon resonance, e.g., using an assay format as defined in Example 3 herein, or a substantially similar assay.

The present disclosure also includes antibodies and antigen-binding fragments thereof that bind monomeric human MET (e.g., hMET.mmh) with a dissociative half-life (t½) of greater than about 1 minute as measured by surface plasmon resonance at 25° C. or 37° C., e.g., using an assay format as defined in Example 3 herein, or a substantially similar assay. According to certain embodiments, anti-MET antibodies are provided that bind monomeric human MET at 37° C. with a t1/2 of greater than about 1 minute, greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or greater than about 20 minutes, or longer, as measured by surface plasmon resonance, e.g., using an assay format as defined in Example 3 herein, or a substantially similar assay.

Provided herein are antibodies and antigen-binding fragments thereof that bind dimeric human MET (e.g., hMET.mFc) with high affinity. For example, the present disclosure includes anti-MET antibodies that bind dimeric human MET with a $K_D$ of less than about 3 nM as measured by surface plasmon resonance at 25° C. or 37° C., e.g., using an assay format as defined in Example 3 herein, or a substantially similar assay. According to certain embodiments, anti-MET antibodies are provided that bind dimeric human MET at 37° C. with a $K_D$ of less than about 3 nM, less than about 2 nM, less than about 1 nM, less than about 0.9 nM, less than about 0.8 nM, less than about 0.7 nM, less than about 0.6 nM, less than about 0.5 nM, less than about 0.4 nM, less than about 0.3 nM, or less than about 0.25 nM, as measured by surface plasmon resonance, e.g., using an assay format as defined in Example 3 herein, or a substantially similar assay.

Also provided herein are antibodies and antigen-binding fragments thereof that bind dimeric human MET (e.g., hMET.mFc) with a dissociative half-life (t½) of greater than about 4 minutes as measured by surface plasmon resonance at 25° C. or 37° C., e.g., using an assay format as defined in Example 3 herein, or a substantially similar assay. According to certain embodiments, anti-MET antibodies are provided that bind dimeric human MET at 37° C. with a t1/2 of greater than about 4 minutes, greater than about 5 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 105 minutes, or longer, as measured by surface plasmon resonance, e.g., using an assay format as defined in Example 3 herein, or a substantially similar assay.

Also provided herein are MET×MET bispecific antigen-binding proteins that bind dimeric human MET (e.g., hMET.mFc) with a dissociative half-life (t½) of greater than about 10 minutes as measured by surface plasmon resonance at 25° C. or 37° C., e.g., using an assay format as defined in Example 5 herein, or a substantially similar assay. According to certain embodiments, MET×MET bispecific antigen-binding proteins are provided that bind dimeric human MET at 37° C. with a t1/2 of greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, greater than about 1100 minutes, or longer, as measured by surface plasmon resonance, e.g., using an assay format as defined in Example 5 herein, or a substantially similar assay.

Also provided herein are anti-MET antibodies and MET×MET bispecific antigen-binding proteins that block the interaction between HGF and MET, e.g., in an in vitro ligand-binding assay. According to certain embodiments provided herein, MET×MET bispecific antigen-binding proteins are provided that block HGF binding to cells expressing human MET, and induce minimal or no MET activation in the absence of HGF signaling. For example, the present disclosure provides MET×MET bispecific antigen-binding proteins that exhibit a degree of MET agonist activity in a cell-based MET activity reporter assay that is less than 50%, less than 40%, less than 30%, less than 20%, less than 10%, less than 5%, less than 3%, less than 2% or less than 1% of the MET agonist activity observed in an equivalent activity reporter assay using a monospecific antibody comprising D1 or D2 alone.

The antibodies and antigen-binding proteins of the present disclosure may possess one or more of the aforementioned biological characteristics, or any combination thereof. The foregoing list of biological characteristics of the antibodies is not intended to be exhaustive. Other biological characteristics of the antibodies provided herein will be evident to a person of ordinary skill in the art from a review of the present disclosure including the working Examples herein.

Antibody-Drug Conjugates (ADCs)

Provided herein are antibody-drug conjugates (ADCs) comprising an anti-MET antibody or a MET×MET bispecific antigen-binding protein conjugated to a therapeutic moiety such as a cytotoxic agent, a chemotherapeutic drug, or a radioisotope.

Cytotoxic agents include any agent that is detrimental to the growth, viability or propagation of cells, including, but not limited to, tubulin-interacting agents and DNA-damaging agents. Examples of suitable cytotoxic agents and chemotherapeutic agents that can be conjugated to anti-MET antibodies in accordance with this aspect of the disclosure include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins (e.g., calicheamicin $\gamma_1$, camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing. According to certain embodiments, the cytotoxic agent that is conjugated to an anti-MET antibody is a maytansinoid such as DM1 or DM4, a tomaymycin derivative, or a dolastatin derivative. According to certain embodiments, the cytotoxic agent that is conjugated to an anti-MET antibody is an auristatin such as MMAE, MMAF, or derivatives thereof. Other cytotoxic agents known in the art are contemplated within the scope of the present disclosure, including, e.g., protein toxins such ricin, *C. difficile* toxin, *pseudomonas* exotoxin, ricin, diphtheria toxin, botulinum toxin, bryodin, saporin, pokeweed toxins (i.e., phytolaccatoxin and phytolaccigenin), and others such as those set forth in Sapra et al., *Pharmacol. & Therapeutics*, 2013, 138:452-469.

In certain embodiments, the cytotoxic agent is a maytansinoid, e.g., derivative of maytansine. Suitable maytansinoids include DM1, DM4, or derivatives, stereoisomers, or isotopologues thereof. Suitable maytansinoids also include, but are not limited to, those disclosed in WO 2014/145090A1, WO 2015/031396A1, US 2016/0375147A1, and US 2017/0209591A1, incorporated herein by reference in their entireties.

In some embodiments, the maytansinoid has the following structure:

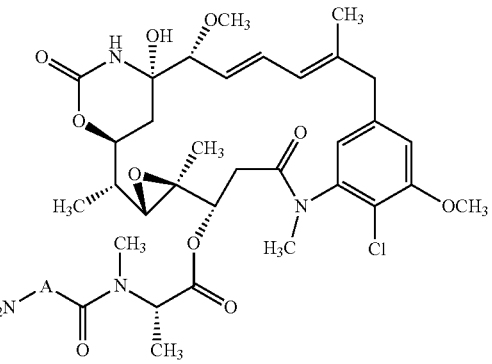

wherein A is an optionally substituted arylene or heteroarylene.

In some embodiments, the maytansinoid has the following structure:

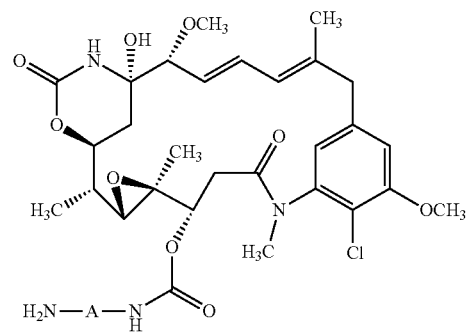

wherein A is an optionally substituted arylene or heteroarylene.

In some embodiments, the maytansinoid has the following structure:

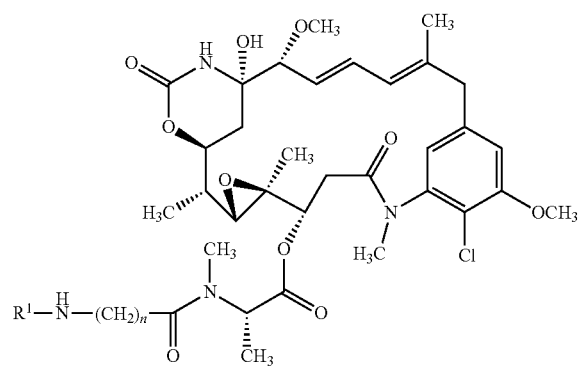

wherein n is an integer from 1-12 and $R^1$ is alkyl.

In some embodiments, the maytansinoid is:
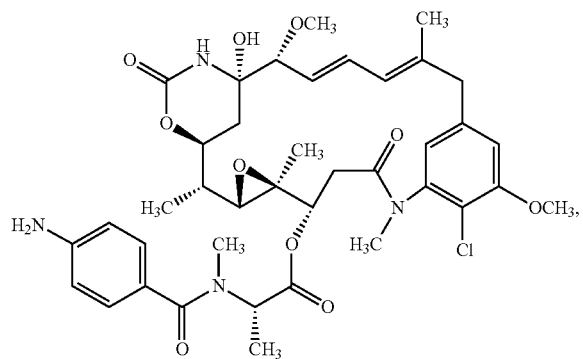
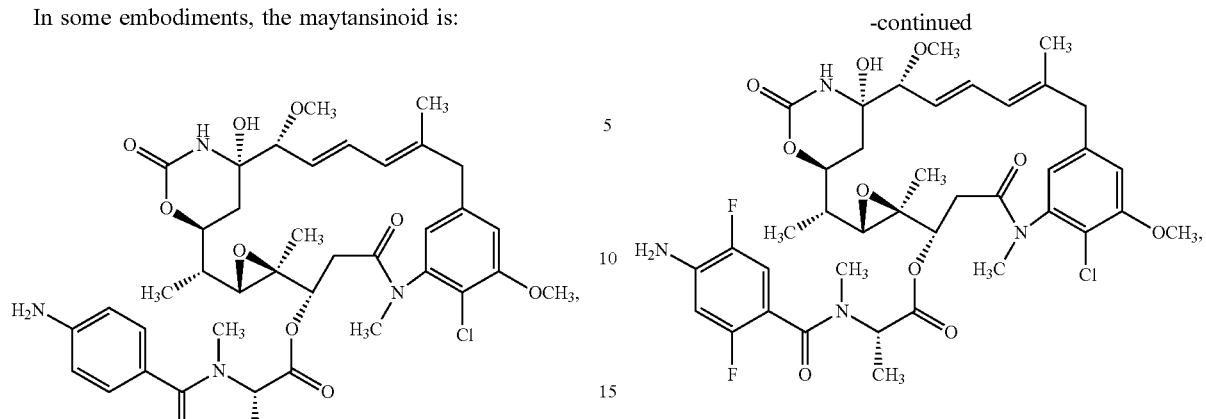
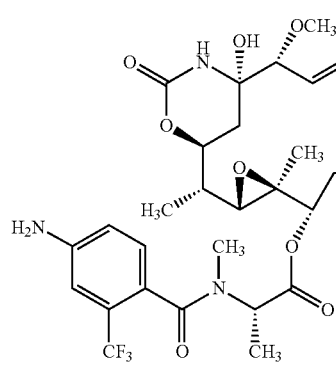
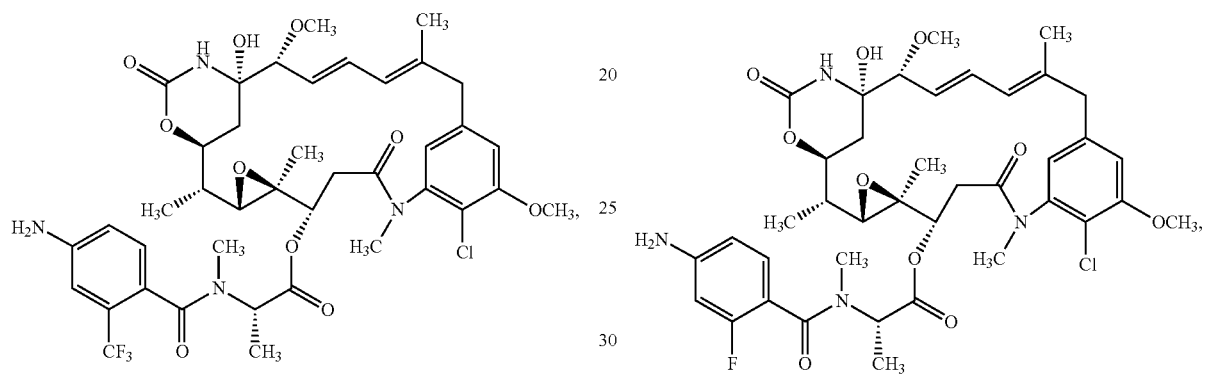
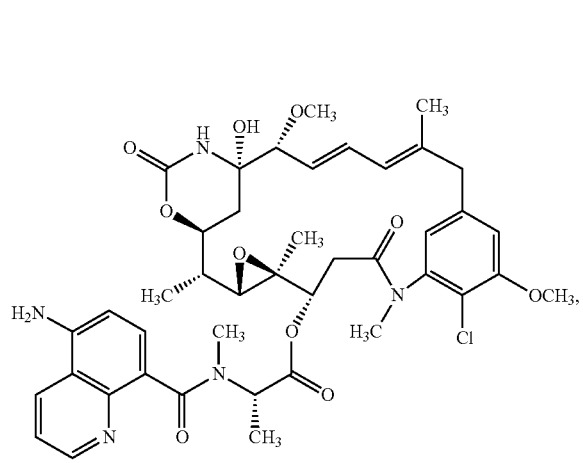
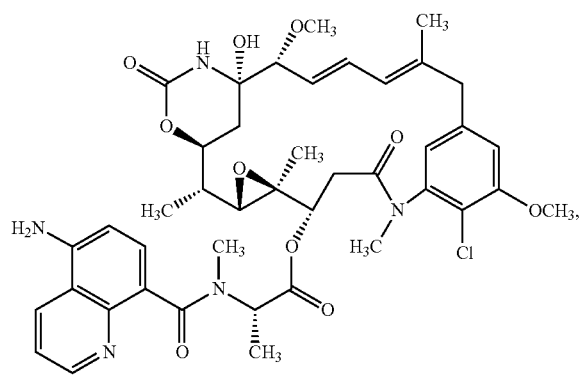
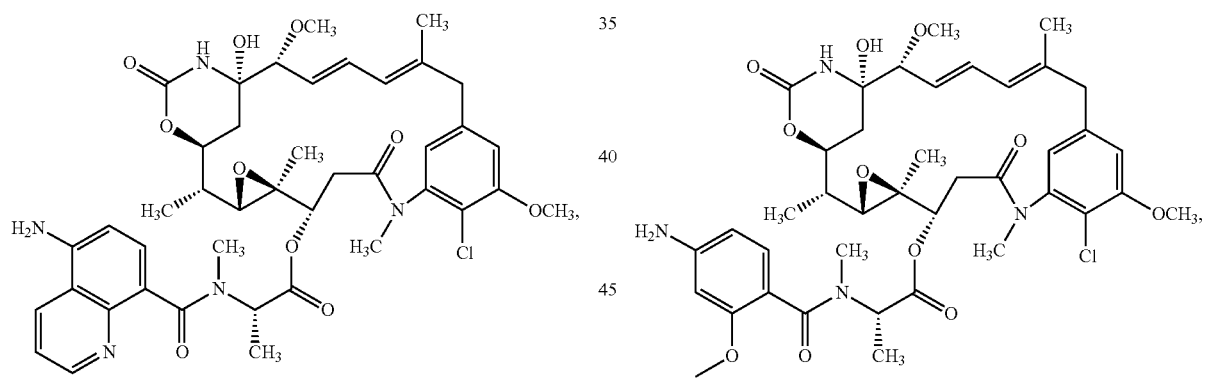
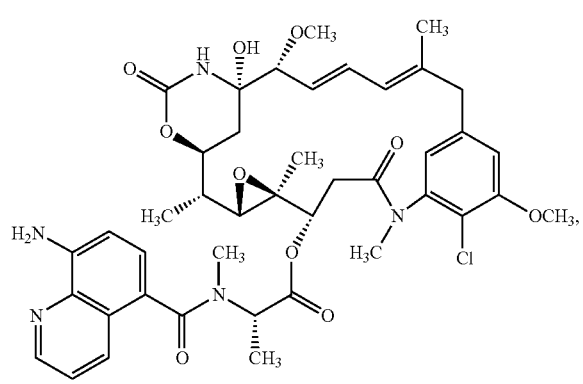

27
-continued
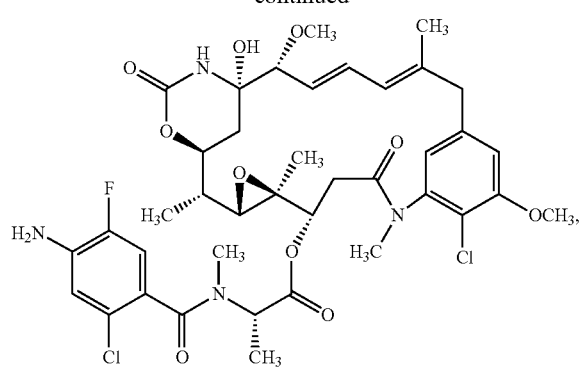
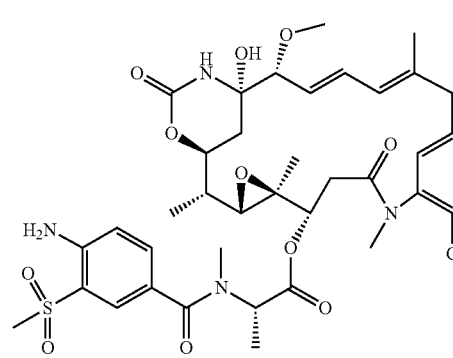
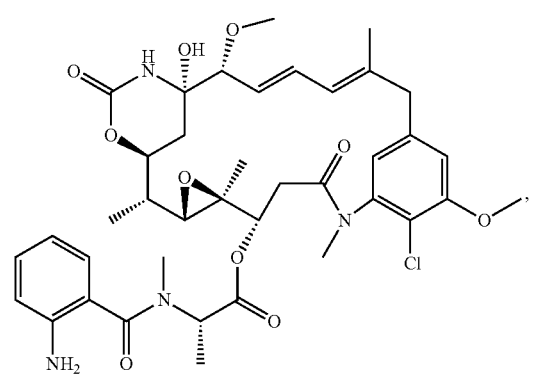
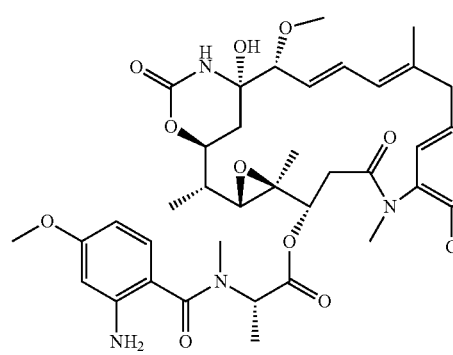
28
-continued
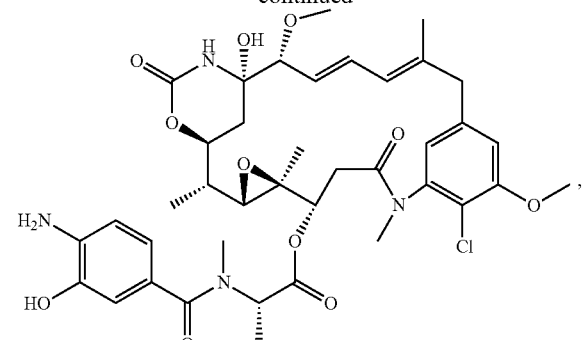
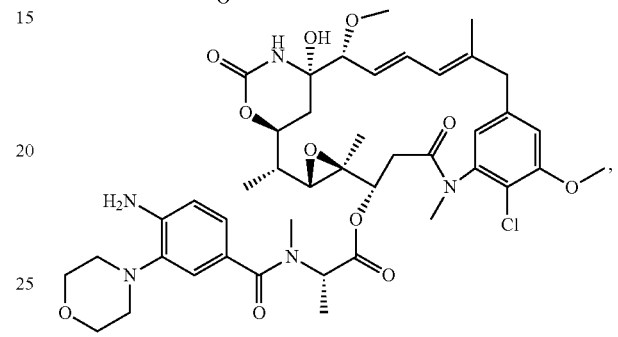

29
-continued
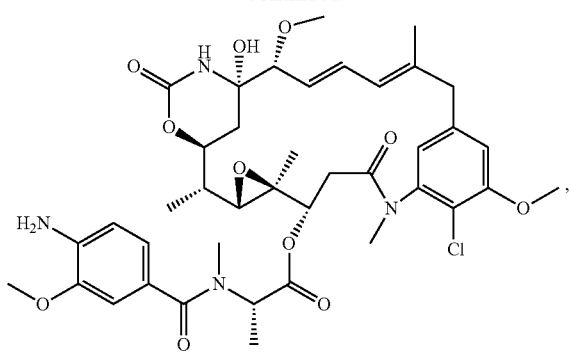
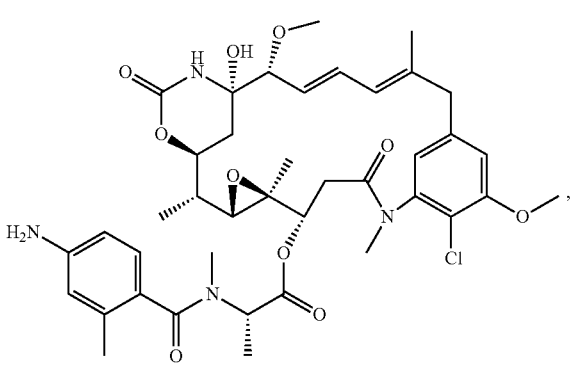
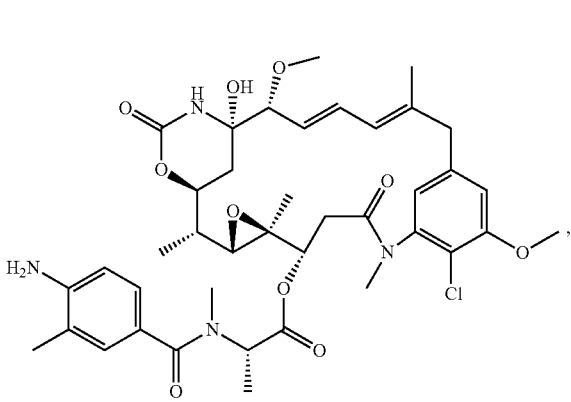
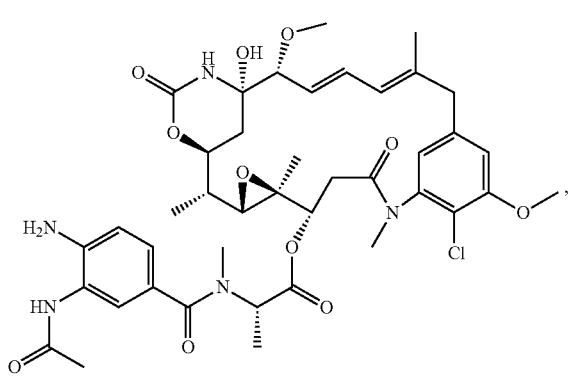
30
-continued
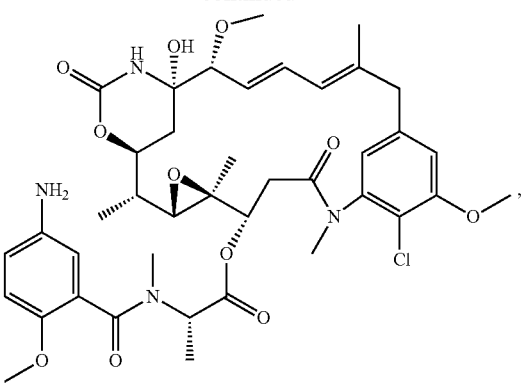
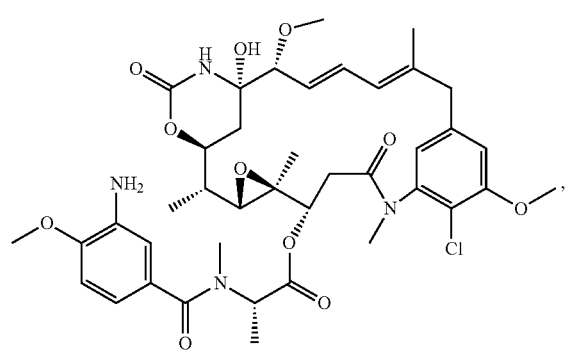

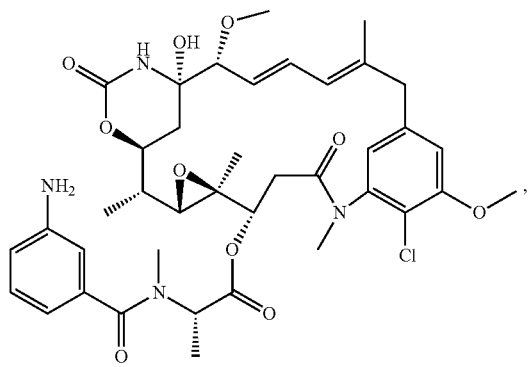
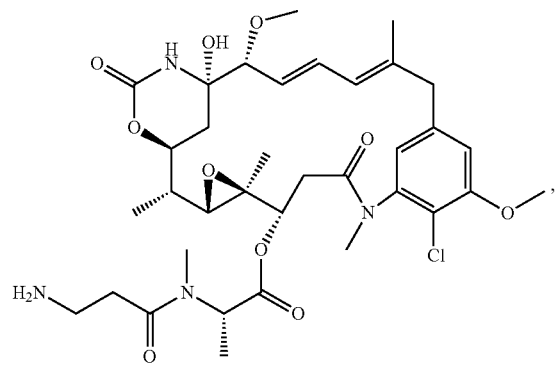
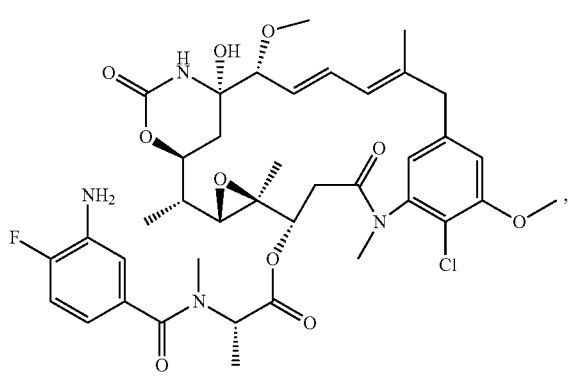
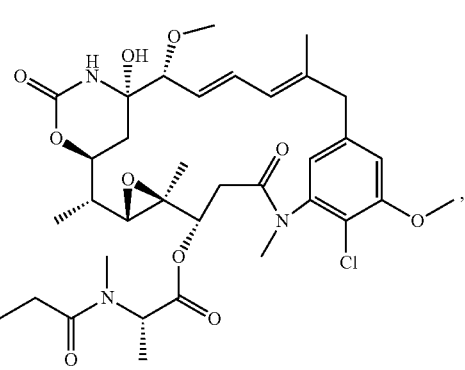
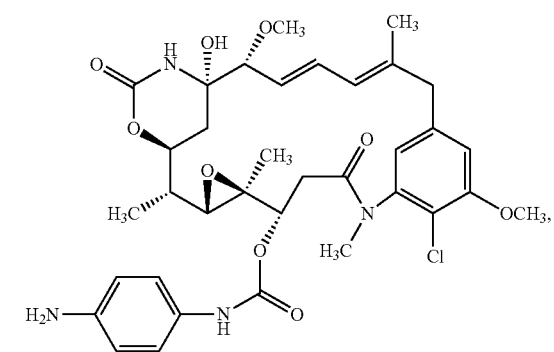
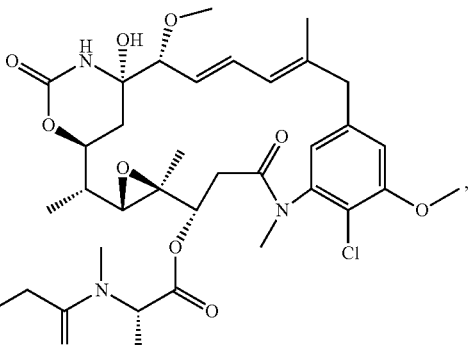
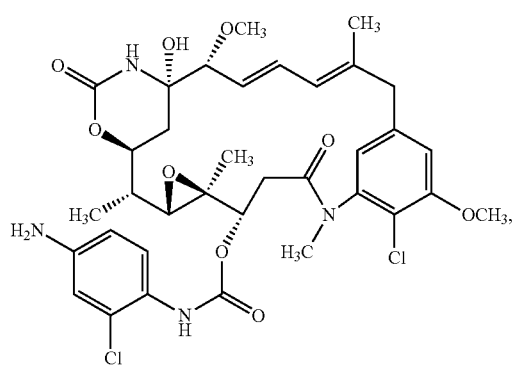
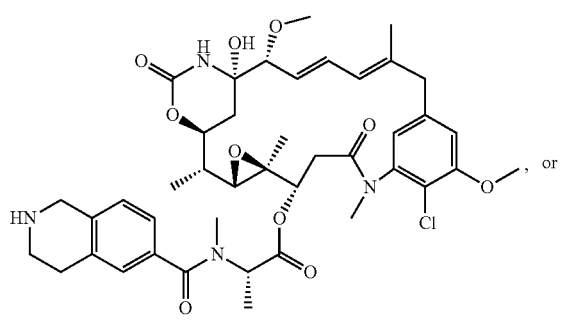

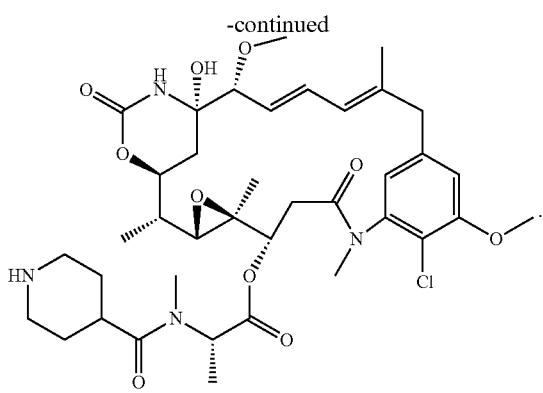

In some embodiments, the maytansinoid is:

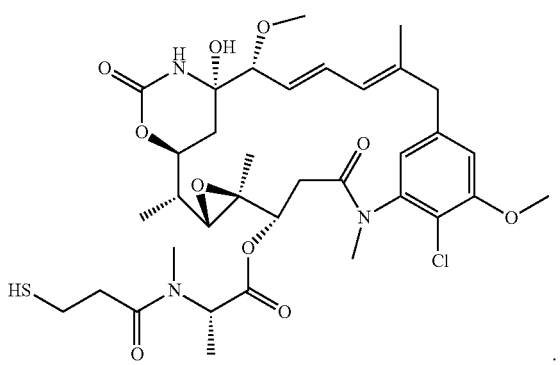 [SMILES: COc1cc2cc(c1Cl)N(C)C(=O)C[C@H](OC(=O)[C@H](C)N(C)C(=O)CCS)[C@]1(C)O[C@H]1[C@H](C)[C@@H]1C[C@@](O)(NC(=O)O1)[C@H](OC)/C=C/C=C(\C)C2]

In some embodiments, the maytansinoid is:

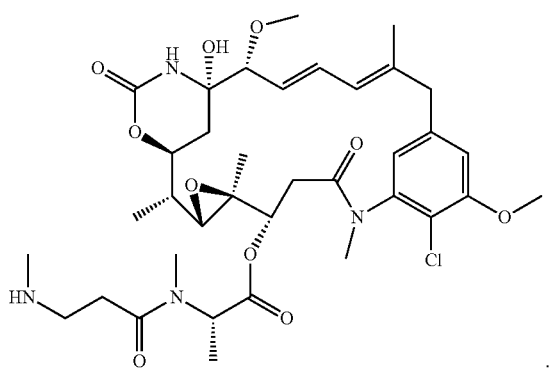 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

Also provided herein are antibody-radionuclide conjugates (ARCs) comprising anti-MET antibodies conjugated to one or more radionuclides. Exemplary radionuclides that can be used in the context of this aspect of the disclosure include, but are not limited to, e.g., $^{225}$Ac, $^{212}$Bi, $^{213}$Bi, $^{131}$I, $^{186}$Re, $^{227}$Th, $^{222}$Rn, $^{223}$Ra, $^{224}$Ra, and $^{90}$Y.

In certain embodiments provided herein, ADCs are provided comprising an anti-MET antibody or a MET×MET bispecific antigen-binding protein conjugated to a cytotoxic agent (e.g., any of the cytotoxic agents disclosed above) via a linker molecule. Linkers are any group or moiety that links, connects, or bonds the antibody or antigen-binding proteins described herein with a therapeutic moiety, e.g. cytotoxic agent. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Any linker molecule or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L- or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

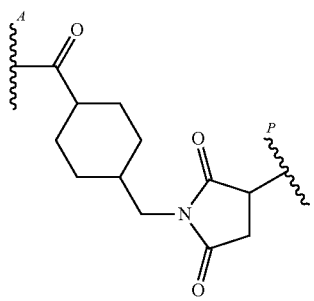

wherein

is a bond to the antibody or antigen-binding protein (e.g., via lysine residue) and

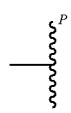

is a bond to the cytotoxic agent (e.g., DM1). In some embodiments, the linker is:

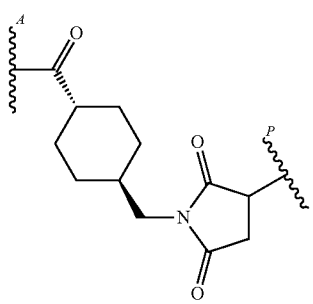

wherein

is a bond to the antibody or antigen-binding protein (e.g., via lysine residue) and

is a bond to the cytotoxic agent (e.g., DM1). In certain embodiments, the linker is:

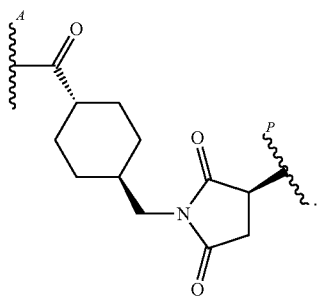

In certain embodiments, the linker is:

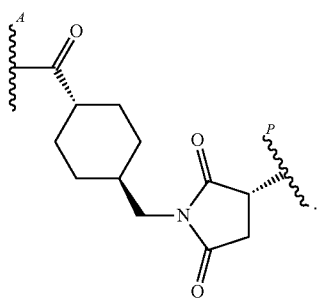

In some embodiments, the linker is derived from male-imidylmethyl-4-trans-cyclohexanecarboxysuccinate:

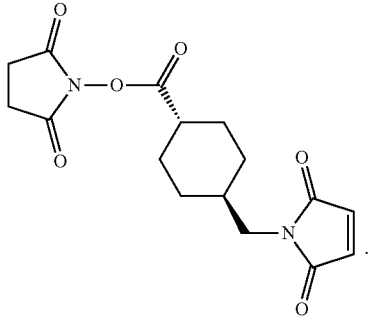 [SMILES: O=C1C=CC(=O)N1C[C@H]1CC[C@H](C(=O)ON2C(=O)CCC2=O)CC1]

In some embodiments, the linker is:

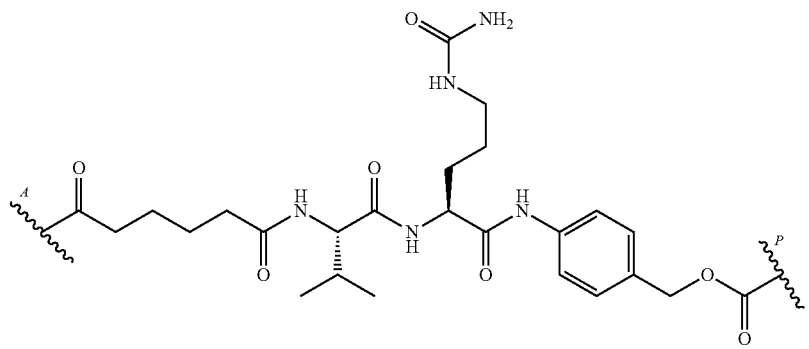

wherein

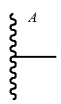

is a bond to the antibody or antigen-binding protein (e.g., via lysine residue) and

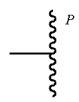

is a bond to the cytotoxic agent (e.g., a compound having the following formula:

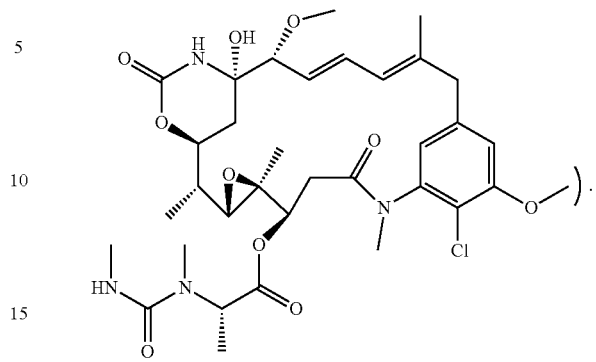

The present disclosure comprises ADCs in which a linker connects an anti-MET antibody or a MET×MET bispecific antigen-binding protein to a drug or cytotoxin through an attachment at a particular amino acid within the antibody or antigen-binding molecule. Exemplary amino acid attachments that can be used in the context of this aspect, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, and Shaunak et al., *Nat. Chem. Biol.,* 2006, 2:312-313). Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques, include, but are not limited to glutamine conjugation via transglutaminase (see e.g., Schibli, Angew Chemie Inter Ed. 2010, 49, 9995).

According to certain embodiments, the present disclosure provides ADCs, wherein an anti-MET antibody or a MET× MET bispecific antigen-binding protein as described herein is conjugated to a linker-drug composition as set forth in International Patent Publication WO2014/145090, (e.g., compound "7," also referred to herein as "M0026" and depicted below), the disclosure of which is hereby incorporated by reference herein in its entirety:

wherein n is an integer from 1-12 and $R^1$ is alkyl. In certain embodiments, the maytansinoid is

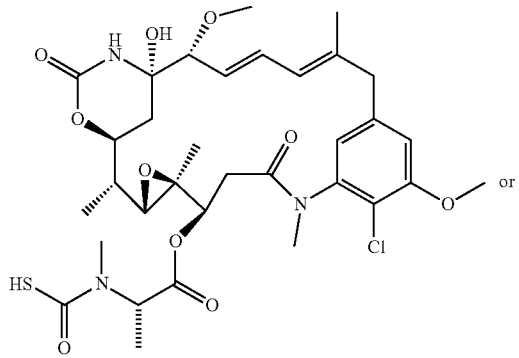

or

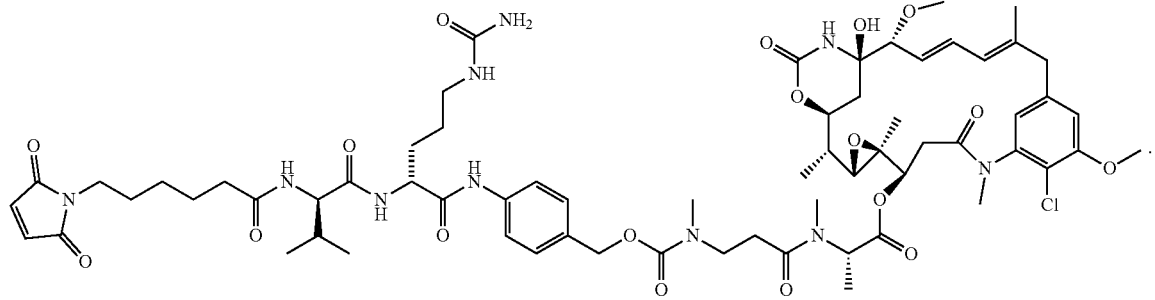

Provided herein are also antibody-drug conjugates comprising the monospecific anti-MET antibodies and MET× MET bispecific antibodies disclosed herein, where said anti-MET antibody or MET×MET bispecific antibody is conjugated to a cytotoxic agent. In certain embodiments, the cytotoxic agent is a maytansinoid. In certain embodiments, the maytansinoid is a compound having the following formula:

-continued

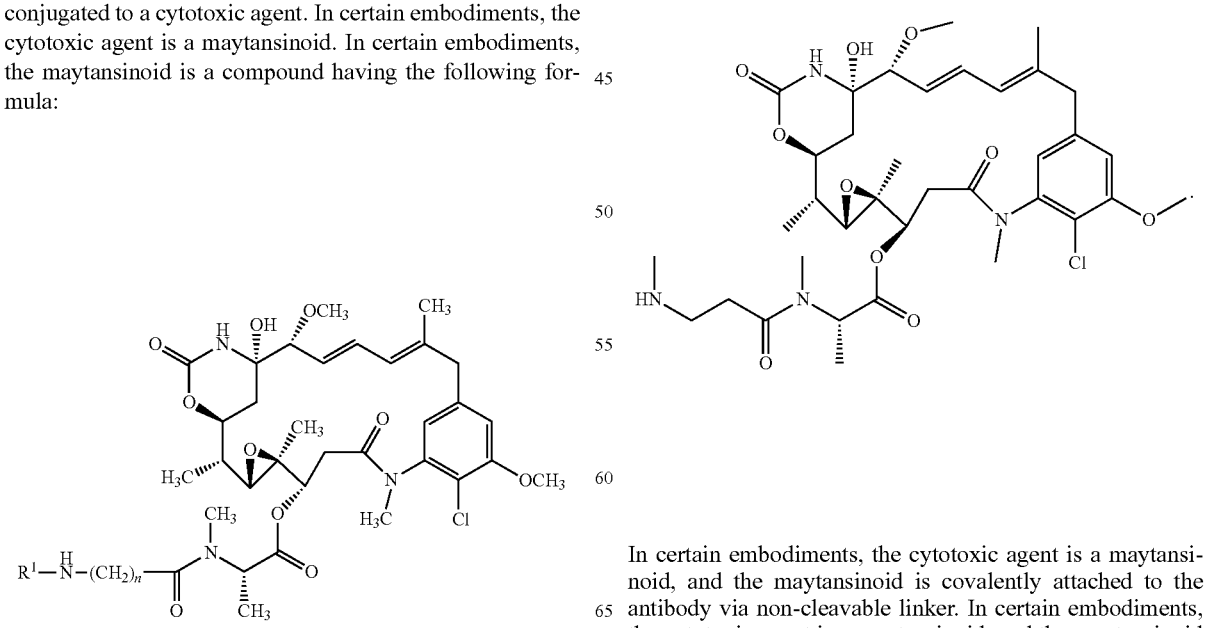

In certain embodiments, the cytotoxic agent is a maytansinoid, and the maytansinoid is covalently attached to the antibody via non-cleavable linker. In certain embodiments, the cytotoxic agent is a maytansinoid, and the maytansinoid is covalently attached to the antibody via cleavable linker.

In one embodiment, the antibody is conjugated to:
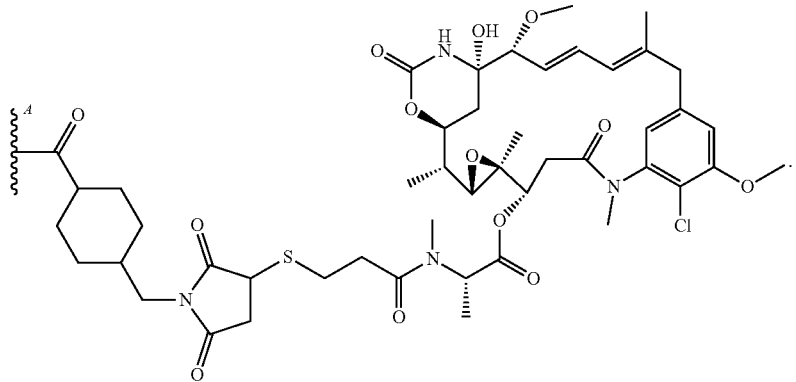
wherein
is a bond to the antibody.
In one embodiment, the antibody is conjugated to:
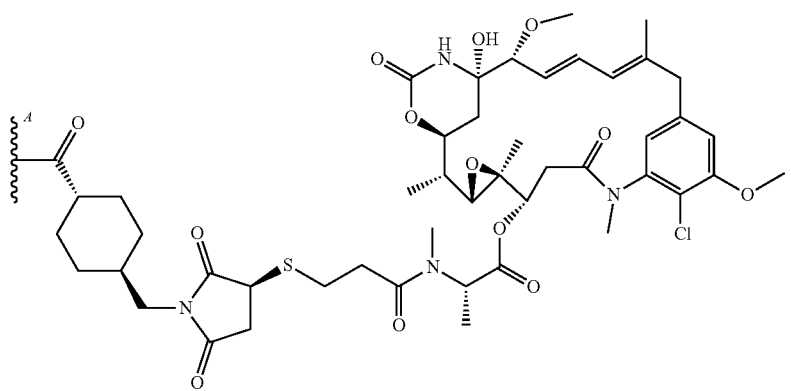
wherein
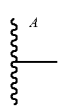
is a bond to the antibody.

In one embodiment, the antibody is conjugated to:

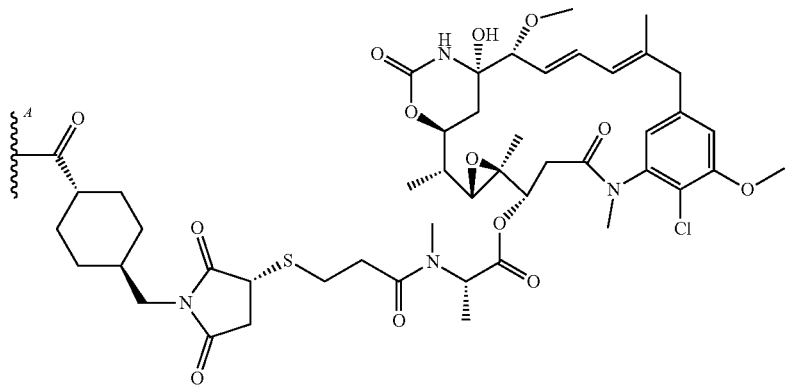

wherein

is a bond to the antibody.

In one embodiment, the antibody is conjugated to:

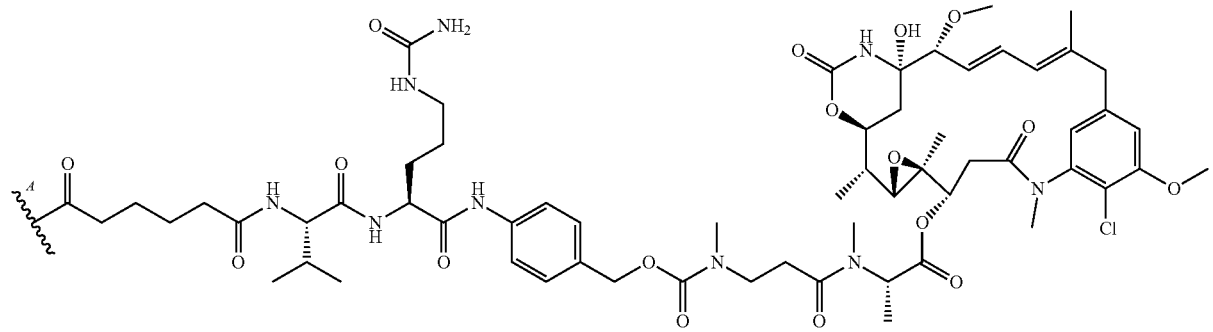

wherein

is a bond to the antibody.

In some embodiments, the conjugates have the following structure:

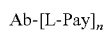

wherein:
Ab is an anti-MET antibody or a MET×MET bispecific antigen-binding protein as described herein;
L is a linker;
Pay is a cytotoxic agent; and
n is an integer from 1-10.

In some embodiments, Ab is an anti-MET antibody comprising the CDRs within the HCVR/LCVR amino acid sequence pair of SEQ ID NOs: 82/138. In some embodiments, Ab is an anti-MET antibody comprising the HCVR amino acid sequence of SEQ ID NO: 82 and the LCVR amino acid sequence of SEQ ID NO: 138.

In some embodiments, Ab is a MET×MET bispecific antigen-binding protein comprising the CDRs within the D1-HCVR amino acid sequence of SEQ ID NO: 58 and the CDRs within the D2-HCVR amino acid sequence of SEQ ID NO: 82. In some aspects, the MET×MET bispecific antigen-binding protein further comprises the CDRs within the LCVR amino acid sequence of SEQ ID NO: 138. In some embodiments, Ab is a MET×MET bispecific antigen-binding protein comprising the D1-HCVR amino acid sequence of SEQ ID NO: 58 and the D2-HCVR amino acid sequence of SEQ ID NO: 82. In some aspects, the MET×MET bispecific antigen-binding protein further comprises the LCVR amino acid sequence of SEQ ID NO: 138.

In some embodiments, Ab is a MET×MET bispecific antigen-binding protein comprising the CDRs within the D1-HCVR amino acid sequence of SEQ ID NO: 18 and the CDRs within the D2-HCVR amino acid sequence of SEQ ID NO: 82. In some aspects, the MET×MET bispecific antigen-binding protein further comprises the CDRs within the LCVR amino acid sequence of SEQ ID NO: 138. In some embodiments, Ab is a MET×MET bispecific antigen-binding protein comprising the D1-HCVR amino acid sequence of SEQ ID NO: 18 and the D2-HCVR amino acid sequence of SEQ ID NO: 82.

In some embodiments, L is a cleavable linker. In some embodiments, L is a non-cleavable linker. In some embodiments, L comprises a dipeptide. In some embodiments, L comprises a PAB moiety.

In some embodiments, L comprises a moiety having the following structure:

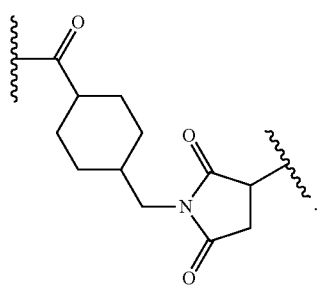 [SMILES: *C(=O)C1CCC(CN2C(=O)CC(*)C2=O)CC1]

In some embodiments, L comprises a moiety having the following structure:

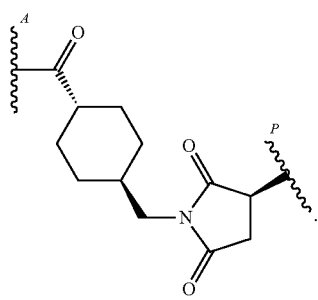

In some embodiments, L comprises a moiety having the following structure:

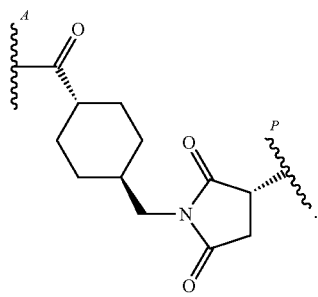

In some embodiments, L comprises a moiety having the following structure:

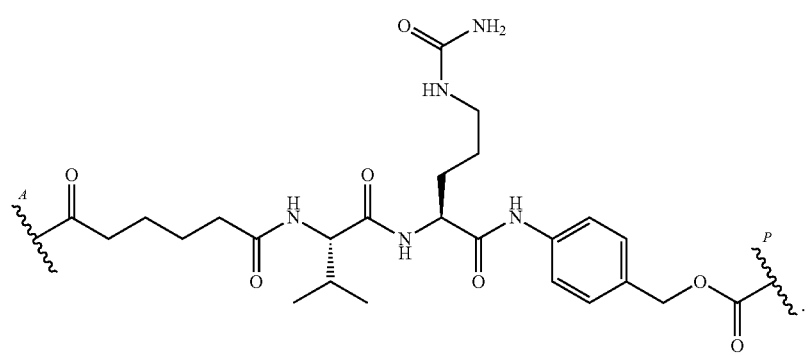

In some embodiments, Pay is a maytansinoid.

In some embodiments, Pay is:

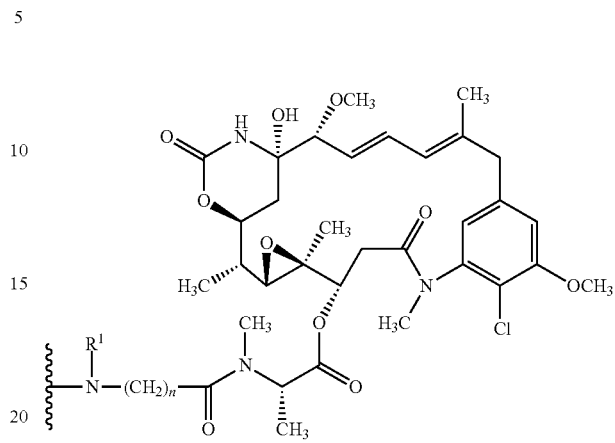

wherein $R^1$ is alkyl.

In some embodiments, Pay is:

In some embodiments, Pay is:
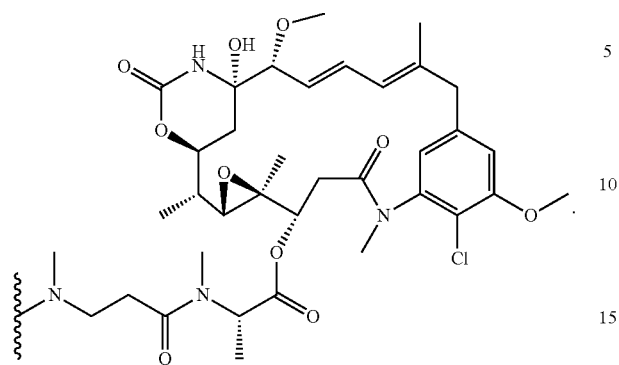
In some embodiments, n is an integer from 2 to 5.
In some embodiments, -L-Pay is:
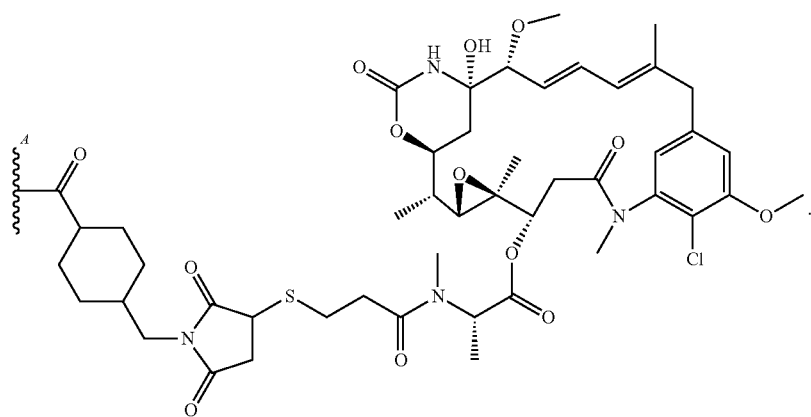
wherein
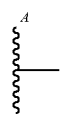
is a bond to the antibody.
In some embodiments, -L-Pay is:
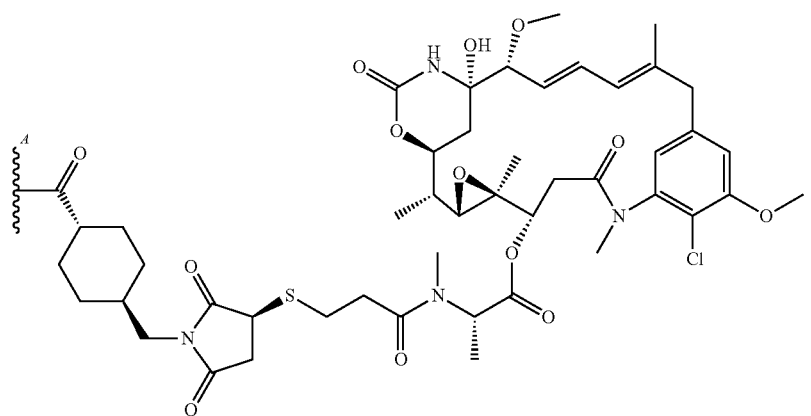

wherein
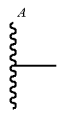
is a bond to the antibody.
In some embodiments, -L-Pay is
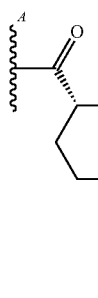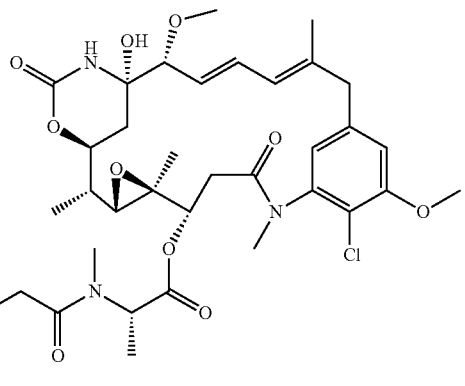
wherein
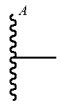
is a bond to the antibody.
In some embodiments, -L-Pay is:
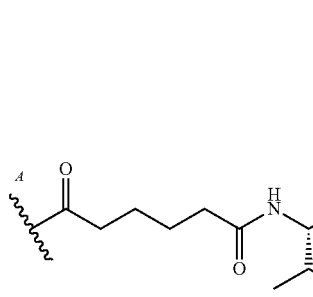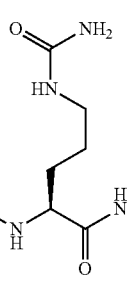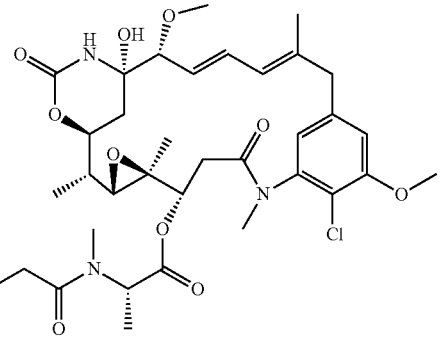
wherein
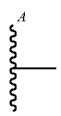
is a bond to the antibody.

In some embodiments, the conjugates have the following structure:

Ab-[L-Pay]$_n$ wherein:
Ab is an anti-MET antibody comprising the HCVR amino acid sequence of SEQ ID NO: 82 and the LCVR amino acid sequence of SEQ ID NO: 138;
L-Pay is

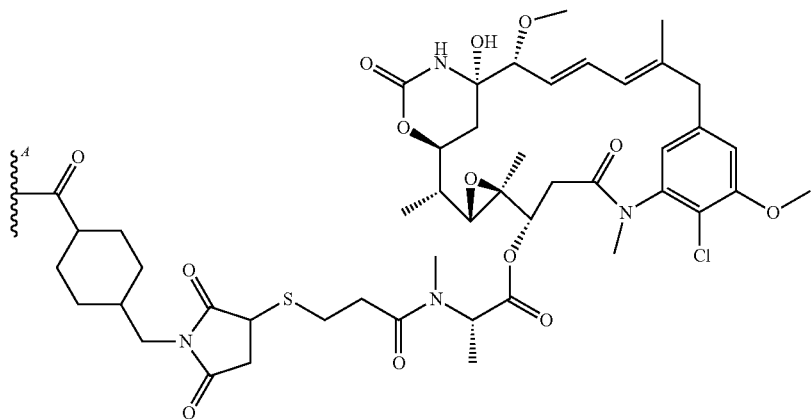

wherein

is a bond to the antibody; and n is an integer from 2-5.

In some embodiments, the conjugates have the following structure:

Ab-[L-Pay]$_n$ wherein:
Ab is an anti-MET antibody comprising the HCVR amino acid sequence of SEQ ID NO: 82 and the LCVR amino acid sequence of SEQ ID NO: 138;
L-Pay is

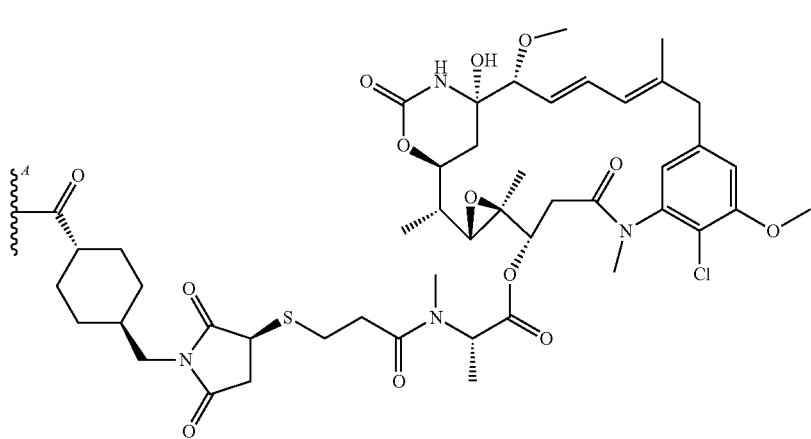

wherein

is a bond to the antibody; and n is an integer from 2-5.

In some embodiments, the conjugates have the following structure:

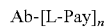

wherein:
Ab is an anti-MET antibody comprising the HCVR amino acid sequence of SEQ ID NO: 82 and the LCVR amino acid sequence of SEQ ID NO: 138;
L-Pay is

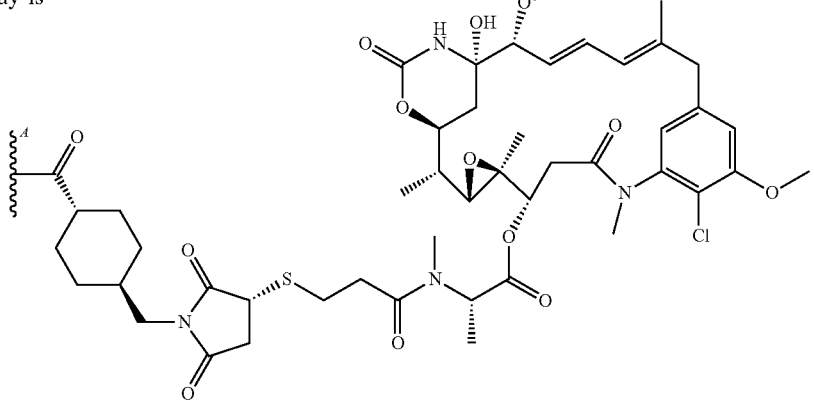

wherein

is a bond to the antibody; and n is an integer from 2-5.

In some embodiments, the conjugates have the following structure:

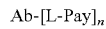

wherein:
Ab is an anti-MET antibody comprising the HCVR amino acid sequence of SEQ ID NO: 82 and the LCVR amino acid sequence of SEQ ID NO: 138;
L-Pay is

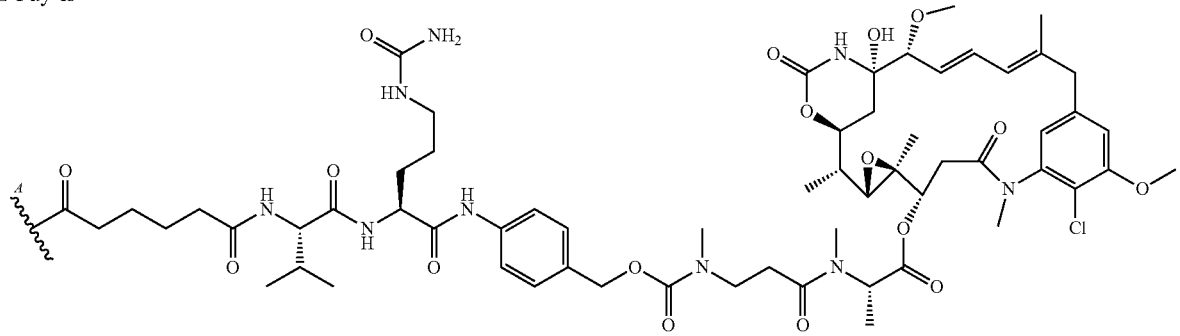

wherein

is a bond to the antibody; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 58 and the D2-HCVR amino acid sequence of SEQ ID NO: 82;
L-Pay is

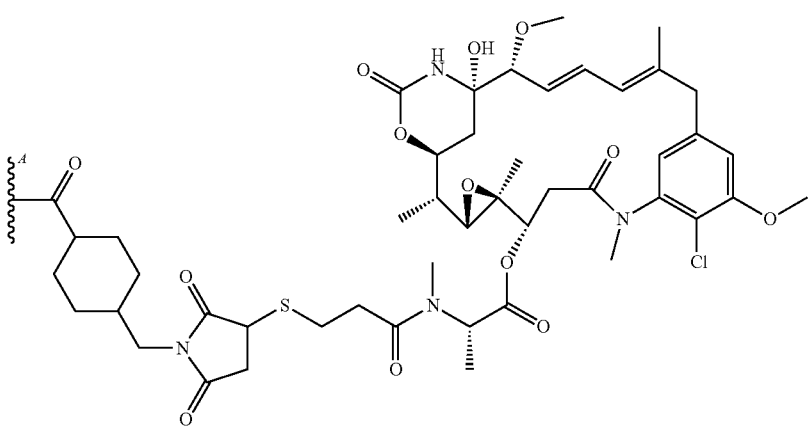

wherein

is a bond to the antigen binding protein; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 58 and the D2-HCVR amino acid sequence of SEQ ID NO: 82;

L-Pay is

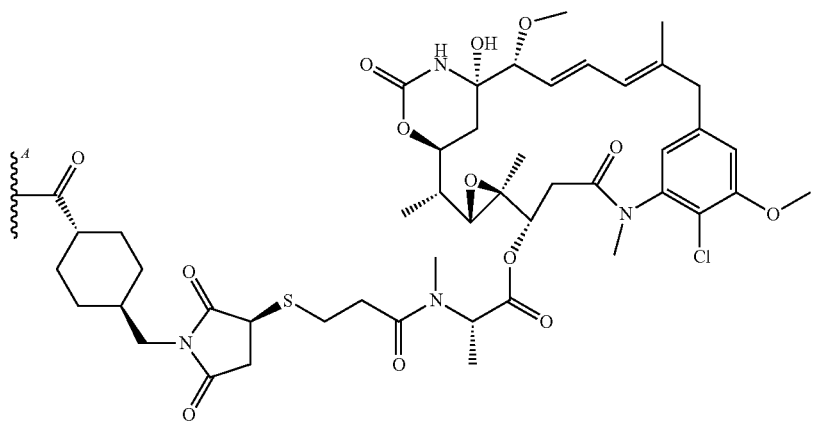

wherein

is a bond to the antigen-binding protein; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 58 and the D2-HCVR amino acid sequence of SEQ ID NO: 82;
L-Pay is

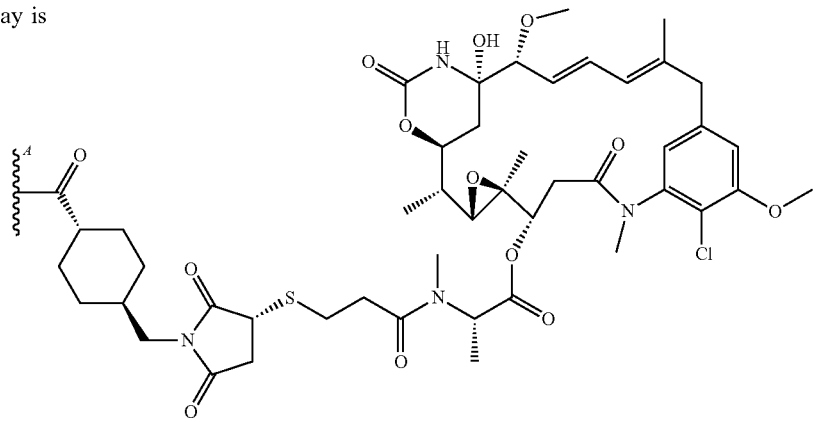

wherein

is a bond to the antigen-binding protein; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 58 and the D2-HCVR amino acid sequence of SEQ ID NO: 82;
L-Pay is

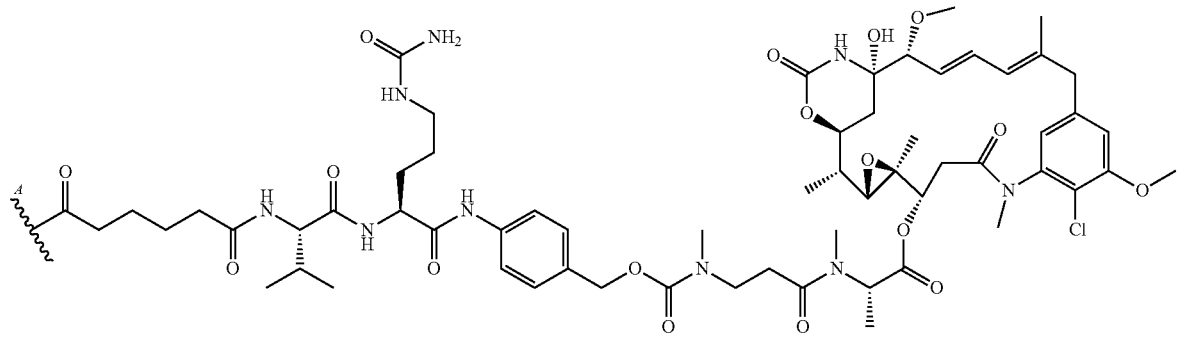

wherein

is a bond to the antigen-binding protein; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 18 and the D2-HCVR amino acid sequence of SEQ ID NO: 82;
L-Pay is

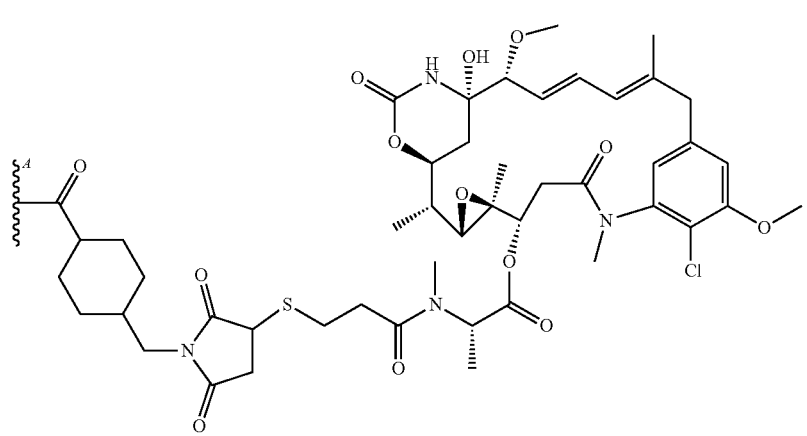

wherein

is a bond to the antigen-binding protein; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 18 and the D2-HCVR amino acid sequence of SEQ ID NO: 82;
L-Pay is

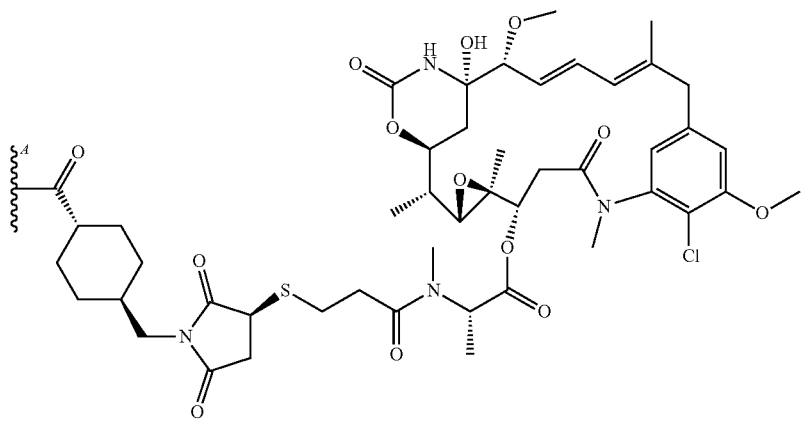

wherein

is a bond to the antigen-binding protein; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 18 and the D2-HCVR amino acid sequence of SEQ ID NO: 82;

L-Pay is

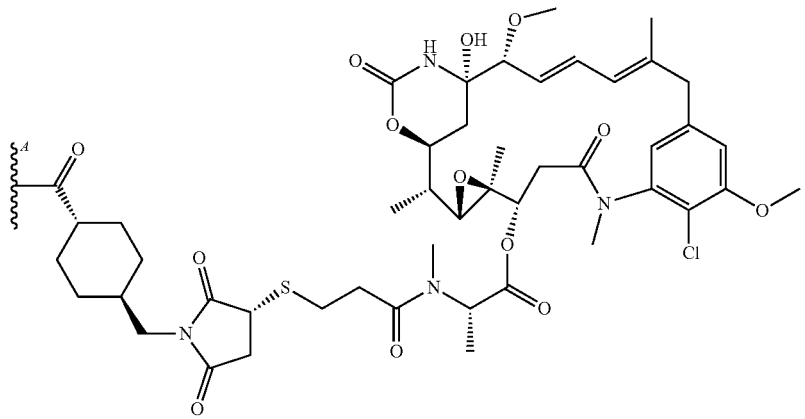

wherein

is a bond to the antigen-binding protein; and n is an integer from 2-5.

In some embodiments, the conjugates have the following structure:

Ab-[L-Pay]$_n$ wherein:
Ab is a MET×MET bispecific antigen-binding protein comprising the D1-HCVR amino acid sequence of SEQ ID NO: 18 and the D2-HCVR amino acid sequence of SEQ ID NO: 82;
L-Pay is

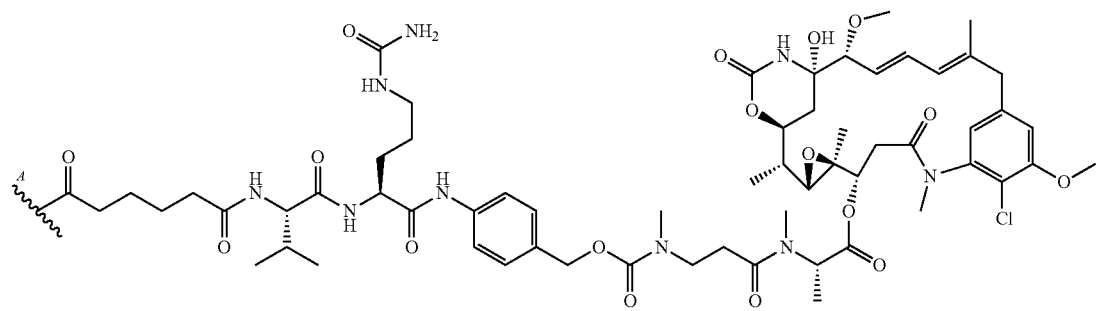

wherein

is a bond to the antigen-binding protein; and n is an integer from 2-5.

The antibody drug conjugates described herein can be prepared using conjugation conditions known to those of ordinary skill in the art, (see, e.g., Doronina et al. *Nature Biotechnology* 2003, 21, 7, 778, which is incorporated herein by reference in its entirety). In some embodiments an anti-MET antibody or a MET×MET bispecific antigen-binding protein antibody drug conjugate is prepared by contacting an anti-MET antibody or a MET×MET bispecific antigen-binding protein described herein with a compound comprising the desired linker and cytotoxic agent, wherein said linker possesses a moiety that is reactive with the antibody or antigen-binding protein, e.g., at the desired residue of the antibody or antigen-binding protein.

In some embodiments, provided herein are processes for preparing an antibody-drug conjugate comprising contacting an anti-MET antibody or a MET×MET bispecific antigen-binding protein described herein with a compound having the following formula $A^1$:

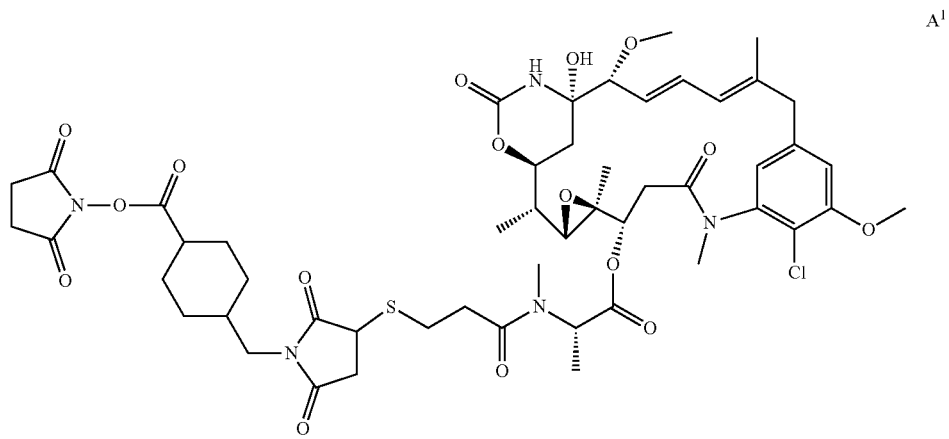 [SMILES: COc1cc2cc(c1Cl)N(C)C(=O)C[C@H](OC(=O)[C@H](C)N(C)C(=O)CCSC1CC(=O)N(CC3CCC(C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

and aqueous diluent.

In some embodiments, the compound of formula $A^1$ is present in stoichiometric excess. In some embodiments, the compound of formula $A^1$ is present in 5-6 fold stoichiometric excess. In some embodiments, the aqueous diluent comprises HEPES. In some embodiments, the aqueous diluent comprises DMA.

In some embodiments, the compound of formula $A^1$ is a compound of formula $A^2$ or $A^3$:

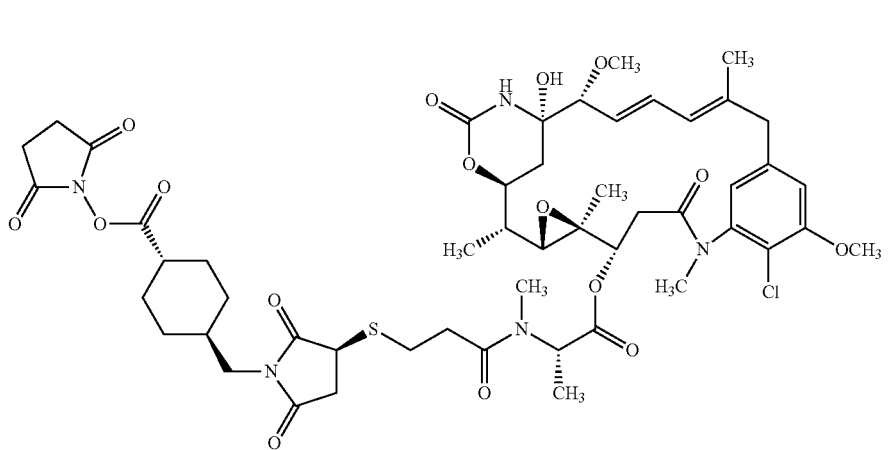

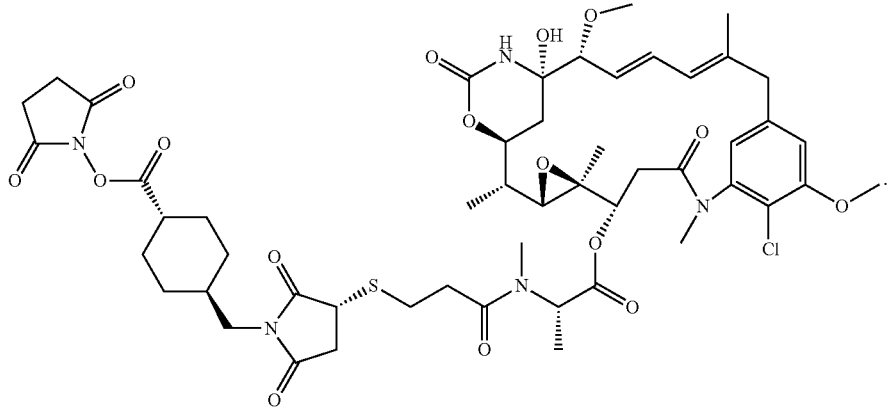

A³

In some embodiments, the compound of formula A² is A³ stereomerically pure. In some embodiments, the compound of formula A¹ comprises a compound of formula A¹ or A², wherein the compound of A¹ or A² is present in a diastereomeric excess of more than 50%. In certain embodiments, the diastereomeric excess is more than 70%. In certain embodiments, the diastereomeric excess is more than 90%. In certain embodiments, the diastereomeric excess is more than 95%.

The term "diastereomeric excess" refers to the difference between the mole fraction of the desired single diastereomer as compared to the remaining diastereomers in a composition. Diastereomeric excess is calculated as follows: (amount of single diastereomer)−(amount of other diastereomers)/1. For example, a composition that contains 90% of 1 and 10% of 2, 3, 4, or a mixture thereof has a diastereomeric excess of 80% [(90−10)/1]. A composition that contains 95% of 1 and 5% of 2, 3, 4, or a mixture thereof has a diastereomeric excess of 90% [(95−5)/1]. A composition that contains 99% of 1 and 1% of 2, 3, 4, or a mixture thereof has a diastereomeric excess of 98% [(99−1)/1]. The diastereomeric excess can similarly be calculated for any one of 1, 2, 3, or 4.

In some embodiments, the compound of formula A¹ is prepared by contacting a compound of formula (a):

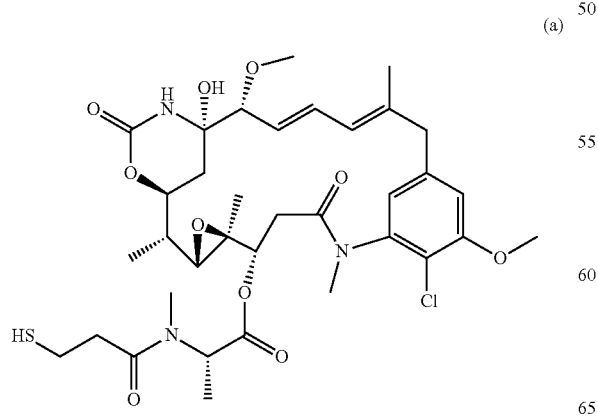

(a)

with a compound of formula (b)

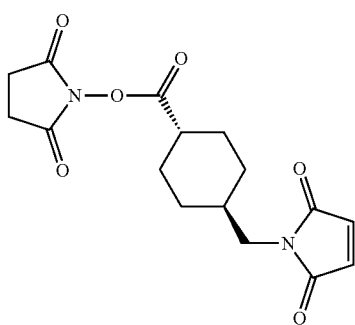

(b)

in the presence of silica gel and diluent. In some embodiments, the diluent comprises an organic solvent and water.

Provided herein is also the product prepared by the process of:
(i) contacting a compound of formula (a):

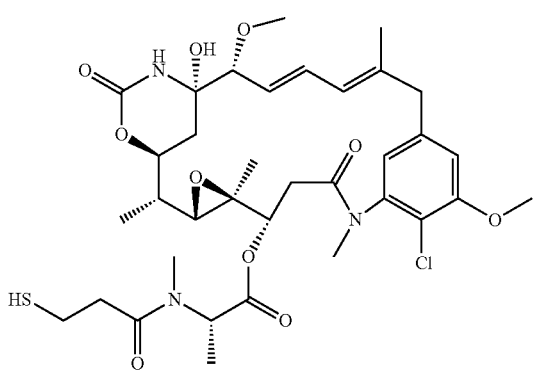

(a)

with a compound of formula (b):

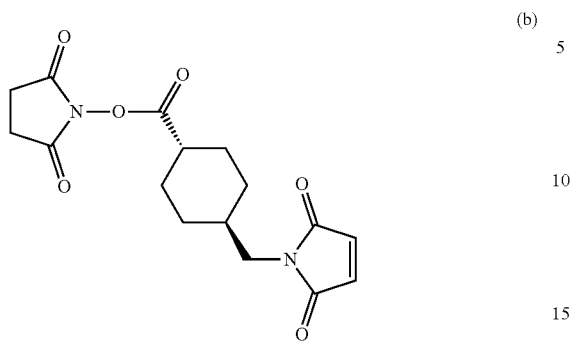

in the presence of silica gel and diluent to synthesize an intermediate; and (ii) contacting an anti-MET antibody or a MET×MET bispecific antigen-binding protein described herein with the intermediate and aqueous diluent.

In some embodiments, provided herein are processes for preparing an antibody-drug conjugate comprising contacting an anti-MET antibody or a MET×MET bispecific antigen-binding protein described herein with a compound having the following formula B:

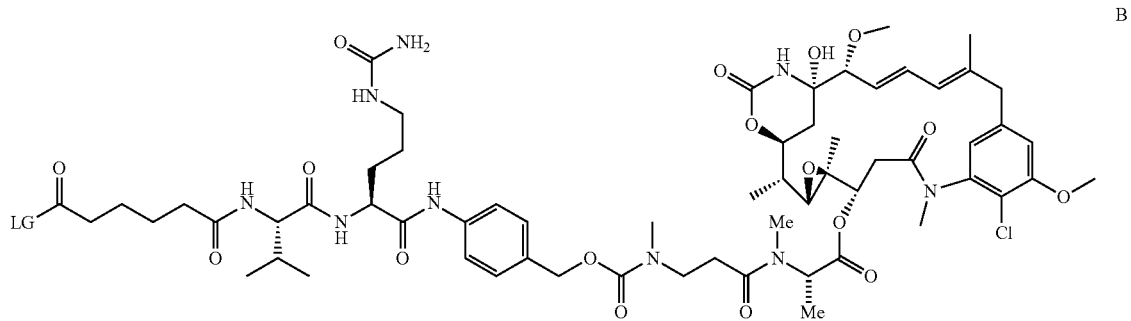

wherein LG is a leaving group, and aqueous diluent.

In some embodiments, the compound of formula B is present in stoichiometric excess. In some embodiments, the compound of formula B is present in 5-6 fold stoichiometric excess. In some embodiments, the aqueous diluent comprises HEPES. In some embodiments, the aqueous diluent comprises DMA. In some embodiments, the —C(O)-LG is an ester, e.g., NHS or trifluorophenyl ester.

In some embodiments, the compound of formula B is a compound of formula $B^1$:

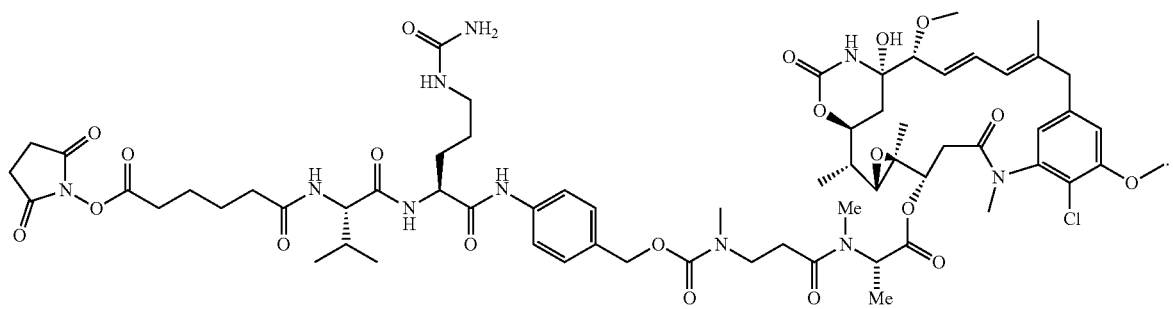

In some embodiments, the compound of formula $B^1$ is prepared by contacting a compound of formula C:

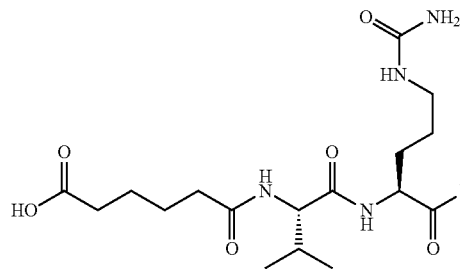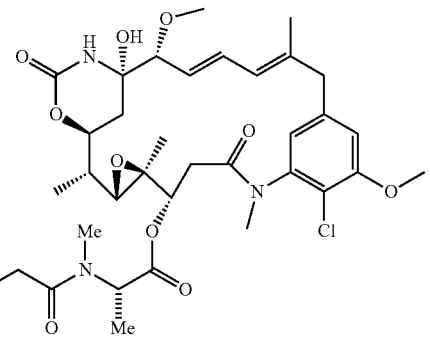

C with N-hydroxysuccinimide (NHS), an peptide coupling reagent, and an organic diluent. Suitable peptide coupling reagents include those that activate, i.e., render reactive, carboxylic acid moieties for reaction with a nucleophile. In certain embodiments, the peptide coupling reagent is N-(3-dimethylaminopropyl)-N'-ethylcarbodiimide hydrochloride (EDC). In some embodiments, the organic solvent is dichloromethane.

In some embodiments, the compound of formula C is prepared by contacting a compound of formula D:

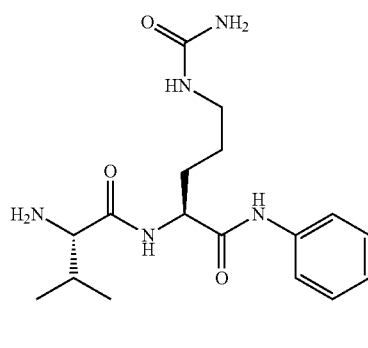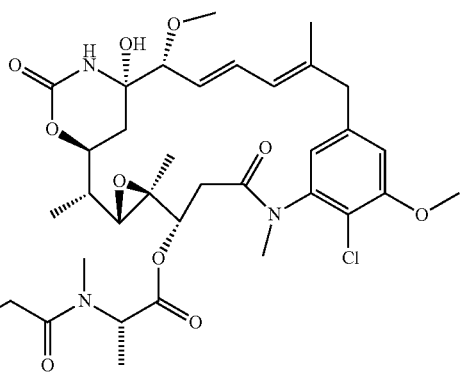

D with adipic acid, a peptide coupling agent, and an organic solvent. In certain embodiments, the peptide coupling agent is 2-ethoxy-1-ethoxycarbonyl-1,2-dihydroquinoline (EEDQ). In certain embodiments, the organic solvent comprises dichloromethane. Compound D can be prepared as described in WO2014/145090.

Epitope Mapping and Related Technologies

The epitope to which the antibodies and antigen-binding domains bind may consist of a single contiguous sequence of 3 or more (e.g., 3, 4, 5, 6, 7, 8, 9, 10, 11, 12, 13, 14, 15, 16, 17, 18, 19, 20 or more) amino acids of a MET protein. Alternatively, the relevant epitope may consist of a plurality of non-contiguous amino acids (or amino acid sequences) of MET. In some embodiments, the epitope is located on or near the ligand-binding domain of MET. In other embodiments, the epitope is located outside of the ligand-binding domain of MET, e.g., at a location on the surface of MET at which an antibody, when bound to such an epitope, does not interfere with HGF binding to MET.

As described elsewhere herein, the individual antigen binding domains (D1 and D2) of the MET×MET bispecific antigen-binding molecules may bind to distinct, or non-overlapping, or partially overlapping epitopes, relative to one another. As used herein, "partially overlapping epitopes" means that the first and second epitopes share less than 5, less than 4, less than 3, or only one common amino acid as determined by any epitope mapping methodology known in the art (e.g., X-ray crystallography, alanine-scan mutagenesis, hydrogen/deuterium exchange [HDX], domain swapping, etc.). The D1 and D2 domains may be non-competitive with one another. For example, in certain embodiments, the binding of a D1 domain of a particular MET×MET bispecific antigen-binding molecule to its epitope on MET does not inhibit (or only minimally inhibits) the binding of the D2 domain of the MET×MET bispecific antigen-binding molecule to its epitope on MET. Due to the non-overlapping (or at most, partially overlapping) nature of the respective epitopes of the D1 and D2 components, the MET×MET bispecific antigen-binding molecules are able to bind to a single MET molecule on a cell surface.

Various techniques known to persons of ordinary skill in the art can be used to determine the epitope on MET with which the antibodies and antigen-binding domains of the present disclosure interact. Exemplary techniques that can be used to determine an epitope or binding domain of a particular antibody or antigen-binding domain include, e.g., point mutagenesis (e.g., alanine scanning mutagenesis, arginine scanning mutagenesis, etc.), peptide blots analysis (Reineke, 2004, Methods Mol Biol 248:443-463), protease protection, and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystal structure analysis can also be used to identify the amino acids within a polypeptide with which an antibody interacts.

Further provided herein are anti-MET antibodies (including bispecific antibodies) that bind to the same epitope as any of the specific exemplary antibodies or antigen-binding domains described herein (e.g. antibodies comprising any of the amino acid sequences as set forth in Table 1 herein). Likewise, also provided herein are anti-MET antibodies that compete for binding to MET with any of the specific exemplary antibodies described herein (e.g. antibodies comprising any of the amino acid sequences as set forth in Table 1 herein). In some embodiments, the human MET epitope to which the anti-MET antibodies bind comprises amino acids 192-204, amino acids 305-315, and/or amino acids 421-455 of SEQ ID NO:155. In some embodiments, the first epitope of human MET comprises amino acids 192-204 of SEQ ID NO:155; and the second epitope of human MET comprises amino acids 305-315 and 421-455 of SEQ ID NO:155.

One can easily determine whether an antibody binds to the same epitope as, or competes for binding with, a reference anti-MET antibody by using routine methods known in the art and exemplified herein. For example, to determine if a test antibody binds to the same epitope as a reference anti-MET antibody provided herein, the reference antibody is allowed to bind to a MET protein. Next, the ability of a test antibody to bind to the MET molecule is assessed. If the test antibody is able to bind to MET following saturation binding with the reference anti-MET antibody, it can be concluded that the test antibody binds to a different epitope than the reference anti-MET antibody. On the other hand, if the test antibody is not able to bind to the MET molecule following saturation binding with the reference anti-MET antibody, then the test antibody may bind to the same epitope as the epitope bound by the reference anti-MET antibody. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-MET antibody, the above-described binding methodology is performed in two orientations: In a first orientation, the reference antibody is allowed to bind to a MET protein under saturating conditions followed by assessment of binding of the test antibody to the MET molecule. In a second orientation, the test antibody is allowed to bind to a MET molecule under saturating conditions followed by assessment of binding of the reference antibody to the MET molecule. If, in both orientations, only the first (saturating) antibody is capable of binding to the MET molecule, then it is concluded that the test antibody and the reference antibody compete for binding to MET. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-MET antibodies and MET×MET bispecific antibodies provided herein can be fully human antibodies. Methods for generating monoclonal antibodies, including fully human monoclonal antibodies are known in the art. Any such known methods can be used in the context of the present disclosure to make human antibodies that specifically bind to human MET.

Using VELOCIMMUNE™ technology, for example, or any other similar known method for generating fully human monoclonal antibodies, high affinity chimeric antibodies to MET are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-MET antibody. While the constant region selected may vary according to specific use, high affinity antigen-binding and target specificity characteristics reside in the variable region. In certain instances, fully human anti-MET antibodies are isolated directly from antigen-positive B cells.

Bioequivalents

The anti-MET antibodies and antibody fragments provided herein encompass proteins having amino acid sequences that vary from those of the described antibodies but that retain the ability to bind human MET. Such variant antibodies and antibody fragments comprise one or more additions, deletions, or substitutions of amino acids when compared to parent sequence, but exhibit biological activity that is essentially equivalent to that of the described antibodies. Likewise, the anti-MET antibody-encoding DNA sequences of the present disclosure encompass sequences that comprise one or more additions, deletions, or substitutions of nucleotides when compared to the disclosed sequence, but that encode an anti-MET antibody or antibody fragment that is essentially bioequivalent to an anti-MET antibody or antibody fragment of the disclosure. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-MET antibodies provided herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-MET antibody variants comprising amino acid changes which modify the glycosylation characteristics of the antibodies, e.g., mutations which eliminate or remove glycosylation.

Species Selectivity and Species Cross-Reactivity

The present disclosure, according to certain embodiments, provides anti-MET antibodies (and antigen-binding molecules comprising anti-MET antigen-binding domains) that bind to human MET but not to MET from other species. The present disclosure also includes anti-MET antibodies (and antigen-binding molecules comprising anti-MET antigen-binding domains) that bind to human MET and to MET from one or more non-human species. For example, the anti-MET antibodies and antigen-binding molecules may bind to human MET and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee MET. According to certain exemplary embodiments, anti-MET antibodies and antigen-binding molecules are provided which specifically bind human MET and cynomolgus monkey (e.g., *Macaca fascicularis*) MET. Other anti-MET antibodies and antigen-binding molecules bind human MET but do not bind, or bind only weakly, to cynomolgus monkey MET.

Multispecific Antibodies

As described elsewhere herein, the present disclosure provides bispecific antigen-binding molecules comprising two different antigen-binding domains, wherein the first antigen-binding domain (D1) binds a first epitope on MET, and wherein the second antigen-binding domain (D2) binds a second epitope on MET. In certain embodiments, the first and second epitopes on MET to which the D1 and D2 domains bind are distinct, or non-overlapping, or partially overlapping. According to this aspect, the D1 domain can comprise any of the HCVR/LCVR or CDR amino acid sequences as set forth in Table 1 herein, and the D2 domain can comprise any other of the HCVR/LCVR or CDR amino acid sequences as set forth in Table 1 herein (so long as the binding specificity of the D1 domain is different from the binding specificity of the D2 domain, and/or the antigen-binding protein from which D1 was obtained does not compete for binding to MET with the antigen-binding protein from which D2 was obtained). In some embodiments, the human MET epitope to which the anti-MET antibodies bind comprise amino acids 192-204, amino acids 305-315, and/or amino acids 421-455 of SEQ ID NO:155. In some embodiments, the first epitope of human MET comprises amino acids 192-204 of SEQ ID NO:155; and the second epitope of human MET comprises amino acids 305-315 and 421-455 of SEQ ID NO:155.

According to a separate aspect of the present disclosure, conventional bispecific antibodies are also provided wherein one arm of the bispecific antibody binds to an epitope on human MET, and the other arm of the bispecific antibody binds to a second antigen other than MET. The MET-binding arm can comprise any of the HCVR/LCVR or CDR amino acid sequences as set forth in Table 1 herein. In certain embodiments, the MET-binding arm binds human MET and blocks HGF binding to MET. In other embodiments, the MET-binding arm binds human MET but does not block HGF binding to MET.

An exemplary bispecific antibody format that can be used in the context of the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

Provided herein are pharmaceutical compositions comprising the anti-MET antibodies or MET×MET bispecific antigen-binding molecules of the present invention. The pharmaceutical compositions may be formulated with suitable carriers, excipients, and other agents that provide improved transfer, delivery, tolerance, and the like.

Therapeutic Uses of the Antibodies

Provided herein are methods comprising administering to a subject in need thereof a therapeutic composition comprising an anti-MET antibody or a MET×MET bispecific antigen-binding molecule (e.g., an anti-MET comprising any of the HCVR/LCVR or CDR sequences as set forth in Table 1 herein, or a MET×MET bispecific antigen-binding molecule comprising any of the D1 and D2 components as set forth in Table 5 herein). The therapeutic composition can comprise any of the anti-MET antibodies or MET×MET bispecific antigen-binding molecules disclosed herein, and a pharmaceutically acceptable carrier or diluent.

The anti-MET antibodies and MET×MET bispecific antigen-binding molecules are useful, inter alia, for the treatment, prevention and/or amelioration of any disease or disorder associated with or mediated by MET expression, signaling or activity, or treatable by blocking the interaction between MET and HGF, or otherwise inhibiting MET activity and/or signaling, and/or promoting receptor internalization and/or decreasing cell surface receptor number.

For example, anti-MET antibodies and MET×MET bispecific antigen-binding molecules of the present disclosure are useful for the treatment of tumors that express (or overexpress) MET. For example, the anti-MET antibodies and MET×MET bispecific antigen-binding molecules may be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the anti-MET antibodies and MET×MET bispecific antigen-binding molecules are used to treat one or more of the following cancers: acute myelogenous leukemia, adult T-cell leukemia, astrocytomas, bladder cancer, breast cancer, cervical cancer, cholangiocarcinoma, chronic myeloid leukemia, colorectal cancer, endometrial cancer, esophageal cancer, gastric cancer (e.g., gastric cancer with MET amplification), glioblastomata, head and neck cancer (e.g., head and neck squamous cell carcinoma [HNSCC]), Kaposi's sarcoma, kidney cancer, leiomyosarcomas, liver cancer, lung cancer (e.g., non-small cell lung cancer [NSCLC]), lymphomas, malignant gliomas, malignant mesothelioma, melanoma, mesothelioma, MFH/fibrosarcoma, multiple myeloma, nasopharyngeal cancer, osteosarcoma, ovarian cancer, pancreatic carcinoma, prostate cancer, renal cell carcinoma, rhabdomyosarcoma, small cell lung cancer, synovial sarcoma, thyroid cancer, and Wilms' tumor.

In the context of the methods of treatment described herein, the anti-MET antibodies and MET×MET bispecific antigen-binding molecules may be administered as a monotherapy (i.e., as the only therapeutic agent) or in combination with one or more additional therapeutic agents (examples of which are described elsewhere herein).

Combination Therapies and Formulations

Provided herein are compositions and therapeutic formulations comprising any of the anti-MET antibodies and MET×MET bispecific antigen-binding molecules described herein in combination with one or more additional therapeutically active components, and methods of treatment comprising administering such combinations to subjects in need thereof.

The anti-MET antibodies and MET×MET bispecific antigen-binding molecules may be co-formulated with and/or administered in combination with one or more additional therapeutically active component(s) selected from the group consisting of: a MET antagonist (e.g., an anti-MET antibody [e.g., onartuzumab, emibetuzumab, and H4H14639D] or small molecule inhibitor of MET), an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an anti-EGFRvIII antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody or small molecule kinase inhibitor such as, e.g., imatinib mesylate or sunitinib malate), a PDGF ligand inhibitor (e.g., anti-PDGF-A, -B, -C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), a CD20×CD3 bispecific antibody, a PD-1 blocking agent (e.g., an anti-PD-1 antibody such as pembrolizumab or nivolumab), etc. Other agents that may be beneficially administered in combination with antibodies provided herein include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

Illustratively, a PD-1 inhibitor such as an anti-PD-1 antibody can be combined with an anti-Met antibody-drug conjugate as described herein. The target patient population includes specifically those patients with tumors that overexpress the c-Met mutation, such as a patient with a c-Met-expressing non-small cell lung cancer.

Provided herein are compositions and therapeutic formulations comprising any of the anti-MET antibodies and MET×MET bispecific antigen-binding molecules described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The anti-MET antibodies and MET×MET bispecific antigen-binding molecules may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an anti-MET antibody or MET×MET bispecific antigen-binding molecule; (for purposes of the present disclosure, such administration regimens are considered the administration of an antibody "in combination with" an additional therapeutically active component). The present disclosure includes pharmaceutical compositions in which an anti-MET antibody or MET×MET bispecific antigen-binding molecule is co-formulated with one or more of the additional therapeutically active component(s) as described elsewhere herein.

Administration Regimens

According to certain embodiments, multiple doses of an anti-MET antibody or MET×MET bispecific antigen-binding molecule (or a pharmaceutical composition comprising a combination of an anti-MET antibody or MET×MET bispecific antigen-binding molecule and any of the additional therapeutically active agents mentioned herein) may be administered to a subject over a defined time course. The methods according to this aspect comprise sequentially administering to a subject multiple doses of an anti-MET antibody or MET×MET bispecific antigen-binding molecule provided herein. As used herein, "sequentially administering" means that each dose of antibody is administered to the subject at a different point in time, e.g., on different days separated by a predetermined interval (e.g., hours, days, weeks or months). The present disclosure includes methods which comprise sequentially administering to the patient a single initial dose of an anti-MET antibody or MET×MET bispecific antigen-binding molecule, followed by one or more secondary doses of the anti-MET antibody or MET×MET bispecific antigen-binding molecule, and optionally followed by one or more tertiary doses of the anti-MET antibody or MET×MET bispecific antigen-binding molecule.

The terms "initial dose," "secondary doses," and "tertiary doses," refer to the temporal sequence of administration of the anti-MET antibody or MET×MET bispecific antigen-binding molecule. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-MET antibody or MET×MET bispecific antigen-binding molecule, but generally may differ from one another in terms of frequency of administration. In certain embodiments, however, the amount of antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Diagnostic Uses of the Antibodies

The anti-MET antibody or MET×MET bispecific antigen-binding molecule of the present disclosure may also be used to detect and/or measure MET, or MET-expressing cells in a sample, e.g., for diagnostic purposes. For example, an anti-MET antibody, or fragment thereof, may be used to diagnose a condition or disease characterized by aberrant expression (e.g., over-expression, under-expression, lack of expression, etc.) of MET. Exemplary diagnostic assays for MET may comprise, e.g., contacting a sample, obtained from a patient, with an anti-MET antibody or MET×MET bispecific antigen-binding molecule, wherein the antibody is labeled with a detectable label or reporter molecule. Alternatively, an unlabeled anti-MET antibody or MET×MET bispecific antigen-binding molecule can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure MET in a sample include enzyme-linked immunosorbent assay (ELISA), radioimmunoassay (RIA), immuno-PET (e.g., $^{89}Zr$, $^{64}Cu$, etc.), and fluorescence-activated cell sorting (FACS).

Samples that can be used in MET diagnostic assays according to the present disclosure include any tissue or fluid sample obtainable from a patient. Generally, levels of MET in a particular sample obtained from a healthy patient (e.g., a patient not afflicted with a disease or condition associated with abnormal MET levels or activity) will be measured to initially establish a baseline, or standard, level of MET. This baseline level of MET can then be compared against the levels of MET measured in samples obtained from individuals suspected of having a MET-related disease or condition.

EXAMPLES

The following examples are put forth so as to provide those of ordinary skill in the art with a complete disclosure and description of how to make and use the methods and compositions provided herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-MET Antibodies

Anti-MET antibodies were obtained by immunizing a genetically engineered mouse comprising DNA encoding human immunoglobulin heavy and kappa light chain variable regions with an immunogen comprising recombinant human MET extracellular domain fused to human Fc (R&D Systems, Catalog #358-MT, Minneapolis, Minn.). The mice used for the immunizations express a "universal light chain." That is, the antibodies produced in this mouse have different heavy chain variable regions but essentially identical light chain variable domains.

The antibody immune response was monitored by a MET-specific immunoassay. When a desired immune response was achieved splenocytes were harvested and fused with mouse myeloma cells to preserve their viability and form hybridoma cell lines. The hybridoma cell lines were screened and selected to identify cell lines that produce MET-specific antibodies. Using this technique several anti-MET chimeric antibodies (i.e., antibodies possessing human variable domains and mouse constant domains) were obtained. In addition, several fully human anti-MET antibodies were isolated directly from antigen-positive B cells without fusion to myeloma cells, as described in US 2007/0280945A1.

Certain biological properties of the exemplary anti-MET antibodies generated in accordance with the methods of this Example, and bispecific antibodies constructed therefrom, are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-MET antibodies described herein. (As noted above, all antibodies generated in Example 1 possess the same light chain variable region, and thus the same light chain CDR sequences as well). The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H13290P2 | 2 | 4 | 6 | 8 | 138 | 140 | 142 | 144 |
| H4H13291P2 | 10 | 12 | 14 | 16 | 138 | 140 | 142 | 144 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H13295P2 | 18 | 20 | 22 | 24 | 138 | 140 | 142 | 144 |
| H4H13299P2 | 26 | 28 | 30 | 32 | 138 | 140 | 142 | 144 |
| H4H13300P2 | 34 | 36 | 38 | 40 | 138 | 140 | 142 | 144 |
| H4H13301P2 | 42 | 44 | 46 | 48 | 138 | 140 | 142 | 144 |
| H4H13302P2 | 50 | 52 | 54 | 56 | 138 | 140 | 142 | 144 |
| H4H13306P2 | 58 | 60 | 62 | 64 | 138 | 140 | 142 | 144 |
| H4H13309P2 | 66 | 68 | 70 | 72 | 138 | 140 | 142 | 144 |
| H4H13311P2 | 74 | 76 | 78 | 80 | 138 | 140 | 142 | 144 |
| H4H13312P2 | 82 | 84 | 86 | 88 | 138 | 140 | 142 | 144 |
| H4H13313P2 | 90 | 92 | 94 | 96 | 138 | 140 | 142 | 144 |
| H4H13316P2 | 98 | 100 | 102 | 104 | 138 | 140 | 142 | 144 |
| H4H13318P2 | 106 | 108 | 110 | 112 | 138 | 140 | 142 | 144 |
| H4H13319P2 | 114 | 116 | 118 | 120 | 138 | 140 | 142 | 144 |
| H4H13325P2 | 122 | 124 | 126 | 128 | 138 | 140 | 142 | 144 |
| H4H13331P2 | 130 | 132 | 134 | 136 | 138 | 140 | 142 | 144 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H13290P2 | 1 | 3 | 5 | 7 | 137 | 139 | 141 | 143 |
| H4H13291P2 | 9 | 11 | 13 | 15 | 137 | 139 | 141 | 143 |
| H4H13295P2 | 17 | 19 | 21 | 23 | 137 | 139 | 141 | 143 |
| H4H13299P2 | 25 | 27 | 29 | 31 | 137 | 139 | 141 | 143 |
| H4H13300P2 | 33 | 35 | 37 | 39 | 137 | 139 | 141 | 143 |
| H4H13301P2 | 41 | 43 | 45 | 47 | 137 | 139 | 141 | 143 |
| H4H13302P2 | 49 | 51 | 53 | 55 | 137 | 139 | 141 | 143 |
| H4H13306P2 | 57 | 59 | 61 | 63 | 137 | 139 | 141 | 143 |
| H4H13309P2 | 65 | 67 | 69 | 71 | 137 | 139 | 141 | 143 |
| H4H13311P2 | 73 | 75 | 77 | 79 | 137 | 139 | 141 | 143 |
| H4H13312P2 | 81 | 83 | 85 | 87 | 137 | 139 | 141 | 143 |
| H4H13313P2 | 89 | 91 | 93 | 95 | 137 | 139 | 141 | 143 |
| H4H13316P2 | 97 | 99 | 101 | 103 | 137 | 139 | 141 | 143 |
| H4H13318P2 | 105 | 107 | 109 | 111 | 137 | 139 | 141 | 143 |
| H4H13319P2 | 113 | 115 | 117 | 119 | 137 | 139 | 141 | 143 |
| H4H13325P2 | 121 | 123 | 125 | 127 | 137 | 139 | 141 | 143 |
| H4H13331P2 | 129 | 131 | 133 | 135 | 137 | 139 | 141 | 143 |

Antibodies are typically referred to herein according to the following nomenclature: Fc prefix (e.g. "H4H"), followed by a numerical identifier (e.g. "13290," "13291," "13295," etc.), followed by a "P2" suffix, as shown in Tables 1 and 2. Thus, according to this nomenclature, an antibody may be referred to herein as, e.g., "H4H13290P2," "H4H13291 P2," "H4H13295P2," etc. The prefix on the antibody designations used herein indicate the particular Fc region isotype of the antibody. In particular, an "H4H" antibody has a human IgG4 Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG4 Fc can be converted to an antibody with a human IgG1, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Example 3. Surface Plasmon Resonance Derived Binding Affinities and Kinetic Constants of Human Monoclonal Anti-MET (Monospecific) Antibodies Binding affinities and kinetic constants of human anti-MET antibodies were determined by surface plasmon resonance (Biacore 4000 or T-200) at 37° C. The anti-Met antibodies tested in this example were bivalent monospecific binders of MET. The antibodies, expressed as human IgG4 (designated "H4H"), were captured onto a CM4 or CM5 Biacore sensor surface derivatized via amine coupling with a monoclonal mouse anti-human Fc antibody (GE, BR-1008-39). Various concentrations of soluble monomeric (human (h) Met.mmh; SEQ ID NO: 152; *macaca fascicularis* (mf) Met.mmh; SEQ ID NO: 154) or dimeric (hMet.mFc; SEQ ID NO: 153) Met proteins were injected over the anti-MET-antibody captured surface at a flow rate of 30 or 50 µL/minute. Association of hMET.mmh or hMET.mFc to the captured monoclonal antibody was monitored for 4 or 5 minutes and the dissociation of hMET.mmh or hMET.mFc in HBS-ET (0.01M HEPES pH 7.4, 0.15M NaCl, 3 mM EDTA, 0.05% v/v Surfactant P20) or PBS-P (0.01M Sodium Phosphate pH 7.4, 0.15M NaCl, 0.05% v/v Surfactant P20) running buffer was monitored for 10 minutes.

Kinetic association ($k_a$) and dissociation ($k_d$) rate constants were determined by fitting the real-time sensorgrams to a 1:1 binding model using Scrubber 2.0c curve fitting software. Binding dissociation equilibrium constant ($K_D$) and dissociative half-life (t½) were calculated from the kinetic rate constants as:

$$K_D(M) = \frac{kd}{ka}, \text{ and } t^{1/2} \text{ (min)} = \frac{\ln(2)}{60 * kd}$$

Binding kinetic parameters for the monospecific anti-Met antibodies to monomeric and dimeric Met protein are shown below in Table 3.

TABLE 3

Biacore Binding Affinities of Monospecific Anti-MET mAbs at 37° C.
Binding at 37° C./Antibody-Capture Format

| Antibody | Analyte | ka (Ms⁻¹) | kd (s⁻¹) | $K_D$ (Molar) | T½ (min) |
|---|---|---|---|---|---|
| H4H13290P2 | hMet.mmh | 2.53E+05 | 8.03E−04 | 3.17E−09 | 14.4 |
|  | hMET.mFc | 6.15E+05 | 3.15E−04 | 5.13E−10 | 36.6 |
|  | mfMet.mmh | 1.23E+05 | 6.33E−04 | 5.16E−09 | 18.2 |
| H4H13291P2 | hMet.mmh | 2.55E+04 | 2.38E−03 | 9.34E−08 | 4.8 |
|  | hMET.mFc | 3.33E+05 | 3.39E−04 | 1.02E−09 | 34 |
|  | mfMet.mmh | 3.70E+04 | 1.39E−03 | 3.76E−08 | 8.3 |
| H4H13295P2 | hMet.mmh | 1.67E+04 | 5.40E−04 | 3.24E−08 | 21.4 |
|  | hMET.mFc | 2.28E+05 | 2.64E−04 | 1.16E−09 | 43.8 |
|  | mfMet.mmh | 1.65E+04 | 9.79E−04 | 5.93E−08 | 11.8 |
| H4H13299P2 | hMet.mmh | 9.10E+04 | 7.80E−04 | 8.57E−09 | 14.8 |
|  | hMET.mFc | 3.57E+05 | 3.14E−04 | 8.78E−10 | 36.8 |
|  | mfMet.mmh | 1.13E+05 | 8.84E−04 | 7.86E−09 | 13.1 |
| H4H13300P2 | hMet.mmh | 3.35E+04 | 2.43E−03 | 7.25E−08 | 4.8 |
|  | hMET.mFc | 2.65E+05 | 2.95E−04 | 1.12E−09 | 39.1 |
|  | mfMet.mmh | 5.13E+04 | 1.94E−03 | 3.77E−08 | 6.0 |
| H4H13301P2 | hMet.mmh | 7.57E+04 | 6.22E−03 | 8.22E−08 | 1.9 |
|  | hMET.mFc | 7.05E+05 | 1.14E−03 | 1.62E−09 | 10.1 |
|  | mfMet.mmh | 6.85E+04 | 5.30E−03 | 7.74E−08 | 2.2 |
| H4H13302P2 | hMet.mmh | 5.24E+04 | 2.46E−03 | 4.70E−08 | 4.7 |
|  | hMET.mFc | 2.51E+05 | 5.84E−04 | 2.33E−09 | 19.8 |
|  | mfMet.mmh | 3.56E+04 | 2.92E−03 | 8.20E−08 | 4.0 |
| H4H13306P2 | hMet.mmh | 1.52E+05 | 1.66E−02 | 1.09E−07 | 0.7 |
|  | hMET.mFc | 1.21E+06 | 2.60E−03 | 2.15E−09 | 4.4 |
|  | mfMet.mmh | 1.21E+06 | 3.11E−02 | 2.58E−08 | 0.4 |
| H4H13309P2 | hMet.mmh | 9.20E+04 | 5.87E−04 | 6.38E−09 | 19.7 |
|  | hMET.mFc | 4.06E+05 | 2.67E−04 | 6.57E−10 | 43.3 |
|  | mfMet.mmh | 1.23E+05 | 6.33E−04 | 5.16E−09 | 18.2 |
| H4H13311P2 | hMet.mmh | 4.48E+04 | 5.19E−03 | 1.16E−07 | 2.2 |
|  | hMET.mFc | 3.02E+05 | 4.68E−04 | 1.55E−09 | 24.7 |
|  | mfMet.mmh | 7.61E+04 | 6.04E−03 | 7.94E−08 | 1.9 |
| H4H13312P2 | hMet.mmh | 7.19E+04 | 1.63E−02 | 2.27E−07 | 0.7 |
|  | hMET.mFc | 6.14E+05 | 1.71E−03 | 2.79E−09 | 6.7 |
|  | mfMet.mmh | 1.47E+05 | 7.72E−03 | 5.24E−08 | 1.5 |
| H4H13313P2 | hMet.mmh | 8.78E+04 | 5.70E−03 | 6.49E−08 | 2 |
|  | hMET.mFc | 7.50E+05 | 8.93E−04 | 1.19E−09 | 12.9 |
|  | mfMet.mmh | 5.10E+04 | 4.08E−03 | 8.00E−08 | 2.8 |
| H4H13316P2 | hMet.mmh | 7.82E+04 | 1.51E−03 | 1.93E−08 | 7.6 |
|  | hMET.mFc | 2.93E+05 | 1.08E−04 | 3.67E−10 | 107.4 |
|  | mfMet.mmh | NB | NB | NB | NB |
| H4H13318P2 | hMet.mmh | 3.30E+04 | 2.92E−03 | 8.83E−08 | 4 |
|  | hMET.mFc | 3.52E+05 | 1.65E−04 | 4.67E−10 | 70.2 |
|  | mfMet.mmh | NB | NB | NB | NB |
| H4H13319P2 | hMet.mmh | 3.11E+04 | 2.38E−03 | 7.65E−08 | 4.9 |
|  | hMET.mFc | 3.82E+05 | 5.42E−04 | 1.42E−09 | 21.3 |
|  | mfMet.mmh | 2.66E+04 | 1.15E−03 | 4.33E−08 | 10.0 |
| H4H13325P2 | hMet.mmh | 9.53E+04 | 2.36E−03 | 2.48E−08 | 4.9 |
|  | hMET.mFc | 3.06E+05 | 1.85E−04 | 6.05E−10 | 62.4 |
|  | mfMet.mmh | NB | NB | NB | NB |
| H4H13331P2 | hMet.mmh | 2.61E+05 | 8.73E−04 | 3.35E−09 | 13.2 |
|  | hMET.mFc | 6.39E+05 | 1.56E−04 | 2.44E−10 | 74.1 |
|  | mfMet.mmh | 1.61E+05 | 1.04E−03 | 6.47E−09 | 11.1 |

NB = No binding observed under conditions used

As shown in Table 3, several antibodies displayed high affinity binding to human and monkey MET protein.

Example 4. Anti-Met Antibodies Bind to Distinct Epitopes on Met Receptor

To assess whether two anti-Met antibodies are able to compete with one another for binding to their respective epitopes on MET, a binding competition assay was conducted using real time, label-free bio-layer interferometry (BLI) on an OCTET® HTX biosensor (FortéBio Corp., Menlo Park, Calif.).

Briefly, approximately 0.25 nM of human MET extracellular domain expressed with a C-terminal myc-myc-hexahistidine tag (hMet.mmh) was first captured onto anti-penta-His antibody coated OCTET® biosensors (FortéBio Corp., #18-5079) by submerging the biosensors for 5 minutes into wells containing a 20 μg/mL solution of hMET.mmh. The antigen-captured biosensors were then saturated with the first anti-MET monoclonal antibody (subsequently referred to as mAb-1) by immersion into wells containing a 50 μg/mL solution of mAb-1 for 5 minutes. The biosensors were then submerged into wells containing a 50 μg/mL solution of a second anti-MET monoclonal antibody (subsequently referred to as mAb-2) for 3 minutes. All of the biosensors were washed in OCTET® HEPES-buffered saline-EDTA polysorbate 20 (HBS-EP) buffer in between each step of the experiment. The real-time binding response was monitored during the course of the experiment and the binding response at the end of each step was recorded. The response of mAb-2 binding to anti-MET pre-complexed with mAb-1 was compared and the competitive/non-competitive behavior of the different anti-MET monoclonal antibodies was determined using a 50% inhibition threshold. Table 4 explicitly defines the relationships of antibodies competing in both directions, independent of the order of binding.

TABLE 4

Cross-competition of anti-MET antibodies for binding to hMET.mmh

| First mAb (mAb-1) Captured using Anti-Penta-His Octet Biosensors | mAb-2 antibodies which Compete with mAb-1 |
|---|---|
| H4H13301P2 | H4H13302P2 |
| H4H13302P2 | H4H13301P2 |
| H4H13290P2 | H4H13306P2 |
|  | H4H13316P2 |
| H4H13306P2 | H4H13290P2 |
|  | H4H13316P2 |
| H4H13316P2 | H4H13290P2 |
|  | H4H13306P2 |
|  | H4H13325P2 |
|  | H4H13331P2 |
| H4H13325P2 | H4H13316P2 |
|  | H4H13331P2 |
| H4H13312P2 | H4H13331P2 |
| H4H13291P2 | H4H13295P2 |
|  | H4H13300P2 |
|  | H4H13311P2 |
|  | H4H13318P2 |
|  | H4H13319P2 |
| H4H13295P2 | H4H13291P2 |
|  | H4H13300P2 |
|  | H4H13311P2 |
|  | H4H13318P2 |
|  | H4H13319P2 |

TABLE 4-continued

Cross-competition of anti-MET antibodies for binding to hMET.mmh

| First mAb (mAb-1) Captured using Anti-Penta-His Octet Biosensors | mAb-2 antibodies which Compete with mAb-1 |
|---|---|
| H4H13300P2 | H4H13291P2 |
|  | H4H13295P2 |
|  | H4H13311P2 |
|  | H4H13318P2 |
|  | H4H13319P2 |
| H4H13311P2 | H4H13291P2 |
|  | H4H13295P2 |
|  | H4H13300P2 |
|  | H4H13318P2 |
|  | H4H13319P2 |
| H4H13318P2 | H4H13291P2 |
|  | H4H13295P2 |
|  | H4H13300P2 |
|  | H4H13311P2 |
|  | H4H13319P2 |
| H4H13319P2 | H4H13291P2 |
|  | H4H13295P2 |
|  | H4H13300P2 |
|  | H4H13311P2 |
|  | H4H13318P2 |
| H4H13331P2 | H4H13316P2 |
|  | H4H13325P2 |
|  | H4H13312P2 |

Example 5. Construction of Bispecific Antibodies Having Two Different Antigen-Binding Domains Specific for Different Epitopes of MET This example describes the construction of bispecific antibodies comprising two different antigen-binding domains (D1 and D2), wherein D1 and D2 are derived from different anti-MET antibodies and, consequently, bind to separate epitopes on the MET extracellular domain.

The individual anti-MET antigen-binding domains used to construct the bispecific antibodies of this Example were derived from various bivalent, monospecific anti-MET antibodies described in Examples 1 through 3, herein. All anti-MET antibodies described herein comprise the same ("common") light chain (comprising the light chain variable region [LCVR] amino acid sequence of SEQ ID NO:138, and light chain CDR [LCDR1, LCDR2 and LCDR3] amino acid sequences of SEQ ID NOs: 140, 142 and 144). In addition, all of the bispecific antibodies illustrated in this Example contain a "D2" arm derived from the exemplary anti-MET antibody H4H13312P2. Thus, both antigen-binding domains (D1 and D2) of all of the bispecific antibodies described in this example comprise this common light chain variable region, and all D2 binding arms comprise the heavy chain variable region from H4H13312P2; however, the bispecific antibodies differ from one another in terms of their D1 heavy chain variable regions (HCVRs) and heavy chain CDRs (HCDRs). The components of the bispecific antibodies of this Example are summarized in Table 5.

TABLE 5

MET × MET Bispecific Antibody Components Summary

SEQ ID NOs: (Amino Acid Sequences)

| Bispecific Antibody | First Antigen-Binding Domain (D1) | | | | Second Antigen-Binding Domain (D2) | | | |
|---|---|---|---|---|---|---|---|---|
| | D1-HCVR | D1-HCDR1 | D1-HCDR2 | D1-HCDR3 | D2-HCVR | D2-HCDR1 | D2-HCDR2 | D2-HCDR3 |
| H4H14634D (No. 10) | 2 | H4H13290P2 4 | 6 | 8 | 82 | H4H13312P2 84 | 86 | 88 |
| H4H14635D (No. 42) | 18 | H4H13295P2 20 | 22 | 24 | 82 | H4H13312P2 84 | 86 | 88 |
| H4H14636D (No. 74) | 26 | H4H13299P2 28 | 30 | 32 | 82 | H4H13312P2 84 | 86 | 88 |
| H4H14637D (No. 90) | 42 | H4H13301P2 44 | 46 | 48 | 82 | H4H13312P2 84 | 86 | 88 |
| H4H14638D (No. 106) | 50 | H4H13302P2 52 | 54 | 56 | 82 | H4H13312P2 84 | 86 | 88 |
| H4H14639D (No. 122) | 58 | H4H13306P2 60 | 62 | 64 | 82 | H4H13312P2 84 | 86 | 88 |
| H4H14640D (No. 138) | 66 | H4H13309P2 68 | 70 | 72 | 82 | H4H13312P2 84 | 86 | 88 |
| H4H14641D (No. 187) | 90 | H4H13313P2 92 | 94 | 96 | 82 | H4H13312P2 84 | 86 | 88 |
| H4H16445D (No. 26) | 10 | H4H13291P2 12 | 14 | 16 | 82 | H4H13312P2 84 | 86 | 88 |
| H4H16446D (No. 58) | 34 | H4H13300P2 36 | 38 | 40 | 82 | H4H13312P2 84 | 86 | 88 |
| H4H16447D (No. 154) | 74 | H4H13311P2 76 | 78 | 80 | 82 | H4H13312P2 84 | 86 | 88 |
| H4H16448D (No. 219) | 106 | H4H13318P2 108 | 110 | 112 | 82 | H4H13312P2 84 | 86 | 88 |
| H4H16449D (No. 235) | 114 | H4H13319P2 116 | 118 | 120 | 82 | H4H13312P2 84 | 86 | 88 |

*The number designation in parentheses under the bispecific antibody identifiers (e.g., "No. 10") indicates the bispecific antibody number depicted in the MET × MET bispecific antibody matrix of FIG. 1.

Example 6. Surface Plasmon Resonance Derived Binding Affinities and Kinetic Constants of MET×MET Human Bispecific Monoclonal Antibodies Binding affinities and kinetic constants of the MET×MET bispecific antibodies constructed in accordance with Example 4 herein were determined by surface plasmon resonance (Biacore 4000 or T-200) at 37° C. The bispecific antibodies, expressed as human IgG4 (designated "H4H"), were captured onto a CM4 or CM5 Biacore sensor surface derivatized via amine coupling with a monoclonal mouse anti-human Fc antibody (GE, BR-1008-39). Various concentrations of soluble monomeric MET protein (hMet.mmh, SEQ ID NO: 152) were injected over the anti-MET×MET bispecific antibody-captured surface at a flow rate of 30 or 50 µL/minute. Association of the analyte to the captured bispecific antibody was monitored for 4 or 5 minutes and the dissociation of the analyte in HBS-ET (0.01M HEPES pH 7.4, 0.15M NaCl, 3 mM EDTA, 0.05% v/v Surfactant P20) or PBS-P (0.01M Sodium Phosphate pH 7.4, 0.15M NaCl, 0.05% v/v Surfactant P20) running buffer was monitored for 10 minutes.

Kinetic association ($k_a$) and dissociation ($k_d$) rate constants were determined as described in Example 3.

Binding kinetic parameters for the bispecific anti-Met antibodies to monomeric Met protein (hMET.mmh) are shown in Table 6.

TABLE 6

Biacore Binding Affinities of Bispecific Anti-MET mAbs at 37° C.
Binding at 37° C./Antibody-Capture Format

| Bispecific Antibody | Analyte | ka (Ms$^{-1}$) | kd (s$^{-1}$) | $K_D$ (Molar) | T½ (min) |
|---|---|---|---|---|---|
| H4H14634D | hMet.mmh | N/A | ≤1E-5 | N/A | ≥1155 |
| H4H14635D | hMet.mmh | N/A | 8.21E-05 | N/A | 140.6 |
| H4H14636D | hMet.mmh | N/A | ≤1E-5 | N/A | ≥1155 |
| H4H14637D | hMet.mmh | N/A | 3.26E-04 | N/A | 35.4 |
| H4H14638D | hMet.mmh | N/A | 1.65E-04 | N/A | 70.2 |
| H4H14639D | hMet.mmh | N/A | 1.63E-04 | N/A | 70.8 |
| H4H14640D | hMet.mmh | N/A | ≤1E-5 | N/A | ≥1155 |
| H4H14641D | hMet.mmh | N/A | 3.27E-04 | N/A | 35.3 |
| H4H16445D | hMet.mmh | N/A | 3.93E-04 | N/A | 29.4 |
| H4H16446D | hMet.mmh | N/A | 1.03E-04 | N/A | 111.8 |
| H4H16447D | hMet.mmh | N/A | 8.48E-04 | N/A | 13.6 |
| H4H16448D | hMet.mmh | N/A | 5.92E-04 | N/A | 19.5 |
| H4H16449D | hMet.mmh | N/A | 2.94E-04 | N/A | 39.3 |

As shown in Table 6, the bispecific "MET×MET" antibodies described herein exhibited T 1/2 values of up to greater than 1155 minutes.

As shown in Table 7, the dissociation rate for the bispecific antibody H4H14639D is significantly lower than the dissociation rates of each of its parental antibodies, H4H13306P2 and H4H13312P2.

TABLE 7

Biacore Binding Affinities of Bispecific Anti-MET mAb and Monospecific Parents at 37° C.
Binding at 37° C./Antibody-Capture Format

| Antibody | Analyte | kd (s$^{-1}$) | T½ (min) |
|---|---|---|---|
| H4H13306P2 | hMet.mmh | 1.66E−02 | 0.7 |
| H4H13312P2 | hMet.mmh | 8.40E−03 | 1.4 |
| H4H14639D | hMet.mmh | 1.63E−04 | 70.8 |

Example 7. Anti-Met Antibodies Block HFG-Mediated Met Activation in SRE-Luciferase Reporter Bioassay The ability of anti-MET antibodies to block hepatocyte growth factor (HGF)-mediated MET activation was examined in a luciferase-based reporter assay. The growth factor HGF binds to the extracellular domain of its receptor c-Met (MET), triggering rapid homodimerization and activating several downstream signaling cascades. The anti-MET antibodies tested in this example were bivalent monospecific binders of MET, or anti-MET "bispecifics", in which each arm of the bispecific antibody bound to a different and distinct epitope on MET.

Figure 3A:
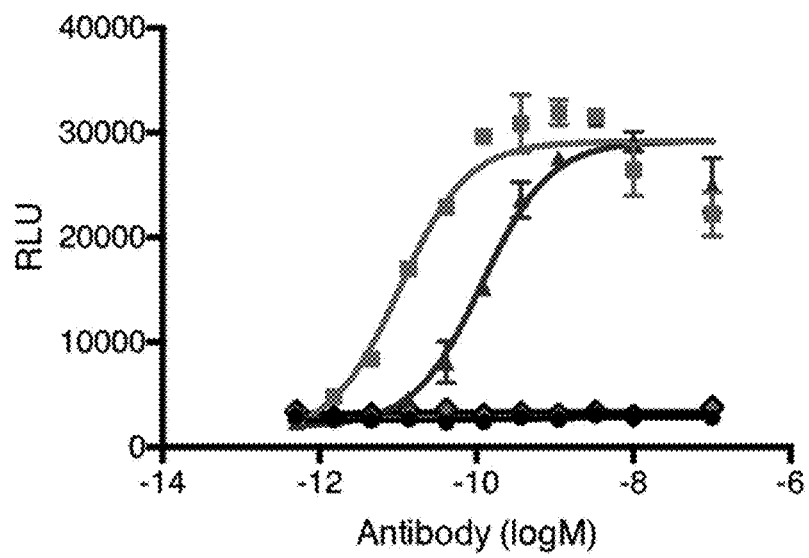
FIG. 3A depicts antibody alone without HGF ligand.
Figure 3B:
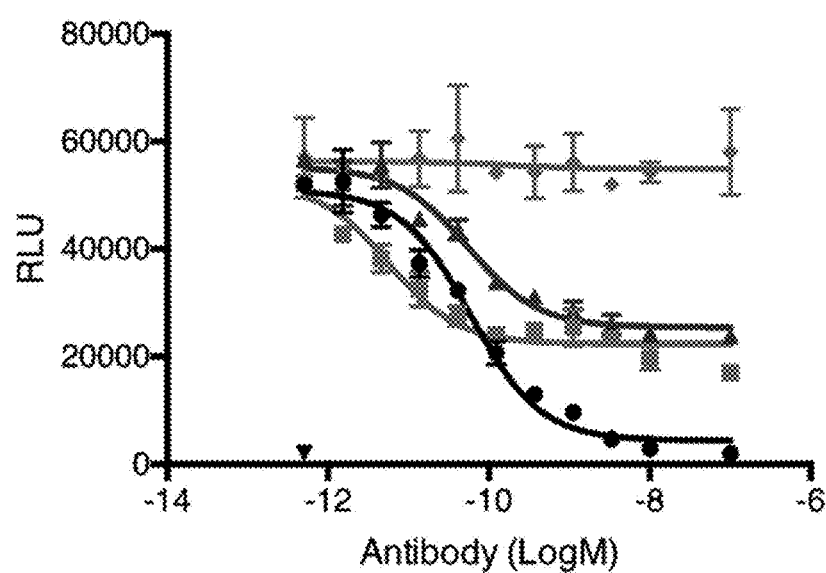
FIG. 3B depicts antibodies plus HGF ligand.

An engineered cell-based luciferase reporter assay (FIG. 2) was used to determine the ability of anti-MET antibodies to activate MET signaling (FIG. 3, panel A; Table 8, columns 3 and 4) and to block ligand-mediated activation of MET (FIG. 3, panel B; Table 8, columns 1 and 2). Briefly, the CIGNAL™ Lenti SRE Reporter (luc) Kit (SABiosciences, Hilden, Del.) was used to generate HEK293/SRE-Luc cells. HEK293 (human embryonic kidney) cells were selected because they endogenously express c-Met. The HEK293/SRE-Luc cells stably incorporated the serum response element (SRE)-dependent luciferase (Luc) reporter (see Dinter et al., PLoS ONE 10(2): e0117774, 2015). HEK293/SRE-Luc cells were cultured in DMEM supplemented with 10% fetal bovine serum (FBS), penicillin/streptomycin/glutamine, and 1 µg/ml puromycin.

Next, 2.0×10$^5$ HEK293/SRE-Luc cells were seeded in luciferase assay media in 96 well plates and incubated overnight at 37° C. in 5% CO$_2$. Hepatocyte growth factor (HGF) dose response curves were generated by adding serially diluted HGF (0.01 pM to 1.0 nM) to cells and recording the luciferase signal after incubation at 37° C. for four to six hours in the absence of antibodies. To generate antibody inhibition curves, cells were pre-incubated for one hour at 37° C. with serially diluted anti-human MET antibodies (1.1 pM to 200 nM). HGF at a concentration of 73 pM or 100 pM was then added for an additional four to six hours before recording the signal. Separately, the ability of the antibodies to activate c-Met in the absence of ligand was also assessed.

Luciferase activity was detected using the ONE-Glo™ Luciferase Assay System (Promega, Madison, Wis.), and emitted light was measured on a Victor or Envision luminometer (Perkin Elmer, Shelton, Conn.) and expressed as relative light units (RLUs). EC50/IC50 values were determined from a four-parameter logistic equation over a 12-point response curve using GRAPHPAD PRISM®. Percent HGF blocking and fold MET activation (mAbs alone) were reported for the highest antibody dose. The results are shown in Table 8.

TABLE 8

Anti-Met Antibody Blocking of HGF-Mediated Signaling and Activation of SRE-Luc in the Absence of Ligand

| | HEK293/SRE-Luc Blocking Activity (1 h mAb pre-bind) | | Ligand (HGF)-Independent HEK293/SRE-Luc Activation | |
|---|---|---|---|---|
| Antibody ID | % Inhibition | IC$_{50}$ (M) | Fold Response | EC$_{50}$ (M) |
| Anti-MET Bivalent Monospecific antibodies Antibodies expressed with a hIgG1-Fc | | | | |
| H1H13301P2 | 42 | 3.3E−09 | 1.4 | ND |
| H1H13316P2 | 86 | 4.0E−11 | 1.7 | ND |
| Antibodies expressed with a hIgG4-Fc | | | | |
| H4H13312P2 | 48 | 7.7E−11 | 10.9 | 1.2E−10 |
| H4H13325P2 | 69 | 1.3E−11 | 4.3 | 1.9E−10 |
| H4H13316P2 | 74 | 7.8E−12 | 2.3 | 4.7E−11 |
| H4H13302P2 | 45 | 1.6E−09 | 1.8 | ND |
| H4H13313P2 | 47 | 2.3E−09 | 1.2 | ND |
| H4H13301P2 | 40 | 1.5E−09 | 1.6 | ND |
| H4H13295P2 | 70 | 5.5E−11 | 2.8 | 3.0E−10 |
| H4H13306P2 | 67 | ND | 9.8 | 1.3E−11 |
| H4H13291P2 | 61 | 1.3E−10 | 2.7 | 3.9E−10 |
| H4H13319P2 | 67 | 5.2E−11 | 4.8 | 1.8E−10 |
| H4H13309P2 | 77 | 2.0E−10 | 9.2 | 3.9E−10 |
| H4H13318P2 | 77 | 1.0E−10 | 3.1 | ND |
| H4H13300P2 | 69 | 1.2E−10 | 2.8 | 4.8E−10 |
| H4H13290P2 | 56 | <2.0E−12 | 9.8 | <2.0E−12 |
| H4H13311P2 | 62 | 3.5E−11 | 5.2 | 3.0E−10 |
| H4H13331P2 | 75 | <1.0E−11 | 7.1 | 2.3E−12 |
| H4H13299P2 | 51 | ND | 14.4 | 3.7E−12 |
| Anti-MET Bispecific Antibodies (hIgG4-Fc) | | | | |
| H4H14639D | 95 | 2.4E−11 | 1.8 | 5.7E−11 |
| H4H14640D | 89 | 5.2E−10 | 2.5 | 6.8E−09 |
| H4H14634D | 85 | 9.7E−12 | 3.4 | 9.0E−11 |
| H4H14635D | 85 | 1.9E−10 | 2.2 | 1.4E−09 |
| H4H14638D | 79 | 1.1E−09 | 2.6 | 5.9E−09 |
| H4H14641D | 75 | 2.7E−09 | 4.4 | 8.4E−08 |
| H4H14636D | 74 | ND | 2.8 | 2.8E−10 |
| H4H14637D | 73 | ND | 2.1 | 4.1E−09 |
| H4H16445D | 81 | 5.2E−10 | 4.3 | 1.0E−09 |
| H4H16446D | 83 | 1.0E−09 | 4.0 | 1.4E−09 |
| H4H16447D | 76 | 8.6E−10 | 5.8 | 1.4E−09 |
| H4H16448D | 87 | 6.2E−10 | 4.3 | 9.1E−10 |
| H4H16449D | 85 | 3.2E−10 | 4.2 | 4.2E−10 |

NT = not tested;
ND = EC50/IC50 not determined due to non-sigmoidal curves or incomplete blocking.

As summarized in Table 8, a majority of the antibodies inhibited activation of the SRE reporter, with IC50 values ranging from <2.0 pM to about 1.0 nM. Several exemplary monospecific bivalent anti-MET antibodies, such as H4H13306P2 and H4H13309P2, were potent inhibitors of SRE-luc activation, with percent inhibition values of 67% and 77%, respectively. Anti-MET bispecific antibodies (MET×MET) exhibited greater inhibition of SRE-luc activation overall. For example, MET×MET bispecific antibody H4H14639D displayed 95 percent inhibition. Additionally, several blocking antibodies were weakly activating in the absence of ligand with fold activation responses ranging from 0.8 to 14.4 above baseline levels.

Also as shown in FIG. 3, the bivalent monospecific antibodies H41413306P2 and H4H13312P2 each activate the Met pathway in the absence of HGF ligand (panel A) and also block HGF activation of the Met (panel B).

Figure 4A:
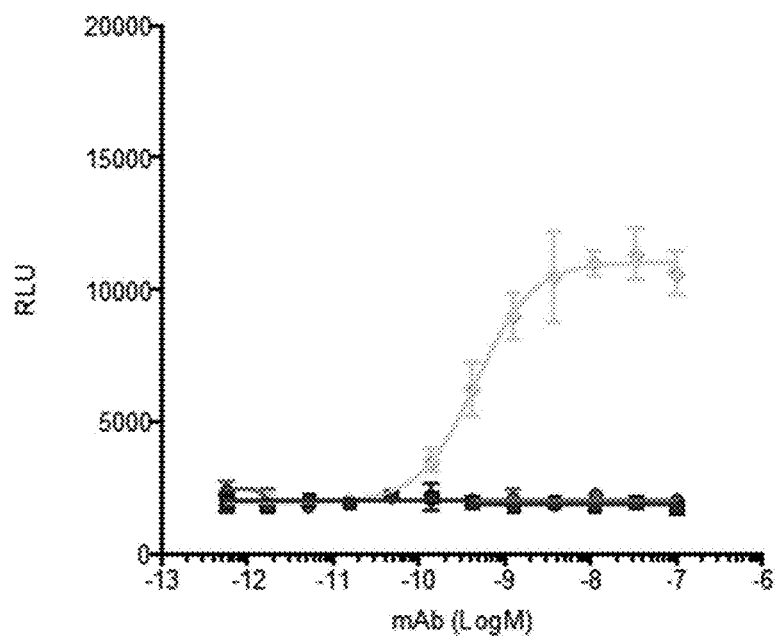
FIG. 4A depicts antibody alone without HGF ligand.
Figure 4B:
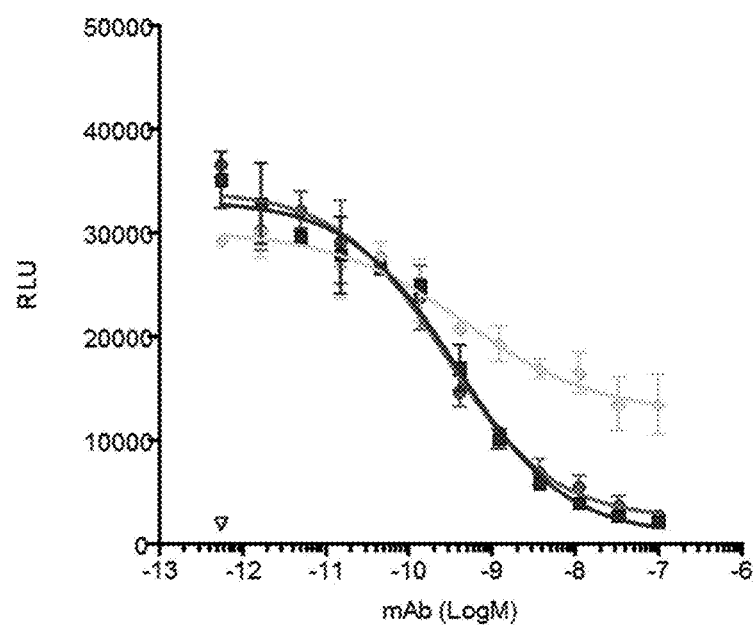
FIG. 4B depicts antibodies plus HGF ligand.

The effect of a bispecific MET×MET antibody (e.g., H4H14639D) on HGF-dependent and HGF-independent MET activation was also assessed using the HEK293/SRE-Luc system. SRE-driven Luciferase activity was measured in HEK293T cells treated with the MET antibodies H4H14639D (the MET×MET bispecific antibody), a monovalent anti-MET antibody, and the H4H14639D parental antibody H4H13312P2 at various concentrations to ascertain the level of HGF-independent MET agonism. While the parental anti-MET monospecific bivalent antibody showed MET agonist activity, neither the monovalent nor the MET×MET bispecific antibody showed MET agonist activity (FIG. 4, panel A).

SRE-driven Luciferase activity was measured in HEK293T cells treated with the MET antibodies H4H14639D (the MET×MET bispecific antibody), a monovalent anti-MET antibody, and the H4H14639D parental antibody H4H13312P2 at various concentrations to ascertain the level of inhibition or blocking of HGF-dependent MET agonism. While the parental anti-MET monospecific bivalent antibody showed some HGF blocking activity, both the monovalent and the MET×MET bispecific antibody showed greater HGF blocking (FIG. 4, panel B).

The MET×MET bispecific antibody blocks HGF signaling and exhibits low MET agonist activity.

Example 8. Anti-Met Antibodies Inhibit Growth of Met-Amplified Cells

Next, selected anti-Met antibodies were tested for their ability to inhibit the growth of MET-amplified SNU5 cells. Briefly, $2.5 \times 10^3$ human gastric carcinoma (SNU5) cells were seeded in complete growth media in the presence of anti-MET antibodies at concentrations ranging from 1.5 pM to 100 nM. The SNU5 complete growth media contained Iscove's Modified Dulbecco's Medium, 10% FBS, and penicillin/streptomycin/glutamine. Cells were incubated for 5 days and the number of viable cells was determined using the CELLTITER-GLO® Luminescent Cell Viability Assay kit (Promega, Madison, Wis.) according to manufacturer instructions.

As summarized in Table 9, several anti-MET antibodies, such as H4H13312P2 and H4H13325P2 blocked SNU5 growth by more than 50%, with overall IC50s ranging from 44 pM to 780 pM.

Figure 5:
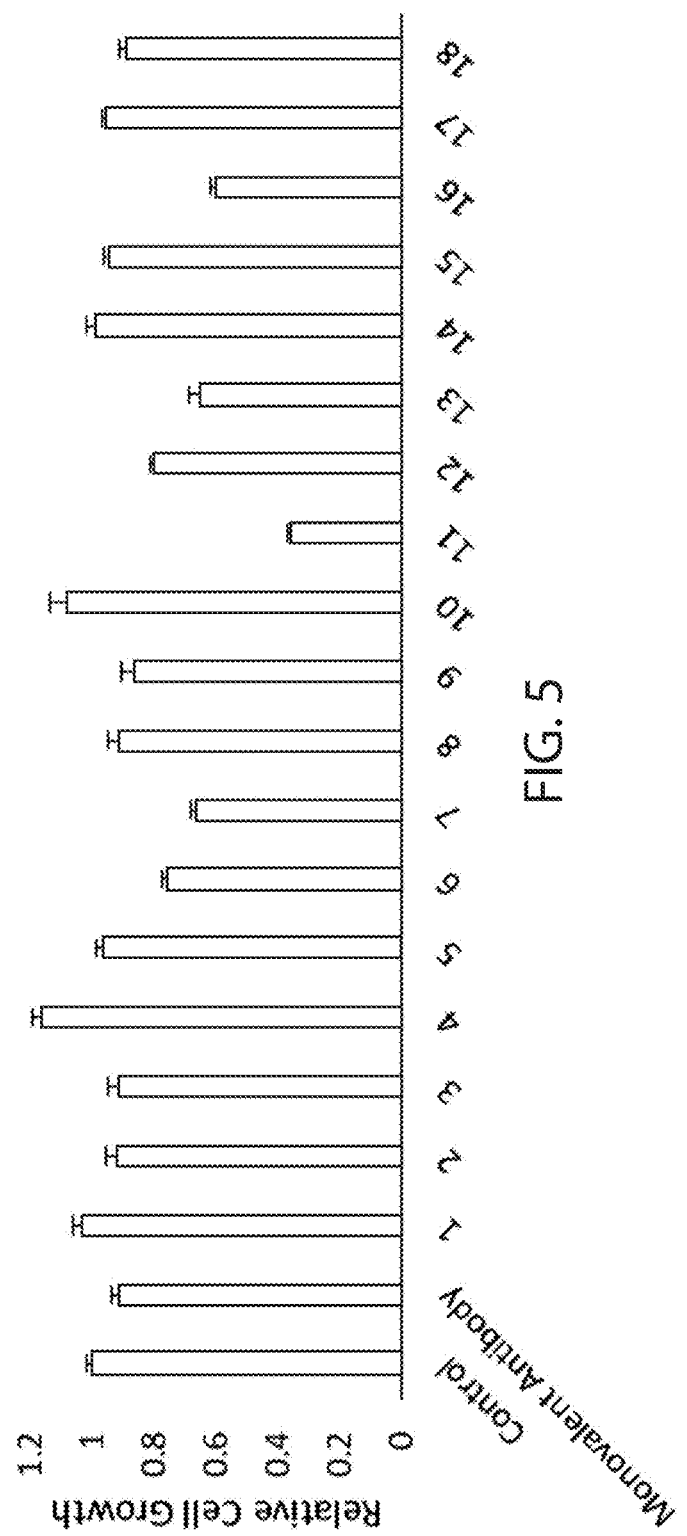
FIG. 5 is a bar chart depicting the relative cell growth of MET-amplified gastric cancer SNU5 cells as a function of treatment with human bivalent monospecific anti-MET antibodies 1-18, a control antibody and an anti-MET monovalent antibody. For comparison purposes, antibody 8 (abscissa) is parental antibody H4H13306P2, and antibody 11 (abscissa) is parental antibody H4H13312P2.

FIG. 5 depicts the relative cell growth of SNU5 cells treated with various anti-MET bivalent monospecific antibodies (i.e., conventional antibodies). A subset of conventional MET antibodies inhibit the growth of SNU5 MET-amplified gastric cancer cells (FIG. 5). SNU5 cells in 96 well plates were treated with each antibody at 10 μg/ml and cell growth was determined after 5 days by reduction of ALAMARBLUE® reagent (Thermo Fisher Scientific, Waltham, Mass.). The monovalent MET antibody (column 2, FIG. 5) was generated using the heavy and light chain variable sequences of MetMab as set forth in U.S. Pat. No. 7,892,550 B2, which is herein incorporated by reference in its entirety. Conventional antibody 8 is H4H13306P2, and conventional antibody 11 is H4H13312P2, which were used to construct the MET×MET bispecfici antibody H4H14639D.

In a separate growth assay, the blocking activity of a MET×MET bispecific antibody (i.e., H4H14639D) was assessed in both SNU5 and the non-small cell lung cancer (NSCLC) cell line EBC-1, which also exhibits amplified Met gene and overexpresses MET (Lutterbach et al., Cancer Res. 67(5): 2081-2088, 2007). Complete growth media for the EBC-1 cells contained MEM Earle's Salts, 10% fetal bovine serum (FBS), penicillin/streptomycin/glutamine, and non-essential amino acids for MEM. H4H14369D exhibited the greatest percent inhibition in MET activity according to the SRE-Luciferase read-out. In the current experiment, $3.0 \times 10^3$ SNU5 or EBC-1 cells were seeded in complete growth media in the presence of H4H14639D at concentrations ranging from 15 pM to 100 nM. Cells were incubated for 3 days at 37° C. in 5% $CO_2$. The cell were then fixed in 4% formaldehyde and stained with 3 μg/ml Hoechst 33342 to label the nuclei. Images were acquired on the IMAGEXPRESS® Micro XL (Molecular Devices, Sunnyvale, Calif.) and nuclear counts were determined via METAXPRESS® Image Analysis software (Molecular Devices, Sunnyvale, Calif.). Background nuclear counts from cells treated with 40 nM digitonin were subtracted from all wells and viability was expressed as a percentage of the untreated controls. IC50 values were determined from a four-parameter logistic equation over a 10-point response curve (GRAPHPAD PRISM®). IC50 values and percent cell killing are shown in Table 9.

TABLE 9

Anti-MET Antibody Blocking of SNU5 Growth

| Antibody | % Growth Inhibition | $IC_{50}$ (M) |
|---|---|---|
| H4H13312P2 | 69 | 7.8E−10 |
| H4H13325P2 | 57 | 4.4E−11 |
| H4H13316P2 | 53 | 1.0E−10 |
| H4H13302P2 | 40 | 1.1E−10 |
| H4H13313P2 | 34 | 4.4E−11 |
| H4H13301P2 | 33 | 7.4E−11 |
| H1H13301P2 | 33 | 1.0E−10 |
| H1H13316P2 | 30 | 2.0E−10 |
| H4H13295P2 | 30 | ND |
| H4H13306P2 | 28 | 7.1E−11 |
| H4H13291P2 | 24 | ND |
| H4H13319P2 | 23 | 1.0E−10 |
| H4H13309P2 | 22 | 1.0E−10 |
| H4H13318P2 | 18 | 5.1E−11 |
| H4H13300P2 | 16 | ND |
| H4H13290P2 | 12 | ND |
| H4H13311P2 | 8 | ND |
| H4H13331P2 | 5 | ND |
| H4H13299P2 | −8 | ND |

ND = $IC_{50}$ not determined due to non-sigmoidal curves or incomplete blocking As summarized in Table 10, below, the MET×MET bispecific antibody H4H14639D inhibited growth of EBC-1 and SNU5 cells by 37 and 40 percent, and with IC50s of 0.82 nM and 0.3 nM, respectively.

TABLE 10

Anti-Met Bispecific Antibody Blocks EBC-1 and SNU5 Growth

| mAb | $IC_{50}$ (nM) | | % Growth Inhibition | |
|---|---|---|---|---|
| | EBC-1 | SNU5 | EBC-1 | SNU5 |
| H4H14639D | 0.82 | 0.30 | 37 | 40 |

Figure 6A:
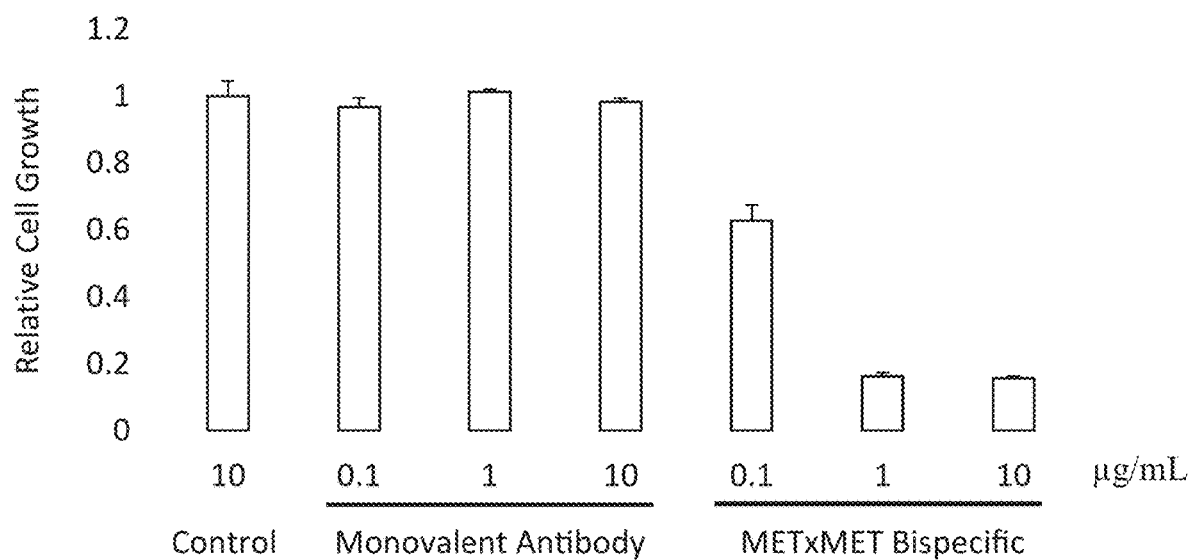
FIG. 6A depicts the relative growth of SNU5 cells as a function of treatment with control antibody, a monovalent antibody at 0.1, 1 and 10 µg/mL, and a MET×MET bispecific antibody at 0.1, 1 and 10 µg/mL.
Figure 6B:
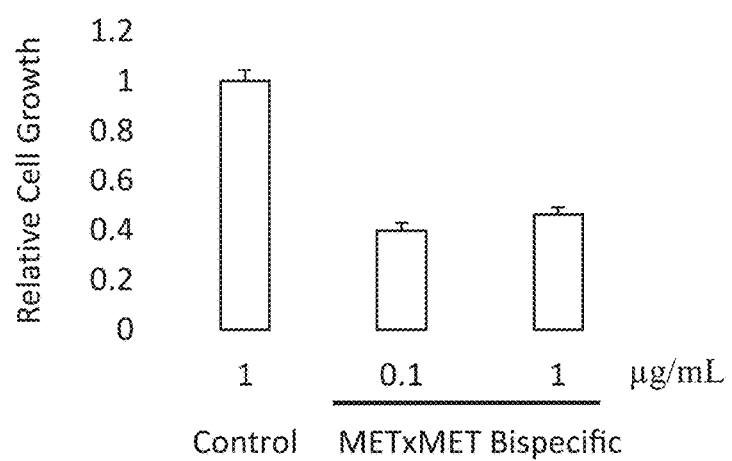
FIG. 6B depicts the relative growth of EBC-1 cells as a function of treatment with control antibody and a MET×MET bispecific antibody at 0.1 and 1 µg/mL.

SNU5 cells (gastric) in 96 well plates were treated with a control antibody, a monovalent MET antibody or a MET×MET bispecific antibody at 0.1 μg/mL, 1 μg/mL, or 10 μg/mL. Cell growth was determined after 5 days by reduction of ALAMARBLUE® reagent (Thermo Fisher Scientific, Waltham, Mass.). The MET×MET bispecific antibody significantly reduced the relative cell growth of SNU5 cells compared to the control and monovalent antibody (FIG. 6, panel A).

Likewise, the effect of MET×MET bispecific antibody on the growth of EBC-1 cells was assessed. 2,500 EBC-1 cells were seeded in a 96 well plate and cultured in Dulbecco's Media supplemented with 10% FBS. The cells were treated with a control antibody or a MET×MET bispecific antibody at 0.1 μg/mL or 1 μg/mL, and were subsequently incubated with 5% $CO_2$ at 37° C. After 5 days, relative cell growth was determined by measuring the reduction of the indicator dye ALAMARBLUE® to its highly fluorescent form in a SPECTRAMAX® M3 plate reader (Molecular Devices, LLC, Sunnyvale, Calif.). The results are shown in Table 11 and FIG. 6, panel B. The MET×MET bispecific antibody (H4H14639D) significantly reduced the relative cell growth of EBC-1 cells compared to the control antibody (FIG. 6, panel B).

Several anti-MET antibodies, both bivalent monospecific and MET×MET bivalent, are potent inhibitors of SRE-Luc activation and inhibit the growth of Met-amplified and MET-overexpressing cell lines.

TABLE 11

Anti-Met Bispecific Antibody Blocks EBC-1 Cell Growth

|  | Relative Cell Growth (n = 3) | Standard Deviation |
| --- | --- | --- |
| Control | 1.000 | 0.045 |
| 0.1 μg/mL H4H14639D | 0.397 | 0.032 |
| 1 μg/mL H4H14639D | 0.462 | 0.028 |

Example 9. A MET×MET Bispecific Antibody Induces Modest and Transient MET Pathway Activity in NCI-H596 NSCLC Cells The effect of a MET×MET bispecific antibody on the MET pathway in human lung adenosquamous carcinoma cells was assessed in vitro.

250,000 NCI-H596 cells were seeded in a 12 well plate and cultured in RPMI Media supplemented with 10% FBS. The cells were treated with hepatocyte growth factor (HGF) at 50 ng/ml or the MET×MET bispecific antibody H4H14639D at 10 μg/ml in duplicate. The cells were subsequently incubated in 5% $CO_2$ at 37° C. After 0, 2, 6 or 18 hours, cell lysates were prepared, protein content was normalized and immunoblot analysis was performed. MET phosphorylation and ERK phosphorylation were quantified with the ImageJ image processing program (T. Collins, BioTechniques 43: S25-S30, 2007). Phosphorylation levels were normalized to the Tubulin loading control and are expressed as fold change relative to control treatment. The results are summarized in Table 12.

TABLE 12

Phosphorylation of MET and ERK

| Treatment (hours) | Phospho-MET (mean ± SD) | Phospho-ERK (mean ± SD) |
| --- | --- | --- |
| Control (hFc) (18) | 1.0 ± 0.5 | 1.0 ± 0.3 |
| HGF (2) | 202.3 ± 38.7 | 16.7 ± 1.6 |
| HGF (6) | 38.9 ± 4.9 | 12.4 ± 3.9 |
| HGF (18) | 59.2 ± 24.4 | 12.4 ± 0.9 |
| H4H14639D (2) | 69.7 ± 7.0 | 2.2 ± 0.9 |
| H4H14639D (6) | 9.9 ± 7.4 | 0.3 ± 0.4 |
| H4H14639D (18) | 1.4 ± 0.1 | 0.1 ± 0.1 |

HGF treatment of NCI-H596 cells induced strong activation of MET and ERK that peaked at 2 hours and was sustained after 18 hours. Modest MET and ERK phosphorylation was detected with the H4H14636D bispecific antibody treatment, which returned to baseline levels by 18 or 6 hours, respectively.

Figure 7A:
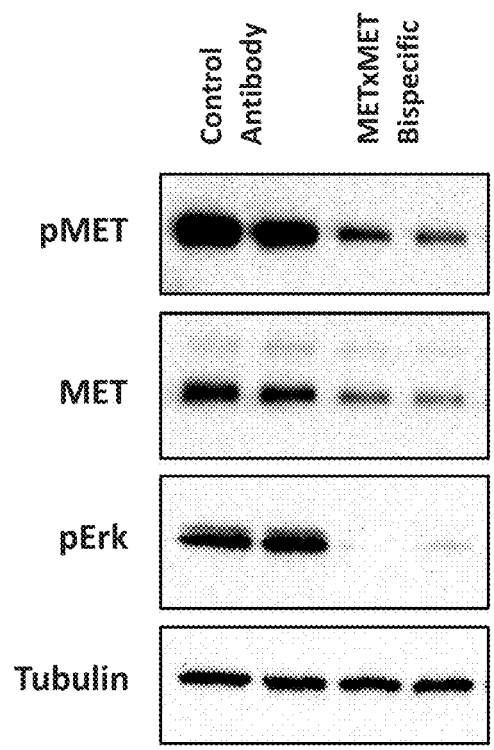
FIGS. 7(A-B) depict immunoblots of pMET (phosphorylated MET), MET, pErk (phosphorylated Erk), and tubulin (for loading control) extracted from Hs746T cells after treatment with a control antibody and a MET×MET bispecific antibody (FIG. 7A), and the expression of MET (and tubulin as a loading control) in Hs746T cells after treatment with the MET×MET bispecific antibody for 0, 2 and 6 hours (FIG. 7B).
Figure 7B:
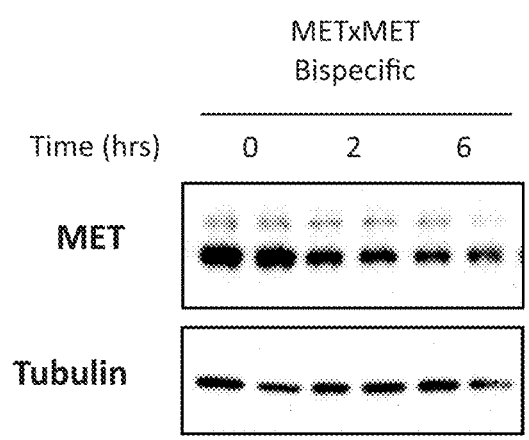

Example 10. A MET×MET Bispecific Antibody Induces MET Degradation and Inhibits Pathway Activity More Potently than Monospecific Antibodies in Hs746T Gastric Cancer Cells The effect of a MET×MET bispecific antibody on MET activity of human gastric carcinoma cells was assessed in vitro. 250,000 Hs746T human gastric carcinoma cells (H. Smith, J. Nat'l. Cancer Inst. 62(2): 225-230, 1979) were seeded in a 12-well plate and cultured in Modified Dulbecco's Media supplemented with 10% FBS. The cells were treated with (1) 5 μg/ml of the hFc control molecule, (2) 5 μg/ml of the parental bivalent monospecific anti-MET antibody H4H13306P2, (3) 5 μg/ml of the parental bivalent monospecific anti-MET antibody H4H13312P2, (4) the combination of 2.5 μg/mL of H4H13306P2 and 2.5 μg/mL of H4H13312P2, or (5) 5 μg/ml of the MET×MET bispecific antibody H4H14639D. The cells were subsequently incubated with 5% $CO_2$ at 37° C. After 18 hours, cell lysates were prepared, protein content was normalized and immunoblot analysis was performed. MET expression, MET phosphorylation, and ERK phosphorylation were quantified with the ImageJ image processing program (T. Collins, BioTechniques 43: S25-S30, 2007). The results are summarized in Table 13 and FIG. 7, panel A, which depicts the raw immunoblot data. Panel B of FIG. 7 depicts MET protein expression in cells that were treated with MET×MET bispecific antibody at 10 μg/ml for 0, 2 or 6 hrs. The total MET levels in Hs747T cells declined over time upon treatment with the MET×MET bispecific antibody. Similar results were obtained for the MET amplified human papillary adenocarcinoma NCI-H820 cell line (Bean et al., "MET amplification occurs with or without T790M mutations in EGFR mutant lung tumors with acquired resistance to getfitnib or erlotinib," Proc. Natl. Acad. Sci. 2007 Dec. 26, 104(52): 20932-20937).

TABLE 13

Relative Levels of MET Protein and MET/ERK Pathway Activation

| Molecule | Relative level MET protein (mean ± SD) | Relative level Phospho-MET (mean ± SD) | Relative level Phospho-ERK (mean ± SD) |
| --- | --- | --- | --- |
| Control (hFc) | 1.00 ± 0.06 | 1.00 ± 0.06 | 1.00 ± 0.03 |
| H4H13306P2 | 0.61 ± 0.09 | 0.57 ± 0.02 | 0.41 ± 0.03 |
| H4H13312P2 | 1.15 ± 0.19 | 0.93 ± 0.04 | 0.39 ± 0.11 |
| H4H13306P2 + H4H13312P2 | 1.06 ± 0.02 | 1.07 ± 0.10 | 1.04 ± 0.23 |
| H4H14639D | 0.41 ± 0.02 | 0.20 ± 0.01 | 0.04 ± 0.01 |

The bispecific antibody, H4H14639D, induced MET degradation more potently than its parental conventional antibodies. Both MET and ERK phosphorylation were more effectively inhibited by treatment with H4H14636D than with the parental antibodies or the combination of the parental antibodies.

Figure 8:
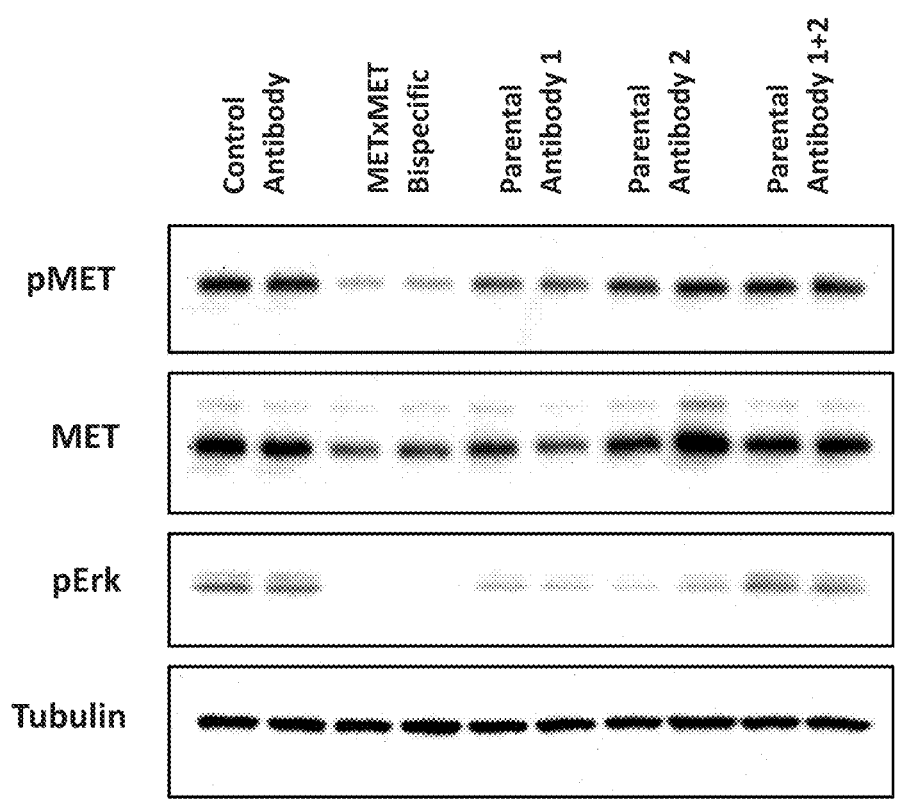
FIG. 8 depicts an immunoblot of pMET, MET, pErk, and tubulin (for loading control) extracted from Hs746T cells after treatment with a control antibody, a MET×MET bispecific antibody, an anti-MET monospecific bivalent parent antibody 1, an anti-MET monospecific bivalent parent antibody 2, and a combination of parental antibodies 1 and 2.

Hs746T gastric cancer cells were treated with control antibody, the MET×MET bispecific antibody H4H14639D, the anti-MET parental antibody H4H13306P2, the anti-MET parental antibody H4H13312P2, and the combination of parental antibodies 1 and 2, each antibody at 10 μg/ml or the combination of parental antibodies at 5 μg/ml each, for 18 hrs. MET expression (MET) and pathway activation (pMET and pErk) were determined by immunoblotting with the indicated antibodies (FIG. 8). MET×MET bispecific antibody inhibits MET pathway activation more effectively than its parental antibodies in Hs746T gastric cancer cells.

Example 11. A MET×MET Bispecific Antibody Induces MET Degradation More Potently than Monospecific Antibodies in NCI-H596 Lung Cancer Cells The effect of a MET×MET bispecific antibody and the parental bivalent monospecific anti-MET antibodies on the expression levels of hepatocyte growth factor receptor (HGFR or MET) on human lung adenosquamous carcinoma cells was assessed. 250,000 NCI-H596 human lung adenosquamous carcinoma cells were seeded in a 12-well plate and cultured in RPMI Media supplemented with 10% FBS. The cells were treated with (1) 5 µg/ml of the hFc control molecule, (2) 5 µg/ml of the parental bivalent monospecific anti-MET antibody H4H13306P2, (3) 5 µg/ml of the parental bivalent monospecific anti-MET antibody H4H13312P2, (4) the combination of 2.5 µg/mL of H4H13306P2 and 2.5 µg/mL of H4H13312P2, or (5) 5 µg/ml of the MET×MET bispecific antibody H4H14639D. The cells were subsequently incubated with 5% $CO_2$ at 37° C. After 18 hours, cell lysates were prepared, protein content was normalized and immunoblot analysis was performed. MET expression was quantified with the ImageJ image processing program (T. Collins, BioTechniques 43: S25-S30, 2007). The results are summarized in Table 14.

TABLE 14

Relative Level of MET Protein

| Molecule | Relative MET Level |
| --- | --- |
| Control (hFc) | 1 ± 0.03 |
| H4H13306P2 | 0.50 ± 0.01 |
| H4H13312P2 | 0.35 ± 0.04 |
| H4H13306P2 + H4H13312P2 | 0.61 ± 0.04 |
| H4H14639D | 0.24 ± 0.01 |

Figure 9:
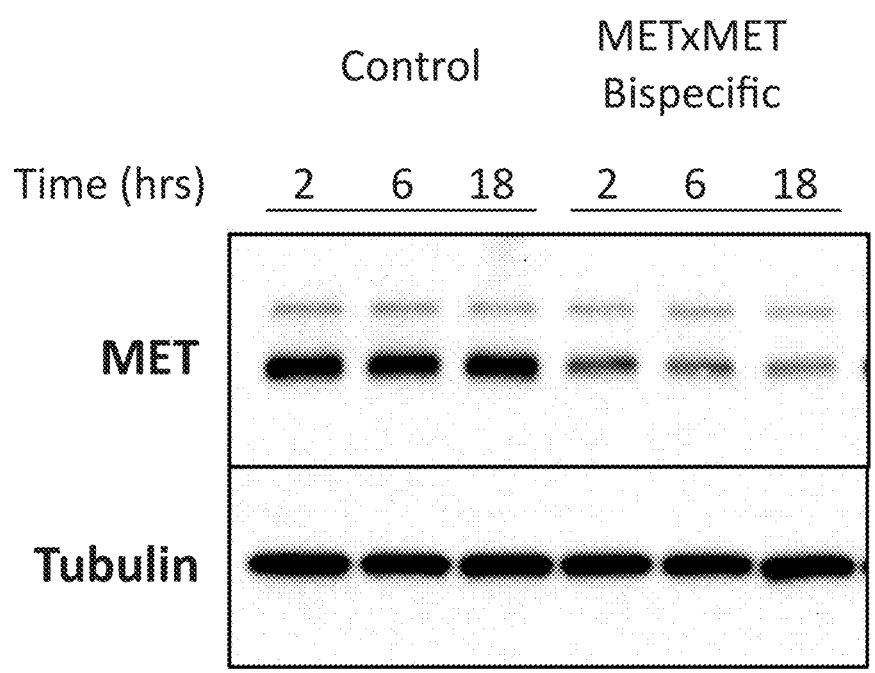
FIG. 9 depicts an immunoblot of the expression of MET (and tubulin as a loading control) in Hs746T cells after treatment with a control antibody and a MET×MET bispecific antibody for 2, 6 and 18 hours.

NCI-H596 (MET exon14 skip mutation) lung cancer cells were also treated with control or MET×MET bispecific antibodies at 10 µg/ml for 2, 6 or 18 hrs. MET expression was determined by immunoblotting (FIG. 9), which shows the MET×MET bispecific antibody-induced degradation of MET with increasing time of treatment.

The bispecific antibody, H4H14636D, induces MET degradation more potently than its parental conventional antibodies in NCI-H596 lung cancer cells.

Example 12. MET×MET Bispecific Antibodies Induce MET Degradation and Inhibit Pathway Activity More Potently than Monospecific Antibodies in SNU5 Gastric Cancer Cells The effect of a bivalent monospecific anti-MET antibody and several MET×MET bispecific antibodies on the expression levels of hepatocyte growth factor receptor (HGFR or MET) on gastric carcinoma cells was assessed. Human gastric carcinoma SNU5 cells were plated in Iscove's medium containing 20% FBS plus pen-strep-glutamine. 24 hours after seeding, the cells were treated with control hFc, the anti-MET parental bivalent monospecific antibody H4H13312P2, or the MET×MET bispecific antibodies (H4H14634D, H4H14635D, H4H14636D, H4H14637D, H4H14638D, H4H14639D, H4H14640D, H4H14641D) for 18 hrs. Cell lysates were then prepared and analyzed by western blotting. Immunoblots were probed for MET and tubulin. The MET protein expression level was quantified and normalized relative to the tubulin loading control. The results are presented in Table 15 and FIG. 10, panel B.

TABLE 15

Relative Level of MET Protein

| Molecule | Relative MET Level |
| --- | --- |
| Control (hFc) | 1 |
| H4H13312P2 | 0.62 |
| H4H14634D | 0.45 |
| H4H14635D | 0.27 |
| H4H14636D | 0.50 |
| H4H14637D | 0.49 |
| H4H14638D | 0.35 |
| H4H14639D | 0.27 |
| H4H14640D | 0.18 |
| H4H14641D | 0.31 |

Figure 10A:
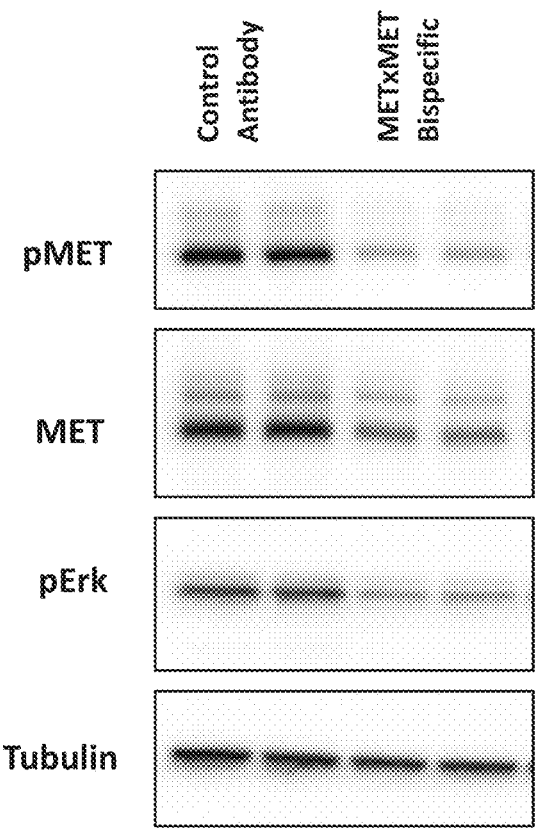
FIGS. 10(A-B) depict immunoblots of pMET, MET, pErk, and tubulin (for loading control) extracted from SNU5 cells after treatment with a control antibody and a MET×MET bispecific antibody (FIG. 10A); and the expression of MET (and tubulin as a loading control) in SNU5 cells after treatment with a control antibody and an anti-MET monovalent antibody (FIG. 10B).
Figure 10B:
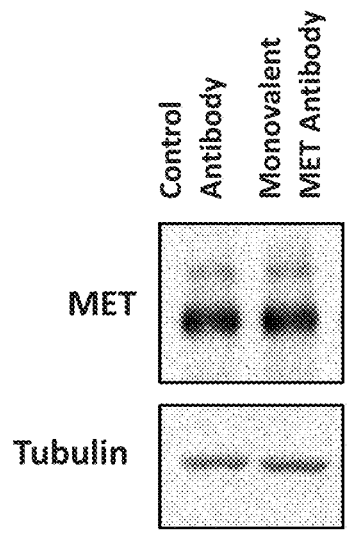

SNU5 cancer cells were treated with control antibody or MET×MET bispecific antibody or monovalent MET antibody at 10 µg/ml for 18 hrs as described above. MET expression (FIG. 10, panels A and B), and pathway activation (i.e., pMET and pERK; panel A) were determined by immunoblotting with the indicated antibodies. The immunoblots are shown in FIG. 10.

Treatment of SNU5 cells with MET×MET bispecific antibodies induced more potent degradation of MET than treatment with the bivalent monospecific anti-MET antibody (H4H13312P2) (FIG. 10, panel B), monovalent MET antibody or control hFc. Treatment of SNU5 cells with the MET×MET bispecific antibody inhibited downstream effectors of the MET pathway. Similar results were obtained for the MET amplified non-small cell lung cancer adenocarcinoma cell line NCI-H1993 (Kubo et al., "MET gene amplification or EGFR mutation activate MET in lung cancers untreated with EGFR tyrosine kinase inhibitors," Int. J. Cancer 2009 Apr. 15; 124(8): 1778-1784).

Figure 11:
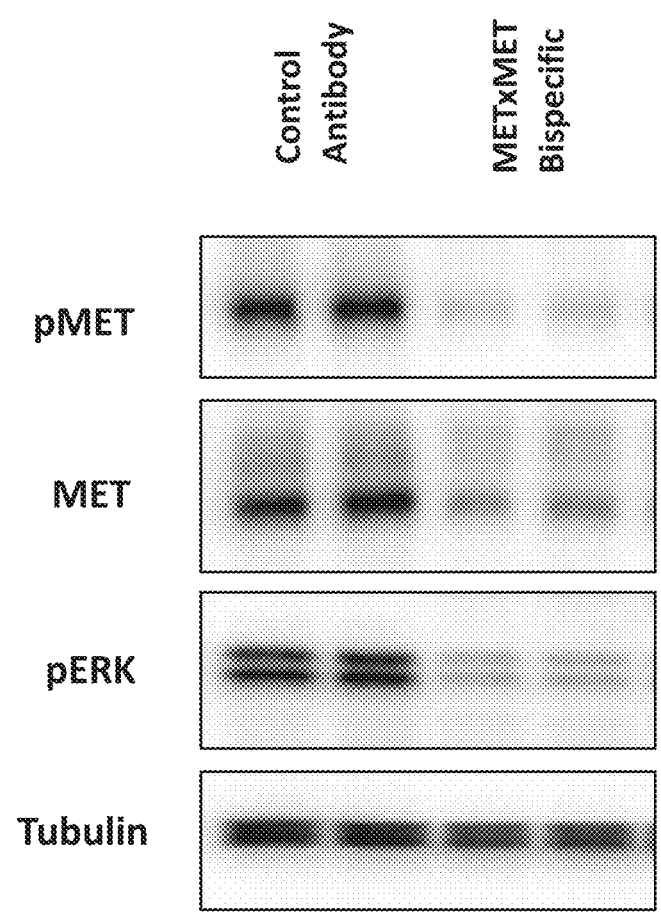
FIG. 11 depicts an immunoblot of pMET, MET, pErk, and tubulin (for loading control) extracted from EBC-1 cells after treatment with a control antibody and a MET×MET bispecific antibody.

Example 13. A MET×MET Bispecific Antibody Induces MET Degradation, Inhibits Pathway Activity, and Inhibits Tumor Growth More Potently than Monospecific Antibodies in EBC-1 Cells MET-amplified human lung squamous cell carcinoma EBC-1 cells (Lutterbach et al., "Lung cancer cell lines harboring MET gene amplification are dependent on Met for growth and survival," Cancer Res. 2007 Mar. 1; 67(5):2081-8) were treated with a control antibody or 10 µg/ml of a MET×MET bispecific antibody for 18 hrs as described above. MET expression and MET pathway activation ascertained by pMET and pErk expression were determined by immunoblotting with the indicated antibodies. The immunoblots are shown in FIG. 11.

Treatment of EBC-1 cells, which harbor MET gene amplification, with MET×MET bispecific antibodies induced more potent degradation of MET than treatment with the control antibody. Treatment of EBC-1 cells with the MET×MET bispecific antibody inhibited downstream effectors of the MET pathway.

Figure 12:
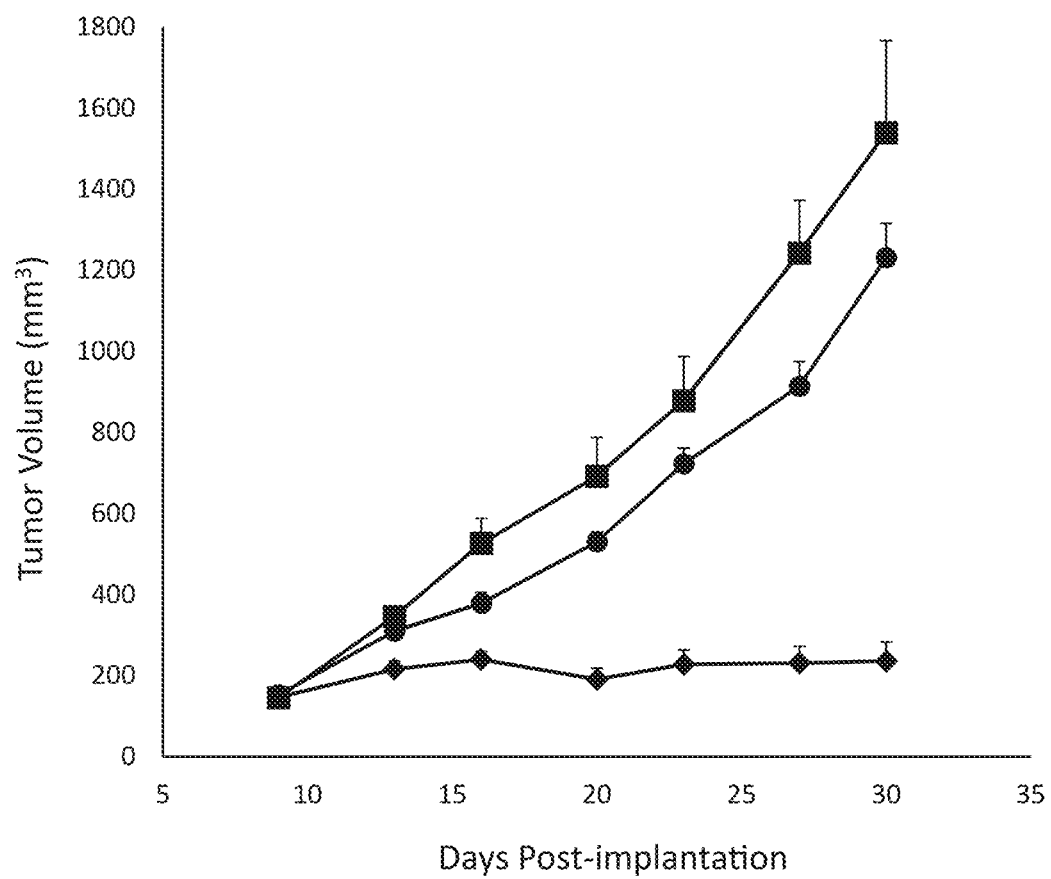
FIG. 12 is a line graph depicting the change in EBC-1 tumor volume in cubic millimeters as a function of time in days after implantation of EBC-1 cells in animals treated with control antibody (filled square ■), MET monovalent antibody (filled circle ●), or MET×MET bispecific antibody (filled diamond ◆).

In another experiment, 5 million EBC-1 cells were implanted subcutaneously into the flank of C.B.-17 SCID mice. Once the tumor volumes reached approximately 150 mm³, mice were randomized into groups of 6 and were treated twice a week with a control antibody at 25 mg/kg or the MET×MET bispecific antibody H4H14639D at 25 mg/kg. Tumor growth was monitored for 30 days post-implantation and tumor volume (mm$^3$) was measured for each experimental group over time. The results are depicted in Table 16 and FIG. 12, which shows that the MET×MET bispecific antibody significantly inhibits the growth of EBC-1 tumors.

TABLE 16

Relative EBC-1 Tumor Growths

| Treatment | Tumor Growth (mm3) form the start of treatment (mean ± SEM) |
|---|---|
| 25 mg/kg Control | 1394 ± 226 |
| 25 mg/kg H4H14639D | 89 ± 47 |

Example 14. A MET×MET Bispecific Antibody Inhibits In Vitro Growth of Hs746T Gastric Cancer Cells More Potently than Monospecific Antibodies The effect of a MET×MET bispecific antibody on the growth of human gastric carcinoma cells was assessed in vitro. 2,500 Hs746T human gastric carcinoma cells (H. Smith, J. Nat'l. Cancer Inst. 62(2): 225-230, 1979) were seeded in a 96 well plate and cultured in Modified Dulbecco's Media supplemented with 10% FBS. The cells were treated with (1) individual bivalent monospecific anti-MET antibodies (H4H13306P2 or H4H13312P2) at 5 µg/ml, (2) a combination of the two bivalent monospecific anti-MET parental antibodies (H4H13306P2 and H4H13312P2) at 2.5 µg/ml each, or (3) the bispecific antibody containing one binding arm from H4H13306P2 and the other binding arm from H4H13312P2 (H4H14639D) at 5 µg/ml. The cells were subsequently incubated with 5% $CO_2$ at 37° C. After 5 days, relative cell growth was determined by measuring the reduction of the indicator dye, ALAMAR BLUE® (ThermoFischer Scientific, Waltham, Mass.), to its highly fluorescent form in a SPECTRAMAX® M3 plate reader (Molecular Devices, Sunnyvale, Calif.). Increasing fluorescence correlates with cell growth. Table 17 depicts the relative Hs746T cell growth for each antibody treatment normalized to control (no treatment) Hs746T cell growth. The bispecific antibody, H4H14639D, inhibits the proliferation of Hs746T cells more potently than its parental monospecific antibodies individually or in combination.

TABLE 17

Normalized Hs746T Cell Growth

| | Relative Cell Growth (n = 3) | Standard Deviation |
|---|---|---|
| Control | 1 | 0.133497801 |
| H4H14639D | 0.647408139 | 0.019090432 |
| H4H13306P2 | 1.623312821 | 0.189647479 |
| H4H13312P2 | 0.852680493 | 0.01728527 |
| H4H13306P2 + H4H13312P2 | 1.767720125 | 0.077445717 |

Figure 13A:
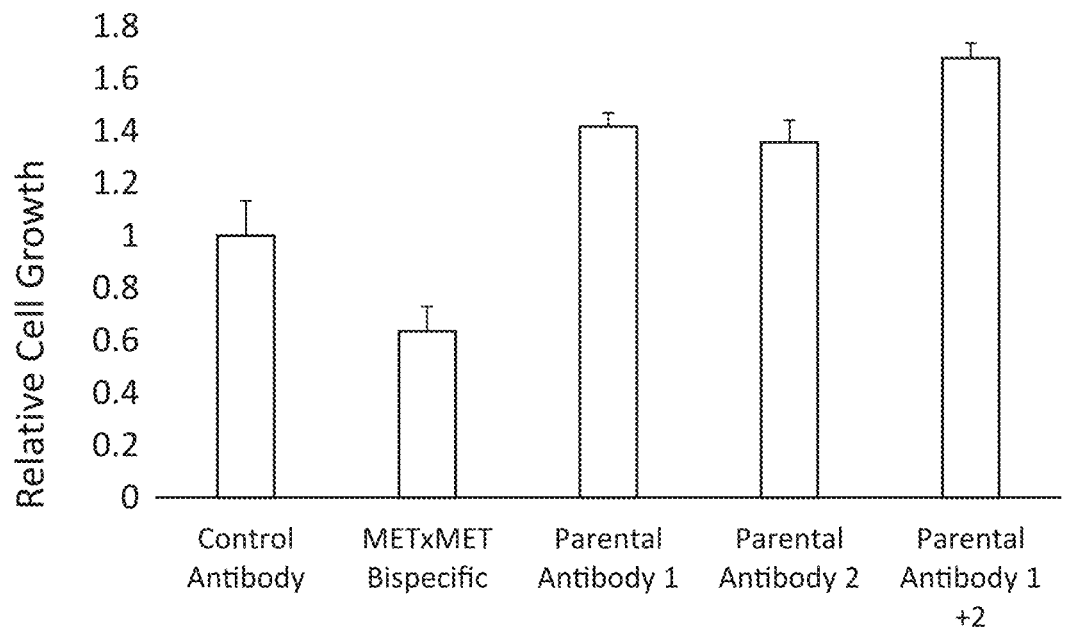
FIG. 13A depicts the relative growth of Hs746T cells as a function of treatment with control antibody, a MET×MET bispecific antibody, the MET×MET parental monospecific antibody 1, the MET×MET parental monospecific antibody 2, and a combination of parental antibodies 1 and 2.
Figure 13B:
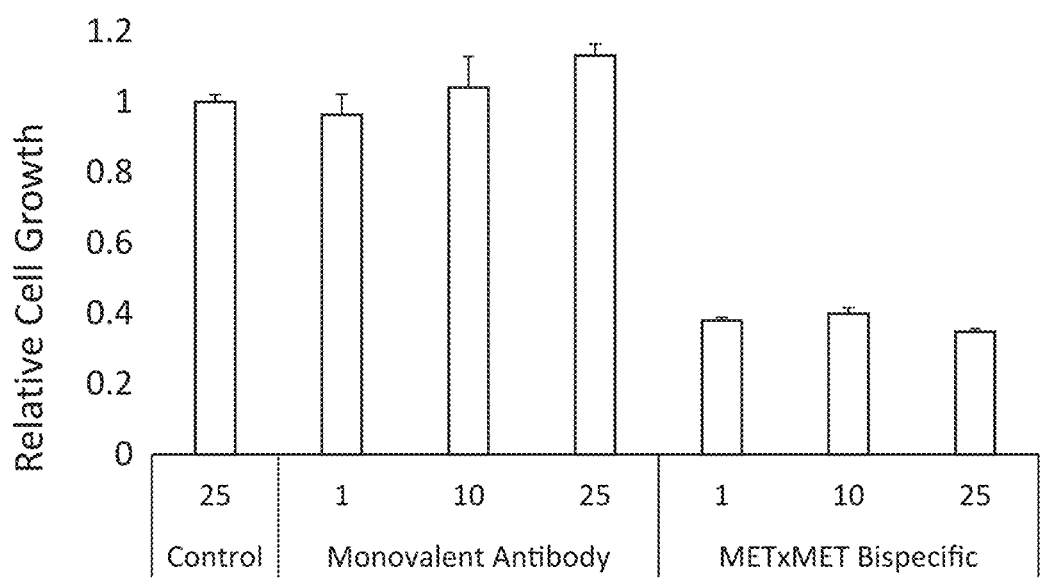
FIG. 13B depicts the relative growth of Hs746T cells as a function of treatment with control antibody, a monovalent antibody at 1, 10 and 25 µg/mL, and a MET×MET bispecific antibody at 1, 10 and 25 µg/mL.

Hs746T gastric cancer cells were treated with control antibody, the MET×MET bispecific antibody H4H14639D, the anti-MET parental antibody H4H13306P2, the anti-MET parental antibody H4H13312P2, and the combination of parental antibodies 1 and 2, each antibody at 2 µg/ml. Cell growth was determined after 5 days by reduction of ALAMAR BLUE® reagent (FIG. 13, panel A). The MET×MET bispecific antibody inhibited cell growth relative to the parental antibodies alone or combined, and inhibited MET pathway activation more effectively than its parental antibodies in Hs746T gastric cancer cells.

Hs746T gastric cancer cells in 96 well plates were treated with 25 µg/mL control antibody, 1 µg/mL, 10 µg/mL or 25 µg/mL monovalent MET antibody, or 1 µg/mL, 10 µg/mL or 25 µg/mL MET×MET bispecific antibody. Hs746T gastric cancer cell growth was determined after 5 days by reduction of ALAMARBLUE® reagent (FIG. 13, panel B). MET× MET bispecific antibody potently inhibits growth of MET-amplified cells.

Figure 14:
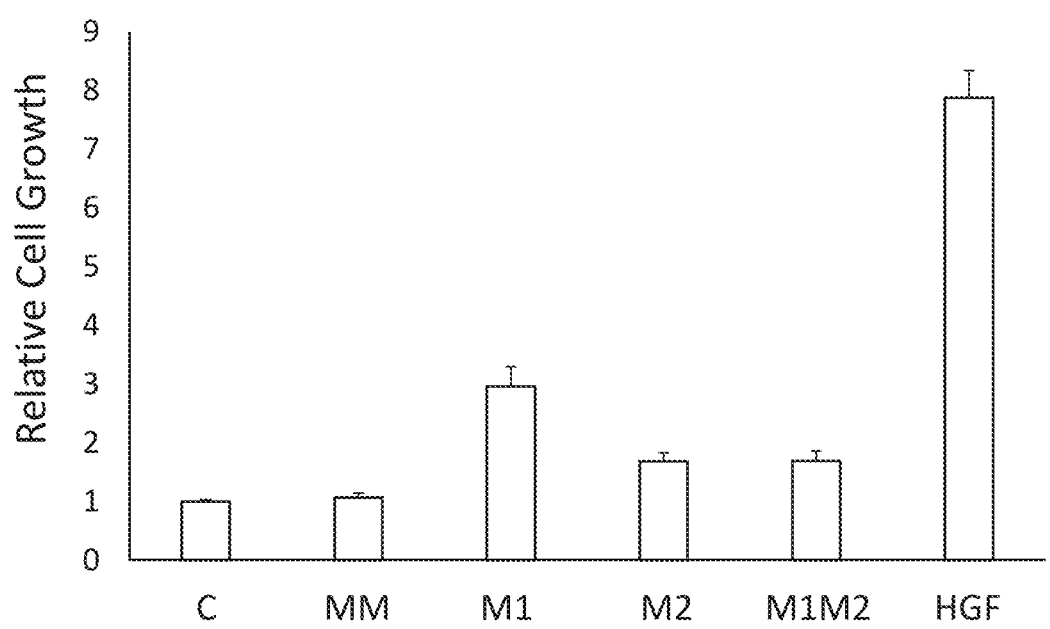
FIG. 14 is a bar chart depicting the relative cell growth of NCI-H596 cells as a function of treatment with a control antibody (C), a MET×MET bispecific antibody (MM), the MET×MET parental monospecific antibody 1 (M1), the MET×MET parental monospecific antibody 2 (M2), a combination of parental antibodies 1 and 2 (M1M2), and the MET-agonist hepatocyte growth factor (HGF).

Example 15. A MET×MET Bispecific Antibody does not Induce Growth of NCI-H596 Lung Cancer Cells In Vitro The effect of a MET×MET bispecific antibody on the growth of human non-small cell lung cancer (NSCLC) cells (NCI-H596) was assessed in vitro. 10,000 NCI-H596 lung adenosquamous carcinoma cells (Nair et al., J. Nat'l. Cancer Inst. 86(5): 378-383, 1994) were seeded in 96 well plates on a layer of 0.66% agar in media supplemented with 1% fetal bovine serum (FBS). The cells were cultured in RPMI 1640 media supplemented with 1% FBS with 0.3% agarose. The cells were treated with (1) individual parental bivalent monospecific anti-MET antibodies (H4H13306P2 or H4H13312P2) at 5 µg/ml, (2) a combination of the two parental bivalent monospecific anti-MET antibodies (H4H13306P2 and H4H13312P2) at 2.5 µg/ml each, (3) a bispecific antibody containing one binding arm from H4H13306P2 and the other binding arm from H4H13312P2 (H4H14639D) at 5 µg/ml, or (4) 100 ng/mL of hepatocyte growth factor (HGF). The cells were subsequently incubated with 5% $CO_2$ at 37° C. After two weeks, relative cell growth was determined by measuring the reduction of the indicator dye, ALAMAR BLUE® (Thermo Fischer Scientific, Waltham, Mass.), to its highly fluorescent form in a SPECTRAMAX® M3 plate reader (Molecular Devices, Sunnyvale, Calif.). Increasing fluorescence correlates with cell growth. Table 18 and FIG. 14 depict the relative NCI-H596 cell growth for each antibody treatment normalized to control (no treatment) NCI-H596 cell growth. Treatment of NCI-H596 lung cancer cells with HGF resulted in potent induction of growth in soft agar. The MET×MET (MM in FIG. 14) bispecific antibody H4H14639D did not significantly alter growth relative to control treated cells. Modest induction of cell growth was observed with each parental bivalent monospecific antibody H4H13306P2 (M1) or H4H13312P2 (M2) individually, or combined (H4H13306P2 and H4H13312P2) (M1M2).

TABLE 18

Normalized NCI-H596 Cell Growth

| | Relative Cell Growth (n = 3) | Standard Deviation |
|---|---|---|
| Control | 1 | 0.030074808 |
| H4H14639D | 1.070339237 | 0.075103746 |
| H4H13306P2 | 2.9593578 | 0.337877264 |
| H4H13312P2 | 1.686580346 | 0.145670753 |
| H4H13306P2 + H4H13312P2 | 1.693724668 | 0.168651046 |
| HGF | 7.87655937 | 0.46057617 |

Example 16. A MET×MET Bispecific Antibody Inhibits In Vitro Growth of SNU5 Gastric Cancer Cells More Potently than Monospecific Antibodies The effect of a MET×MET bispecific antibody on the growth of human gastric carcinoma cells was assessed in vitro. 2,500 SNU5 human gastric carcinoma cells (Ku and Park, Cancer Res. Treat. 37(1): 1-19, 2005) were seeded in a 96 well plate and cultured in Iscove's Modified Dulbecco's Media supplemented with 20% FBS. The cells were treated with (1) individual bivalent monospecific anti-MET antibodies (H4H13306P2 or H4H13312P2) at 5 µg/ml, (2) a combination of the two bivalent monospecific anti-MET antibodies (H4H13306P2 and H4H13312P2) at 2.5 µg/ml each, or (3) a bispecific antibody containing one binding arm from H4H13306P2 and the other binding arm from H4H13312P2 (H4H14639D) at 5 µg/ml. The cells were subsequently incubated with 5% $CO_2$ at 37° C. After 5 days, relative cell growth was determined by measuring the reduction of the indicator dye, ALAMAR BLUE® (Thermo Fischer Scientific, Waltham, Mass.), to its highly fluorescent form in a SPECTRAMAX® M3 plate reader (Molecular Devices, Sunnyvale, Calif.). Increasing fluorescence correlates with cell growth. Table 19 depicts the relative SNU5 cell growth for each antibody treatment normalized to control (no treatment) SNU5 cell growth. The bispecific antibody, H4H14639D, inhibits the proliferation of SNU5 cells more potently than its parental monospecific antibodies.

TABLE 19

Normalized SNU5 Cell Growth

| | Relative Cell Growth (n = 3) | Standard Deviation |
|---|---|---|
| Control | 1 | 0.070814765 |
| H4H14639D | 0.271100069 | 0.01324024 |
| H4H13306P2 | 0.766317547 | 0.061930288 |
| H4H13312P2 | 0.431990234 | 0.033183065 |
| H4H13306P2 + H4H13312P2 | 0.331287005 | 0.012042949 |

Example 17. A MET×MET Bispecific Antibody Induces Regression of Hs746T Tumor Xenograft The effect of a MET×MET bispecific antibody on a human gastric carcinoma tumor in an immunocompromised mouse model was assessed. Three million Hs746T human gastric carcinoma cells were implanted subcutaneously into the flank of CB-17 SCID mice (Bancroft et al., J. Immunol. 137(1): 4-9, 1986). Once the tumor volumes reached approximately 200 $mm^3$, the mice were randomized into groups of six and were treated twice per week with a control antibody at 25 mg/kg or with a MET×MET bispecific antibody (H4H14639D) at 25 mg/kg. Tumor growth was monitored for 16 days post-implantation for the control group, when the control-treated tumors reached protocol size limits. Tumor growth was monitored for 30 days post-implantation for the H4H14639-treated group.

Figure 15:
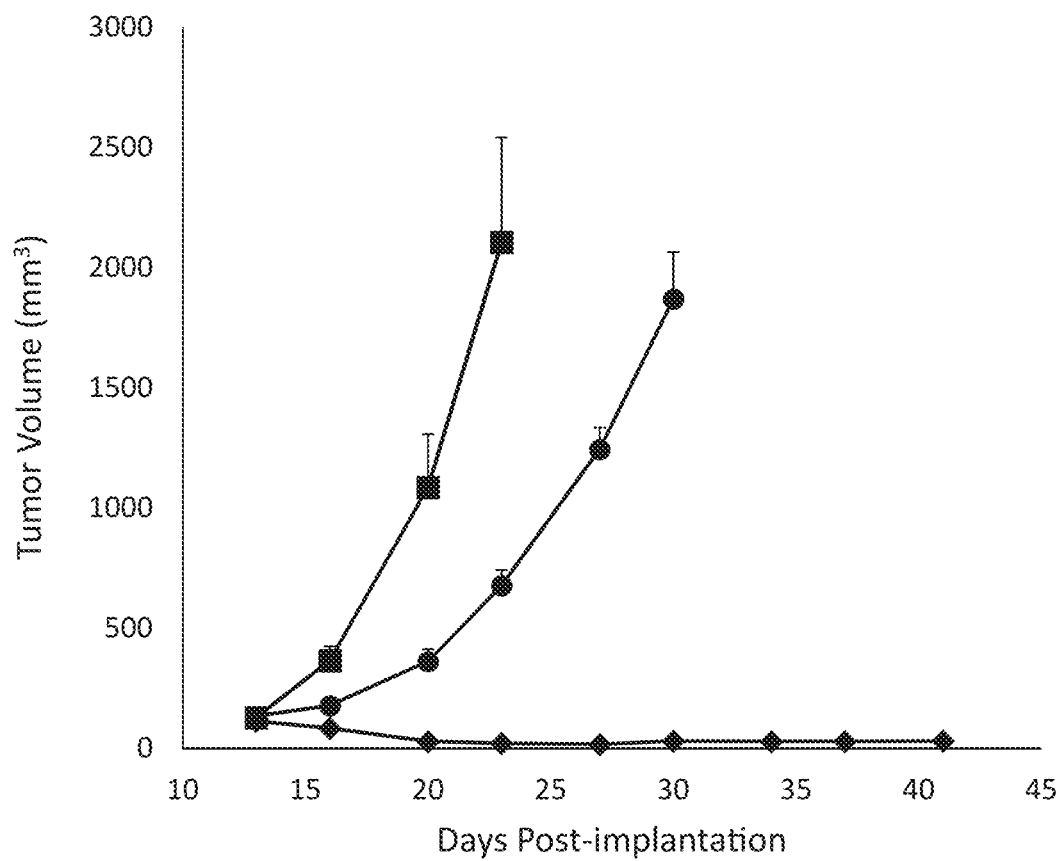
FIG. 15 is a line graph depicting the change in Hs746T tumor volume in cubic millimeters as a function of time in days after implantation of Hs746T cells in animals treated with control antibody (filled square ■), MET monovalent antibody (filled circle ●), or MET×MET bispecific antibody (filled diamond ◆).

Treatment of tumors with the MET×MET bispecific antibody induced regression of tumor size over 21 days relative to the beginning of treatment. The control-treated tumors showed a mean increase in volume of about 12-fold over 16 days of growth (Table 20). Tumor volume over time, which shows Hs746T tumor regression due to the MET×MET bispecific antibody, is shown in FIG. 15.

TABLE 20

Hs746T Gastric Tumor Growth

| Antibody (mg/kg) | Tumor growth ($mm^3$) from the start of treatment (mean ± SEM) |
|---|---|
| Control (10) | 1164 ± 138 |
| H4H14639D (25) | −215 ± 8.3 |

Example 18. A MET×MET Bispecific Antibody Induces Regression of SNU5 Tumor Xenograft The effect of a MET×MET bispecific antibody on a human gastric carcinoma tumor in an immunocompromised mouse model was assessed. Ten million SNU5 human gastric carcinoma cells were implanted subcutaneously into the flank of CB-17 SCID mice. Once the tumor volumes reached approximately 500 $mm^3$, the mice were randomized into groups of five and were treated twice per week with a control antibody at 10 mg/kg or with a MET×MET bispecific antibody (H4H14639D) at either 1 mg/kg or 10 mg/kg. Tumor growth was monitored for 81 days post-implantation when the control-treated tumors reached protocol size limits.

The tumors of mice treated with 1 mg/kg or 10 mg/kg of the MET×MET antibody demonstrated a mean reduction in size of about 95% or 98%, respectively. The control-treated tumors showed a mean increase in volume of about 12-fold from the start of treatment (Table 21).

TABLE 21

SNU5 Gastric Tumor Growth

| Antibody (mg/kg) | Tumor growth ($mm^3$) from the start of treatment (mean ± SEM) |
|---|---|
| Control (10) | 1123 ± 194 |
| H4H14639D (1) | −477 ± 43 |
| H4H14639D (10) | −492 ± 18 |

Figure 16A:
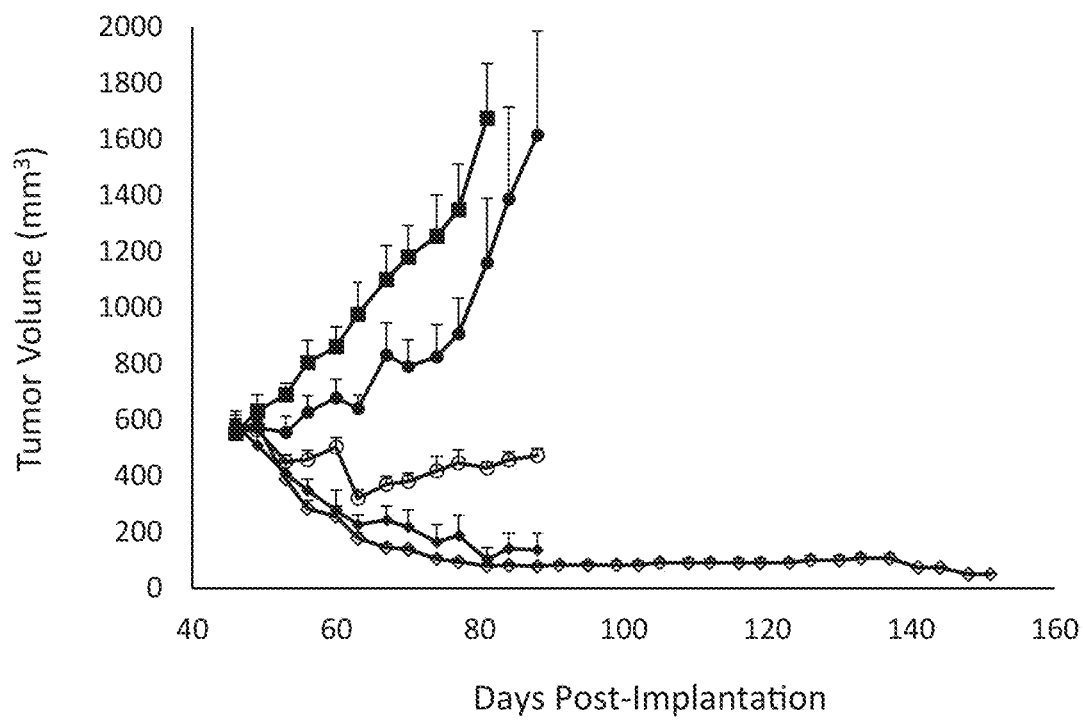
FIG. 16A, is a line graph depicting the change in SNU5 tumor volume in cubic millimeters as a function of time in days after implantation of SNU5 cells in animals treated with control antibody (filled square ■), MET monovalent antibody at 1 mg/mL (filled circle ●), MET monovalent antibody at 10 mg/mL (open circle ○), MET×MET bispecific antibody at 1 mg/mL (filled diamond ◆), or MET×MET bispecific antibody at 10 mg/mL (open diamond ◇).
Figure 16B:
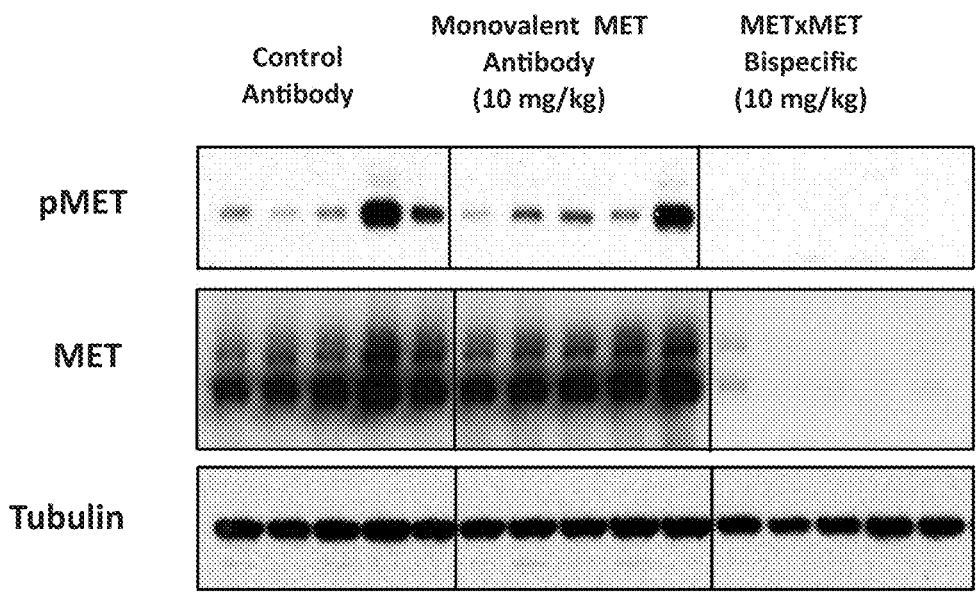
FIG. 16B, is an immunoblot of pMET, MET, and tubulin (loading control) extracted from an SNU5 tumor removed from a mouse xenograft model after treatment with a control antibody, 10 mg/kg of an anti-MET monovalent antibody, and 10 mg/kg of a MET×MET bispecific antibody.

Subcutaneously implanted SNU5 tumors were treated twice weekly with control antibody, monovalent MET antibody at 1 mg/kg or 10 mg/kg, or MET×MET bispecific antibody at 1 mg/kg or 10 mg/kg. Potent and sustained regression of MET-amplified SNU5 tumors (i.e., reduction in tumor volume) was observed over time in those mice treated with MET×MET bispecific antibody (FIG. 16, panel A). Protein was extracted from the end-of-study tumors and MET expression and pathway activation as indicated by MET phosphorylation (pMET expression) were determined by immunoblotting. The MET×MET treated mice (tumors) showed reduction in MET and pMET expression relative to the controls (FIG. 16, panel B). The MET×MET bispecific antibody is a potent inhibitor of tumors harboring MET amplification.

Example 19. A MET×MET Bispecific Antibody Induces Regression of U87-MG Tumor Xenograft The effect of a MET×MET bispecific antibody on a human glioblastoma tumor in an immunocompromised mouse model was assessed. Five million U87-MG human glioblastoma cells (Vordermark and Brown, Int. J. Radiation Biol. 56(4): 1184-1193, 2003) were implanted subcutaneously into the flank of CB-17 SCID mice. U87-MG glioblastoma xenograft models are driven by autocrine HGF signaling. Once the tumor volumes reached approximately 100 mm³, the mice were randomized into groups of six and were treated with a control antibody or the MET×MET bispecific antibody (H4H14639D). 25 mg/kg of antibody (control or MET×MET) was administered to each mouse twice per week. Tumor growth was monitored for 29 days post-implantation when the control-treated tumors reached protocol size limits.

Figure 17:
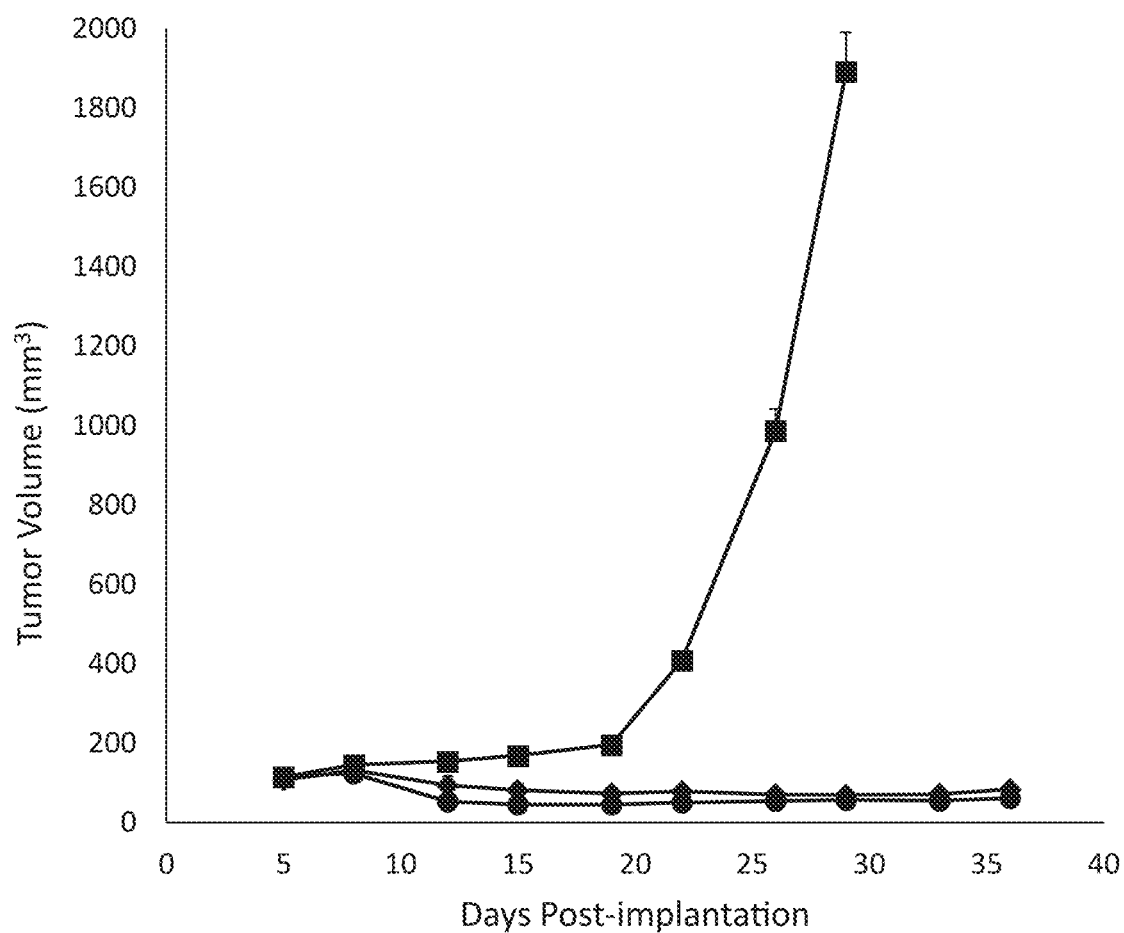
FIG. 17 is a line graph depicting the change in U87-MG tumor volume in cubic millimeters as a function of time in days after implantation of U87-MG cells in animals treated with control antibody (filled square ■), MET monovalent antibody (filled circle ●), or MET×MET bispecific antibody (filled diamond ◆).

The tumors of mice treated with the MET×MET antibody demonstrated a mean reduction in size of about 38%, whereas the control-treated tumors showed a mean increase in volume of about 19-fold over 29 days of growth (Table 22). Tumor volume over time, which shows U87-MG tumor regression due to the MET×MET bispecific antibody, is shown in FIG. 17.

TABLE 22

Glioblastoma Tumor Growth

| Antibody (mg/kg) | Tumor growth (mm3) from the start of treatment (mean ± SEM) |
|---|---|
| Control (25) | 1777 ± 98 |
| H4H14639D (25) | −38 ± 18 |

Example 20. A MET×MET Bispecific Antibody Inhibits Growth of U118-MG Tumor Xenograft The effect of a MET×MET bispecific antibody on a human glioblastoma tumor in an immunocompromised mouse model was assessed. U118-MG glioblastoma xenograft models are driven by autocrine HGF signaling. Five million U118-MG human glioblastoma cells (Olopade et al., Cancer Research 52: 2523-2529, 1992) were implanted subcutaneously into the flank of CB-17 SCID mice. Once the tumor volumes reached approximately 100 mm³, the mice were randomized into groups of six and were treated with a control antibody or the MET×MET bispecific antibody (H4H14639D). 25 mg/kg of antibody (control or MET×MET) was administered to each mouse twice per week. Tumor growth was monitored for 72 days post-implantation.

The MET antibody inhibited tumor growth by 99% over the 72 day period (Table 23).

TABLE 23

Glioblastoma Tumor Growth

| Antibody (mg/kg) | Tumor growth (mm3) from the start of treatment (mean ± SEM) | % Decrease in tumor growth versus control |
|---|---|---|
| Control (25) | 1228 ± 123 | — |
| H4H14639D (25) | 11 ± 18 | 99.1 |

Figure 18:
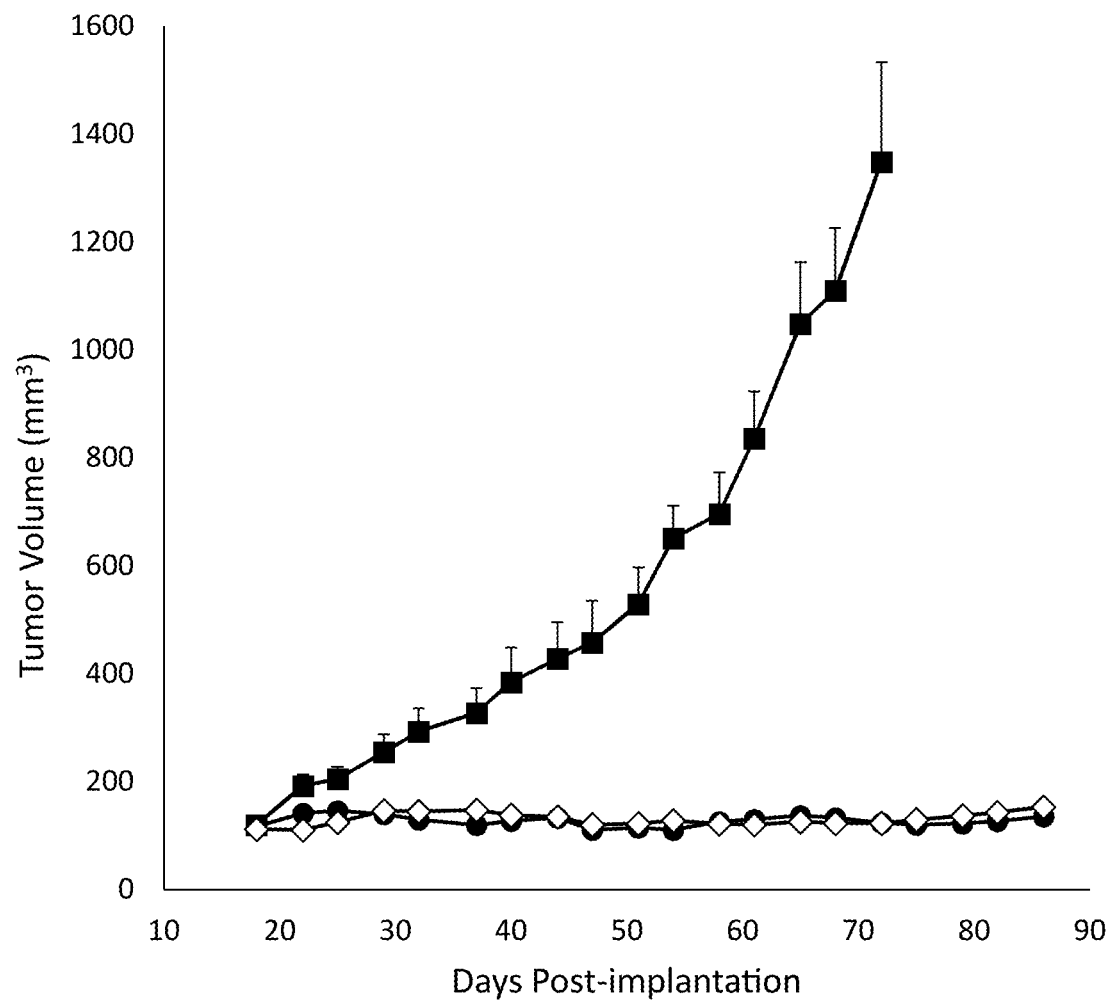
FIG. 18 is a line graph depicting the change in U118-MG tumor volume in cubic millimeters as a function of time in days after implantation of U118-MG cells in animals treated with control antibody (filled square ■), MET monovalent antibody (filled circle ●), or MET×MET bispecific antibody (open diamond ◇).

In another experiment, subcutaneously implanted U118-MG glioblastoma tumors in mice were treated twice weekly with 25 mg/kg control antibody, monovalent MET antibody or MET×MET bispecific antibody. Tumor volume (mm³) was measured for each experimental group over time. The results are depicted in FIG. 18, which shows the MET×MET bispecific antibody inhibits growth of U118-MG tumors.

Example 21: Maytansinoid Synthesis

Maytansin-3-N-methyl-L-alanine-N-Me-beta-alanine-carbamyl-(p-amino)benzyl-citrulline-valine-adipoyl-succinate (Compound 1 in FIG. 20) was synthesized from compound 2 (FIG. 19) as described below.

Figure 19:
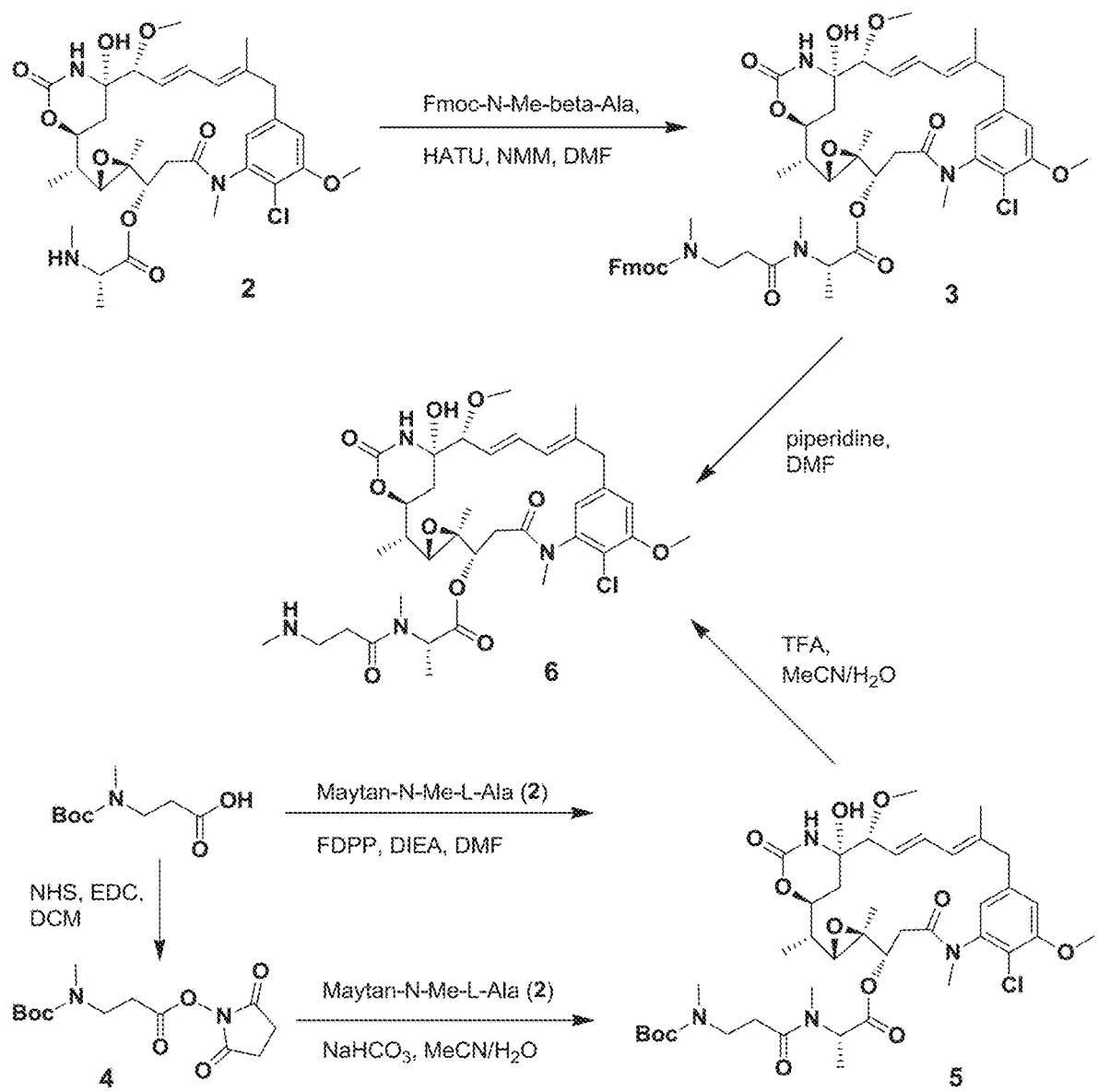
FIG. 19 is a schematic illustrating the synthesis of maytansinoid 6.

Maytansin-3-N-methyl-L-alanine-Fmoc-N-Me-beta-alanine (Compound 3, FIG. 19)

Des-acetyl-maytansine (Compound 2, FIG. 19, 0.433 g, 0.666 mmol), Fmoc-N-Me-beta-Ala (0.434 g, 1.33 mmol), and HATU (0.757 g, 1.99 mmol) were weighed to a dry flask, dissolved in anhydrous DMF (9 mL), and treated with 4-methylmorpholine (0.300 mL, 2.73 mmol). The flask was sealed with a rubber septum, purged with argon, and the reaction stirred at ambient temperature. After 3 days the mixture was evaporated to an oil, dissolved in acetonitrile and water, and purified by flash chromatography on a 275 g C18 silica column (30-90% acetonitrile in water over 20 min, 0.05% acetic acid in both phases). Lyophilization of the product fractions gave the title compound as a white solid. The crude was purified on an 80 g silica gel column (EtOAc—5:5:1 EtOAc:DCM:MeOH over 17 min). The pure fractions were combined, evaporated, and dried in vacuo overnight giving the title compound as a white solid (0.424 g, 66%). MS (ESI, pos.): calc'd for $C_{51}H_{61}ClN_4O_{12}$, 956.4; found 956.9 (M+H), 979.0 (M+Na), 939.0 (M−H$_2$O+H).

N-tert-Butoxycarbonyl-N-methyl-beta-alanine succinate ester (Compound 4, FIG. 19)

The title compound was prepared from commercial Boc-N-Me-beta-Ala-OH by a method well known in the art (cf.-Widdison et al., J. Med. Chem., 2006, 49 (14), 4401). $^1$H NMR (300 MHz, CDCl$_3$): δ 3.62 (bm, 2H), 2.88 (m, 9H), 1.47 (s, 9H).

Maytansin-3-N-methyl-L-alanine-Boc-N-Me-beta-alanine (Compound 5, FIG. 19)

Method A:
The product of the preceding step (Compound 4, FIG. 19, 0.453 g, 1.51 mmol) and des-acetyl-maytansine (Compound 2, FIG. 19, 0.304 g, 0.468 mmol) were dissolved in 3:1 acetonitrile:water (8 mL), treated with 1M aqueous NaHCO$_3$ (0.5 mL), and stirred at ambient temperature for 18 hours. When the reaction was complete as determined by TLC, it was then stirred with brine for 10 min and extracted thrice with ethyl acetate (EtOAc). The combined organic layers were then dried over Na$_2$SO$_4$, filtered, and the filtrate concentrated and dried in vacuo to a gold syrup that was purified by flash column chromatography on a 20 g silica gel cartridge (0-10% MeOH in EtOAc over 15 min) giving the title compound as a white solid (0.084 g, 43%). MS (ESI, pos.): calc'd for $C_{41}H_{59}ClN_4O_{12}$, 834.4; found 835.2 (M+H), 857.2 (M+Na), 817.4 (M−H$_2$O+H).

Method B:
Boc-N-Me-beta-Ala-OH (0.294 g, 1.45 mmol) was dissolved in anhydrous DMF (5 mL), treated with pentafluorophenyl diphenylphosphinate (FDPP, 0.555 g, 1.44 mmol), and the reaction stirred at ambient temperature for 30 min. The mixture was then transferred to a larger flask containing a mixture of des-acetyl-maytansine (Compound 2, FIG. 19, 0.462 g, 0.711 mmol) and diisopropylethylamine (DIEA, 0.250 mL, 1.44 mmol) in anhydrous DMF (7 mL), the flask sealed with a rubber septum, purged with argon, and reaction stirred again at ambient temperature. After 24 hours the reaction was concentrated in vacuo to an oil, dissolved in ethyl acetate (EtOAc, 2 mL), and purified on a 40 g silica gel cartridge (EtOAc—5:5:1 EtOAc/DCM/MeOH over 15 min), giving the title compound as a pale yellow solid (0.468 g, 79%). MS (ESI, pos.): calc'd for $C_{41}H_{59}ClN_4O_{12}$, 834.4; found 857.2 (M+Na), 817.2 (M–$H_2O$+H).

Maytansin-3-N-methyl-L-alanine-N-Me-beta-alanine (Compound 6, FIG. 19). Method A Maytansin-N-Me-L-Ala-Boc-N-Me-beta-Ala (Compound 5, FIG. 19, 0.464 g, 0.555 mmol) was dissolved in a 3:1:1 mixture of acetonitrile/water/trifluoroacetic acid (7 mL), the flask sealed with a rubber septum, purged with argon, and the reaction stirred at ambient temperature for 24 hours, then capped and stored at −20° C. for 3 days. The crude reaction mixture was warmed to ambient temperature for 2 hours, briefly concentrated in vacuo, purified on a 100 g C18 RediSep Gold column (20-80% acetonitrile in water over 25 min, 0.1% TFA in both solvents), and the combined pure fractions were partially evaporated at ambient temperature, frozen in a dry ice bath, and lyophilized to give the title compound as a pale yellow solid (0.295 g, 63%). MS (ESI, pos.): calc'd for $C_{36}H_{51}ClN_4O_{10}$, 734.3; found 735.7 (M+H), 1471.3 (2M+H).

Method B:

Maytansin-N-Me-L-Ala-Fmoc-beta-Ala (Compound 3, FIG. 19, 0.422 g, 0.441 mmol) was dissolved in 5% piperidine in DMF (6.00 mL, 3.04 mmol), the reaction flask sealed with a rubber septum, purged with argon, and the mixture stirred at ambient temperature. After 3 hours the reaction was complete by LCMS, so it was concentrated in vacuo, sealed, and stored at −20° C. overnight. The crude product was warmed to ambient temperature, treated with acetonitrile and 10% aq. acetic acid (3 mL each), and purified by flash chromatography on a 275 g C18 silica column (10-90% acetonitrile in water over 20 min, 0.05% acetic acid in both solvents). Lyophilization of the product fractions gave the title compound as a white solid. The solid was triturated thrice with dry diethyl ether, filtered, the solids washed off the frit with DCM, and the filtrate evaporated and dried in vacuo giving the title compound as a white solid (0.311 g, 89%). MS (ESI, pos.): calc'd for $C_{36}H_{51}ClN_4O_{10}$, 734.3; found 735.0 (M+H).

Figure 20:
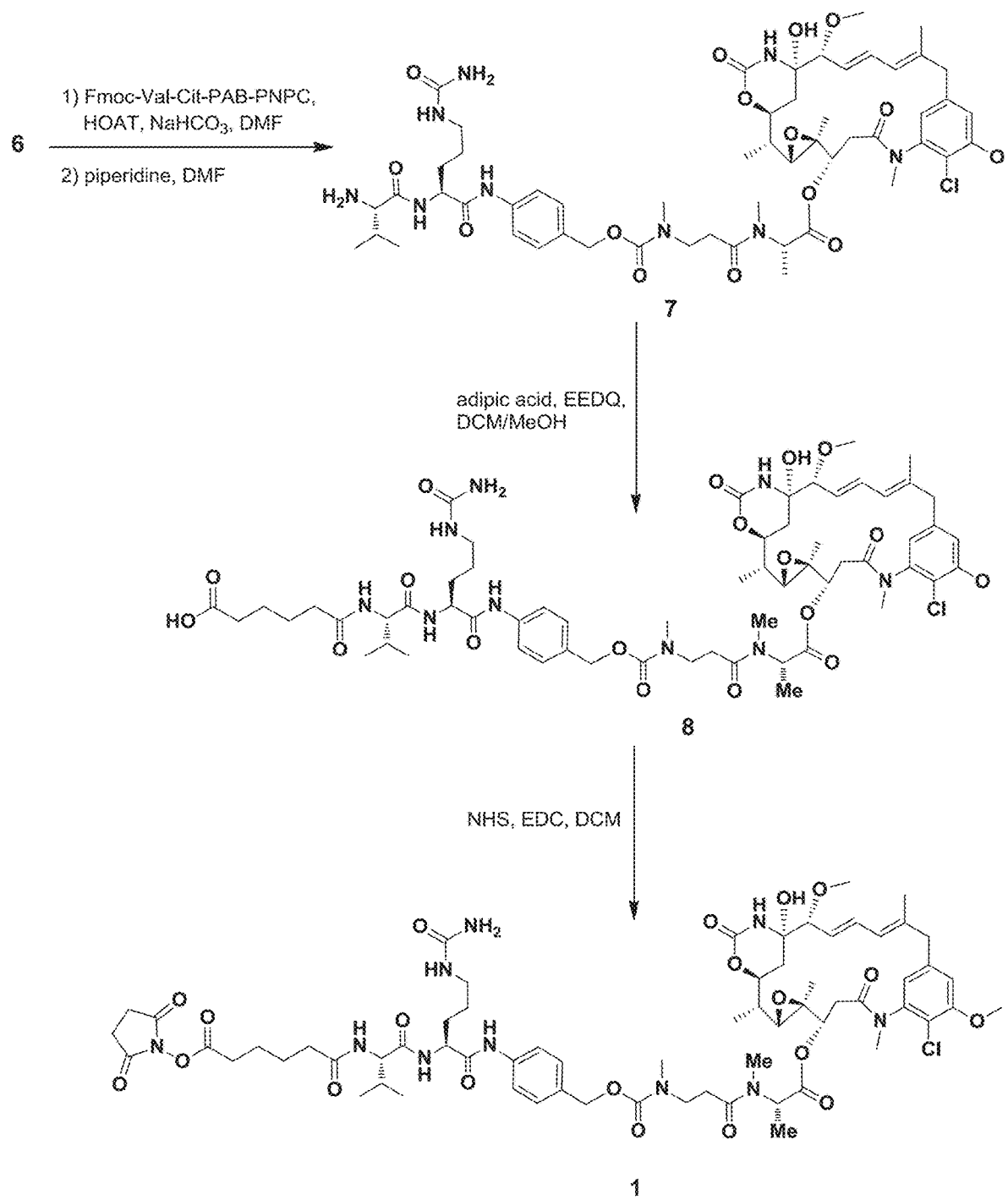
FIG. 20 is a schematic illustrating the synthesis of maytansinoid intermediate 1.

Maytansin-3-N-methyl-L-alanine-N-Me-beta-alanine-carbamyl-(p-amino)benzyl-citrulline-valine-Fmoc (Compound 7, FIG. 20). Step 1

The product of the preceding step (Compound 6, FIG. 19, 0.310 g, 0.390 mmol), 1-hydroxy-7-azabenzotriazole (HOAT, 0.164 g, 1.20 mmol), sodium bicarbonate (0.138 g, 1.64 mmol), and Fmoc-valine-citrulline-(p-amino)benzyl-(p-nitrophenyl)carbonate (0.595 g, 0.776 mmol, prepared by method known in the art, cf.-Gangwar et al., U.S. Pat. No. 7,714,016 B2) were dissolved in anhydrous DMF (10 mL), the reaction flask sealed with a rubber septum, purged with argon, and the mixture stirred at ambient temperature. After 24 hours the reaction was partially evaporated in vacuo to ca. 2-3 mL, treated with 10% aq. acetic acid and water (ca. 1 mL each), dissolved in acetonitrile (ca. 6 mL), and purified by flash chromatography on a 275 g C18 silica column (30-90% acetonitrile in water over 20 min, 0.05% acetic acid in both solvents). Partial evaporation, freezing, and lyophilization gave the title compound as a white solid (0.362 g, 68%). MS (ESI, pos.): calc'd for $C_{70}H_{88}ClN_9O_{17}$, 1361.6; found 1362.1 (M+H), 1384.1 (M+Na), 1344.1 (M–$H_2O$+H).

Step 2:

The product of the preceding step (0.360 g, 0.264 mmol) was dissolved in 5% piperidine in DMF (7 mL), the reaction flask sealed with a rubber septum, purged with argon, and the mixture stirred at ambient temperature. After 3 hours the reaction was evaporated in vacuo, the residue treated with 10% aq. acetic acid (2 mL), dissolved in acetonitrile (4 mL), and purified by flash chromatography on a 275 g C18 silica column (10-70% acetonitrile in water over 20 min, 0.05% acetic acid in both solvents). The pure fractions were combined, stored at −20° C. overnight, partially evaporated in vacuo at 25-30° C., frozen on dry ice, and lyophilized for 6 days giving the title compound as a pale yellow solid (0.303 g, 95%). MS (ESI, pos.): calc'd for $C_{15}H_{78}ClN_9O_{15}$, 1139.5; found 1140.1 (M+H), 1162.0 (M+Na).

Maytansin-3-N-methyl-L-alanine-N-Me-beta-alanine-carbamyl-(p-amino)benzyl-citrulline-valine-adipic acid (Compound 8, FIG. 20)

The product of the preceding step (Compound 7, FIG. 20, 0.205 g, 0.171 mmol), adipic acid (0.258 g, 1.77 mmol), and 2-ethoxy-1-ethoxycarbonyl-1,2-dihydroquinoline (EEDQ, 0.215 g, 0.869 mmol) were dissolved in dry DCM (10 mL) and anhydrous methanol (5 mL), the reaction flask was sealed with a rubber septum, purged with argon, and the mixture stirred at ambient temperature. After 21 hours the reaction was evaporated in vacuo, the residue dissolved in a few mL of acetonitrile/water, and purified by flash chromatography on a 150 g C18 silica column (20-80% acetonitrile in water over 17 min, 0.05% acetic acid in both solvents). Partial evaporation, freezing, and lyophilization of the pure fractions for 18 hours gave the title compound as a white solid (0.140 g, 65%). MS (ESI, pos.): calc'd for $C_{61}H_{86}ClN_9O_{18}$, 1267.6; found 1268.9 (M+H), 1290.9 (M+Na).

Maytansin-3-N-methyl-L-alanine-N-Me-beta-alanine-carbamyl-(p-amino)benzyl-citrulline-valine-adipoyl-succinate (Compound 1, FIG. 20)

The product of the preceding step (Compound 8, FIG. 20, 0.061 g, 0.048 mmol), N-hydroxysuccinimide (0.063 g, 0.55 mmol), and N-(3-Dimethylaminopropyl)-N'-ethylcarbodiimide hydrochloride (EDC-HCl, 0.071 g, 0.37 mmol) were dissolved in dry DCM (7 mL), the reaction flask sealed with a rubber septum, purged with argon, and the mixture stirred at ambient temperature. After 5 days the reaction was evaporated in vacuo, the residue dissolved in a few mL of acetonitrile/water, and purified by flash chromatography on a 100 g C18 silica column (30-90% acetonitrile in water over 15 min, 0.05% acetic acid in both solvents). Partial evaporation, freezing, and lyophilization of the cleanest product fractions for 18 hours gave the title compound as a white solid (0.044 g, 67%). MS (ESI, pos.): calc'd for $C_{65}H_{89}ClN_{10}O_{20}$, 1364.6; found 1365.7 (M+H), 1387.7 (M+Na), 1347.7 (M–$H_2O$+H). $^1$H-NMR (500 MHz; $CDCl_3$): δ 7.56 (d, J=8.3 Hz, 2H), 7.20 (d, J=8.7 Hz, 1H), 6.80 (s, 1H), 6.71 (m, 1H), 6.62 (d, J=10.0 Hz, 1H), 6.39 (dd, J=15.1, 11.3 Hz, 1H), 5.68 (dd, J=15.3, 9.1 Hz, 1H), 5.38-5.32 (m, 1H), 5.03 (t, J=15.1 Hz, 1H), 4.88 (d, J=12.3 Hz, 1H), 4.73 (d, J=11.3 Hz, 1H), 4.61 (dd, J=9.1, 3.6 Hz, 1H), 4.26 (d, J=7.0 Hz, 1H), 4.17 (t, J=7.1 Hz, 1H), 3.95 (s, 3H), 3.61 (d, J=11.7 Hz, 1H), 3.57 (d, J=12.4 Hz, 1H), 3.46 (d, J=9.1 Hz, 2H), 3.33 (s, 3H), 3.27 (t, J=6.9 Hz, 1H), 3.17-3.07 (m, 5H), 2.97 (dd, J=16.6, 9.9 Hz, 1H), 2.88 (d, J=11.7 Hz, 3H), 2.84 (s, 4H), 2.77 (s, 2H), 2.66 (s, 2H), 2.62 (t, J=4.8 Hz, 2H), 2.56 (d, J=13.1 Hz, 1H), 2.32 (t, J=6.6 Hz, 2H), 2.15 (d, J=14.0 Hz, 1H), 2.10 (q, J=6.8 Hz, 1H), 1.92

(s, 4H), 1.75 (m, 5H), 1.61 (s, 3H), 1.52 (s, 3H), 1.27 (d, J=6.3 Hz, 3H), 1.22 (dt, J=12.7, 6.3 Hz, 6H), 0.95 (t, J=5.9 Hz, 7H), 0.78 (s, 3H).

DM1 was synthesized as a single diastereomer based on the procedures described in WO 2015/031396 (e.g., Example 2, paragraph [00106]), incorporated herein by reference in its entirety.

Example 22. Antibody Conjugation and Characterization of Conjugates

Antibody Conjugation

The antibodies (H4H14639D, H4H13312P, H4H14635D, and isotype control; 10-20 mg/ml) in 50 mM HEPES, 150 mM NaCl, pH 8.0, and 10-15% (v/v) DMA were conjugated with a 5-6 fold excess of SMCC-DM1 diastereomer prepared as described in Example 21 (Maytansinoid A) or maytansin-3-N-methyl-L-alanine-N-Me-beta-alanine-carbamyl-(p-amino)benzyl-citrulline-valine-adipoyl-succinate (Compound 1, FIG. 20) (Maytansinoid B) for 2 hours at ambient temperature. The conjugates were purified by size exclusion chromatography or extensive ultrafiltration and sterile filtered. Protein concentrations were determined by UV spectral analysis. Size-exclusion HPLC established that all conjugates used were >90% monomeric, and RP-HPLC established that there was <1% unconjugated linker payload. All conjugated antibodies were analyzed by UV for linker payload loading values according to Hamblett et al. (American Association for Cancer Research. 2004 Oct. 15; 10(20): 7063-70) and/or by mass difference, native versus conjugated. Payload to antibody ratios are reported in Table 24.

TABLE 24

Percent Yield and Payload to Antibody Ratios for Each of the Antibody Drug Conjugates

| Antibody | Yield (%) | DAR (MS) | DAR (UV) |
|---|---|---|---|
| H4H14639D-maytansinoid A | 60 | 3.8 | 3.7 |
| H4H14639D-maytasinoid B | 50 | 2.4 | 2.4 |
| H4H13312P-maytansinoid A | 60 | 4.1 | 4.1 |
| H4H13312P-maytansinoid B | 50 | 2.3 | 2.5 |
| Isotype Control REGN1945-maytansinoid B | 70 | 2.3 | 2.5 |
| Isotype Control REGN1945-maytansinoid A | 80 | 3.7 | 3.7 |

Characterization of Conjugates by Liquid Chromatography-Mass Spectrometry

To determine the loading of the linker-payloads on the antibody, the conjugates were deglycosylated, and analyzed by LC-MS.

For the assay, 50 μg of the conjugate was diluted with milli-Q water to a final concentration of 1 mg/mL. Ten μL of PNGase F solution [PNGase F solution was prepared by adding 150μ of PNGase F stock (New England Biolabs, Cat#P0704L) and 850μ of milli-Q water and mixed well] was added to the diluted conjugate solution and then incubated at 37° C. overnight. Injections of 5 μL of each sample were made onto LC-MS (Waters Synat G2-Si) and eluted with 0.1 mL/minute of a gradient mobile phase 20-40% over 25 minutes (Mobile Phase A: 0.1% v/v FA in $H_2O$; Mobile Phase B: 0.1% v/v FA in Acetonitrile). The LC separation was achieved on a Waters Acquity BEH C4 column (1.0×50 mM, 1.7 μM) at 80° C.

The mass spectrometry spectra were deconvoluted using Masslynx software and the drug to antibody ratio (DAR) was calculated using the following equations:

1. Relative Percentage (%) of Drug (Dn) by Distribution Peak Intensity (PI):

$$Dn\ \% = PIn/\Sigma(PI0+PI1+PI2+ \ldots +PIi) \times 100$$

(n=0, 1, 2, 3, ..., i)

2. Average DAR Calculation:

$$DAR = \Sigma(1 \times D1\% + 2 \times D2\% + 3 \times D3\% + \ldots + i \times Di\ \%)$$

Example 23. Surface Plasmon Resonance Derived Binding Affinities and Kinetic Constants of Conjugated Human Monoclonal Anti-MET (Monospecific and Bispecific) Antibodies Equilibrium dissociation constants ($K_D$ values) for MET binding to anti-MET antibodies conjugated with either MCC-DM1 diastereomer (maytansinoid A) or maytansin-3-N-methyl-L-alanine-N-Me-beta-alanine-carbamyl-(p-amino)benzyl-citrulline-valine-adipoyl-succinate (Compound 1, FIG. 20) (maytansinoid B) were determined using a real-time surface plasmon resonance biosensor assay on a Biacore 2000 instrument. The Biacore sensor surface was derivatized by amine coupling with a monoclonal mouse anti-human Fc antibody (GE Healthcare, #BR-1008-39) to capture anti-MET ADC and parent unmodified antibodies expressed with human constant regions. Biacore binding studies were performed in HEPES Buffered Saline (HBS)-EP running buffer (0.01M HEPES pH 7.4, 0.15M NaCl, 3 mM EDTA, 0.05% v/v Surfactant P20). Human MET was prepared in-house expressing a C-terminal myc-myc-hexahistidine tag (hMET-mmh). Different concentrations (3-fold dilutions) of hMET-mmh (ranging from 30 nM to 1.1 nM) prepared in HBS-EP running buffer were injected over the anti-MET ADC or antibody captured surface at a flow rate of 40 μL/min. Association of hMET-mmh to each of the captured ADCs and monoclonal antibodies was monitored for 4 minutes. Subsequently, hMET-mmh dissociation was monitored for 6 minutes in HBS-EP running buffer. Anti-human Fc surface was regenerated by a brief injection of 20 mM $H_3PO_4$. All binding kinetic experiments were performed at 25° C.

Kinetic association ($k_a$) and dissociation ($k_d$) rate constants were determined by fitting the real-time sensorgrams to a 1:1 binding model using Scrubber 2.0c curve fitting software. All sensorgrams were double referenced by subtracting buffer injection sensorgram signal from the corresponding analyte sensorgram, thereby removing artifacts caused by dissociation of the antibody from the capture surface. Binding dissociation equilibrium constants ($K_D$) and dissociative half-lives (t1/2) were calculated from the kinetic rate constants as:

$$K_D(M) = \frac{kd}{ka}, \text{ and } t^{1/2} \text{ (min)} = \frac{\ln(2)}{60 * kd}$$

Binding kinetic parameters for Maytansinoid A or Maytansinoid B conjugated anti-Met monospecific and bispecific antibodies are shown below in Table 25, with some experiments run in duplicate.

TABLE 25

Biacore Binding Affinities of Conjugated Mono- and Bi-specific Monoclonal Anti-MET Antibodies at 25° C.

| Antibody | mAb Captured (RU) | Antigen Bound (RU) | ka (1/Ms) | kd (1/s) | $K_D$ (M) | t½ (min) |
|---|---|---|---|---|---|---|
| H4H13312P2 | 148.1 ± 1.2 | 12.3 | 2.59E+05 | 5.35E−03 | 2.07E−08 | 2.2 |
| H4H13312P2 | 142.7 ± 0.3 | 12.1 | 1.87E+05 | 4.85E−03 | 2.59E−08 | 2.4 |
| H4H13312P2-Maytansinoid A | 232.6 ± 0.5 | 11.9 | 1.82E+05 | 7.18E−03 | 3.94E−08 | 1.6 |
| H4H13312P2-Maytansinoid B | 263.0 ± 2.6 | 10.9 | 1.80E+05 | 6.32E−03 | 3.51E−08 | 1.8 |
| H4H14639D | 283.6 ± 4.4 | 82.8 | 5.90E+05 | 1.56E−03 | 2.64E−09 | 7.4 |
| H4H14639D-Maytansinoid A | 207.7 ± 0.8 | 55.8 | 4.95E+05 | 1.81E−03 | 3.65E−09 | 6.4 |
| H4H14639D-Maytansinoid B | 227.5 ± 0.4 | 55.4 | 4.83E+05 | 1.87E−03 | 3.86E−09 | 6.2 |
| H4H14639D-Maytansinoid A | 284.0 ± 1.1 | 62.8 | 4.70E+05 | 1.76E−03 | 3.74E−09 | 6.6 |
| H4H14639D-Maytansinoid B | 268.7 ± 0.7 | 72.8 | 4.91E+05 | 1.45E−03 | 2.95E−09 | 8.0 |

Example 24: In Vitro Potencies of Anti-MET Antibody Drug Conjugates (ADCs)

To determine the relative cell-killing potency of anti-MET antibody drug conjugates (ADCs) described herein, cell-killing assays were run on multiple cells lines expressing varying levels of endogenous MET. EBC-1 (Riken Cell Bank; # RBRC-RCB1965), MKN-45 (JCRB; # JCRB0254), NCI-H1993 (ATCC; # CRL-5909), and J.RT3 (ATCC; # TIB-153) cell lines were maintained in RPMI+10% FBS+1× penicillin/streptomycin/L-glutamine (P/S/G), SNU-5 (ATCC; # CRL-5973) were maintained in Iscove's+10% FBS+1×P/S/G, Hs746t (ATCC; # HTB-135) and HEK293 (ATCC; #003041) were maintained in DME+10% FBS+1× P/S/G, MDA-MB-231 (ATCC; # HTB-26) were maintained in Liebowitz's L-15+10% FBS+1×P/S/G+1×nonessential amino acids (NEAA) without $CO_2$, U87MG (ATCC; # HTB-14) were maintained in MEM Earle's Salts+15% FBS+1×P/S/G+1×NEAA, T47D (ATCC; # HTB-133) were maintained in RPM1 1640+10% FBS+1×P/S/G+10 mM HEPES+1 mM sodium pyruvate+10 ug/ml Bovine Insulin, and A549 (ATCC; # CCL-185) were maintained in Kaighn's Nutrient Mixture F-12 (HAM's F-12K)+10% FBS+1×P/S/G.

Initially, relative binding of the anti-MET antibodies was assessed with unconjugated H4H14635D, H4H14639D and H4H13312P2 antibodies across the entire panel of cell lines via flow cytometry. Briefly, 1×10⁶ cells were incubated with 10 µg/ml of H4H14635D, H4H14639D, H4H13312P2 or an isotype control antibody (REGN1945) for 30 minutes on ice in PBS+2% FBS (FACS buffer). Following one wash with FACS buffer, cells were incubated with 10 µg/ml of Alexa647 conjugated anti-human secondary antibody (Jackson ImmunoResearch, #109-606-170) for 30 minutes on ice. After one additional wash with FACS buffer, samples were fixed with Cytofix (BD Biosciences, #554655), filtered with FACS buffer and run on an iQue flow cytometer (Intelicyte). Mean fluorescence intensity (MFI) data was determined using FlowJo software (FlowJo LLC). FACS binding is expressed as fold MFI binding above isotype control levels, and results are summarized in Table 26. Relative binding of the three anti-Met antibodies was comparable on each cell line and ranged from 447-fold to 7-fold above isotype controls. No detectable binding of any of the 3 anti-MET antibodies tested was observed on T47D, HEK293, or J.RT3 cells.

To measure in vitro cytotoxicity of anti-MET ADCs, nuclear counts after a 3 or 6-day treatment with the ADCs was assessed. Briefly, cells were seeded in 96 well collagen coated plates (Greiner, VWR; #82050-812) at 750-3000 cells/well in complete growth media and grown overnight at 37° C., 5%$00_2$. For cell viability curves, serially diluted ADCs, unconjugated antibodies, or free payloads were added to the cells at final concentrations ranging from 100 nM to 0.01 nM (based on toxin concentration) and incubated for 3 or 6 days at 37° C. in 5% $CO_2$. Cells were subsequently treated with 3 ug/ml Hoechst 33342 nuclear stain (Invitrogen, # H3570) while being fixed with 4% formaldehyde. Images were acquired on the ImageXpress micro XL (Molecular Devices, Sunnyvale, Calif.) and nuclear counts were determined via MetaXpress image analysis software (Molecular Devices, Sunnyvale, Calif.). Background nuclear counts from cells treated with 40 nM digitonin were subtracted from all wells and viability was expressed as a percentage of the untreated controls. $IC_{50}$ values were determined from a four-parameter logistic equation over a 10-point response curve (Graph Pad Prism). The untreated condition for each dose-response curve is also included in the analysis and is represented as the lowest dose. $IC_{50}$ values and percent cell killing are shown in Tables 27 and 28.

As summarized in Table 27, the anti-MET antibody-drug conjugate H4H14639D-Maytansinoid A specifically reduced cell viability in Met amplified EBC-1, SNU-5, MKN-45, NCI-H1993, and Hs746t cell backgrounds with $IC_{50}$ values ranging from 0.35 nM to 0.96 nM. The percentage of cells killed (max % kill) ranged from 73% to 100%. H4H14639D-Maytansinoid A also specifically killed 84% of A549 cells with an $IC_{50}$ values of 13.91 nM. H4H14639D-Maytansinoid A $IC_{50}$ values were greater than 37 nM in low expressing (MDA-MB-231 and U87MG) and non-expressing (T47D, HEK293, and J.RT3) cell lines. The similarly conjugated isotype control antibody killed all cell lines with $IC_{50}$ values greater than 35 nM. The methyl disulfide version of DM1 (MeS-DM1) killed all tested lines with $IC_{50}$ values ranging from 0.07 nM to 2.86 nM.

In a separate experiment, three anti-Met antibodies (H4H14639D, H4H14635D, and H4H13312P2) were conjugated to Maytansinoid A or Maytansinoid B maytansinoid payloads, and in vitro cytotoxicity was assessed in EBC-1, Hs746t, A549, ant T47D cells following a 6 day treatment.

As summarized in Table 28, all anti-Met antibody-drug conjugates potently and specifically reduced cell viability in Met positive cells, with $IC_{50}$ values as low as 10 pM in EBC-1 cells, 0.82 nM in Hs746t cells, and 3.5 nM in A549 cells. The percentage of cells killed was greater than 95% in EBC-1 cells, greater than 86% in Hs746t cells, and greater than 72% in A549 cells. T47D cells (Met negative) were not specifically killed by the anti-Met ADCs. The similarly conjugated isotype control antibodies reduced cell viability in all of the tested cell lines with $IC_{50}$ values greater than 5 nM in EBC-1 cells, greater than 33 nM in Hs746t cells, and greater than 90 nM in A549 and T47D cells. Unconjugated H4H14639D reduced cell viability in EBC-1, Hs746t, and A549 cells but at a lower percentage than the conjugated antibodies. Unconjugated H4H14635D and H4H13312P2 had little to no impact on viability in any of the tested cell lines. The methyl disulfide version of DM1 (MeS-DM1) killed all tested lines with $IC_{50}$ values ranging from 0.12 nM to 1.39 nM. In contrast, M24 (the payload released from Maytansinoid B) killed cells with IC50s >100 nM.

TABLE 26

FACS Binding of Unconjugated MET Antibodies to Tumor Cell Lines.

| | FACS Binding (MFI Fold Above Isotype Control) | | | | | |
|---|---|---|---|---|---|---|
| Cell Line | Unstained | Secondary Alone | REGN1945 (Isotype Control) | H4H14635D | H4H14639D | H4H13312P2 |
| EBC-1 | 0.7 | 0.6 | 1 | 263 | 252 | 147 |
| SNU-5 | 1 | 1.2 | 1 | 477 | 454 | 235 |
| MKN-45 | 1 | 0.8 | 1 | 183 | 156 | 94 |
| NCI-H1993* | 1 | 2 | ND | ND | 188 | 188 |
| Hs746t | 0.8 | 1.1 | 1 | 39 | 34 | 27 |
| MDA-MB-231 | 3 | 5.6 | 1 | 11 | 12 | 7 |
| U87MG | 1.6 | 1.7 | 1 | 18 | 18 | 10 |
| T47D | 1 | 0.9 | 1 | 1.3 | 1 | 1.4 |
| A549 | 0.7 | 0.5 | 1 | 12 | 10 | 7 |
| HEK293 | 0.2 | 0.2 | 1 | 1.8 | 1.8 | 1.2 |
| J.RT3 | 0.8 | 1 | 1 | 1.6 | 1.4 | 1.1 |

*Expressed as fold above unstained for NCI-H1993.

TABLE 27

$IC_{50}$ and Max % Kill of Anti-MET ADCs in 3-Day in vitro Cytotoxicity Assay.

| | EBC-1 | | SNU-5 | | MKN-45 | | NCI-H1993 | |
|---|---|---|---|---|---|---|---|---|
| Antibody-Drug Conjugate | $IC_{50}$ (nM) | Max % Kill | $IC_{50}$ (nM) | Max % Kill | $IC_{50}$ (nM) | Max % Kill | $IC_{50}$ (nM) | Max % Kill |
| DM1 (MeS-DM1) | 2.22 | 90 | 1.22 | 99 | 2.73 | 85 | 2.86 | 81 |
| H4H14639D | 0.82 | 37 | 0.30 | 40 | ND | 0 | ND | 0 |
| H4H14639D-Maytansinoid A | 0.96 | 89 | 0.40 | 100 | 0.35 | 86 | 0.41 | 94 |
| REGN1945-Maytansinoid A | 35.06 | 65 | >100 | 14 | >100 | 39 | 49.42 | 68 |

| | Hs746t | | MDA-MB-231 | | U87MG | |
|---|---|---|---|---|---|---|
| Antibody-Drug Conjugate | $IC_{50}$ (nM) | Max % Kill | $IC_{50}$ (nM) | Max % Kill | $IC_{50}$ (nM) | Max % Kill |
| DM1 (free drug) | 1.46 | 81 | 1.53 | 89 | 0.61 | 89 |
| H4H14639D | 0.42 | 7 | >100 | 6 | >100 | 6 |
| H4H14639D-Maytansinoid A | 0.56 | 73 | >100 | 48 | 100 | 58 |
| REGN1945-Maytansinoid A | 33.22 | 44 | >100 | 42 | 94.71 | 58 |

| | T47D | | A549 | | HEK293 | | J.RT3 | |
|---|---|---|---|---|---|---|---|---|
| Antibody-Drug Conjugate | $IC_{50}$ (nM) | Max % Kill | $IC_{50}$ (nM) | Max % Kill | $IC_{50}$ (nM) | Max % Kill | $IC_{50}$ (nM) | Max % Kill |
| DM1 (free drug) | 1.33 | 91 | 2.56 | 97 | 0.15 | 95 | 0.07 | 100 |
| H4H14639D | >100 | 0 | >100 | 37 | ND | 0 | >100 | 5 |
| H4H14639D-Maytansinoid A | >100 | 6 | 13.91 | 84 | 40.90 | 65 | 37.82 | 59 |
| REGN1945-Maytansinoid A | >100 | 1 | >100 | 63 | >100 | 44 | 39.79 | 70 |

TABLE 28

IC$_{50}$ and Max % Kill of Anti-MET ADCs in 6-day in vitro Cytotoxicity Assay.

| Antibody-Drug Conjugate | EBC-1 IC$_{50}$ (nM) | EBC-1 Max % Kill | Hs746t IC$_{50}$ (nM) | Hs746t Max % Kill | T47D IC$_{50}$ (nM) | T47D Max % Kill | A549 IC$_{50}$ (nM) | A549 Max % Kill |
|---|---|---|---|---|---|---|---|---|
| DM1 (MeS-DM1) | 0.12 | 62 | 1.39 | 88 | 0.24 | 96 | 0.49 | 90 |
| M24 (Maytansinoid B released payload) | >100 | 32 | >100 | 10 | >100 | 0 | >100 | 10 |
| H4H14639D | 0.37 | 66 | 0.44 | 35 | >100 | 0 | 0.17 | 29 |
| H4H14639D-Maytansinoid A | 0.27 | 97 | 0.82 | 87 | >100 | 3 | 6.01 | 86 |
| H4H14639D-Maytansinoid B | 0.01 | 96 | 0.86 | 90 | >100 | 0 | 3.54 | 80 |
| H4H13312P2 | >100 | 30 | >100 | 0 | >100 | 0 | >100 | 7 |
| H4H13312P2-Maytansinoid A | 0.39 | 95 | 1.59 | 87 | >100 | 6 | 18.30 | 89 |
| H4H13312P2-Maytansinoid B | 0.07 | 95 | 0.89 | 90 | >100 | 3 | 27.10 | 85 |
| H4H14635D | >100 | 11 | >100 | 7 | >100 | 7 | >100 | 0 |
| H4H14635D-Maytansinoid A | 0.76 | 96 | 1.76 | 86 | >100 | 92 | 6.78 | 91 |
| H4H14635D-Maytansinoid B | 0.26 | 96 | 2.32 | 89 | >100 | 2 | 21.40 | 72 |
| REGN1945 | >100 | 0 | >100 | 0 | >100 | 0 | >100 | 1 |
| REGN1945-Maytansinoid A | 28.08 | 93 | 33.06 | 76 | >100 | 14 | 93.40 | 49 |
| REGN1945-Maytansinoid B | 5.01 | 97 | >100 | 0 | >100 | 1 | >100 | 15 |

Example 25: In Vivo Efficacy Against Gastric Cancer Cells 3 million Hs746T gastric cancer cells were implanted subcutaneously into the flank of C.B.-17 SCID mice. Once the tumor volumes reached approximately 150 mm$^3$, mice were randomized into groups of 6 and were treated with control antibodies REGN1945-Maytansinoid B or REGN1945-Maytansinoid A at 10 mg/kg or with H4H14639D-Maytansinoid A or H4H14639D-Maytansinoid B at 3 or 10 mg/kg. All antibodies were administered three times at a frequency of once per week. Tumor growth was monitored for 37 days post-implantation.

The effect of H4H14639D-Maytansinoid A or H4H14639D-Maytansinoid B on the growth of human tumor xenografts in immunocompromised mice was assessed, and the results are shown in Table 29. Tumors treated with the control antibodies, REGN1945-Maytansinoid B or REGN1945-Maytansinoid A, grew to reach protocol size limits within 20 days. Tumors treated with H4H14639D-Maytansinoid A at 3 mg/kg grew to reach protocol size limits within 27 days. Growth of tumors treated with H4H14639D-Maytansinoid B at 3 mg/kg was inhibited for the duration of the experiment. Treatment of tumors with H4H14639D-Maytansinoid A or H4H14639D-Maytansinoid B at 10 mg/kg induced regression of tumor size relative to the beginning of treatment.

TABLE 29

Tumor Growth in SCID Mice Treated with Anti-Met-C Antibody Conjugates

| Antibody (mg/kg) | Tumor growth (mm$^3$) from start of treatment (mean ± SD) |
|---|---|
| REGN1945-Maytansinoid A 10 mg/kg | 1244 ± 199 |
| REGN1945-Maytansinoid B 10 mg/kg | 1345 ± 121 |
| H4H14639D-Maytansinoid A 3 mg/kg | 832 ± 15 |
| H4H14639D-Maytansinoid A 10 mg/kg | −148 ± 0.17 |
| H4H14639D-Maytansinoid B 3 mg/kg | 19 ± 147 |
| H4H14639D-Maytansinoid B 10 mg/kg | −137 ± 0 |

Example 26: In Vivo Efficacy Against Lung Cancer Cells 5 million EBC1 lung cancer cells were implanted subcutaneously into the flank of C.B.-17 SCID mice. Once the tumor volumes reached approximately 170 mm$^3$, mice were randomized into groups of 6 and were treated with control antibody REGN1945-Maytansinoid B at 15 mg/kg or H4H14639D-Maytansinoid B at 2.5, 5, 10 or 15 mg/kg. Antibodies were administered two times at a frequency of once per week. Tumor growth was monitored for 73 days post-implantation.

The effect of H4H14639D on the growth of human tumor xenografts in immunocompromised mice was assessed. Tumors treated with the control antibody, REGN1945-Maytansinoid B, grew to reach protocol size limits within 24 days (IACUC protocols require sacrifice of animals harboring tumors that exceed 2 cm in diameter, approximately 1500 mm$^3$). Treatment of tumors with H4H14639D-Maytansinoid B at 2.5, 5, 10 or 15 mg/kg induced regression of tumor size relative to the beginning of treatment. Results are shown in Table 30.

TABLE 30

Tumor Growth in SCID Mice Treated with Anti-Met-C Antibody Conjugates

| Antibody (mg/kg) | Tumor growth (mm³) from start of treatment (mean ± SD) |
|---|---|
| REGN1945-Maytansinoid B 15 mg/kg | 1106 ± 165 |
| H4H14639D-Maytansinoid B 2.5 mg/kg | −142 ± 24 |
| H4H14639D-Maytansinoid B 5 mg/kg | −163 ± 0 |
| H4H14639D-Maytansinoid B 10 mg/kg | −173 ± 0 |
| H4H14639D-Maytansinoid B 15 mg/kg | −179 ± 0 |

Example 26: In Vivo Efficacy Against Patient-Derived NSCLC Tumors

Met-expressing NSCLC CTG-0165 patient-derived tumors were implanted subcutaneously into the flank of nu/nu Nude mice. Once the tumor volumes reached approximately 150 mm³, mice were randomized into groups of 6 and were treated with control antibodies REGN1945-Maytansinoid B or REGN1945-Maytansinoid A at 10 mg/kg or with H4H14639D-Maytansinoid A or H4H14639D-Maytansinoid B at 3 or 10 mg/kg. All antibodies were administered three times at a frequency of once per week. Tumor growth was monitored for 61 days post-implantation.

The effect of H4H14639D-Maytansinoid A or H4H14639D-Maytansinoid B on the growth of human tumor xenografts in immunocompromised mice was assessed. Tumors treated with the control antibodies REGN1945-Maytansinoid A or REGN1945-Maytansinoid B grew to reach protocol size limits within 27 days. Growth of tumors treated with H4H14639D-Maytansinoid A or H4H14639D-Maytansinoid B at 3 mg/kg was inhibited for 27 days. Treatment of tumors with H4H14639D-Maytansinoid A or H4H14639D-Maytansinoid B at 10 mg/kg induced regression of tumor size relative to the beginning of treatment. Data are provided in Table 31.

TABLE 31

Tumor Growth in Nude Mice Treated with Anti-Met-C Antibody Conjugates

| Antibody (mg/kg) | Tumor growth (mm³) from start of treatment (mean ± SD) |
|---|---|
| REGN1945-Maytansinoid A 10 mg/kg | 967 ± 136 |
| REGN1945-Maytansinoid B 10 mg/kg | 1537 ± 373 |
| H4H14639D-Maytansinoid A 3 mg/kg | 154 ± 227 |
| H4H14639D-Maytansinoid A 10 mg/kg | "−141 ± 2.3 |
| H4H14639D-Maytansinoid B 3 mg/kg | 517 ± 362 |
| H4H14639D-Maytansinoid B 10 mg/kg | "−145 ± 2 |

Example 27: Hydrogen/Deuterium (H/D) Exchange Based Epitope Mapping Epitope Mapping of Anti-Met Antibodies H4H13312P2, H4H13306P2 and H4H14639D Binding to Human MET Experiments were conducted to determine the specific regions of human hepatocyte growth factor receptor ectodomain (SEQ ID NO:155: human Met isoform 1 (Uniprot ID: P08581) expressed with a myc-myc-hexahistidine(.mmh) tag; hereafter referred to as hMet) with which anti-Met antibodies H4H13312P2, H4H13306P2 and H4H14639D interact. H4H13312P2 and H4H13306P2 are bivalent-monospecific anti-Met antibodies; H4H14639D is a bispecific antibody comprising two heavy chains binding to distinct epitopes on Met, each from H4H13312P2 and H4H13306P2, respectively, and a universal light chain. (See Example 5).

Hydrogen/Deuterium (H/D) Exchange epitope mapping with mass spectrometry (HDX-MS) was utilized to determine the binding epitopes of the antibodies mentioned above. A general description of the HDX method is set forth in e.g., Ehring (1999) *Analytical Biochemistry* 267(2):252-259; and Engen and Smith (2001) Anal. Chem. 73:256A-265A.

Experimental Procedure

To map the binding epitope(s) of anti-Met antibodies H4H13312P2, H4H13306P2 and H4H14639D on hMET via HDX, the individual antibodies were separately covalently attached to NHS-activated Sepharose 4 Fast Flow beads (GE Healthcare, Pittsburgh, Pa.). Two methods "On-Antigen" and "On-Complex", as described below, were utilized to confirm the binding epitopes of the anti-Met antibodies.

In the 'On-Antigen' experimental condition, hMET was deuterated for 5.0 mins or 10.0 mins in PBS buffer prepared with $D_2O$. The deuterated antigen was bound to H4H13312P2 or H4H13306P2 antibody beads through a short incubation, and then eluted from beads with an ice-cold low pH quench buffer. The eluted sample was manually loaded to a Waters H/DX-MS system consisting of integrated online peptide digestion, trapping, 9.0 minute Liquid Chromatography (LC) separation, and Synapt G2-Si MS data acquisition.

In the 'On-Complex' experimental condition, hMET was first bound to H4H13312P2 or H4H13306P2 beads and then deuterated for 5.0 mins or 10.0 mins via incubation in PBS buffer prepared with $D_2O$. The deuterated hMET was eluted and analyzed by the Waters H/DX-MS system as mentioned above.

For the identification of the peptic peptides from hMET, LC-MS$^E$ data from the un-deuterated sample were processed and searched against human MET using Waters ProteinLynx Global Server (PLGS) software. The identified peptides were imported to DynamX 3.0 software and filtered by the following two criteria: 1) minimum products per amino acid is 0.3; 2) replication file threshold is 3.0. DynamX 3.0 software subsequently automatically calculated the deuterium uptake difference of each identified peptide between 'On-Antigen' and 'On-Complex" across both 5 min and 10 min deuteration time points. The individual isotopic peak of each peptide picked up by DynamX software for the centroid value calculation was also manually examined to ensure the accuracy of the deuterium uptake calculation.

In general, delta values for deuteration above 0.2 were used as the cut-off point for determining a specific binding epitope.

Results

Using online pepsin digestion via Waters Enzymate™ BEH Pepsin Column (2.1×30 mm, 5 μm) coupled with 9.0 minute LC-MS$^E$ data acquisition, a total of 162 peptic peptides from human MET were reproducibly identified with traceable deuterium uptake for both 'On-Antigen' and 'On-Complex' experiments when the H4H13312P2 antibody beads were used. These peptides represent 55.7% sequence coverage. Among all these peptides, only five were found to have significantly reduced deuteration uptake upon binding H4H13312P2 (On-Complex') as compared to the deuteration of the antigen alone ('On-Antigen'). The centroid values of these five peptides under both the experimental conditions were illustrated in Table 32. The region corresponding to the residues 192-204 covered by these five peptides were defined as the binding epitope for the antibody H4H13312P2 based on HDX data.

TABLE 32 hMET peptic peptides with reduced deuterium uptake upon binding to H4H13312P2

| Residues of hMET | 5 min Deuteration | | | 10 min Deuteration | | |
|---|---|---|---|---|---|---|
| | On-Complex Centroid MH+ | On-Antigen Centroid MH+ | Δ | On-Complex Centroid MH+ | On-Antigen Centroid MH+ | Δ |
| 192-202 | 1351.25 | 1351.83 | −0.58 | 1351.39 | 1352.27 | −0.88 |
| 192-203 | 1482.34 | 1482.94 | −0.60 | 1482.50 | 1483.40 | −0.90 |
| 192-204 | 1629.84 | 1630.71 | −0.87 | 1630.01 | 1631.10 | −1.09 |
| 193-202 | 1252.07 | 1252.79 | −0.72 | 1252.25 | 1253.08 | −0.83 |
| 193-203 | 1383.22 | 1383.79 | −0.57 | 1383.40 | 1384.17 | −0.77 |

For the HDX experiment carried out using H4H13306P2 antibody beads, a total of 98 peptic peptides from hMET were reproducibly identified with traceable deuterium uptake during both 'On-Antigen' and 'On-Complex' experiments. These 98 peptides represent 52.1% sequence coverage. Among all these peptides, twelve were observed to have reduced have significantly reduced deuteration uptake upon binding H4H13306P2 ('On-Complex') as compared to the deuteration of the antigen alone ('On-Antigen'). The centroid values of these twelve peptides under both the experimental conditions were illustrated in Table 33. The regions corresponding to residues 305-315 and residues 421-455 covered by these peptides were defined as the binding epitope for the antibody H4H13306P2 based on HDX data.

TABLE 33 hMET peptic peptides with reduced deuterium uptake upon binding to H4H13306P2

| Residues of hMET | 5 min Deuteration | | | 10 min Deuteration | | |
|---|---|---|---|---|---|---|
| | On-Complex Centroid MH+ | On-Antigen Centroid MH+ | Δ | On-Complex Centroid MH+ | On-Antigen Centroid MH+ | Δ |
| 305-312 | 818.20 | 818.83 | −0.63 | 818.31 | 819.13 | −0.82 |
| 305-315 | 1161.50 | 1162.58 | −1.08 | 1161.80 | 1162.95 | −1.15 |
| 306-313 | 818.48 | 818.97 | −0.49 | 818.71 | 819.28 | −0.57 |
| 421-431 | 1206.24 | 1206.75 | −0.51 | 1206.28 | 1206.95 | −0.67 |
| 421-435 | 1581.28 | 1581.84 | −0.56 | 1581.41 | 1582.09 | −0.68 |
| 421-438 | 1941.58 | 1942.15 | −0.57 | 1941.71 | 1942.39 | −0.68 |
| 422-438 | 1794.58 | 1795.04 | −0.46 | 1794.72 | 1795.34 | −0.62 |
| 439-447 | 963.90 | 964.83 | −0.93 | 963.97 | 965.24 | −1.27 |
| 439-455 | 1846.58 | 1847.79 | −1.21 | 1847.24 | 1847.85 | −0.61 |
| 439-456 | 1960.24 | 1961.32 | −1.08 | 1960.83 | 1961.42 | −0.59 |
| 441-455 | 1586.30 | 1587.71 | −1.41 | 1587.33 | 1587.79 | −0.46 |
| 442-455 | 1487.50 | 1488.50 | −1.00 | 1487.92 | 1488.54 | −0.62 |

The same methodology as outlined above was used to determine the binding epitopes for bispecific anti-Met antibody H4H14639D. The H4H14639D binding epitopes on hMET, determined by this methodology, correspond to the epitopes determined for the parental antibodies.

Binding epitope of Anti-Met antibody H4H13312P2: AA 192-204: VRRLKETKDGFMF (SEQ ID NO: 156) of SEQ ID NO: 155.

Binding epitope of Anti-Met antibody H4H13306P2: AA 305-315: LARQIGASLND (SEQ ID NO: 157) of SEQ ID NO: 155 and AA 421-455: FIKGDLTIANLGTSEG-RFMQVVVSRSGPSTPHVNF (SEQ ID NO: 158) of SEQ ID NO: 155.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

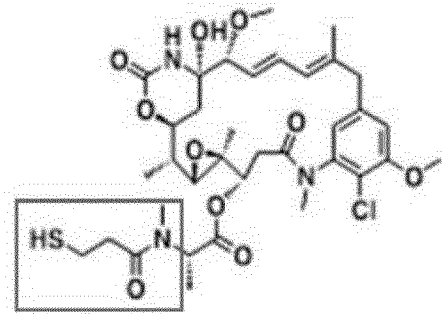

What is claimed is:

1. A bispecific antigen-binding molecule comprising:
   a first antigen-binding domain (D1) comprising three heavy chain complementarity determining regions (HCDR1, HCDR2 and HCDR3) within a heavy chain variable region (HCVR) comprising the amino acid sequence of SEQ ID NO: 58 and three light chain complementarity determining regions (LCDR1, LCDR2 and LCDR3) within a light chain variable region (LCVR) comprising the amino acid sequence of SEQ ID NO: 138; and
   a second antigen-binding domain (D2) comprising three heavy chain complementarity determining regions (HCDR1, HCDR2 and HCDR3) within a heavy chain variable region (HCVR) comprising the amino acid sequence of SEQ ID NO: 82 and three light chain complementarity determining regions (LCDR1, LCDR2 and LCDR3) within a light chain variable region (LCVR) comprising the amino acid sequence of SEQ ID NO: 138;
   wherein D1 specifically binds a first epitope of human MET; and
   wherein D2 specifically binds a second epitope of human MET.

2. The bispecific antigen-binding molecule of claim 1, wherein the bispecific antigen-binding molecule is conjugated to a cytotoxin.

3. The bispecific antigen-binding molecule of claim 2, wherein the cytotoxin is selected from the group consisting of biotoxins, chemotherapeutic agents, and radioisotopes.

4. The bispecific antigen-binding molecule of claim 2, wherein the cytotoxin is selected from the group consisting of maytansinoids, auristatins, duocarmycins, $^{225}$Ac, $^{227}$Th, and any derivatives thereof. and any derivatives thereof.

5. The bispecific antigen-binding molecule of claim 1, wherein the bispecific antigen-binding molecule is conjugated to a cytotoxic agent through a linker.

6. The bispecific antigen-binding molecule of claim 5, wherein the cytotoxic agent is a maytansinoid.

7. The bispecific antigen-binding molecule of claim 6, wherein the maytansinoid is:

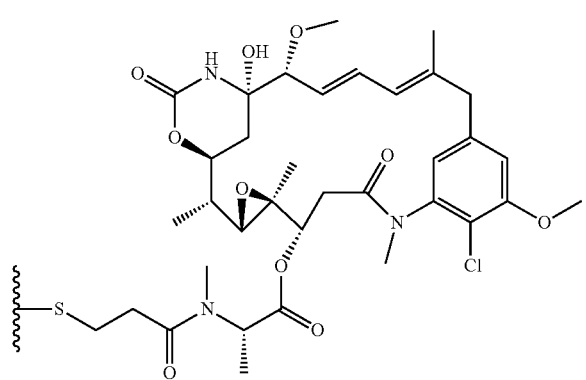 [SMILES: *SCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

wherein the

is the bond to the linker.

8. The bispecific antigen-binding molecule of claim 7, wherein the linker is:

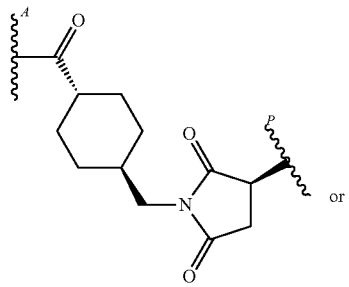

or

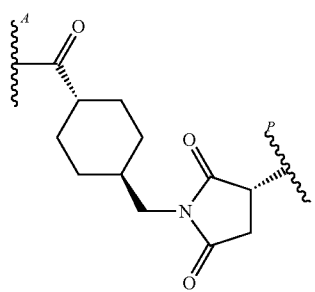

wherein the bond noted with

represents the bond to the bispecific antigen-binding molecule and the bond noted with

represents the bond to the maytansinoid.

9. The bispecific antigen-binding molecule of claim 6, wherein the maytansinoid is

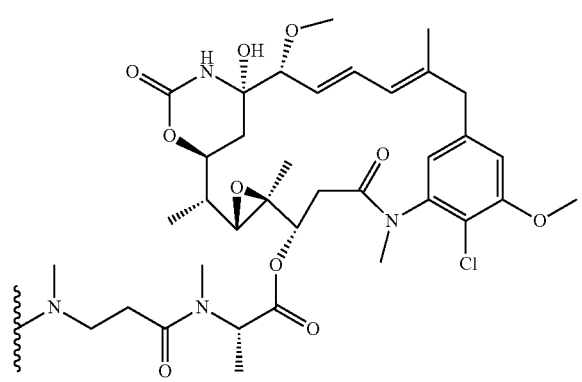 [SMILES: *N(C)CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

wherein the

is the bond to the linker.

10. The bispecific antigen-binding molecule of claim 9, wherein the linker is:

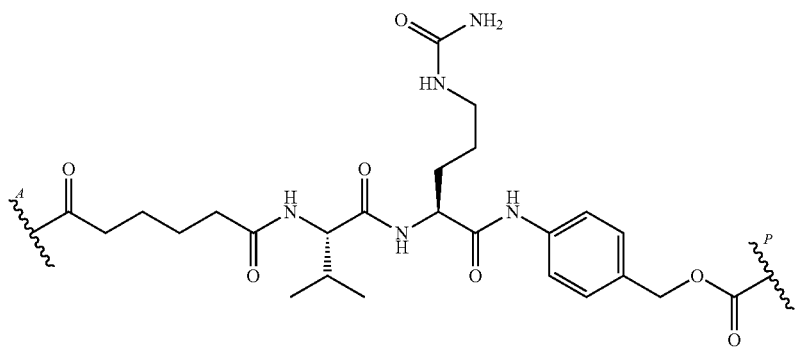

wherein the bond noted with

represents the bond to the bispecific antigen-binding molecule and the bond noted with

represents the bond to the maytansinoid.

11. A pharmaceutical composition comprising the bispecific antigen-binding molecule of claim 1, and a pharmaceutically acceptable carrier.

12. A method of treating a cancer in a subject suffering from a tumor harboring a MET genetic alteration and/or a tumor whose growth is driven by autocrine HGF signaling, the method comprising administering to the subject the bispecific antigen-binding molecule of claim 1.

13. A method of treating a cancer, reducing tumor growth, and/or causing tumor regression in a subject suffering from a MET positive tumor, the method comprising administering to a subject in need thereof the bispecific antigen-binding molecule of claim 2.

14. A bispecific antigen-binding molecule comprising:
a first antigen-binding domain D1 comprising an HCDR1 comprising the amino acid sequence of SEQ ID NO:60; HCDR2 comprising the amino acid sequence of SEQ ID NO:62; HCDR3 comprising the amino acid sequence of SEQ ID NO:64; LCDR1 comprising the amino acid sequence of SEQ ID NO:140; LCDR2 comprising the amino acid sequence of SEQ ID NO:142; and LCDR3 comprising the amino acid sequence of SEQ ID NO:144; wherein D1 specifically binds a first epitope of human MET; and
a second antigen-binding domain D2 comprising an HCDR1 comprising the amino acid sequence of SEQ ID NO: 84; an HCDR2 comprising the amino acid sequence of SEQ ID NO: 86; an HCDR3 comprising the amino acid sequence of SEQ ID NO: 88; an LCDR1 comprising the amino acid sequence of SEQ ID NO: 140; an LCDR2 comprising the amino acid sequence of SEQ ID NO: 142; and an LCDR3 comprising the amino acid sequence of SEQ ID NO: 144; wherein D2 specifically binds a second epitope of human MET.

15. The bispecific antigen-binding molecule of claim 14, wherein D1 comprises: an HCVR comprising the amino acid sequence of SEQ ID NO: 58 or an amino acid sequence that is at least 95% identical thereto; and an LCVR comprising the amino acid sequence of SEQ ID NO: 138 or an amino acid sequence that is at least 95% identical thereto.

16. The bispecific antigen-binding molecule of claim 15, wherein D1 comprises: an HCVR comprising the amino acid sequence of SEQ ID NO: 58; and an LCVR comprising the amino acid sequence of SEQ ID NO: 138.

17. The bispecific antigen-binding molecule of claim 14, wherein D2 comprises: an HCVR comprising the amino acid sequence of SEQ ID NO: 82 or an amino acid sequence that is at least 95% identical thereto; and an LCVR comprising the amino acid sequence of SEQ ID NO: 138 or an amino acid sequence that is at least 95% identical thereto.

18. The bispecific antigen-binding molecule of claim 17, wherein D2 comprises: an HCVR comprising the amino acid sequence of SEQ ID NO: 82; and an LCVR comprising the amino acid sequence of SEQ ID NO: 138.

19. The bispecific antigen-binding molecule of claim 14, wherein the bispecific antigen-binding molecule is conjugated to a maytansinoid through a linker, and wherein the maytansinoid is

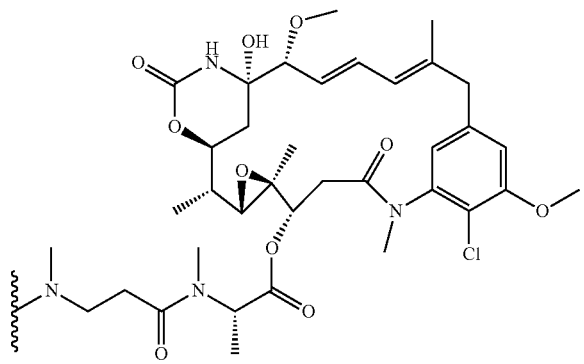 [SMILES: *N(C)CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

wherein the

is the bond to the linker.

20. The bispecific antigen-binding molecule of claim 19, wherein the linker is:

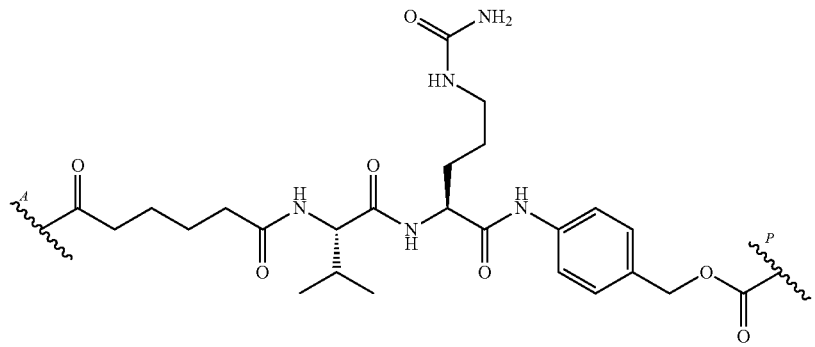

wherein the bond noted with

represents the bond to the bispecific antigen-binding molecule and the bond noted with

represents the bond to the maytansinoid.

21. The bispecific antigen-binding molecule of claim 20, wherein:

D1 comprises an HCVR comprising the amino acid sequence of SEQ ID NO: 58 and an LCVR comprising the amino acid sequence of SEQ ID NO: 138; and D2 comprises an HCVR comprising the amino acid sequence of SEQ ID NO: 82; and an LCVR comprising the amino acid sequence of SEQ ID NO: 138.

22. A method for preparing an antibody-drug conjugate comprising contacting:

(a) an anti-MET antibody comprising the three heavy chain complementarity determining regions (HCDR1, HCDR2 and HCDR3) within a heavy chain variable region (HCVR) comprising the amino acid sequence of SEQ ID NO: 58 and three light chain complementarity determining regions (LCDR1, LCDR2 and LCDR3) within a light chain variable region (LCVR) comprising the amino acid sequence of SEQ ID NO: 138; or (b) a MET×MET bispecific antigen-binding protein comprising:

a first antigen binding domain D1 comprising three heavy chain complementarity determining regions (HCDR1, HCDR2 and HCDR3) within a heavy chain variable region (HCVR) comprising the amino acid sequence of SEQ ID NO: 58 and three light chain complementarity determining regions (LCDR1, LCDR2 and LCDR3) within a light chain variable region (LCVR) comprising the amino acid sequence of SEQ ID NO: 138, wherein D1 specifically binds a first epitope of human MET and a second antigen binding domain D2 comprising three heavy chain complementarity determining regions (HCDR1, HCDR2 and HCDR3) within a heavy chain variable region (HCVR) comprising the amino acid sequence of SEQ ID NO: 82 and three light chain complementarity determining regions (LCDR1, LCDR2 and LCDR3) within a light chain variable region (LCVR) comprising the amino acid sequence of SEQ ID NO: 138 wherein D2 specifically binds a second epitope of human MET, with a compound having the following formula A¹:

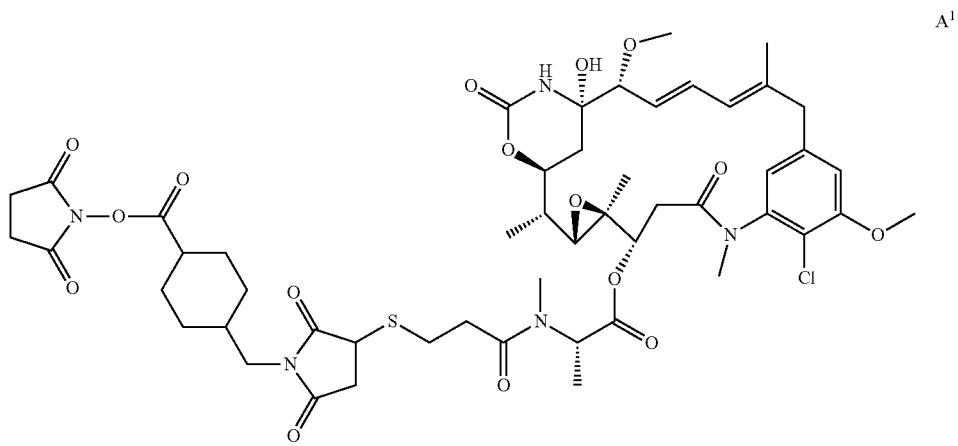 [SMILES: COc1cc2cc(c1Cl)N(C)C(=O)C[C@H](OC(=O)[C@H](C)N(C)C(=O)CCSC1CC(=O)N(CC3CCC(C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

and aqueous diluent.

23. An antibody-drug conjugate prepared by the process of:
(i) contacting a compound of formula (a):

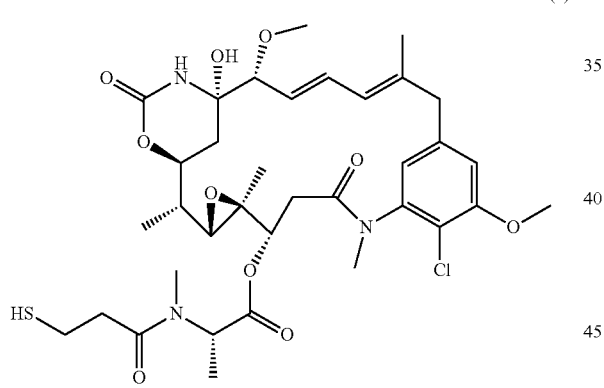

with a compound of formula (b):

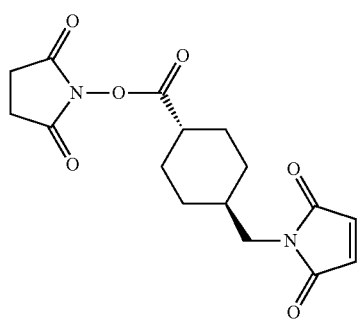

in the presence of silica gel and diluent to synthesize an intermediate; and (ii) contacting:
(a) an anti-MET antibody comprising the three heavy chain complementarity determining regions (HCDR1, HCDR2 and HCDR3) within a heavy chain variable region (HCVR) comprising the amino acid sequence of SEQ ID NO:58 and three light chain complementarity determining regions (LCDR1, LCDR2 and LCDR3) within a light chain variable region (LCVR) comprising the amino acid sequence of SEQ ID NO:138; or
(b) a MET×MET bispecific antigen-binding protein comprising:
a first antigen binding domain D1 comprising three heavy chain complementarity determining regions (HCDR1, HCDR2 and HCDR3) within a heavy chain variable region (HCVR) comprising the amino acid sequence of SEQ ID NO: 58 and three light chain complementarity determining regions (LCDR1, LCDR2 and LCDR3) within a light chain variable region (LCVR) comprising the amino acid sequence of SEQ ID NO: 138, wherein D1 specifically binds a first epitope of human MET, and
a second antigen binding domain D2 comprising three heavy chain complementarity determining regions (HCDR1, HCDR2 and HCDR3) within a heavy chain variable region (HCVR) comprising the amino acid sequence of SEQ ID NO: 82 and three light chain complementarity determining regions (LCDR1, LCDR2 and LCDR3) within a light chain variable region (LCVR) comprising the amino acid sequence of SEQ ID NO: 138 wherein D2 specifically binds a second epitope of human MET, with the intermediate and aqueous diluent.

24. A bispecific antigen-binding molecule comprising:
a first antigen binding domain D1 comprising an HCDR1 comprising the amino acid sequence of SEQ ID NO:20; HCDR2 comprising the amino acid sequence of SEQ ID NO:22; HCDR3 comprising the amino acid sequence of SEQ ID NO:24; LCDR1 comprising the amino acid sequence of SEQ ID NO:140; LCDR2 comprising the amino acid sequence of SEQ ID NO:142; and LCDR3 comprising the amino acid sequence of SEQ ID NO:144; wherein D1 specifically binds a first epitope of human MET; and
a second antigen binding domain D2 comprising an HCDR1 comprising the amino acid sequence of SEQ ID NO: 84; an HCDR2 comprising the amino acid sequence of SEQ ID NO: 86; an HCDR3 comprising the amino acid sequence of SEQ ID NO: 88; an LCDR1 comprising the amino acid sequence of SEQ ID NO: 140; an LCDR2 comprising the amino acid sequence of SEQ ID NO: 142; and an LCDR3 comprising the amino acid sequence of SEQ ID NO: 144; wherein D2 specifically binds a second epitope of human MET.

25. The bispecific antigen-binding molecule of claim 24, wherein:
   D1 comprises an HCVR comprising the amino acid sequence of SEQ ID NO: 18 and an LCVR comprising the amino acid sequence of SEQ ID NO: 138; and
   D2 comprises an HCVR comprising the amino acid sequence of SEQ ID NO: 82; and an LCVR comprising the amino acid sequence of SEQ ID NO: 138.

26. A bispecific antigen-binding molecule comprising:
   a first antigen-binding domain (D1) wherein D1 specifically binds a first epitope of human MET; and
   a second antigen-binding domain (D2) wherein D2 specifically binds a second epitope of human MET; and
   wherein D1 comprises the CDRs within the D1-HCVR amino acid sequence of SEQ ID NO: 18 and the CDRs within the D1-LCVR amino acid sequence of SEQ ID NO: 138, and D2 comprises the CDRs within the D2-HCVR amino acid sequence of SEQ ID NO: 82 and the D2-LCVR amino acid sequence of SEQ ID NO: 138.

* * * * *

UNITED STATES PATENT AND TRADEMARK OFFICE
CERTIFICATE OF CORRECTION

PATENT NO. : 11,142,578 B2
APPLICATION NO. : 15/814095
DATED : October 12, 2021
INVENTOR(S) : Babb et al.

Page 1 of 2

It is certified that error appears in the above-identified patent and that said Letters Patent is hereby corrected as shown below:

In the Specification

Column 38, between Line 10 and Line 15:
The chemical structure is missing an ethyl group ($CH_3$-NH-$CH_2$-$CH_2$-R):

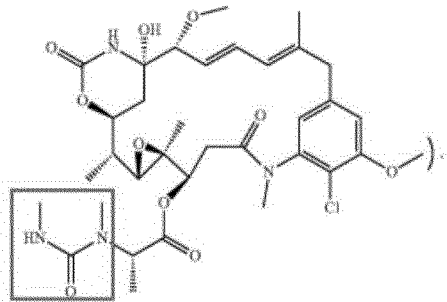

Should be:

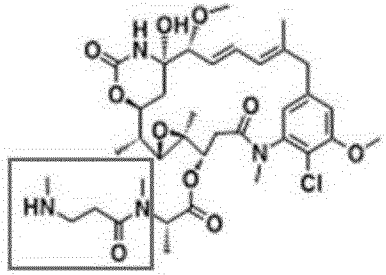

Signed and Sealed this
Eleventh Day of October, 2022

*Katherine Kelly Vidal*

Katherine Kelly Vidal
*Director of the United States Patent and Trademark Office*

CERTIFICATE OF CORRECTION (continued)　　　　　　　　　　　　　　　Page 2 of 2
U.S. Pat. No. 11,142,578 B2

Column 39, between Line 15 and Line 40:
The chemical structure:

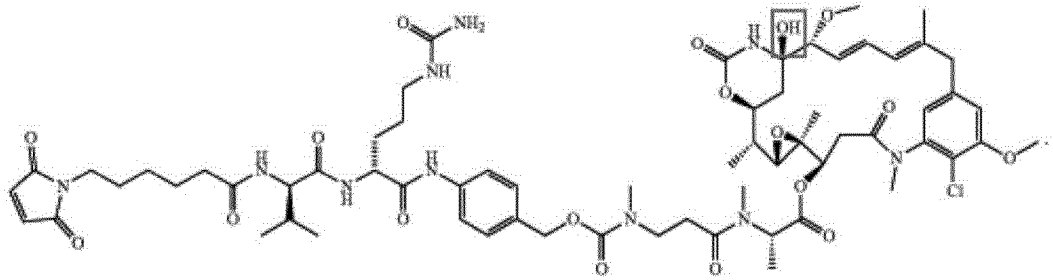

Should be:

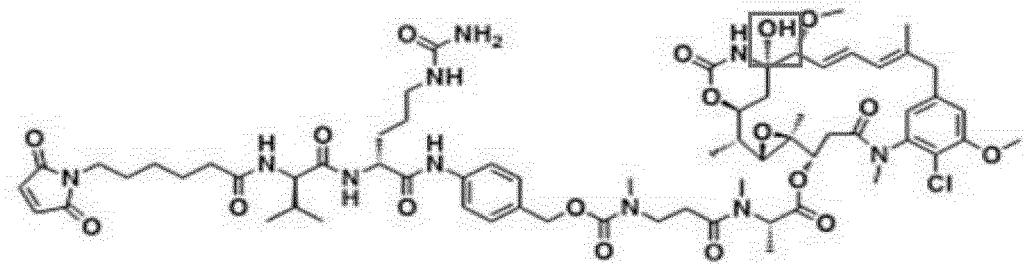

Column 40, between Line 10 and Line 15:
The chemical structure is missing an ethyl group ($CH_3$-NH-$CH_2$-$CH_2$-R):

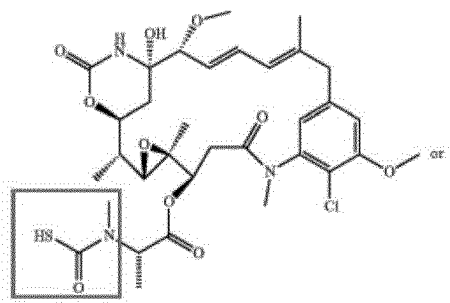

Should be:

SEQUENCE LISTING

<160> NUMBER OF SEQ ID NOS: 158

<210> SEQ ID NO 1
<211> LENGTH: 372
<212> TYPE: DNA
<213> ORGANISM: Homo sapiens

<400> SEQUENCE: 1

```
caggtgcagc tgcaggagtc gggcccagga ctggtgaagc cttcggagac cctgtccctc        60
acctgcactg tctctggtga ctccatcagt agttactatt ggacctggat ccggcagccc       120
ccagggaagg gactggagtg gattgggtat atctttaca ggggggcac cacctacaac         180 ccctccctca agagtcgagt caccatatca gtagacacgt ccaagaacca gttctccctg       240
aagttgaggt ctgtgaccgc cgcagacacg gccgtgtatt actgtgcgag gggagacgat       300
```

```
cttttagtgg tgacaagtgt ctactggtac atcgatctct ggggccgtgg caccctggtc    360
accgtctcct ca                                                        372
```

<210> SEQ ID NO 2
<211> LENGTH: 124
<212> TYPE: PRT
<213> ORGANISM: Homo sapiens

<400> SEQUENCE: 2

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Thr Trp Ile Arg Gln Pro Pro Gly Lys Gly Leu Glu Trp Ile
        35                  40                  45

Gly Tyr Ile Phe Tyr Arg Gly Gly Thr Thr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Gly Asp Asp Leu Leu Val Val Thr Ser Val Tyr Trp Tyr Ile Asp
            100                 105                 110

Leu Trp Gly Arg Gly Thr Leu Val Thr Val Ser Ser
        115                 120
```

<210> SEQ ID NO 3
<211> LENGTH: 24
<212> TYPE: DNA
<213> ORGANISM: Homo sapiens

<400> SEQUENCE: 3

```
ggtgactcca tcagtagtta ctat                                            24
```

<210> SEQ ID NO 4
<211> LENGTH: 8
<212> TYPE: PRT
<213> ORGANISM: Homo sapiens

<400> SEQUENCE: 4

```
Gly Asp Ser Ile Ser Ser Tyr Tyr
1               5
```

<210> SEQ ID NO 5
<211> LENGTH: 21
<212> TYPE: DNA
<213> ORGANISM: Homo sapiens

<400> SEQUENCE: 5

```
atcttttaca gggggggcac c                                               21
```

<210> SEQ ID NO 6
<211> LENGTH: 7
<212> TYPE: PRT
<213> ORGANISM: Homo sapiens

<400> SEQUENCE: 6

```
Ile Phe Tyr Arg Gly Gly Thr
1               5
```

<210> SEQ ID NO 7
<211> LENGTH: 54
<212> TYPE: DNA
<213> ORGANISM: Homo sapiens

<400> SEQUENCE: 7
gcgaggggag acgatctttt agtggtgaca agtgtctact ggtacatcga tctc        54

<210> SEQ ID NO 8
<211> LENGTH: 18
<212> TYPE: PRT
<213> ORGANISM: Homo sapiens

<400> SEQUENCE: 8

Ala Arg Gly Asp Asp Leu Leu Val Val Thr Ser Val Tyr Trp Tyr Ile
1               5                   10                  15

Asp Leu

<210> SEQ ID NO 9
<211> LENGTH: 360
<212> TYPE: DNA
<213> ORGANISM: Homo sapiens

<400> SEQUENCE: 9
caggtgcagc tggtggagtc tgggggaggc gtggtccagc ctggggggtc cctgagactc        60
tcctgtgcag cgtccggatt caccttcagt ggctatggca tgcactgggt ccgccaggct       120
ccaggcaagg ggctggagtg gatggcagtt atatggtatg atggaagtaa tgattactat       180
ccagactccg tgaagggccg attcaccatc tccagagaca attccaagaa cacgctgtat       240
ctgcaaatga acagcctgag agtcgaggac acggctgtgt attactgtgc gcgagatgcg       300
tgggacctac tacgttcctt tgactactgg ggccaggaa ccctggtcac cgtctcctca       360

<210> SEQ ID NO 10
<211> LENGTH: 120
<212> TYPE: PRT
<213> ORGANISM: Homo sapiens

<400> SEQUENCE: 10

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Gly Tyr
                20                  25                  30

Gly Met His Trp Val Arg Gln Ala Pro Gly Lys Gly Leu Glu Trp Met
            35                  40                  45

Ala Val Ile Trp Tyr Asp Gly Ser Asn Asp Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Ala Trp Asp Leu Leu Arg Ser Phe Asp Tyr Trp Gly Gln
            100                 105                 110

Gly Thr Leu Val Thr Val Ser Ser
        115                 120

<210> SEQ ID NO 11
<211> LENGTH: 24
<212> TYPE: DNA

<213> ORGANISM: Homo sapiens

<400> SEQUENCE: 11
ggattcacct tcagtggcta tggc                                              24

<210> SEQ ID NO 12
<211> LENGTH: 8
<212> TYPE: PRT
<213> ORGANISM: Homo sapiens

<400> SEQUENCE: 12

Gly Phe Thr Phe Ser Gly Tyr Gly
1               5

<210> SEQ ID NO 13
<211> LENGTH: 24
<212> TYPE: DNA
<213> ORGANISM: Homo sapiens

<400> SEQUENCE: 13
atatggtatg atggaagtaa tgat                                              24

<210> SEQ ID NO 14
<211> LENGTH: 8
<212> TYPE: PRT
<213> ORGANISM: Homo sapiens

<400> SEQUENCE: 14

Ile Trp Tyr Asp Gly Ser Asn Asp
1               5

<210> SEQ ID NO 15
<211> LENGTH: 39
<212> TYPE: DNA
<213> ORGANISM: Homo sapiens

<400> SEQUENCE: 15
gcgcgagatg cgtgggacct actacgttcc tttgactac                              39

<210> SEQ ID NO 16
<211> LENGTH: 13
<212> TYPE: PRT
<213> ORGANISM: Homo sapiens

<400> SEQUENCE: 16

Ala Arg Asp Ala Trp Asp Leu Leu Arg Ser Phe Asp Tyr
1               5                   10

<210> SEQ ID NO 17
<211> LENGTH: 363
<212> TYPE: DNA
<213> ORGANISM: Homo sapiens

<400> SEQUENCE: 17
caggtgcagc tggtggagtc tgggggaggc gtggtccagc ctggggaggtc cctgagagtc       60 tcttgtgtag tgtctggatt caccttcagc agctttggca tgcattgggt ccgccaggct      120
ccagacaagg gctggagtg gtggcagtt atatggtatg atggaagtaa tgattactat        180
tcagactccg tgaagggccg attcaccatc tccagagaca attccaagaa cacgctgttt      240
ctacaaatga accgcctgag agccgaagac acggctgttt attactgtgc gcgagctaat     300
aactggaacc gttttgatgc ctttgatctc tggggccaag gacaatggt caccgtctct      360

```
tca                                                         363
```

```
<210> SEQ ID NO 18
<211> LENGTH: 121
<212> TYPE: PRT
<213> ORGANISM: Homo sapiens

<400> SEQUENCE: 18
```

Gln Val Gln Leu Val Glu Ser Gly Gly Val Val Gln Pro Gly Arg
1               5                   10                  15

Ser Leu Arg Val Ser Cys Val Val Ser Gly Phe Thr Phe Ser Ser Phe
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Asp Tyr Tyr Ser Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Arg Leu Arg Ala Glu Asp Thr Ala Val Tyr Tyr Cys
                85                  90                  95

Ala Arg Ala Asn Asn Trp Asn Arg Phe Asp Ala Phe Asp Leu Trp Gly
            100                 105                 110

Gln Gly Thr Met Val Thr Val Ser Ser
        115                 120

```
<210> SEQ ID NO 19
<211> LENGTH: 24
<212> TYPE: DNA
<213> ORGANISM: Homo sapiens

<400> SEQUENCE: 19
ggattcacct tcagcagctt tggc                                  24

<210> SEQ ID NO 20
<211> LENGTH: 8
<212> TYPE: PRT
<213> ORGANISM: Homo sapiens

<400> SEQUENCE: 20
```

Gly Phe Thr Phe Ser Ser Phe Gly
1               5

```
<210> SEQ ID NO 21
<211> LENGTH: 24
<212> TYPE: DNA
<213> ORGANISM: Homo sapiens

<400> SEQUENCE: 21
atatggtatg atggaagtaa tgat                                  24

<210> SEQ ID NO 22
<211> LENGTH: 8
<212> TYPE: PRT
<213> ORGANISM: Homo sapiens

<400> SEQUENCE: 22
```

Ile Trp Tyr Asp Gly Ser Asn Asp
1               5

```
<210> SEQ ID NO 23
<211> LENGTH: 42
```

```
<212> TYPE: DNA
<213> ORGANISM: Homo sapiens

<400> SEQUENCE: 23
gcgcgagcta ataactggaa ccgttttgat gcctttgatc tc                          42

<210> SEQ ID NO 24
<211> LENGTH: 14
<212> TYPE: PRT
<213> ORGANISM: Homo sapiens

<400> SEQUENCE: 24

Ala Arg Ala Asn Asn Trp Asn Arg Phe Asp Ala Phe Asp Leu
1               5                  10

<210> SEQ ID NO 25
<211> LENGTH: 372
<212> TYPE: DNA
<213> ORGANISM: Homo sapiens

<400> SEQUENCE: 25
gaggtgcagc tggtggagtc tgggggaggc ttggttcagc ctggagggtc cctgagactc        60
tcctgtgcag cctctggatt catcttcagt aattatgaaa tgaactgggt ccgccaggct       120
ccagggaagg gactggaatg gatttcatac attactagta gtggtaatat gaaatattac       180
gcagactctg tgaagggccg attcaccatc tccagagaca cgacaagaa ttcactgtat        240 ctgcaaatga gtagtctgag agtcgaggac acggctgttt attattgtgt gagaggaggg       300
cgatttttgg agtggttgac ctactacgtt atggtcgtct ggggccaagg gaccacggtc       360
accgtctcct ca                                                          372

<210> SEQ ID NO 26
<211> LENGTH: 124
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn Tyr
            20                  25                  30

Glu Met Asn Trp Val Arg Gln Ala Pro Gly Lys Gly Leu Glu Trp Ile
        35                  40                  45

Ser Tyr Ile Thr Ser Ser Gly Asn Met Lys Tyr Tyr Ala Asp Ser Val
    50                  55                  60

Lys Gly Arg Phe Thr Ile Ser Arg Asp Asn Asp Lys Asn Ser Leu Tyr
65                  70                  75                  80

Leu Gln Met Ser Ser Leu Arg Val Glu Asp Thr Ala Val Tyr Tyr Cys
                85                  90                  95

Val Arg Gly Gly Arg Phe Leu Glu Trp Leu Thr Tyr Tyr Val Met Val
            100                 105                 110

Val Trp Gly Gln Gly Thr Thr Val Thr Val Ser Ser
        115                 120

<210> SEQ ID NO 27
<211> LENGTH: 24
<212> TYPE: DNA
<213> ORGANISM: Homo sapiens

<400> SEQUENCE: 27
```

```
ggattcatct tcagtaatta tgaa                                              24
```

<210> SEQ ID NO 28
<211> LENGTH: 8
<212> TYPE: PRT
<213> ORGANISM: Homo sapiens

<400> SEQUENCE: 28

Gly Phe Ile Phe Ser Asn Tyr Glu
1               5

<210> SEQ ID NO 29
<211> LENGTH: 24
<212> TYPE: DNA
<213> ORGANISM: Homo sapiens

<400> SEQUENCE: 29

```
attactagta gtggtaatat gaaa                                              24
```

<210> SEQ ID NO 30
<211> LENGTH: 8
<212> TYPE: PRT
<213> ORGANISM: Homo sapiens

<400> SEQUENCE: 30

Ile Thr Ser Ser Gly Asn Met Lys
1               5

<210> SEQ ID NO 31
<211> LENGTH: 51
<212> TYPE: DNA
<213> ORGANISM: Homo sapiens

<400> SEQUENCE: 31

```
gtgagaggag ggcgattttt ggagtggttg acctactacg ttatggtcgt c                51
```

<210> SEQ ID NO 32
<211> LENGTH: 17
<212> TYPE: PRT
<213> ORGANISM: Homo sapiens

<400> SEQUENCE: 32

Val Arg Gly Gly Arg Phe Leu Glu Trp Leu Thr Tyr Tyr Val Met Val
1               5                   10                  15
Val

<210> SEQ ID NO 33
<211> LENGTH: 360
<212> TYPE: DNA
<213> ORGANISM: Homo sapiens

<400> SEQUENCE: 33

```
caggtgcagc tggtggagtc tgggggaggc gtggtccagc ctggggaggtc cctgagactc       60 tcctgtgcag tgtctggatt caccttcagt agctatggca tgcactgggt ccgccaggct      120
ccaggcaagg ggctggagtg gtggcaaat atttggtatg atggaactaa tgattactat       180
ccatactccg tgaagggccg attcaccatc tccagagaca attcccagaa cacactatat      240
ctgcaaatga acagcctgag agccgaggac acggctgtat attactgtgc gagagaggac      300
ttcattaact accggtcttt tgactattgg ggccagggaa ccctggtcac cgtctcctca      360
```

<210> SEQ ID NO 34
<211> LENGTH: 120
<212> TYPE: PRT
<213> ORGANISM: Homo sapiens

<400> SEQUENCE: 34

```
Gln Val Gln Leu Val Glu Ser Gly Gly Val Val Gln Pro Gly Arg
1               5                   10                  15

Ser Leu Arg Leu Ser Cys Ala Val Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Asn Ile Trp Tyr Asp Gly Thr Asn Asp Tyr Tyr Pro Tyr Ser Val
50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Phe Ile Asn Tyr Arg Ser Phe Asp Tyr Trp Gly Gln
            100                 105                 110

Gly Thr Leu Val Thr Val Ser Ser
        115                 120
```

<210> SEQ ID NO 35
<211> LENGTH: 24
<212> TYPE: DNA
<213> ORGANISM: Homo sapiens

<400> SEQUENCE: 35
ggattcacct tcagtagcta tggc                                          24

<210> SEQ ID NO 36
<211> LENGTH: 8
<212> TYPE: PRT
<213> ORGANISM: Homo sapiens

<400> SEQUENCE: 36

```
Gly Phe Thr Phe Ser Ser Tyr Gly
1               5
```

<210> SEQ ID NO 37
<211> LENGTH: 24
<212> TYPE: DNA
<213> ORGANISM: Homo sapiens

<400> SEQUENCE: 37
atttggtatg atggaactaa tgat                                          24

<210> SEQ ID NO 38
<211> LENGTH: 8
<212> TYPE: PRT
<213> ORGANISM: Homo sapiens

<400> SEQUENCE: 38

```
Ile Trp Tyr Asp Gly Thr Asn Asp
1               5
```

<210> SEQ ID NO 39
<211> LENGTH: 39
<212> TYPE: DNA
<213> ORGANISM: Homo sapiens

<400> SEQUENCE: 39

```
gcgagagagg acttcattaa ctaccggtct tttgactat                                 39
```

<210> SEQ ID NO 40
<211> LENGTH: 13
<212> TYPE: PRT
<213> ORGANISM: Homo sapiens

<400> SEQUENCE: 40

Ala Arg Glu Asp Phe Ile Asn Tyr Arg Ser Phe Asp Tyr
1               5                   10

<210> SEQ ID NO 41
<211> LENGTH: 372
<212> TYPE: DNA
<213> ORGANISM: Homo sapiens

<400> SEQUENCE: 41

```
caggtgcagc tggtggagtc tgggggaggc gtggtccagc cagggacgtc cctgagactc          60
tcctgtgtcg cgtctggatt caccttcaga aattttggaa tgcactgggt ccgccaggct         120
ccaggcaagg ggctggagtg gtggcaaat atatggtttg acggaagtaa tgagaactat          180
gtcgagtcca ttcagggccg attcaccatc tccagagaca attccaagaa cacactgaat         240
ctgcagatga acagcctgag agccgaggac tcggctgtct attactgtgt gagagaggga         300
atcctaggaa ctactaatcc ttatgatgct tttgatgtct ggggccaagg gacaatggtc         360
accgtctctt ca                                                              372
```

<210> SEQ ID NO 42
<211> LENGTH: 124
<212> TYPE: PRT
<213> ORGANISM: Homo sapiens

<400> SEQUENCE: 42

Gln Val Gln Leu Val Glu Ser Gly Gly Gly Val Gln Pro Gly Thr
1               5                   10                  15

Ser Leu Arg Leu Ser Cys Val Ala Ser Gly Phe Thr Phe Arg Asn Phe
            20                  25                  30

Gly Met His Trp Val Arg Gln Ala Pro Gly Lys Gly Leu Glu Trp Val
        35                  40                  45

Ala Asn Ile Trp Phe Asp Gly Ser Asn Glu Asn Tyr Val Glu Ser Ile
    50                  55                  60

Gln Gly Arg Phe Thr Ile Ser Arg Asp Asn Ser Lys Asn Thr Leu Asn
65                  70                  75                  80

Leu Gln Met Asn Ser Leu Arg Ala Glu Asp Ser Ala Val Tyr Tyr Cys
                85                  90                  95

Val Arg Glu Gly Ile Leu Gly Thr Thr Asn Pro Tyr Asp Ala Phe Asp
            100                 105                 110

Val Trp Gly Gln Gly Thr Met Val Thr Val Ser Ser
        115                 120

<210> SEQ ID NO 43
<211> LENGTH: 24
<212> TYPE: DNA
<213> ORGANISM: Homo sapiens

<400> SEQUENCE: 43

```
ggattcacct tcagaaattt tgga                                                 24
```

<210> SEQ ID NO 44
<211> LENGTH: 8
<212> TYPE: PRT
<213> ORGANISM: Homo sapiens

<400> SEQUENCE: 44

Gly Phe Thr Phe Arg Asn Phe Gly
1               5

<210> SEQ ID NO 45
<211> LENGTH: 24
<212> TYPE: DNA
<213> ORGANISM: Homo sapiens

<400> SEQUENCE: 45
atatggtttg acggaagtaa tgag                                          24

<210> SEQ ID NO 46
<211> LENGTH: 8
<212> TYPE: PRT
<213> ORGANISM: Homo sapiens

<400> SEQUENCE: 46

Ile Trp Phe Asp Gly Ser Asn Glu
1               5

<210> SEQ ID NO 47
<211> LENGTH: 51
<212> TYPE: DNA
<213> ORGANISM: Homo sapiens

<400> SEQUENCE: 47
gtgagagagg gaatcctagg aactactaat ccttatgatg cttttgatgt c            51

<210> SEQ ID NO 48
<211> LENGTH: 17
<212> TYPE: PRT
<213> ORGANISM: Homo sapiens

<400> SEQUENCE: 48

Val Arg Glu Gly Ile Leu Gly Thr Thr Asn Pro Tyr Asp Ala Phe Asp
1               5                   10                  15
Val

<210> SEQ ID NO 49
<211> LENGTH: 378
<212> TYPE: DNA
<213> ORGANISM: Homo sapiens

<400> SEQUENCE: 49
caggtgcagc tggtggagtc tgggggaggc gtggtccagc ctggaggtc cctgagactc    60 tcctgtgcag cgtctggatt cacctttagt aactttggaa tgcactgggt ccgccaggcg  120
ccaggcaagg gactggagtg gtggcaggt atatggtttg atggaagtaa taaaaactat  180
atagactccg tgaagggccg attcaccatc tcaagagaca attccaagaa cacgctgtat  240
ctgcaaatga acagcctgag agccgaggac acggctgtgt attactgtgc gagagagggc  300
tatgattcgg ggactgatta tatccccct gatattttg atatttgggg ccaagggaca  360
atggtcaccg tctcttca                                                378

<210> SEQ ID NO 50

```
<211> LENGTH: 126
<212> TYPE: PRT
<213> ORGANISM: Homo sapiens

<400> SEQUENCE: 50

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Gly Ile Trp Phe Asp Gly Ser Asn Lys Asn Tyr Ile Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Asp Ser Gly Thr Asp Tyr Ile Pro Tyr Asp Ile
            100                 105                 110

Phe Asp Ile Trp Gly Gln Gly Thr Met Val Thr Val Ser Ser
        115                 120                 125

<210> SEQ ID NO 51
<211> LENGTH: 24
<212> TYPE: DNA
<213> ORGANISM: Homo sapiens

<400> SEQUENCE: 51
ggattcacct ttagtaactt tgga                                          24

<210> SEQ ID NO 52
<211> LENGTH: 8
<212> TYPE: PRT
<213> ORGANISM: Homo sapiens

<400> SEQUENCE: 52

Gly Phe Thr Phe Ser Asn Phe Gly
1               5

<210> SEQ ID NO 53
<211> LENGTH: 24
<212> TYPE: DNA
<213> ORGANISM: Homo sapiens

<400> SEQUENCE: 53
atatggtttg atggaagtaa taaa                                          24

<210> SEQ ID NO 54
<211> LENGTH: 8
<212> TYPE: PRT
<213> ORGANISM: Homo sapiens

<400> SEQUENCE: 54

Ile Trp Phe Asp Gly Ser Asn Lys
1               5

<210> SEQ ID NO 55
<211> LENGTH: 57
<212> TYPE: DNA
<213> ORGANISM: Homo sapiens

<400> SEQUENCE: 55
```
gcgagagagg gctatgattc ggggactgat tatatcccct atgatatttt tgatatt        57

<210> SEQ ID NO 56
<211> LENGTH: 19
<212> TYPE: PRT
<213> ORGANISM: Homo sapiens

<400> SEQUENCE: 56

Ala Arg Glu Gly Tyr Asp Ser Gly Thr Asp Tyr Ile Pro Tyr Asp Ile
1               5                   10                  15

Phe Asp Ile

<210> SEQ ID NO 57
<211> LENGTH: 363
<212> TYPE: DNA
<213> ORGANISM: Homo sapiens

<400> SEQUENCE: 57
gaagtgcagc tggtggagtc tgggggaggc ttggtacagc ctggcacgtc cctgagactc        60
tcctgtgcag cctctggatt cacctttgat gattatgcca tgcactgggt ccggcaagct       120
ccagggaagg gcctggagtg gtctcaggt attacttgga atagttataa catagactat        180
gctgactctg tgaagggccg attcaccatc tccagagaca acgccaagaa ctccctgtat       240
ctgcaaatga acagtctgag agctgaggac acggccttgt attactgtgc aaaagatgat       300
gactacagta actacgttta ctttgactac tggggccagg aaccctggt caccgtctcc        360
tca                                                                      363

<210> SEQ ID NO 58
<211> LENGTH: 121
<212> TYPE: PRT
<213> ORGANISM: Homo sapiens

<400> SEQUENCE: 58

Glu Val Gln Leu Val Glu Ser Gly Gly Gly Leu Val Gln Pro Gly Thr
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Tyr Asn Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asp Asp Tyr Ser Asn Tyr Val Tyr Phe Asp Tyr Trp Gly
            100                 105                 110

Gln Gly Thr Leu Val Thr Val Ser Ser
        115                 120

<210> SEQ ID NO 59
<211> LENGTH: 24
<212> TYPE: DNA
<213> ORGANISM: Homo sapiens

<400> SEQUENCE: 59
ggattcacct ttgatgatta tgcc                                                24

<210> SEQ ID NO 60
<211> LENGTH: 8
<212> TYPE: PRT
<213> ORGANISM: Homo sapiens

<400> SEQUENCE: 60

Gly Phe Thr Phe Asp Asp Tyr Ala
1               5

<210> SEQ ID NO 61
<211> LENGTH: 24
<212> TYPE: DNA
<213> ORGANISM: Homo sapiens

<400> SEQUENCE: 61
attacttgga atagttataa cata                                              24

<210> SEQ ID NO 62
<211> LENGTH: 8
<212> TYPE: PRT
<213> ORGANISM: Homo sapiens

<400> SEQUENCE: 62

Ile Thr Trp Asn Ser Tyr Asn Ile
1               5

<210> SEQ ID NO 63
<211> LENGTH: 42
<212> TYPE: DNA
<213> ORGANISM: Homo sapiens

<400> SEQUENCE: 63
gcaaaagatg atgactacag taactacgtt tactttgact ac                          42

<210> SEQ ID NO 64
<211> LENGTH: 14
<212> TYPE: PRT
<213> ORGANISM: Homo sapiens

<400> SEQUENCE: 64

Ala Lys Asp Asp Asp Tyr Ser Asn Tyr Val Tyr Phe Asp Tyr
1               5                   10

<210> SEQ ID NO 65
<211> LENGTH: 360
<212> TYPE: DNA
<213> ORGANISM: Homo sapiens

<400> SEQUENCE: 65
caggttcagc tggtgcagtc cggaactgag gtgaaggagc tggggcctc agtgaaggtc         60 tcctgtaagg cctctggtta ctcctttacc acctatggta tcagctggct gcgacaggcc      120
cctggacaag gacttgagtg gatgggatgg atcagcactt acaatggtga cacaatctct      180
gcacagatgc tccaggacag agtcaccctg accgcagaca catccacgcg cacagcctac      240
atggaactga aagcctgag atctgacgac acggccgtgt attactgtgc gagaggtcat      300
gagtatgata gtcttgttta ttcttactgg ggccagggaa ccctggtcac cgtctcctca      360

<210> SEQ ID NO 66
<211> LENGTH: 120
<212> TYPE: PRT
<213> ORGANISM: Homo sapiens

<400> SEQUENCE: 66

Gln Val Gln Leu Val Gln Ser Gly Thr Glu Val Lys Glu Pro Gly Ala
1               5                   10                  15

Ser Val Lys Val Ser Cys Lys Ala Ser Gly Tyr Ser Phe Thr Thr Tyr
            20                  25                  30

Gly Ile Ser Trp Leu Arg Gln Ala Pro Gly Gln Gly Leu Glu Trp Met
        35                  40                  45

Gly Trp Ile Ser Thr Tyr Asn Gly Asp Thr Ile Ser Ala Gln Met Leu
    50                  55                  60

Gln Asp Arg Val Thr Leu Thr Ala Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Gly His Glu Tyr Asp Ser Leu Val Tyr Ser Tyr Trp Gly Gln
            100                 105                 110

Gly Thr Leu Val Thr Val Ser Ser
        115                 120

<210> SEQ ID NO 67
<211> LENGTH: 24
<212> TYPE: DNA
<213> ORGANISM: Homo sapiens

<400> SEQUENCE: 67
ggttactcct ttaccaccta tggt                                         24

<210> SEQ ID NO 68
<211> LENGTH: 8
<212> TYPE: PRT
<213> ORGANISM: Homo sapiens

<400> SEQUENCE: 68

Gly Tyr Ser Phe Thr Thr Tyr Gly
1               5

<210> SEQ ID NO 69
<211> LENGTH: 24
<212> TYPE: DNA
<213> ORGANISM: Homo sapiens

<400> SEQUENCE: 69
atcagcactt acaatggtga caca                                         24

<210> SEQ ID NO 70
<211> LENGTH: 8
<212> TYPE: PRT
<213> ORGANISM: Homo sapiens

<400> SEQUENCE: 70

Ile Ser Thr Tyr Asn Gly Asp Thr
1               5

<210> SEQ ID NO 71
<211> LENGTH: 39
<212> TYPE: DNA
<213> ORGANISM: Homo sapiens

<400> SEQUENCE: 71
gcgagaggtc atgagtatga tagtcttgtt tattcttac                         39

<210> SEQ ID NO 72
<211> LENGTH: 13
<212> TYPE: PRT
<213> ORGANISM: Homo sapiens

<400> SEQUENCE: 72

Ala Arg Gly His Glu Tyr Asp Ser Leu Val Tyr Ser Tyr
1               5                   10

<210> SEQ ID NO 73
<211> LENGTH: 360
<212> TYPE: DNA
<213> ORGANISM: Homo sapiens

<400> SEQUENCE: 73
caggtgcagc tggtggagtc tgggggaggc gtggtccagc ctggggaggtc cctgagactc      60 tcctgtgcag cgtctggatt caccttcagt agttatgcca tgcactgggt ccgccaggct     120
ccaggcaggg ggctggagtg ggtggcggtt atatggcatg atggagatgt tgaatactat     180
gtagactccg tgaaggaccg attcaccatc tccagagaca attccaagag cacgctgtat     240
ctgcaaatga acagcctgag agccgaagat acggctttat attattgtgc gagagaggcg     300
tgggacctac tacgtccctt tgactattgg ggccaggaa ccctggtcac cgtctcctca      360

<210> SEQ ID NO 74
<211> LENGTH: 120
<212> TYPE: PRT
<213> ORGANISM: Homo sapiens

<400> SEQUENCE: 74

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Arg Gly Leu Glu Trp Val
        35                  40                  45

Ala Val Ile Trp His Asp Gly Asp Val Glu Tyr Tyr Val Asp Ser Val
    50                  55                  60

Lys Asp Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Leu Tyr Tyr Cys
                85                  90                  95

Ala Arg Glu Ala Trp Asp Leu Leu Arg Pro Phe Asp Tyr Trp Gly Gln
            100                 105                 110

Gly Thr Leu Val Thr Val Ser Ser
        115                 120

<210> SEQ ID NO 75
<211> LENGTH: 24
<212> TYPE: DNA
<213> ORGANISM: Homo sapiens

<400> SEQUENCE: 75
ggattcacct tcagtagtta tgcc                                              24

<210> SEQ ID NO 76
<211> LENGTH: 8
<212> TYPE: PRT
<213> ORGANISM: Homo sapiens

```
<400> SEQUENCE: 76

Gly Phe Thr Phe Ser Ser Tyr Ala
1               5

<210> SEQ ID NO 77
<211> LENGTH: 24
<212> TYPE: DNA
<213> ORGANISM: Homo sapiens

<400> SEQUENCE: 77
atatggcatg atggagatgt tgaa                                            24

<210> SEQ ID NO 78
<211> LENGTH: 8
<212> TYPE: PRT
<213> ORGANISM: Homo sapiens

<400> SEQUENCE: 78

Ile Trp His Asp Gly Asp Val Glu
1               5

<210> SEQ ID NO 79
<211> LENGTH: 39
<212> TYPE: DNA
<213> ORGANISM: Homo sapiens

<400> SEQUENCE: 79
gcgagagagg cgtgggacct actacgtccc tttgactat                            39

<210> SEQ ID NO 80
<211> LENGTH: 13
<212> TYPE: PRT
<213> ORGANISM: Homo sapiens

<400> SEQUENCE: 80

Ala Arg Glu Ala Trp Asp Leu Leu Arg Pro Phe Asp Tyr
1               5                   10

<210> SEQ ID NO 81
<211> LENGTH: 351
<212> TYPE: DNA
<213> ORGANISM: Homo sapiens

<400> SEQUENCE: 81
gaggtgcagc tggtggagtc tggaggaggc ttggtccagc ctgggggtc  cctgagactc      60 tcctgtgcag cctctgggtt catcgtcacc accaactaca tgacctggct ccgccaggct    120
ccagggaagg ggctggagtg ggtctcactt atttatagca gtggtcacac atactacgca    180
gactccgtga agggccgatt caccatctcc agacacaatt ccaagaacac actgtatcta    240
caaatggaca gcctgagagc tgaggacacg gccgtgtatt actgtgcgag tgctttcgca    300
gcggatgttt ttgatatctg gggccaaggg acaatggtca ccgtctcttc a             351

<210> SEQ ID NO 82
<211> LENGTH: 117
<212> TYPE: PRT
<213> ORGANISM: Homo sapiens

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Val Thr Thr Asn
```

```
                 20                  25                  30
Tyr Met Thr Trp Leu Arg Gln Ala Pro Gly Lys Gly Leu Glu Trp Val
             35                  40                  45

Ser Leu Ile Tyr Ser Ser Gly His Thr Tyr Tyr Ala Asp Ser Val Lys
 50                  55                  60

Gly Arg Phe Thr Ile Ser Arg His Asn Ser Lys Asn Thr Leu Tyr Leu
 65                  70                  75                  80

Gln Met Asp Ser Leu Arg Ala Glu Asp Thr Ala Val Tyr Tyr Cys Ala
                 85                  90                  95

Ser Ala Phe Ala Ala Asp Val Phe Asp Ile Trp Gly Gln Gly Thr Met
             100                 105                 110

Val Thr Val Ser Ser
        115

<210> SEQ ID NO 83
<211> LENGTH: 24
<212> TYPE: DNA
<213> ORGANISM: Homo sapiens

<400> SEQUENCE: 83
gggttcatcg tcaccaccaa ctac                                            24

<210> SEQ ID NO 84
<211> LENGTH: 8
<212> TYPE: PRT
<213> ORGANISM: Homo sapiens

<400> SEQUENCE: 84

Gly Phe Ile Val Thr Thr Asn Tyr
 1               5

<210> SEQ ID NO 85
<211> LENGTH: 21
<212> TYPE: DNA
<213> ORGANISM: Homo sapiens

<400> SEQUENCE: 85
atttatagca gtggtcacac a                                               21

<210> SEQ ID NO 86
<211> LENGTH: 7
<212> TYPE: PRT
<213> ORGANISM: Homo sapiens

<400> SEQUENCE: 86

Ile Tyr Ser Ser Gly His Thr
 1               5

<210> SEQ ID NO 87
<211> LENGTH: 33
<212> TYPE: DNA
<213> ORGANISM: Homo sapiens

<400> SEQUENCE: 87
gcgagtgctt tcgcagcgga tgtttttgat atc                                  33

<210> SEQ ID NO 88
<211> LENGTH: 11
<212> TYPE: PRT
<213> ORGANISM: Homo sapiens

<400> SEQUENCE: 88
```

Ala Ser Ala Phe Ala Ala Asp Val Phe Asp Ile
1               5                   10

<210> SEQ ID NO 89
<211> LENGTH: 372
<212> TYPE: DNA
<213> ORGANISM: Homo sapiens

<400> SEQUENCE: 89

```
caggtgcagc tggtggagtc tgggggaggc gtggtccagc ctggagggtc cctgagactc    60
tcctgttcag cgtctggatt ctccttcagt cactttggca tgcactgggt ccgccaggtt   120
ccaggcgggg gcctggagtg ggtgacaagt atatggtttg atggaagtaa tagatattat   180
gcagactcct tgaagggccg attcaccatc tccagagaca attccaagaa tactctgtat   240
ctggaaatga acagcctgag agccgaggac acggctgtgt attactgtgt gagagagggg   300
atactgggaa ctactaatcc ttatgatgtt tttgatgtct ggggtcaggg gacaatggtc   360
accgtctctt ca                                                       372
```

<210> SEQ ID NO 90
<211> LENGTH: 124
<212> TYPE: PRT
<213> ORGANISM: Homo sapiens

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ser Ala Ser Gly Phe Ser Phe Ser His Phe
            20                  25                  30

Gly Met His Trp Val Arg Gln Val Pro Gly Gly Gly Leu Glu Trp Val
        35                  40                  45

Thr Ser Ile Trp Phe Asp Gly Ser Asn Arg Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Val Arg Glu Gly Ile Leu Gly Thr Thr Asn Pro Tyr Asp Val Phe Asp
            100                 105                 110

Val Trp Gly Gln Gly Thr Met Val Thr Val Ser Ser
        115                 120

<210> SEQ ID NO 91
<211> LENGTH: 24
<212> TYPE: DNA
<213> ORGANISM: Homo sapiens

<400> SEQUENCE: 91

```
ggattctcct tcagtcactt tggc                                           24
```

<210> SEQ ID NO 92
<211> LENGTH: 8
<212> TYPE: PRT
<213> ORGANISM: Homo sapiens

<400> SEQUENCE: 92

Gly Phe Ser Phe Ser His Phe Gly
1               5

<210> SEQ ID NO 93
<211> LENGTH: 24
<212> TYPE: DNA
<213> ORGANISM: Homo sapiens

<400> SEQUENCE: 93
atatggtttg atggaagtaa taga                                           24

<210> SEQ ID NO 94
<211> LENGTH: 8
<212> TYPE: PRT
<213> ORGANISM: Homo sapiens

<400> SEQUENCE: 94

Ile Trp Phe Asp Gly Ser Asn Arg
1               5

<210> SEQ ID NO 95
<211> LENGTH: 51
<212> TYPE: DNA
<213> ORGANISM: Homo sapiens

<400> SEQUENCE: 95
gtgagagagg ggatactggg aactactaat ccttatgatg ttttgatgt c              51

<210> SEQ ID NO 96
<211> LENGTH: 17
<212> TYPE: PRT
<213> ORGANISM: Homo sapiens

<400> SEQUENCE: 96

Val Arg Glu Gly Ile Leu Gly Thr Thr Asn Pro Tyr Asp Val Phe Asp
1               5                   10                  15

Val

<210> SEQ ID NO 97
<211> LENGTH: 372
<212> TYPE: DNA
<213> ORGANISM: Homo sapiens

<400> SEQUENCE: 97
gaggtgcagc tggtggagtc tgggggaggc ttggtacagc cgggggggtc cctgagactc    60
tcctgtgcag cctctggatt cacctttaga agctatgtca tgagctggtt ccgccaggct   120
ccagggaagg ggctggagtg ggtctcagga atgagtggga gtggtggaag cacatcctac   180
gcagactccg tgaagggccg gttcaccatc tccagagaca attcaaagaa tacgctgtat   240
ctgctaatga acagcctgag aaccgaggac acggccgtat attattgtgc gaaagaaaac   300
ggggctaact ggaactacgg ctactacggt atggacgtct ggggccaagg gaccacggtc   360
accgtctcct ca                                                      372

<210> SEQ ID NO 98
<211> LENGTH: 124
<212> TYPE: PRT
<213> ORGANISM: Homo sapiens

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

```
Val Met Ser Trp Phe Arg Gln Ala Pro Gly Lys Gly Leu Glu Trp Val
        35                  40                  45
Ser Gly Met Ser Gly Ser Gly Gly Ser Thr Ser Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Leu Met Asn Ser Leu Arg Thr Glu Asp Thr Ala Val Tyr Tyr Cys
                 85                  90                  95
Ala Lys Glu Asn Gly Ala Asn Trp Asn Tyr Gly Tyr Tyr Gly Met Asp
            100                 105                 110
Val Trp Gly Gln Gly Thr Thr Val Thr Val Ser Ser
            115                 120
```

<210> SEQ ID NO 99
<211> LENGTH: 24
<212> TYPE: DNA
<213> ORGANISM: Homo sapiens

<400> SEQUENCE: 99
ggattcacct ttagaagcta tgtc                                          24

<210> SEQ ID NO 100
<211> LENGTH: 8
<212> TYPE: PRT
<213> ORGANISM: Homo sapiens

<400> SEQUENCE: 100

```
Gly Phe Thr Phe Arg Ser Tyr Val
 1               5
```

<210> SEQ ID NO 101
<211> LENGTH: 24
<212> TYPE: DNA
<213> ORGANISM: Homo sapiens

<400> SEQUENCE: 101
atgagtggga gtggtggaag caca                                          24

<210> SEQ ID NO 102
<211> LENGTH: 8
<212> TYPE: PRT
<213> ORGANISM: Homo sapiens

<400> SEQUENCE: 102

```
Met Ser Gly Ser Gly Gly Ser Thr
 1               5
```

<210> SEQ ID NO 103
<211> LENGTH: 51
<212> TYPE: DNA
<213> ORGANISM: Homo sapiens

<400> SEQUENCE: 103
gcgaaagaaa acggggctaa ctggaactac ggctactacg gtatggacgt c            51

<210> SEQ ID NO 104
<211> LENGTH: 17
<212> TYPE: PRT
<213> ORGANISM: Homo sapiens

<400> SEQUENCE: 104

Ala Lys Glu Asn Gly Ala Asn Trp Asn Tyr Gly Tyr Tyr Gly Met Asp
1               5                   10                  15

Val

<210> SEQ ID NO 105
<211> LENGTH: 360
<212> TYPE: DNA
<213> ORGANISM: Homo sapiens

<400> SEQUENCE: 105
caggtgcagc tggtggagtc tgggggaggc gtggtccagc ctggagggtc cctgagactc      60
tcctgtgtag cgtctggatt ctccttcagt aactttggca tgcactgggt ccgccaggct     120
ccaggcaagg ggctggagtg ggtggcaatt atatggtatg atggaagtaa taaatactat     180
tcagactccg tgaagggccg cttcaccatc tccagagaca attccaagaa cacgctgtat     240
ctgcaaatga acagcctgag agtcgacgac acggctgtgt attactgtgc gagattcgat     300
cgctggaaat ttgacgcttt tgatatctgg ggccaaggga caatggtcac cgtctcttca     360

<210> SEQ ID NO 106
<211> LENGTH: 120
<212> TYPE: PRT
<213> ORGANISM: Homo sapiens

<400> SEQUENCE: 106

Gln Val Gln Leu Val Glu Ser Gly Gly Gly Val Val Gln Pro Gly Arg
1               5                   10                  15

Ser Leu Arg Leu Ser Cys Val Ala Ser Gly Phe Ser Phe Ser Asn Phe
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Asp Asp Thr Ala Val Tyr Tyr Cys
                85                  90                  95

Ala Arg Phe Asp Arg Trp Lys Phe Asp Ala Phe Asp Ile Trp Gly Gln
            100                 105                 110

Gly Thr Met Val Thr Val Ser Ser
        115                 120

<210> SEQ ID NO 107
<211> LENGTH: 24
<212> TYPE: DNA
<213> ORGANISM: Homo sapiens

<400> SEQUENCE: 107
ggattctcct tcagtaactt tggc      24

<210> SEQ ID NO 108
<211> LENGTH: 8
<212> TYPE: PRT
<213> ORGANISM: Homo sapiens

<400> SEQUENCE: 108

Gly Phe Ser Phe Ser Asn Phe Gly
1               5

-continued

<210> SEQ ID NO 109
<211> LENGTH: 24
<212> TYPE: DNA
<213> ORGANISM: Homo sapiens

<400> SEQUENCE: 109
atatggtatg atggaagtaa taaa                                          24

<210> SEQ ID NO 110
<211> LENGTH: 8
<212> TYPE: PRT
<213> ORGANISM: Homo sapiens

<400> SEQUENCE: 110

Ile Trp Tyr Asp Gly Ser Asn Lys
1               5

<210> SEQ ID NO 111
<211> LENGTH: 39
<212> TYPE: DNA
<213> ORGANISM: Homo sapiens

<400> SEQUENCE: 111
gcgagattcg atcgctggaa atttgacgct tttgatatc                          39

<210> SEQ ID NO 112
<211> LENGTH: 13
<212> TYPE: PRT
<213> ORGANISM: Homo sapiens

<400> SEQUENCE: 112

Ala Arg Phe Asp Arg Trp Lys Phe Asp Ala Phe Asp Ile
1               5                   10

<210> SEQ ID NO 113
<211> LENGTH: 360
<212> TYPE: DNA
<213> ORGANISM: Homo sapiens

<400> SEQUENCE: 113
caggtgcagc tggtggagtc tgggggaggc gtggtccagc ctggggaggtc cctgagactc      60 tcctgtgcag cgtctggatt caccttcagt agctttgcca tgcactgggt ccgccaggct     120
ccaggcaagg ggctgagtg gtggcagtt atatggtatg atggaagtaa tgattactat      180
gcagcctccg tgaagggccg tttcaccatc tccagagaca attccaagaa cacgctgtat     240
ctggaaatga acagactgag agccgaggac acggctgtgt atcactgtgc gagagataac     300
tggaattact ggggggggtat ggacgtctgg ggccaaggga ccacggtcac cgtctcctca     360

<210> SEQ ID NO 114
<211> LENGTH: 120
<212> TYPE: PRT
<213> ORGANISM: Homo sapiens

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Ala Met His Trp Val Arg Gln Ala Pro Gly Lys Gly Leu Glu Trp Val
        35                  40                  45

Ala Val Ile Trp Tyr Asp Gly Ser Asn Asp Tyr Tyr Ala Ala Ser Val

```
                    50                  55                  60

Lys Gly Arg Phe Thr Ile Ser Arg Asp Asn Ser Lys Asn Thr Leu Tyr
 65                  70                  75                  80

Leu Glu Met Asn Arg Leu Arg Ala Glu Asp Thr Ala Val Tyr His Cys
                 85                  90                  95

Ala Arg Asp Asn Trp Asn Tyr Trp Gly Gly Met Asp Val Trp Gly Gln
            100                 105                 110

Gly Thr Thr Val Thr Val Ser Ser
        115                 120

<210> SEQ ID NO 115
<211> LENGTH: 24
<212> TYPE: DNA
<213> ORGANISM: Homo sapiens

<400> SEQUENCE: 115
ggattcacct tcagtagctt tgcc                                          24

<210> SEQ ID NO 116
<211> LENGTH: 8
<212> TYPE: PRT
<213> ORGANISM: Homo sapiens

<400> SEQUENCE: 116

Gly Phe Thr Phe Ser Ser Phe Ala
 1               5

<210> SEQ ID NO 117
<211> LENGTH: 24
<212> TYPE: DNA
<213> ORGANISM: Homo sapiens

<400> SEQUENCE: 117
atatggtatg atggaagtaa tgat                                          24

<210> SEQ ID NO 118
<211> LENGTH: 8
<212> TYPE: PRT
<213> ORGANISM: Homo sapiens

<400> SEQUENCE: 118

Ile Trp Tyr Asp Gly Ser Asn Asp
 1               5

<210> SEQ ID NO 119
<211> LENGTH: 39
<212> TYPE: DNA
<213> ORGANISM: Homo sapiens

<400> SEQUENCE: 119
gcgagagata actggaatta ctggggggt atggacgtc                           39

<210> SEQ ID NO 120
<211> LENGTH: 13
<212> TYPE: PRT
<213> ORGANISM: Homo sapiens

<400> SEQUENCE: 120

Ala Arg Asp Asn Trp Asn Tyr Trp Gly Gly Met Asp Val
 1               5                  10

<210> SEQ ID NO 121
```

-continued

```
<211> LENGTH: 375
<212> TYPE: DNA
<213> ORGANISM: Homo sapiens

<400> SEQUENCE: 121
gaggtgcagc tgttggagtc tgggggaggc tgggtgcagc cggggggtc cctgagactc      60 tcctgtgcag cctctggatt cgcctttagt aattatgcca tgaactgggt ccgccagact    120
ccagggaagg gctggagtg gtctcagtt attagtagta gtggtggaaa cacatactac     180
gcagactccg tgaagggccg gttcgccatc tccagagaca attccaggga tacgctgcat    240
ctgcaaatga acagactgag agtcgaggac acggccgtct attactgtgc gaaagaaata    300
cgtccgtatt acgatctttc ctactattac ggtatggacg tctggggcca agggaccacg    360
gtcaccgtct cctca                                                     375

<210> SEQ ID NO 122
<211> LENGTH: 125
<212> TYPE: PRT
<213> ORGANISM: Homo sapiens

<400> SEQUENCE: 122

Glu Val Gln Leu Leu Glu Ser Gly Gly Gly Trp Val Gln Pro Gly Gly
1               5                   10                  15

Ser Leu Arg Leu Ser Cys Ala Ala Ser Gly Phe Ala Phe Ser Asn Tyr
            20                  25                  30

Ala Met Asn Trp Val Arg Gln Thr Pro Gly Lys Gly Leu Glu Trp Val
        35                  40                  45

Ser Val Ile Ser Ser Ser Gly Gly Asn Thr Tyr Tyr Ala Asp Ser Val
    50                  55                  60

Lys Gly Arg Phe Ala Ile Ser Arg Asp Asn Ser Arg Asp Thr Leu His
65                  70                  75                  80

Leu Gln Met Asn Arg Leu Arg Val Glu Asp Thr Ala Val Tyr Tyr Cys
                85                  90                  95

Ala Lys Glu Ile Arg Pro Tyr Tyr Asp Leu Ser Tyr Tyr Tyr Gly Met
            100                 105                 110

Asp Val Trp Gly Gln Gly Thr Thr Val Thr Val Ser Ser
        115                 120                 125

<210> SEQ ID NO 123
<211> LENGTH: 24
<212> TYPE: DNA
<213> ORGANISM: Homo sapiens

<400> SEQUENCE: 123
ggattcgcct ttagtaatta tgcc                                            24

<210> SEQ ID NO 124
<211> LENGTH: 8
<212> TYPE: PRT
<213> ORGANISM: Homo sapiens

<400> SEQUENCE: 124

Gly Phe Ala Phe Ser Asn Tyr Ala
1               5

<210> SEQ ID NO 125
<211> LENGTH: 24
<212> TYPE: DNA
<213> ORGANISM: Homo sapiens
```

```
<400> SEQUENCE: 125
attagtagta gtggtggaaa caca                                             24

<210> SEQ ID NO 126
<211> LENGTH: 8
<212> TYPE: PRT
<213> ORGANISM: Homo sapiens

<400> SEQUENCE: 126

Ile Ser Ser Ser Gly Gly Asn Thr
1               5

<210> SEQ ID NO 127
<211> LENGTH: 54
<212> TYPE: DNA
<213> ORGANISM: Homo sapiens

<400> SEQUENCE: 127
gcgaaagaaa tacgtccgta ttacgatctt tcctactatt acggtatgga cgtc           54

<210> SEQ ID NO 128
<211> LENGTH: 18
<212> TYPE: PRT
<213> ORGANISM: Homo sapiens

<400> SEQUENCE: 128

Ala Lys Glu Ile Arg Pro Tyr Tyr Asp Leu Ser Tyr Tyr Tyr Gly Met
1               5                   10                  15

Asp Val

<210> SEQ ID NO 129
<211> LENGTH: 348
<212> TYPE: DNA
<213> ORGANISM: Homo sapiens

<400> SEQUENCE: 129
caggtgcagc tgcaggagtc gggcccagga ctggtgaagt cttcggagac cctgtccctc     60
acctgcactg tctctggtgg ctccatcaga aatttctact ggagctggct ccggcagccc   120
ccagggaagg gactagagtg gattgggcac atcaattaca tgggggcac cgactacaac    180 ccctccctca agagtcgagt caccatatca gtagacacgt ccaagaatca gttctccctg   240
aatttgaact ctgtgaccgc cgcagacacg gccgtgtatt actgtgcgag acagagattc   300
tacggtatgg acgtctgggg tccagggacc acggtcaccg tctcctca                348

<210> SEQ ID NO 130
<211> LENGTH: 116
<212> TYPE: PRT
<213> ORGANISM: Homo sapiens

<400> SEQUENCE: 130

Gln Val Gln Leu Gln Glu Ser Gly Pro Gly Leu Val Lys Ser Ser Glu
1               5                   10                  15

Thr Leu Ser Leu Thr Cys Thr Val Ser Gly Gly Ser Ile Arg Asn Phe
            20                  25                  30

Tyr Trp Ser Trp Leu Arg Gln Pro Pro Gly Lys Gly Leu Glu Trp Ile
        35                  40                  45

Gly His Ile Asn Tyr Asn Gly Gly Thr Asp Tyr Asn Pro Ser Leu Lys
    50                  55                  60

Ser Arg Val Thr Ile Ser Val Asp Thr Ser Lys Asn Gln Phe Ser Leu
```

```
                65                  70                  75                  80
Asn Leu Asn Ser Val Thr Ala Ala Asp Thr Ala Val Tyr Tyr Cys Ala
                    85                  90                  95

Arg Gln Arg Phe Tyr Gly Met Asp Val Trp Gly Pro Gly Thr Thr Val
            100                 105                 110

Thr Val Ser Ser
        115
```

<210> SEQ ID NO 131
<211> LENGTH: 24
<212> TYPE: DNA
<213> ORGANISM: Homo sapiens

<400> SEQUENCE: 131
ggtggctcca tcagaaattt ctac                                          24

<210> SEQ ID NO 132
<211> LENGTH: 8
<212> TYPE: PRT
<213> ORGANISM: Homo sapiens

<400> SEQUENCE: 132

Gly Gly Ser Ile Arg Asn Phe Tyr
1               5

<210> SEQ ID NO 133
<211> LENGTH: 21
<212> TYPE: DNA
<213> ORGANISM: Homo sapiens

<400> SEQUENCE: 133
atcaattaca atgggggcac c                                             21

<210> SEQ ID NO 134
<211> LENGTH: 7
<212> TYPE: PRT
<213> ORGANISM: Homo sapiens

<400> SEQUENCE: 134

Ile Asn Tyr Asn Gly Gly Thr
1               5

<210> SEQ ID NO 135
<211> LENGTH: 30
<212> TYPE: DNA
<213> ORGANISM: Homo sapiens

<400> SEQUENCE: 135
gcgagacaga gattctacgg tatggacgtc                                    30

<210> SEQ ID NO 136
<211> LENGTH: 10
<212> TYPE: PRT
<213> ORGANISM: Homo sapiens

<400> SEQUENCE: 136

Ala Arg Gln Arg Phe Tyr Gly Met Asp Val
1               5                   10

<210> SEQ ID NO 137
<211> LENGTH: 324
<212> TYPE: DNA
<213> ORGANISM: Homo sapiens

<400> SEQUENCE: 137

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 138
<211> LENGTH: 108
<212> TYPE: PRT
<213> ORGANISM: Homo sapiens

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 139
<211> LENGTH: 18
<212> TYPE: DNA
<213> ORGANISM: Homo sapiens

<400> SEQUENCE: 139

```
cagagcatta gcagctat                                                  18
```

<210> SEQ ID NO 140
<211> LENGTH: 6
<212> TYPE: PRT
<213> ORGANISM: Homo sapiens

<400> SEQUENCE: 140

Gln Ser Ile Ser Ser Tyr
1               5

<210> SEQ ID NO 141
<211> LENGTH: 9
<212> TYPE: DNA
<213> ORGANISM: Homo sapiens

<400> SEQUENCE: 141

```
gctgcatcc                                                             9
```

<210> SEQ ID NO 142
<211> LENGTH: 3
<212> TYPE: PRT

<213> ORGANISM: Homo sapiens

<400> SEQUENCE: 142

Ala Ala Ser
1

<210> SEQ ID NO 143
<211> LENGTH: 30
<212> TYPE: DNA
<213> ORGANISM: Homo sapiens

<400> SEQUENCE: 143
caacagagtt acagtacccc tccgatcacc                                      30

<210> SEQ ID NO 144
<211> LENGTH: 10
<212> TYPE: PRT
<213> ORGANISM: Homo sapiens

<400> SEQUENCE: 144

Gln Gln Ser Tyr Ser Thr Pro Pro Ile Thr
1               5                   10

<210> SEQ ID NO 145
<211> LENGTH: 1408
<212> TYPE: PRT
<213> ORGANISM: Homo sapiens

<400> SEQUENCE: 145

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu

-continued

```
               225                 230                 235                 240

Phe Arg Asp Ser Tyr Pro Ile Lys Tyr Val His Ala Phe Glu Ser Asn
                        245                 250                 255

Asn Phe Ile Tyr Phe Leu Thr Val Gln Arg Glu Thr Leu Asp Ala Gln
                    260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
        305                 310                 315                 320

Tyr Val Ser Lys Pro Gly Ala Gln Leu Ala Arg Gln Ile Gly Ala Ser
                        325                 330                 335

Leu Asn Asp Asp Ile Leu Phe Gly Val Phe Ala Gln Ser Lys Pro Asp
                    340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Val Arg
                370                 375                 380

Cys Leu Gln His Phe Tyr Gly Pro Asn His Glu His Cys Phe Asn Arg
        385                 390                 395                 400

Thr Leu Leu Arg Asn Ser Ser Gly Cys Glu Ala Arg Arg Asp Glu Tyr
                        405                 410                 415

Arg Thr Glu Phe Thr Thr Ala Leu Gln Arg Val Asp Leu Phe Met Gly
                    420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
        465                 470                 475                 480

Leu Asp Ser His Pro Val Ser Pro Glu Val Ile Val Glu His Thr Leu
                        485                 490                 495

Asn Gln Asn Gly Tyr Thr Leu Val Ile Thr Gly Lys Lys Ile Thr Lys
                    500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
                530                 535                 540

Cys Val Arg Ser Glu Glu Cys Leu Ser Gly Thr Trp Thr Gln Gln Ile
        545                 550                 555                 560

Cys Leu Pro Ala Ile Tyr Lys Val Phe Pro Asn Ser Ala Pro Leu Glu
                        565                 570                 575

Gly Gly Thr Arg Leu Thr Ile Cys Gly Trp Asp Phe Gly Phe Arg Arg
                    580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
        625                 630                 635                 640

Ser Asn Gly His Gly Thr Thr Gln Tyr Ser Thr Phe Ser Tyr Val Asp
                        645                 650                 655
```

```
Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Thr Trp Lys Glu Pro Leu Asn Ile Val Ser Phe Leu
            755                 760                 765

Phe Cys Phe Ala Ser Gly Ser Thr Ile Thr Gly Val Gly Lys Asn
            770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
            805                 810                 815

Ile Cys Cys Thr Thr Pro Ser Leu Gln Gln Leu Asn Leu Gln Leu Pro
            820                 825                 830

Leu Lys Thr Lys Ala Phe Phe Met Leu Asp Gly Ile Leu Ser Lys Tyr
            835                 840                 845

Phe Asp Leu Ile Tyr Val His Asn Pro Val Phe Lys Pro Phe Glu Lys
850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
            900                 905                 910

Thr Val Pro Asn Asp Leu Leu Lys Leu Asn Ser Glu Leu Asn Ile Glu
            915                 920                 925

Trp Lys Gln Ala Ile Ser Ser Thr Val Leu Gly Lys Val Ile Val Gln
930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
            980                 985                 990

Val His Thr Pro His Leu Asp Arg Leu Val Ser Ala Arg Ser Val Ser
            995                 1000                1005

Pro Thr Thr Glu Met Val Ser Asn Glu Ser Val Asp Tyr Arg Ala
    1010                1015                1020

Thr Phe Pro Glu Asp Gln Phe Pro Asn Ser Ser Gln Asn Gly Ser
    1025                1030                1035

Cys Arg Gln Val Gln Tyr Pro Leu Thr Asp Met Ser Pro Ile Leu
    1040                1045                1050

Thr Ser Gly Asp Ser Asp Ile Ser Ser Pro Leu Leu Gln Asn Thr
    1055                1060                1065
```

| | | | | | | | | | | | |
|---|---|---|---|---|---|---|---|---|---|---|---|
|Val|His|Ile|Asp|Leu|Ser|Ala|Leu|Asn|Pro|Glu|Leu|Val|Gln|Ala|
|1070| | | | |1075| | | | |1080| | | | |

Val Gln His Val Val Ile Gly Pro Ser Ser Leu Ile Val His Phe
1085                1090                1095

Asn Glu Val Ile Gly Arg Gly His Phe Gly Cys Val Tyr His Gly
1100                1105                1110

Thr Leu Leu Asp Asn Asp Gly Lys Lys Ile His Cys Ala Val Lys
1115                1120                1125

Ser Leu Asn Arg Ile Thr Asp Ile Gly Glu Val Ser Gln Phe Leu
1130                1135                1140

Thr Glu Gly Ile Ile Met Lys Asp Phe Ser His Pro Asn Val Leu
1145                1150                1155

Ser Leu Leu Gly Ile Cys Leu Arg Ser Glu Gly Ser Pro Leu Val
1160                1165                1170

Val Leu Pro Tyr Met Lys His Gly Asp Leu Arg Asn Phe Ile Arg
1175                1180                1185

Asn Glu Thr His Asn Pro Thr Val Lys Asp Leu Ile Gly Phe Gly
1190                1195                1200

Leu Gln Val Ala Lys Gly Met Lys Tyr Leu Ala Ser Lys Lys Phe
1205                1210                1215

Val His Arg Asp Leu Ala Ala Arg Asn Cys Met Leu Asp Glu Lys
1220                1225                1230

Phe Thr Val Lys Val Ala Asp Phe Gly Leu Ala Arg Asp Met Tyr
1235                1240                1245

Asp Lys Glu Tyr Tyr Ser Val His Asn Lys Thr Gly Ala Lys Leu
1250                1255                1260

Pro Val Lys Trp Met Ala Leu Glu Ser Leu Gln Thr Gln Lys Phe
1265                1270                1275

Thr Thr Lys Ser Asp Val Trp Ser Phe Gly Val Leu Leu Trp Glu
1280                1285                1290

Leu Met Thr Arg Gly Ala Pro Pro Tyr Pro Asp Val Asn Thr Phe
1295                1300                1305

Asp Ile Thr Val Tyr Leu Leu Gln Gly Arg Arg Leu Leu Gln Pro
1310                1315                1320

Glu Tyr Cys Pro Asp Pro Leu Tyr Glu Val Met Leu Lys Cys Trp
1325                1330                1335

His Pro Lys Ala Glu Met Arg Pro Ser Phe Ser Glu Leu Val Ser
1340                1345                1350

Arg Ile Ser Ala Ile Phe Ser Thr Phe Ile Gly Glu His Tyr Val
1355                1360                1365

His Val Asn Ala Thr Tyr Val Asn Val Lys Cys Val Ala Pro Tyr
1370                1375                1380

Pro Ser Leu Leu Ser Ser Glu Asp Asn Ala Asp Asp Glu Val Asp
1385                1390                1395

Thr Arg Pro Ala Ser Phe Trp Glu Thr Ser
1400                1405

<210> SEQ ID NO 146
<211> LENGTH: 1390
<212> TYPE: PRT
<213> ORGANISM: Homo sapiens

<400> SEQUENCE: 146

Met Lys Ala Pro Ala Val Leu Ala Pro Gly Ile Leu Val Leu Leu Phe
1               5                   10                  15

-continued

```
Thr Leu Val Gln Arg Ser Asn Gly Glu Cys Lys Glu Ala Leu Ala Lys
             20                  25                  30

Ser Glu Met Asn Val Asn Met Lys Tyr Gln Leu Pro Asn Phe Thr Ala
         35                  40                  45

Glu Thr Pro Ile Gln Asn Val Ile Leu His Glu His Ile Phe Leu
 50                  55                  60

Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430
```

-continued

```
Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
```

-continued

```
            850                 855                 860
Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
                980                 985                 990

Thr Glu Met Val Ser Asn Glu Ser  Val Asp Tyr Arg Ala  Thr Phe Pro
            995                 1000                1005

Glu Asp Gln Phe Pro Asn Ser  Ser Gln Asn Gly Ser  Cys Arg Gln
        1010                1015                1020

Val Gln Tyr Pro Leu Thr Asp  Met Ser Pro Ile Leu  Thr Ser Gly
        1025                1030                1035

Asp Ser Asp Ile Ser Ser Pro  Leu Leu Gln Asn Thr  Val His Ile
        1040                1045                1050

Asp Leu Ser Ala Leu Asn Pro  Glu Leu Val Gln Ala  Val Gln His
        1055                1060                1065

Val Val Ile Gly Pro Ser Ser  Leu Ile Val His Phe  Asn Glu Val
        1070                1075                1080

Ile Gly Arg Gly His Phe Gly  Cys Val Tyr His Gly  Thr Leu Leu
        1085                1090                1095

Asp Asn Asp Gly Lys Lys Ile  His Cys Ala Val Lys  Ser Leu Asn
        1100                1105                1110

Arg Ile Thr Asp Ile Gly Glu  Val Ser Gln Phe Leu  Thr Glu Gly
        1115                1120                1125

Ile Ile Met Lys Asp Phe Ser  His Pro Asn Val Leu  Ser Leu Leu
        1130                1135                1140

Gly Ile Cys Leu Arg Ser Glu  Gly Ser Pro Leu Val  Val Leu Pro
        1145                1150                1155

Tyr Met Lys His Gly Asp Leu  Arg Asn Phe Ile Arg  Asn Glu Thr
        1160                1165                1170

His Asn Pro Thr Val Lys Asp  Leu Ile Gly Phe Gly  Leu Gln Val
        1175                1180                1185

Ala Lys Gly Met Lys Tyr Leu  Ala Ser Lys Lys Phe  Val His Arg
        1190                1195                1200

Asp Leu Ala Ala Arg Asn Cys  Met Leu Asp Glu Lys  Phe Thr Val
        1205                1210                1215

Lys Val Ala Asp Phe Gly Leu  Ala Arg Asp Met Tyr  Asp Lys Glu
        1220                1225                1230

Tyr Tyr Ser Val His Asn Lys  Thr Gly Ala Lys Leu  Pro Val Lys
        1235                1240                1245

Trp Met Ala Leu Glu Ser Leu  Gln Thr Gln Lys Phe  Thr Thr Lys
        1250                1255                1260
```

```
Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 147
<211> LENGTH: 934
<212> TYPE: PRT
<213> ORGANISM: Homo sapiens

<400> SEQUENCE: 147

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
```

```
                225                 230                 235                 240
        Phe Arg Asp Ser Tyr Pro Ile Lys Tyr Val His Ala Phe Glu Ser Asn
                        245                 250                 255
        Asn Phe Ile Tyr Phe Leu Thr Val Gln Arg Glu Thr Leu Asp Ala Gln
                        260                 265                 270
        Thr Phe His Thr Arg Ile Ile Arg Phe Cys Ser Ile Asn Ser Gly Leu
                        275                 280                 285
        His Ser Tyr Met Glu Met Pro Leu Glu Cys Ile Leu Thr Glu Lys Arg
                        290                 295                 300
        Lys Lys Arg Ser Thr Lys Lys Glu Val Phe Asn Ile Leu Gln Ala Ala
        305                 310                 315                 320
        Tyr Val Ser Lys Pro Gly Ala Gln Leu Ala Arg Gln Ile Gly Ala Ser
                        325                 330                 335
        Leu Asn Asp Asp Ile Leu Phe Gly Val Phe Ala Gln Ser Lys Pro Asp
                        340                 345                 350
        Ser Ala Glu Pro Met Asp Arg Ser Ala Met Cys Ala Phe Pro Ile Lys
                        355                 360                 365
        Tyr Val Asn Asp Phe Phe Asn Lys Ile Val Asn Lys Asn Asn Val Arg
                        370                 375                 380
        Cys Leu Gln His Phe Tyr Gly Pro Asn His Glu His Cys Phe Asn Arg
        385                 390                 395                 400
        Thr Leu Leu Arg Asn Ser Ser Gly Cys Glu Ala Arg Arg Asp Glu Tyr
                        405                 410                 415
        Arg Thr Glu Phe Thr Thr Ala Leu Gln Arg Val Asp Leu Phe Met Gly
                        420                 425                 430
        Gln Phe Ser Glu Val Leu Leu Thr Ser Ile Ser Thr Phe Ile Lys Gly
                        435                 440                 445
        Asp Leu Thr Ile Ala Asn Leu Gly Thr Ser Glu Gly Arg Phe Met Gln
                        450                 455                 460
        Val Val Val Ser Arg Ser Gly Pro Ser Thr Pro His Val Asn Phe Leu
        465                 470                 475                 480
        Leu Asp Ser His Pro Val Ser Pro Glu Val Ile Val Glu His Thr Leu
                        485                 490                 495
        Asn Gln Asn Gly Tyr Thr Leu Val Ile Thr Gly Lys Lys Ile Thr Lys
                        500                 505                 510
        Ile Pro Leu Asn Gly Leu Gly Cys Arg His Phe Gln Ser Cys Ser Gln
                        515                 520                 525
        Cys Leu Ser Ala Pro Pro Phe Val Gln Cys Gly Trp Cys His Asp Lys
                        530                 535                 540
        Cys Val Arg Ser Glu Glu Cys Leu Ser Gly Thr Trp Thr Gln Gln Ile
        545                 550                 555                 560
        Cys Leu Pro Ala Ile Tyr Lys Val Phe Pro Asn Ser Ala Pro Leu Glu
                        565                 570                 575
        Gly Gly Thr Arg Leu Thr Ile Cys Gly Trp Asp Phe Gly Phe Arg Arg
                        580                 585                 590
        Asn Asn Lys Phe Asp Leu Lys Lys Thr Arg Val Leu Leu Gly Asn Glu
                        595                 600                 605
        Ser Cys Thr Leu Thr Leu Ser Glu Ser Thr Met Asn Thr Leu Lys Cys
                        610                 615                 620
        Thr Val Gly Pro Ala Met Asn Lys His Phe Asn Met Ser Ile Ile Ile
        625                 630                 635                 640
        Ser Asn Gly His Gly Thr Thr Gln Tyr Ser Thr Phe Ser Tyr Val Asp
                        645                 650                 655
```

```
Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Val Gly
            900                 905                 910

Phe Leu His Ser Ser His Asp Val Asn Lys Glu Ala Ser Val Ile Met
        915                 920                 925

Leu Phe Ser Gly Leu Lys
    930

<210> SEQ ID NO 148
<211> LENGTH: 281
<212> TYPE: PRT
<213> ORGANISM: Homo sapiens

<400> SEQUENCE: 148

Lys Glu Ala Leu Ala Lys Ser Glu Met Asn Val Asn Met Lys Tyr Gln
1               5                   10                  15

Leu Pro Asn Phe Thr Ala Glu Thr Pro Ile Gln Asn Val Ile Leu His
            20                  25                  30

Glu His His Ile Phe Leu Gly Ala Thr Asn Tyr Ile Tyr Val Leu Asn
        35                  40                  45

Glu Glu Asp Leu Gln Lys Val Ala Glu Tyr Lys Thr Gly Pro Val Leu
    50                  55                  60

Glu His Pro Asp Cys Phe Pro Cys Gln Asp Cys Ser Ser Lys Ala Asn
65                  70                  75                  80

Leu Ser Gly Gly Val Trp Lys Asp Asn Ile Asn Met Ala Leu Val Val
```

```
                        85                  90                  95
Asp Thr Tyr Tyr Asp Asp Gln Leu Ile Ser Cys Gly Ser Val Asn Arg
                100                 105                 110

Gly Thr Cys Gln Arg His Val Phe Pro His Asn His Thr Ala Asp Ile
            115                 120                 125

Gln Ser Glu Val His Cys Ile Phe Ser Pro Gln Ile Glu Glu Pro Ser
        130                 135                 140

Gln Cys Pro Asp Cys Val Val Ser Ala Leu Gly Ala Lys Val Leu Ser
145                 150                 155                 160

Ser Val Lys Asp Arg Phe Ile Asn Phe Phe Val Gly Asn Thr Ile Asn
                165                 170                 175

Ser Ser Tyr Phe Pro Asp His Pro Leu His Ser Ile Ser Val Arg Arg
                180                 185                 190

Leu Lys Glu Thr Lys Asp Gly Phe Met Phe Leu Thr Asp Gln Ser Tyr
                195                 200                 205

Ile Asp Val Leu Pro Glu Phe Arg Asp Ser Tyr Pro Ile Lys Tyr Val
        210                 215                 220

His Ala Phe Glu Ser Asn Asn Phe Ile Tyr Phe Leu Thr Val Gln Arg
225                 230                 235                 240

Glu Thr Leu Asp Ala Gln Thr Phe His Thr Arg Ile Ile Arg Phe Cys
                245                 250                 255

Ser Ile Asn Ser Gly Leu His Ser Tyr Met Glu Met Pro Leu Glu Cys
                260                 265                 270

Ile Leu Thr Glu Lys Arg Lys Lys Arg
                275                 280

<210> SEQ ID NO 149
<211> LENGTH: 1101
<212> TYPE: PRT
<213> ORGANISM: Homo sapiens

<400> SEQUENCE: 149

Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
                20                  25                  30

Asp Ile Leu Phe Gly Val Phe Ala Gln Ser Lys Pro Asp Ser Ala Glu
            35                  40                  45

Pro Met Asp Arg Ser Ala Met Cys Ala Phe Pro Ile Lys Tyr Val Asn
    50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Thr Glu
                100                 105                 110

Phe Thr Thr Ala Leu Gln Arg Val Asp Leu Phe Met Gly Gln Phe Ser
            115                 120                 125

Glu Val Leu Leu Thr Ser Ile Ser Thr Phe Ile Lys Gly Asp Leu Thr
        130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser
                165                 170                 175
```

```
His Pro Val Ser Pro Glu Val Ile Val Glu His Thr Leu Asn Gln Asn
                180                 185                 190

Gly Tyr Thr Leu Val Ile Thr Gly Lys Lys Ile Thr Lys Ile Pro Leu
            195                 200                 205

Asn Gly Leu Gly Cys Arg His Phe Gln Ser Cys Ser Gln Cys Leu Ser
        210                 215                 220

Ala Pro Pro Phe Val Gln Cys Gly Trp Cys His Asp Lys Cys Val Arg
225                 230                 235                 240

Ser Glu Glu Cys Leu Ser Gly Thr Trp Thr Gln Gln Ile Cys Leu Pro
                245                 250                 255

Ala Ile Tyr Lys Val Phe Pro Asn Ser Ala Pro Leu Glu Gly Gly Thr
            260                 265                 270

Arg Leu Thr Ile Cys Gly Trp Asp Phe Gly Phe Arg Arg Asn Asn Lys
        275                 280                 285

Phe Asp Leu Lys Lys Thr Arg Val Leu Leu Gly Asn Glu Ser Cys Thr
290                 295                 300

Leu Thr Leu Ser Glu Ser Thr Met Asn Thr Leu Lys Cys Thr Val Gly
305                 310                 315                 320

Pro Ala Met Asn Lys His Phe Asn Met Ser Ile Ile Ser Asn Gly
            325                 330                 335

His Gly Thr Thr Gln Tyr Ser Thr Phe Ser Tyr Val Asp Pro Val Ile
            340                 345                 350

Thr Ser Ile Ser Pro Lys Tyr Gly Pro Met Ala Gly Gly Thr Leu Leu
            355                 360                 365

Thr Leu Thr Gly Asn Tyr Leu Asn Ser Gly Asn Ser Arg His Ile Ser
            370                 375                 380

Ile Gly Gly Lys Thr Cys Thr Leu Lys Ser Val Ser Asn Ser Ile Leu
385                 390                 395                 400

Glu Cys Tyr Thr Pro Ala Gln Thr Ile Ser Thr Glu Phe Ala Val Lys
                405                 410                 415

Leu Lys Ile Asp Leu Ala Asn Arg Glu Thr Ser Ile Phe Ser Tyr Arg
            420                 425                 430

Glu Asp Pro Ile Val Tyr Glu Ile His Pro Thr Lys Ser Phe Ile Ser
            435                 440                 445

Thr Trp Trp Lys Glu Pro Leu Asn Ile Val Ser Phe Leu Phe Cys Phe
450                 455                 460

Ala Ser Gly Gly Ser Thr Ile Thr Gly Val Gly Lys Asn Leu Asn Ser
465                 470                 475                 480

Val Ser Val Pro Arg Met Val Ile Asn Val His Glu Ala Gly Arg Asn
                485                 490                 495

Phe Thr Val Ala Cys Gln His Arg Ser Asn Ser Glu Ile Ile Cys Cys
            500                 505                 510

Thr Thr Pro Ser Leu Gln Gln Leu Asn Leu Gln Leu Pro Leu Lys Thr
            515                 520                 525

Lys Ala Phe Phe Met Leu Asp Gly Ile Leu Ser Lys Tyr Phe Asp Leu
            530                 535                 540

Ile Tyr Val His Asn Pro Val Phe Lys Pro Phe Glu Lys Pro Val Met
545                 550                 555                 560

Ile Ser Met Gly Asn Glu Asn Val Leu Glu Ile Lys Gly Asn Asp Ile
                565                 570                 575

Asp Pro Glu Ala Val Lys Gly Glu Val Leu Lys Val Gly Asn Lys Ser
            580                 585                 590

Cys Glu Asn Ile His Leu His Ser Glu Ala Val Leu Cys Thr Val Pro
```

```
                595                 600                 605
        Asn Asp Leu Leu Lys Leu Asn Ser Glu Leu Asn Ile Glu Trp Lys Gln
            610                 615                 620
        Ala Ile Ser Ser Thr Val Leu Gly Lys Val Ile Val Gln Pro Asp Gln
        625                 630                 635                 640
        Asn Phe Thr Gly Leu Ile Ala Gly Val Val Ser Ile Ser Thr Ala Leu
                        645                 650                 655
        Leu Leu Leu Leu Gly Phe Phe Leu Trp Leu Lys Lys Arg Lys Gln Ile
                    660                 665                 670
        Lys Asp Leu Gly Ser Glu Leu Val Arg Tyr Asp Ala Arg Val His Thr
                675                 680                 685
        Pro His Leu Asp Arg Leu Val Ser Ala Arg Ser Val Ser Pro Thr Thr
            690                 695                 700
        Glu Met Val Ser Asn Glu Ser Val Asp Tyr Arg Ala Thr Phe Pro Glu
        705                 710                 715                 720
        Asp Gln Phe Pro Asn Ser Ser Gln Asn Gly Ser Cys Arg Gln Val Gln
                        725                 730                 735
        Tyr Pro Leu Thr Asp Met Ser Pro Ile Leu Thr Ser Gly Asp Ser Asp
                    740                 745                 750
        Ile Ser Ser Pro Leu Leu Gln Asn Thr Val His Ile Asp Leu Ser Ala
                755                 760                 765
        Leu Asn Pro Glu Leu Val Gln Ala Val Gln His Val Val Ile Gly Pro
            770                 775                 780
        Ser Ser Leu Ile Val His Phe Asn Glu Val Ile Gly Arg Gly His Phe
        785                 790                 795                 800
        Gly Cys Val Tyr His Gly Thr Leu Leu Asp Asn Asp Gly Lys Lys Ile
                        805                 810                 815
        His Cys Ala Val Lys Ser Leu Asn Arg Ile Thr Asp Ile Gly Glu Val
                    820                 825                 830
        Ser Gln Phe Leu Thr Glu Gly Ile Ile Met Lys Asp Phe Ser His Pro
                835                 840                 845
        Asn Val Leu Ser Leu Leu Gly Ile Cys Leu Arg Ser Glu Gly Ser Pro
            850                 855                 860
        Leu Val Val Leu Pro Tyr Met Lys His Gly Asp Leu Arg Asn Phe Ile
        865                 870                 875                 880
        Arg Asn Glu Thr His Asn Pro Thr Val Lys Asp Leu Ile Gly Phe Gly
                        885                 890                 895
        Leu Gln Val Ala Lys Gly Met Lys Tyr Leu Ala Ser Lys Lys Phe Val
                    900                 905                 910
        His Arg Asp Leu Ala Ala Arg Asn Cys Met Leu Asp Glu Lys Phe Thr
                915                 920                 925
        Val Lys Val Ala Asp Phe Gly Leu Ala Arg Asp Met Tyr Asp Lys Glu
            930                 935                 940
        Tyr Tyr Ser Val His Asn Lys Thr Gly Ala Lys Leu Pro Val Lys Trp
        945                 950                 955                 960
        Met Ala Leu Glu Ser Leu Gln Thr Gln Lys Phe Thr Thr Lys Ser Asp
                        965                 970                 975
        Val Trp Ser Phe Gly Val Leu Leu Trp Glu Leu Met Thr Arg Gly Ala
                    980                 985                 990
        Pro Pro Tyr Pro Asp Val Asn Thr Phe Asp Ile Thr Val Tyr Leu Leu
                995                 1000                1005
        Gln Gly Arg Arg Leu Leu Gln Pro Glu Tyr Cys Pro Asp Pro Leu
            1010                1015                1020
```

```
Tyr Glu Val Met Leu Lys Cys Trp His Pro Lys Ala Glu Met Arg
    1025                1030                1035

Pro Ser Phe Ser Glu Leu Val Ser Arg Ile Ser Ala Ile Phe Ser
    1040                1045                1050

Thr Phe Ile Gly Glu His Tyr Val His Val Asn Ala Thr Tyr Val
    1055                1060                1065

Asn Val Lys Cys Val Ala Pro Tyr Pro Ser Leu Leu Ser Ser Glu
    1070                1075                1080

Asp Asn Ala Asp Asp Glu Val Asp Thr Arg Pro Ala Ser Phe Trp
    1085                1090                1095

Glu Thr Ser
    1100

<210> SEQ ID NO 150
<211> LENGTH: 1082
<212> TYPE: PRT
<213> ORGANISM: Homo sapiens

<400> SEQUENCE: 150

Thr Lys Lys Glu Val Phe Asn Ile Leu Gln Ala Ala Tyr Val Ser Lys
1               5                   10                  15

Pro Gly Ala Gln Leu Ala Arg Gln Ile Gly Ala Ser Leu Asn Asp Asp
                20                  25                  30

Ile Leu Phe Gly Val Phe Ala Gln Ser Lys Pro Asp Ser Ala Glu Pro
            35                  40                  45

Met Asp Arg Ser Ala Met Cys Ala Phe Pro Ile Lys Tyr Val Asn Asp
        50                  55                  60

Phe Phe Asn Lys Ile Val Asn Lys Asn Asn Val Arg Cys Leu Gln His
65                  70                  75                  80

Phe Tyr Gly Pro Asn His Glu His Cys Phe Asn Arg Thr Leu Leu Arg
                85                  90                  95

Asn Ser Ser Gly Cys Glu Ala Arg Arg Asp Glu Tyr Arg Thr Glu Phe
                100                 105                 110

Thr Thr Ala Leu Gln Arg Val Asp Leu Phe Met Gly Gln Phe Ser Glu
            115                 120                 125

Val Leu Leu Thr Ser Ile Ser Thr Phe Ile Lys Gly Asp Leu Thr Ile
        130                 135                 140

Ala Asn Leu Gly Thr Ser Glu Gly Arg Phe Met Gln Val Val Val Ser
145                 150                 155                 160

Arg Ser Gly Pro Ser Thr Pro His Val Asn Phe Leu Leu Asp Ser His
                165                 170                 175

Pro Val Ser Pro Glu Val Ile Val Glu His Thr Leu Asn Gln Asn Gly
                180                 185                 190

Tyr Thr Leu Val Ile Thr Gly Lys Lys Ile Thr Lys Ile Pro Leu Asn
            195                 200                 205

Gly Leu Gly Cys Arg His Phe Gln Ser Cys Ser Gln Cys Leu Ser Ala
        210                 215                 220

Pro Pro Phe Val Gln Cys Gly Trp Cys His Asp Lys Cys Val Arg Ser
225                 230                 235                 240

Glu Glu Cys Leu Ser Gly Thr Trp Thr Gln Gln Ile Cys Leu Pro Ala
                245                 250                 255

Ile Tyr Lys Val Phe Pro Asn Ser Ala Pro Leu Glu Gly Gly Thr Arg
                260                 265                 270

Leu Thr Ile Cys Gly Trp Asp Phe Gly Phe Arg Arg Asn Asn Lys Phe
```

```
                275                 280                 285
Asp Leu Lys Lys Thr Arg Val Leu Leu Gly Asn Glu Ser Cys Thr Leu
290                 295                 300
Thr Leu Ser Glu Ser Thr Met Asn Thr Leu Lys Cys Thr Val Gly Pro
305                 310                 315                 320
Ala Met Asn Lys His Phe Asn Met Ser Ile Ile Ser Asn Gly His
                325                 330                 335
Gly Thr Thr Gln Tyr Ser Thr Phe Ser Tyr Val Asp Pro Val Ile Thr
                340                 345                 350
Ser Ile Ser Pro Lys Tyr Gly Pro Met Ala Gly Thr Leu Leu Thr
                355                 360                 365
Leu Thr Gly Asn Tyr Leu Asn Ser Gly Asn Ser Arg His Ile Ser Ile
370                 375                 380
Gly Gly Lys Thr Cys Thr Leu Lys Ser Val Ser Asn Ser Ile Leu Glu
385                 390                 395                 400
Cys Tyr Thr Pro Ala Gln Thr Ile Ser Thr Glu Phe Ala Val Lys Leu
                405                 410                 415
Lys Ile Asp Leu Ala Asn Arg Glu Thr Ser Ile Phe Ser Tyr Arg Glu
                420                 425                 430
Asp Pro Ile Val Tyr Glu Ile His Pro Thr Lys Ser Phe Ile Ser Gly
                435                 440                 445
Gly Ser Thr Ile Thr Gly Val Gly Lys Asn Leu Asn Ser Val Ser Val
                450                 455                 460
Pro Arg Met Val Ile Asn Val His Glu Ala Gly Arg Asn Phe Thr Val
465                 470                 475                 480
Ala Cys Gln His Arg Ser Asn Ser Glu Ile Ile Cys Cys Thr Thr Pro
                485                 490                 495
Ser Leu Gln Gln Leu Asn Leu Gln Leu Pro Leu Lys Thr Lys Ala Phe
                500                 505                 510
Phe Met Leu Asp Gly Ile Leu Ser Lys Tyr Phe Asp Leu Ile Tyr Val
                515                 520                 525
His Asn Pro Val Phe Lys Pro Phe Glu Lys Pro Val Met Ile Ser Met
530                 535                 540
Gly Asn Glu Asn Val Leu Glu Ile Lys Gly Asn Asp Ile Asp Pro Glu
545                 550                 555                 560
Ala Val Lys Gly Glu Val Leu Lys Val Gly Asn Lys Ser Cys Glu Asn
                565                 570                 575
Ile His Leu His Ser Glu Ala Val Leu Cys Thr Val Pro Asn Asp Leu
                580                 585                 590
Leu Lys Leu Asn Ser Glu Leu Asn Ile Glu Trp Lys Gln Ala Ile Ser
                595                 600                 605
Ser Thr Val Leu Gly Lys Val Ile Val Gln Pro Asp Gln Asn Phe Thr
                610                 615                 620
Gly Leu Ile Ala Gly Val Val Ser Ile Ser Thr Ala Leu Leu Leu Leu
625                 630                 635                 640
Leu Gly Phe Phe Leu Trp Leu Lys Lys Arg Lys Gln Ile Lys Asp Leu
                645                 650                 655
Gly Ser Glu Leu Val Arg Tyr Asp Ala Arg Val His Thr Pro His Leu
                660                 665                 670
Asp Arg Leu Val Ser Ala Arg Ser Val Ser Pro Thr Thr Glu Met Val
                675                 680                 685
Ser Asn Glu Ser Val Asp Tyr Arg Ala Thr Phe Pro Glu Asp Gln Phe
690                 695                 700
```

Pro Asn Ser Ser Gln Asn Gly Ser Cys Arg Gln Val Gln Tyr Pro Leu
705                 710                 715                 720

Thr Asp Met Ser Pro Ile Leu Thr Ser Gly Asp Ser Asp Ile Ser Ser
            725                 730                 735

Pro Leu Leu Gln Asn Thr Val His Ile Asp Leu Ser Ala Leu Asn Pro
        740                 745                 750

Glu Leu Val Gln Ala Val Gln His Val Val Ile Gly Pro Ser Ser Leu
    755                 760                 765

Ile Val His Phe Asn Glu Val Ile Gly Arg Gly His Phe Gly Cys Val
770                 775                 780

Tyr His Gly Thr Leu Leu Asp Asn Asp Gly Lys Lys Ile His Cys Ala
785                 790                 795                 800

Val Lys Ser Leu Asn Arg Ile Thr Asp Ile Gly Glu Val Ser Gln Phe
            805                 810                 815

Leu Thr Glu Gly Ile Ile Met Lys Asp Phe Ser His Pro Asn Val Leu
        820                 825                 830

Ser Leu Leu Gly Ile Cys Leu Arg Ser Glu Gly Ser Pro Leu Val Val
    835                 840                 845

Leu Pro Tyr Met Lys His Gly Asp Leu Arg Asn Phe Ile Arg Asn Glu
850                 855                 860

Thr His Asn Pro Thr Val Lys Asp Leu Ile Gly Phe Gly Leu Gln Val
865                 870                 875                 880

Ala Lys Gly Met Lys Tyr Leu Ala Ser Lys Lys Phe Val His Arg Asp
            885                 890                 895

Leu Ala Ala Arg Asn Cys Met Leu Asp Glu Lys Phe Thr Val Lys Val
        900                 905                 910

Ala Asp Phe Gly Leu Ala Arg Asp Met Tyr Asp Lys Glu Tyr Tyr Ser
    915                 920                 925

Val His Asn Lys Thr Gly Ala Lys Leu Pro Val Lys Trp Met Ala Leu
930                 935                 940

Glu Ser Leu Gln Thr Gln Lys Phe Thr Thr Lys Ser Asp Val Trp Ser
945                 950                 955                 960

Phe Gly Val Leu Leu Trp Glu Leu Met Thr Arg Gly Ala Pro Pro Tyr
            965                 970                 975

Pro Asp Val Asn Thr Phe Asp Ile Thr Val Tyr Leu Leu Gln Gly Arg
        980                 985                 990

Arg Leu Leu Gln Pro Glu Tyr Cys Pro Asp Pro Leu Tyr Glu Val Met
    995                 1000                1005

Leu Lys Cys Trp His Pro Lys Ala Glu Met Arg Pro Ser Phe Ser
    1010                1015                1020

Glu Leu Val Ser Arg Ile Ser Ala Ile Phe Ser Thr Phe Ile Gly
    1025                1030                1035

Glu His Tyr Val His Val Asn Ala Thr Tyr Val Asn Val Lys Cys
    1040                1045                1050

Val Ala Pro Tyr Pro Ser Leu Leu Ser Ser Glu Asp Asn Ala Asp
    1055                1060                1065

Asp Glu Val Asp Thr Arg Pro Ala Ser Phe Trp Glu Thr Ser
    1070                1075                1080

<210> SEQ ID NO 151
<211> LENGTH: 626
<212> TYPE: PRT
<213> ORGANISM: Homo sapiens

<400> SEQUENCE: 151

```
Thr Lys Lys Glu Val Phe Asn Ile Leu Gln Ala Ala Tyr Val Ser Lys
  1               5                  10                  15
Pro Gly Ala Gln Leu Ala Arg Gln Ile Gly Ala Ser Leu Asn Asp Asp
             20                  25                  30
Ile Leu Phe Gly Val Phe Ala Gln Ser Lys Pro Asp Ser Ala Glu Pro
         35                  40                  45
Met Asp Arg Ser Ala Met Cys Ala Phe Pro Ile Lys Tyr Val Asn Asp
     50                  55                  60
Phe Phe Asn Lys Ile Val Asn Lys Asn Asn Val Arg Cys Leu Gln His
 65                  70                  75                  80
Phe Tyr Gly Pro Asn His Glu His Cys Phe Asn Arg Thr Leu Leu Arg
                 85                  90                  95
Asn Ser Ser Gly Cys Glu Ala Arg Arg Asp Glu Tyr Arg Thr Glu Phe
            100                 105                 110
Thr Thr Ala Leu Gln Arg Val Asp Leu Phe Met Gly Gln Phe Ser Glu
        115                 120                 125
Val Leu Leu Thr Ser Ile Ser Thr Phe Ile Lys Gly Asp Leu Thr Ile
    130                 135                 140
Ala Asn Leu Gly Thr Ser Glu Gly Arg Phe Met Gln Val Val Val Ser
145                 150                 155                 160
Arg Ser Gly Pro Ser Thr Pro His Val Asn Phe Leu Leu Asp Ser His
                165                 170                 175
Pro Val Ser Pro Glu Val Ile Val Glu His Thr Leu Asn Gln Asn Gly
            180                 185                 190
Tyr Thr Leu Val Ile Thr Gly Lys Lys Ile Thr Lys Ile Pro Leu Asn
        195                 200                 205
Gly Leu Gly Cys Arg His Phe Gln Ser Cys Ser Gln Cys Leu Ser Ala
    210                 215                 220
Pro Pro Phe Val Gln Cys Gly Trp Cys His Asp Lys Cys Val Arg Ser
225                 230                 235                 240
Glu Glu Cys Leu Ser Gly Thr Trp Thr Gln Gln Ile Cys Leu Pro Ala
                245                 250                 255
Ile Tyr Lys Val Phe Pro Asn Ser Ala Pro Leu Glu Gly Gly Thr Arg
            260                 265                 270
Leu Thr Ile Cys Gly Trp Asp Phe Gly Phe Arg Arg Asn Asn Lys Phe
        275                 280                 285
Asp Leu Lys Lys Thr Arg Val Leu Leu Gly Asn Glu Ser Cys Thr Leu
    290                 295                 300
Thr Leu Ser Glu Ser Thr Met Asn Thr Leu Lys Cys Thr Val Gly Pro
305                 310                 315                 320
Ala Met Asn Lys His Phe Asn Met Ser Ile Ile Ser Asn Gly His
                325                 330                 335
Gly Thr Thr Gln Tyr Ser Thr Phe Ser Tyr Val Asp Pro Val Ile Thr
            340                 345                 350
Ser Ile Ser Pro Lys Tyr Gly Pro Met Ala Gly Gly Thr Leu Leu Thr
        355                 360                 365
Leu Thr Gly Asn Tyr Leu Asn Ser Gly Asn Ser Arg His Ile Ser Ile
    370                 375                 380
Gly Gly Lys Thr Cys Thr Leu Lys Ser Val Ser Asn Ser Ile Leu Glu
385                 390                 395                 400
Cys Tyr Thr Pro Ala Gln Thr Ile Ser Thr Glu Phe Ala Val Lys Leu
                405                 410                 415
```

```
Lys Ile Asp Leu Ala Asn Arg Glu Thr Ser Ile Phe Ser Tyr Arg Glu
            420                 425                 430

Asp Pro Ile Val Tyr Glu Ile His Pro Thr Lys Ser Phe Ile Ser Gly
        435                 440                 445

Gly Ser Thr Ile Thr Gly Val Gly Lys Asn Leu Asn Ser Val Ser Val
    450                 455                 460

Pro Arg Met Val Ile Asn Val His Glu Ala Gly Arg Asn Phe Thr Val
465                 470                 475                 480

Ala Cys Gln His Arg Ser Asn Ser Glu Ile Ile Cys Cys Thr Thr Pro
                485                 490                 495

Ser Leu Gln Gln Leu Asn Leu Gln Leu Pro Leu Lys Thr Lys Ala Phe
                500                 505                 510

Phe Met Leu Asp Gly Ile Leu Ser Lys Tyr Phe Asp Leu Ile Tyr Val
            515                 520                 525

His Asn Pro Val Phe Lys Pro Phe Glu Lys Pro Val Met Ile Ser Met
        530                 535                 540

Gly Asn Glu Asn Val Leu Glu Ile Lys Gly Asn Asp Ile Asp Pro Glu
545                 550                 555                 560

Ala Val Lys Gly Glu Val Leu Lys Val Gly Asn Lys Ser Cys Glu Asn
                565                 570                 575

Ile His Leu His Ser Glu Ala Val Leu Cys Thr Val Pro Asn Asp Leu
                580                 585                 590

Leu Lys Leu Asn Ser Glu Leu Asn Ile Glu Val Gly Phe Leu His Ser
            595                 600                 605

Ser His Asp Val Asn Lys Glu Ala Ser Val Ile Met Leu Phe Ser Gly
        610                 615                 620

Leu Lys
625

<210> SEQ ID NO 152
<211> LENGTH: 650
<212> TYPE: PRT
<213> ORGANISM: Artificial
<220> FEATURE:
<223> OTHER INFORMATION: synthetic

<400> SEQUENCE: 152

Thr Lys Lys Glu Val Phe Asn Ile Leu Gln Ala Ala Tyr Val Ser Lys
1               5                   10                  15

Pro Gly Ala Gln Leu Ala Arg Gln Ile Gly Ala Ser Leu Asn Asp Asp
            20                  25                  30

Ile Leu Phe Gly Val Phe Ala Gln Ser Lys Pro Asp Ser Ala Glu Pro
        35                  40                  45

Met Asp Arg Ser Ala Met Cys Ala Phe Pro Ile Lys Tyr Val Asn Asp
    50                  55                  60

Phe Phe Asn Lys Ile Val Asn Lys Asn Asn Val Arg Cys Leu Gln His
65                  70                  75                  80

Phe Tyr Gly Pro Asn His Glu His Cys Phe Asn Arg Thr Leu Leu Arg
                85                  90                  95

Asn Ser Ser Gly Cys Glu Ala Arg Arg Asp Glu Tyr Arg Thr Glu Phe
            100                 105                 110

Thr Thr Ala Leu Gln Arg Val Asp Leu Phe Met Gly Gln Phe Ser Glu
        115                 120                 125

Val Leu Leu Thr Ser Ile Ser Thr Phe Ile Lys Gly Asp Leu Thr Ile
    130                 135                 140
```

```
Ala Asn Leu Gly Thr Ser Glu Gly Arg Phe Met Gln Val Val Ser
145                 150                 155                 160

Arg Ser Gly Pro Ser Thr Pro His Val Asn Phe Leu Leu Asp Ser His
            165                 170                 175

Pro Val Ser Pro Glu Val Ile Val Glu His Thr Leu Asn Gln Asn Gly
        180                 185                 190

Tyr Thr Leu Val Ile Thr Gly Lys Lys Ile Thr Lys Ile Pro Leu Asn
        195                 200                 205

Gly Leu Gly Cys Arg His Phe Gln Ser Cys Ser Gln Cys Leu Ser Ala
        210                 215                 220

Pro Pro Phe Val Gln Cys Gly Trp Cys His Asp Lys Cys Val Arg Ser
225                 230                 235                 240

Glu Glu Cys Leu Ser Gly Thr Trp Thr Gln Gln Ile Cys Leu Pro Ala
                245                 250                 255

Ile Tyr Lys Val Phe Pro Asn Ser Ala Pro Leu Glu Gly Gly Thr Arg
                260                 265                 270

Leu Thr Ile Cys Gly Trp Asp Phe Gly Phe Arg Arg Asn Asn Lys Phe
            275                 280                 285

Asp Leu Lys Lys Thr Arg Val Leu Leu Gly Asn Glu Ser Cys Thr Leu
        290                 295                 300

Thr Leu Ser Glu Ser Thr Met Asn Thr Leu Lys Cys Thr Val Gly Pro
305                 310                 315                 320

Ala Met Asn Lys His Phe Asn Met Ser Ile Ile Ser Asn Gly His
                325                 330                 335

Gly Thr Thr Gln Tyr Ser Thr Phe Ser Tyr Val Asp Pro Val Ile Thr
                340                 345                 350

Ser Ile Ser Pro Lys Tyr Gly Pro Met Ala Gly Gly Thr Leu Leu Thr
            355                 360                 365

Leu Thr Gly Asn Tyr Leu Asn Ser Gly Asn Ser Arg His Ile Ser Ile
        370                 375                 380

Gly Gly Lys Thr Cys Thr Leu Lys Ser Val Ser Asn Ser Ile Leu Glu
385                 390                 395                 400

Cys Tyr Thr Pro Ala Gln Thr Ile Ser Thr Glu Phe Ala Val Lys Leu
                405                 410                 415

Lys Ile Asp Leu Ala Asn Arg Glu Thr Ser Ile Phe Ser Tyr Arg Glu
                420                 425                 430

Asp Pro Ile Val Tyr Glu Ile His Pro Thr Lys Ser Phe Ile Ser Thr
            435                 440                 445

Trp Trp Lys Glu Pro Leu Asn Ile Val Ser Phe Leu Phe Cys Phe Ala
        450                 455                 460

Ser Gly Gly Ser Thr Ile Thr Gly Val Gly Lys Asn Leu Asn Ser Val
465                 470                 475                 480

Ser Val Pro Arg Met Val Ile Asn Val His Glu Ala Gly Arg Asn Phe
                485                 490                 495

Thr Val Ala Cys Gln His Arg Ser Asn Ser Glu Ile Ile Cys Cys Thr
                500                 505                 510

Thr Pro Ser Leu Gln Gln Leu Asn Leu Gln Leu Pro Leu Lys Thr Lys
            515                 520                 525

Ala Phe Phe Met Leu Asp Gly Ile Leu Ser Lys Tyr Phe Asp Leu Ile
        530                 535                 540

Tyr Val His Asn Pro Val Phe Lys Pro Phe Glu Lys Pro Val Met Ile
545                 550                 555                 560
```

Ser Met Gly Asn Glu Asn Val Leu Glu Ile Lys Gly Asn Asp Ile Asp
                565                 570                 575

Pro Glu Ala Val Lys Gly Glu Val Leu Lys Val Gly Asn Lys Ser Cys
            580                 585                 590

Glu Asn Ile His Leu His Ser Glu Ala Val Leu Cys Thr Val Pro Asn
        595                 600                 605

Asp Leu Leu Lys Leu Asn Ser Glu Leu Asn Ile Glu Trp Lys Gln Ala
    610                 615                 620

Glu Gln Lys Leu Ile Ser Glu Glu Asp Leu Glu Gln Lys Leu Ile Ser
625                 630                 635                 640

Glu Glu Asp Leu His His His His His His
            645                 650

<210> SEQ ID NO 153
<211> LENGTH: 838
<212> TYPE: PRT
<213> ORGANISM: Artificial
<220> FEATURE:
<223> OTHER INFORMATION: synthetic

<400> SEQUENCE: 153

Thr Lys Lys Glu Val Phe Asn Ile Leu Gln Ala Ala Tyr Val Ser Lys
1               5                   10                  15

Pro Gly Ala Gln Leu Ala Arg Gln Ile Gly Ala Ser Leu Asn Asp Asp
            20                  25                  30

Ile Leu Phe Gly Val Phe Ala Gln Ser Lys Pro Asp Ser Ala Glu Pro
        35                  40                  45

Met Asp Arg Ser Ala Met Cys Ala Phe Pro Ile Lys Tyr Val Asn Asp
    50                  55                  60

Phe Phe Asn Lys Ile Val Asn Lys Asn Val Arg Cys Leu Gln His
65                  70                  75                  80

Phe Tyr Gly Pro Asn His Glu His Cys Phe Asn Arg Thr Leu Leu Arg
                85                  90                  95

Asn Ser Ser Gly Cys Glu Ala Arg Arg Asp Glu Tyr Arg Thr Glu Phe
            100                 105                 110

Thr Thr Ala Leu Gln Arg Val Asp Leu Phe Met Gly Gln Phe Ser Glu
        115                 120                 125

Val Leu Leu Thr Ser Ile Ser Thr Phe Ile Lys Gly Asp Leu Thr Ile
    130                 135                 140

Ala Asn Leu Gly Thr Ser Glu Gly Arg Phe Met Gln Val Val Val Ser
145                 150                 155                 160

Arg Ser Gly Pro Ser Thr Pro His Val Asn Phe Leu Leu Asp Ser His
                165                 170                 175

Pro Val Ser Pro Glu Val Ile Val Glu His Thr Leu Asn Gln Asn Gly
            180                 185                 190

Tyr Thr Leu Val Ile Thr Gly Lys Lys Ile Thr Lys Ile Pro Leu Asn
        195                 200                 205

Gly Leu Gly Cys Arg His Phe Gln Ser Cys Ser Gln Cys Leu Ser Ala
    210                 215                 220

Pro Pro Phe Val Gln Cys Gly Trp Cys His Asp Lys Cys Val Arg Ser
225                 230                 235                 240

Glu Glu Cys Leu Ser Gly Thr Trp Thr Gln Gln Ile Cys Leu Pro Ala
                245                 250                 255

Ile Tyr Lys Val Phe Pro Asn Ser Ala Pro Leu Glu Gly Gly Thr Arg
            260                 265                 270

```
Leu Thr Ile Cys Gly Trp Asp Phe Gly Phe Arg Arg Asn Asn Lys Phe
            275                 280                 285

Asp Leu Lys Lys Thr Arg Val Leu Leu Gly Asn Glu Ser Cys Thr Leu
290                 295                 300

Thr Leu Ser Glu Ser Thr Met Asn Thr Leu Lys Cys Thr Val Gly Pro
305                 310                 315                 320

Ala Met Asn Lys His Phe Asn Met Ser Ile Ile Ser Asn Gly His
                325                 330                 335

Gly Thr Thr Gln Tyr Ser Thr Phe Ser Tyr Val Asp Pro Val Ile Thr
            340                 345                 350

Ser Ile Ser Pro Lys Tyr Gly Pro Met Ala Gly Thr Leu Leu Thr
        355                 360                 365

Leu Thr Gly Asn Tyr Leu Asn Ser Gly Asn Ser Arg His Ile Ser Ile
        370                 375                 380

Gly Gly Lys Thr Cys Thr Leu Lys Ser Val Ser Asn Ser Ile Leu Glu
385                 390                 395                 400

Cys Tyr Thr Pro Ala Gln Thr Ile Ser Thr Glu Phe Ala Val Lys Leu
                405                 410                 415

Lys Ile Asp Leu Ala Asn Arg Glu Thr Ser Ile Phe Ser Tyr Arg Glu
            420                 425                 430

Asp Pro Ile Val Tyr Glu Ile His Pro Thr Lys Ser Phe Ile Ser Thr
            435                 440                 445

Trp Trp Lys Glu Pro Leu Asn Ile Val Ser Phe Leu Phe Cys Phe Ala
        450                 455                 460

Ser Gly Gly Ser Thr Ile Thr Gly Val Gly Lys Asn Leu Asn Ser Val
465                 470                 475                 480

Ser Val Pro Arg Met Val Ile Asn Val His Glu Ala Gly Arg Asn Phe
                485                 490                 495

Thr Val Ala Cys Gln His Arg Ser Asn Ser Glu Ile Ile Cys Cys Thr
                500                 505                 510

Thr Pro Ser Leu Gln Gln Leu Asn Leu Gln Leu Pro Leu Lys Thr Lys
            515                 520                 525

Ala Phe Phe Met Leu Asp Gly Ile Leu Ser Lys Tyr Phe Asp Leu Ile
        530                 535                 540

Tyr Val His Asn Pro Val Phe Lys Pro Phe Glu Lys Pro Val Met Ile
545                 550                 555                 560

Ser Met Gly Asn Glu Asn Val Leu Glu Ile Lys Gly Asn Asp Ile Asp
                565                 570                 575

Pro Glu Ala Val Lys Gly Glu Val Leu Lys Val Gly Asn Lys Ser Cys
            580                 585                 590

Glu Asn Ile His Leu His Ser Glu Ala Val Leu Cys Thr Val Pro Asn
        595                 600                 605

Asp Leu Leu Lys Leu Asn Ser Glu Leu Asn Ile Glu Trp Lys Gln Ala
        610                 615                 620

Met Glu Val Ser Ser Val Phe Ile Phe Pro Pro Lys Pro Lys Asp Val
625                 630                 635                 640

Leu Thr Ile Thr Leu Thr Pro Lys Val Thr Cys Val Val Asp Ile
                645                 650                 655

Ser Lys Asp Asp Pro Glu Val Gln Phe Ser Trp Phe Val Asp Val
            660                 665                 670

Glu Val His Thr Ala Gln Thr Gln Pro Arg Glu Glu Gln Phe Asn Ser
        675                 680                 685

Thr Phe Arg Ser Val Ser Glu Leu Pro Ile Met His Gln Asp Trp Leu
```

```
            690                 695                 700
Asn Gly Lys Glu Phe Lys Cys Arg Val Asn Ser Ala Ala Phe Pro Ala
705                 710                 715                 720

Pro Ile Glu Lys Thr Ile Ser Lys Thr Lys Gly Arg Pro Lys Ala Pro
                725                 730                 735

Gln Val Tyr Thr Ile Pro Pro Lys Glu Gln Met Ala Lys Asp Lys
                740                 745                 750

Val Ser Leu Thr Cys Met Ile Thr Asp Phe Phe Pro Glu Asp Ile Thr
                755                 760                 765

Val Glu Trp Gln Trp Asn Gly Gln Pro Ala Glu Asn Tyr Lys Asn Thr
                770                 775                 780

Gln Pro Ile Met Asp Thr Asp Gly Ser Tyr Phe Val Tyr Ser Lys Leu
785                 790                 795                 800

Asn Val Gln Lys Ser Asn Trp Glu Ala Gly Asn Thr Phe Thr Cys Ser
                805                 810                 815

Val Leu His Glu Gly Leu His Asn His His Thr Glu Lys Ser Leu Ser
                820                 825                 830

His Ser Pro Gly Lys Glu
            835

<210> SEQ ID NO 154
<211> LENGTH: 1100
<212> TYPE: PRT
<213> ORGANISM: Artificial
<220> FEATURE:
<223> OTHER INFORMATION: synthetic

<400> SEQUENCE: 154

Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
                20                  25                  30

Asp Ile Leu Phe Gly Val Phe Ala Gln Ser Lys Pro Asp Ser Ala Glu
            35                  40                  45

Pro Met Asp Arg Ser Ala Met Cys Ala Phe Pro Ile Lys Tyr Val Asn
        50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Ala Glu
                100                 105                 110

Phe Thr Thr Ala Leu Gln Arg Val Asp Leu Phe Met Gly Gln Phe Ser
            115                 120                 125

Glu Val Leu Leu Thr Ser Ile Ser Thr Phe Val Lys Gly Asp Leu Thr
        130                 135                 140

Ile Ala Asn Leu Gly Thr Ser Glu Gly Arg Phe Met Gln Val Val
145                 150                 155                 160

Ser Arg Ser Gly Pro Ser Thr Pro His Val Asn Phe Leu Leu Asp Ser
                165                 170                 175

His Pro Val Ser Pro Glu Val Ile Val Glu His Pro Leu Asn Gln Asn
            180                 185                 190

Gly Tyr Thr Leu Val Val Thr Gly Lys Lys Ile Thr Lys Ile Pro Leu
        195                 200                 205

Asn Gly Leu Gly Cys Arg His Phe Gln Ser Cys Ser Gln Cys Leu Ser
```

-continued

```
              210                 215                 220
Ala Pro Pro Phe Val Gln Cys Gly Trp Cys His Asp Lys Cys Val Arg
225                 230                 235                 240

Ser Glu Glu Cys Pro Ser Gly Thr Trp Thr Gln Gln Ile Cys Leu Pro
                    245                 250                 255

Ala Ile Tyr Lys Val Phe Pro Thr Ser Ala Pro Leu Glu Gly Gly Thr
                260                 265                 270

Arg Leu Thr Ile Cys Gly Trp Asp Phe Gly Phe Arg Arg Asn Asn Lys
            275                 280                 285

Phe Asp Leu Lys Lys Thr Arg Val Leu Leu Gly Asn Glu Ser Cys Thr
        290                 295                 300

Leu Thr Leu Ser Glu Ser Thr Met Asn Thr Leu Lys Cys Thr Val Gly
305                 310                 315                 320

Pro Ala Met Asn Lys His Phe Asn Met Ser Ile Ile Ile Ser Asn Gly
                    325                 330                 335

His Gly Thr Thr Gln Tyr Ser Thr Phe Ser Tyr Val Asp Pro Ile Ile
                340                 345                 350

Thr Ser Ile Ser Pro Lys Tyr Gly Pro Met Ala Gly Gly Thr Leu Leu
            355                 360                 365

Thr Leu Thr Gly Asn Tyr Leu Asn Ser Gly Asn Ser Arg His Ile Ser
        370                 375                 380

Ile Gly Gly Lys Thr Cys Thr Leu Lys Ser Val Ser Asn Ser Ile Leu
385                 390                 395                 400

Glu Cys Tyr Thr Pro Ala Gln Thr Ile Ser Thr Glu Phe Ala Val Lys
                    405                 410                 415

Leu Lys Ile Asp Leu Ala Asn Arg Glu Thr Ser Ile Phe Ser Tyr Arg
                420                 425                 430

Glu Asp Pro Ile Val Tyr Glu Ile His Pro Thr Lys Ser Phe Ile Ser
            435                 440                 445

Gly Gly Ser Thr Ile Thr Gly Val Gly Lys Asn Leu His Ser Val Ser
        450                 455                 460

Val Pro Arg Met Val Ile Asn Val His Glu Ala Gly Arg Asn Phe Thr
465                 470                 475                 480

Val Ala Cys Gln His Arg Ser Asn Ser Glu Ile Ile Cys Cys Thr Thr
                    485                 490                 495

Pro Ser Leu Gln Gln Leu Asn Leu Gln Leu Pro Leu Lys Thr Lys Ala
                500                 505                 510

Phe Phe Met Leu Asp Gly Ile Leu Ser Lys Tyr Phe Asp Leu Ile Tyr
            515                 520                 525

Val His Asn Pro Val Phe Lys Pro Phe Glu Lys Pro Val Met Ile Ser
        530                 535                 540

Met Gly Asn Glu Asn Val Leu Glu Ile Lys Gly Asn Asp Ile Asp Pro
545                 550                 555                 560

Glu Ala Val Lys Gly Glu Val Leu Lys Val Gly Asn Lys Ser Cys Glu
                    565                 570                 575

Asn Ile His Leu His Ser Glu Ala Val Leu Cys Thr Val Pro Asn Asp
                580                 585                 590

Leu Leu Lys Leu Asn Ser Glu Leu Asn Ile Glu Trp Lys Gln Ala Ile
            595                 600                 605

Ser Ser Thr Val Leu Gly Lys Val Ile Val Gln Pro Asp Gln Asn Phe
        610                 615                 620

Thr Gly Leu Ile Ala Gly Val Val Ser Ile Ser Ile Ala Leu Leu Leu
625                 630                 635                 640
```

Leu Leu Gly Leu Phe Leu Trp Leu Lys Lys Arg Lys Gln Ile Lys Asp
                645                 650                 655

Leu Gly Ser Glu Leu Val Arg Tyr Asp Ala Arg Val His Thr Pro His
            660                 665                 670

Leu Asp Arg Leu Val Ser Ala Arg Ser Val Ser Pro Thr Thr Glu Met
            675                 680                 685

Val Ser Asn Glu Ser Val Asp Tyr Arg Ala Thr Phe Pro Glu Asp Gln
        690                 695                 700

Phe Pro Asn Ser Ser Gln Asn Gly Ser Cys Arg Gln Val Gln Tyr Pro
705                 710                 715                 720

Leu Thr Asp Met Ser Pro Ile Leu Thr Ser Gly Asp Ser Asp Ile Ser
                725                 730                 735

Ser Pro Leu Leu Gln Asn Thr Val His Ile Asp Leu Ser Ala Leu Asn
                740                 745                 750

Pro Glu Leu Val Gln Ala Val Gln His Val Val Ile Gly Pro Ser Ser
            755                 760                 765

Leu Ile Val His Phe Asn Glu Val Ile Gly Arg Gly His Phe Gly Cys
        770                 775                 780

Val Tyr His Gly Thr Leu Leu Asp Asn Asp Gly Lys Lys Ile His Cys
785                 790                 795                 800

Ala Val Lys Ser Leu Asn Arg Ile Thr Asp Ile Gly Glu Val Ser Gln
                805                 810                 815

Phe Leu Thr Glu Gly Ile Ile Met Lys Asp Phe Ser His Pro Asn Val
                820                 825                 830

Leu Ser Leu Leu Gly Ile Cys Leu Arg Ser Glu Gly Ser Pro Leu Val
            835                 840                 845

Val Leu Pro Tyr Met Lys His Gly Asp Leu Arg Asn Phe Ile Arg Asn
850                 855                 860

Glu Thr His Asn Pro Thr Val Lys Asp Leu Ile Gly Phe Gly Leu Gln
865                 870                 875                 880

Val Ala Lys Gly Met Lys Tyr Leu Ala Ser Lys Lys Phe Val His Arg
                885                 890                 895

Asp Leu Ala Ala Arg Asn Cys Met Leu Asp Glu Lys Phe Thr Val Lys
            900                 905                 910

Val Ala Asp Phe Gly Leu Ala Arg Asp Met Tyr Asp Lys Glu Tyr Tyr
        915                 920                 925

Ser Val His Asn Lys Thr Gly Ala Lys Leu Pro Val Lys Trp Met Ala
930                 935                 940

Leu Glu Ser Leu Gln Thr Gln Lys Phe Thr Thr Lys Ser Asp Val Trp
945                 950                 955                 960

Ser Phe Gly Val Leu Leu Trp Glu Leu Met Thr Arg Gly Ala Pro Pro
                965                 970                 975

Tyr Pro Asp Val Asn Thr Phe Asp Ile Thr Val Tyr Leu Leu Gln Gly
            980                 985                 990

Arg Arg Leu Leu Gln Pro Glu Tyr Cys Pro Asp Pro Leu Tyr Glu Val
        995                 1000                1005

Met Leu Lys Cys Trp His Pro Lys Ala Glu Met Arg Pro Ser Phe
1010                1015                1020

Ser Glu Leu Val Ser Arg Ile Ser Ala Ile Phe Ser Thr Phe Ile
    1025                1030                1035

Gly Glu His Tyr Val His Val Asn Ala Thr Tyr Val Asn Val Lys
    1040                1045                1050

```
Cys Val Ala Pro Tyr Pro Ser Leu Leu Ser Ser Glu Asp Asn Ala
    1055                1060                1065

Asp Asp Glu Val Asp Thr Glu Gln Lys Leu Ile Ser Glu Glu Asp
    1070                1075                1080

Leu Glu Gln Lys Leu Ile Ser Glu Glu Asp Leu His His His His
    1085                1090                1095

His His
    1100

<210> SEQ ID NO 155
<211> LENGTH: 936
<212> TYPE: PRT
<213> ORGANISM: Artificial Sequence
<220> FEATURE:
<223> OTHER INFORMATION: synthetic

<400> SEQUENCE: 155

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
                20                  25                  30

Leu His Glu His His Ile Phe Leu Gly Ala Thr Asn Tyr Ile Tyr Val
            35                  40                  45

Leu Asn Glu Glu Asp Leu Gln Lys Val Ala Glu Tyr Lys Thr Gly Pro
        50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
        275                 280                 285

Val Phe Asn Ile Leu Gln Ala Ala Tyr Val Ser Lys Pro Gly Ala Gln
    290                 295                 300
```

```
Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
            325                 330                 335

Ala Met Cys Ala Phe Pro Ile Lys Tyr Val Asn Asp Phe Phe Asn Lys
            340                 345                 350

Ile Val Asn Lys Asn Val Arg Cys Leu Gln His Phe Tyr Gly Pro
            355                 360                 365

Asn His Glu His Cys Phe Asn Arg Thr Leu Leu Arg Asn Ser Ser Gly
            370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
                420                 425                 430

Thr Ser Glu Gly Arg Phe Met Gln Val Val Ser Arg Ser Gly Pro
            435                 440                 445

Ser Thr Pro His Val Asn Phe Leu Leu Asp Ser His Pro Val Ser Pro
450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Arg Ser Glu Glu Cys Leu
            515                 520                 525

Ser Gly Thr Trp Thr Gln Gln Ile Cys Leu Pro Ala Ile Tyr Lys Val
            530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
            580                 585                 590

Ser Thr Met Asn Thr Leu Lys Cys Thr Val Gly Pro Ala Met Asn Lys
            595                 600                 605

His Phe Asn Met Ser Ile Ile Ile Ser Asn Gly His Gly Thr Thr Gln
610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
            645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
            690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
```

```
                        725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
            755                 760                 765

Arg Ser Asn Ser Glu Ile Ile Cys Cys Thr Thr Pro Ser Leu Gln Gln
        770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
            820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
        850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr Glu Gln Lys Leu
            900                 905                 910

Ile Ser Glu Glu Asp Leu Gly Gly Gln Lys Leu Ile Ser Glu Glu
            915                 920                 925

Asp Leu His His His His His His
        930                 935

<210> SEQ ID NO 156
<211> LENGTH: 12
<212> TYPE: PRT
<213> ORGANISM: Artificial Sequence
<220> FEATURE:
<223> OTHER INFORMATION: synthetic

<400> SEQUENCE: 156

Val Arg Arg Leu Lys Glu Thr Lys Asp Gly Phe Met
1               5                   10

<210> SEQ ID NO 157
<211> LENGTH: 11
<212> TYPE: PRT
<213> ORGANISM: Artificial Sequence
<220> FEATURE:
<223> OTHER INFORMATION: synthetic

<400> SEQUENCE: 157

Leu Ala Arg Gln Ile Gly Ala Ser Leu Asn Asp
1               5                   10

<210> SEQ ID NO 158
<211> LENGTH: 35
<212> TYPE: PRT
<213> ORGANISM: Artificial Sequence
<220> FEATURE:
<223> OTHER INFORMATION: synthetic

<400> SEQUENCE: 158

Phe Ile Lys Gly Asp Leu Thr Ile Ala Asn Leu Gly Thr Ser Glu Gly
1               5                   10                  15
```

Arg Phe Met Gln Val Val Val Ser Arg Ser Gly Pro Ser Thr Pro His
            20                  25                  30
Val Asn Phe
        35